(12) United States Patent
Hindson et al.

(10) Patent No.: US 10,323,279 B2
(45) Date of Patent: *Jun. 18, 2019

(54) METHODS AND SYSTEMS FOR PROCESSING POLYNUCLEOTIDES

(71) Applicant: 10X GENOMICS, INC., Pleasanton, CA (US)

(72) Inventors: Christopher Hindson, Pleasanton, CA (US); Michael Schnall-Levin, Palo Alto, CA (US); Andrew Price, Dublin, CA (US); Paul Hardenbol, San Francisco, CA (US); Yuan Li, Dublin, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/052,486

(22) Filed: Aug. 1, 2018

(65) Prior Publication Data

US 2018/0371540 A1  Dec. 27, 2018

Related U.S. Application Data

(63) Continuation-in-part of application No. 16/000,803, filed on Jun. 5, 2018, which is a continuation of application No. 15/850,241, filed on Dec. 21, 2017, which is a continuation of application No. 15/588,519, filed on May 5, 2017, now Pat. No. 9,856,530, which is a continuation of application No. 15/376,582, filed on Dec. 12, 2016, now Pat. No. 9,701,998, which is a continuation-in-part of application No. 14/104,650, filed on Dec. 12, 2013, now Pat. No. 9,567,631, and a continuation-in-part of application No. 14/250,701, filed on Apr. 11, 2014, now abandoned, which is a continuation of application No. 14/175,973, filed on Feb. 7, 2014, now Pat. No. 9,388,465, application No. 16/052,486, filed on Aug. 1, 2018, which is a continuation-in-part of application No. 14/316,447, filed on Jun. 26, 2014, which is a continuation-in-part of application No. 13/966,150, filed on Aug. 13, 2013, and a continuation-in-part of application No. PCT/US2013/054797, filed on Aug. 13, 2013.

(60) Provisional application No. 61/737,374, filed on Dec. 14, 2012, provisional application No. 61/844,804, filed on Jul. 10, 2013, provisional application No. 61/840,403, filed on Jun. 27, 2013, provisional application No. 61/800,223, filed on Mar. 15, 2013, provisional application No. 61/762,435, filed on Feb. 8, 2013, provisional application No. 61/683,192, filed on Aug. 14, 2012, provisional application No. 61/896,060, filed on Oct. 26, 2013, provisional application No. 61/909,974, filed on Nov. 27, 2013, provisional application No. 61/937,344, filed on Feb. 7, 2014, provisional application No. 61/940,318, filed on Feb. 14, 2014, provisional application No. 61/991,018, filed on May 9, 2014.

(51) Int. Cl.
| | | |
|---|---|---|
| C12Q 1/68 | (2018.01) | |
| C12Q 1/6874 | (2018.01) | |
| C12Q 1/6806 | (2018.01) | |
| C12Q 1/6855 | (2018.01) | |
| C12Q 1/6869 | (2018.01) | |

(52) U.S. Cl.
CPC ......... *C12Q 1/6874* (2013.01); *C12Q 1/6806* (2013.01); *C12Q 1/6855* (2013.01); *C12Q 1/6869* (2013.01)

(58) Field of Classification Search
CPC ............... C12Q 1/6855; C12Q 1/6869; C12Q 2563/159; C12Q 2563/179
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | William et al. |
| 4,124,638 A | 11/1978 | Hansen |

(Continued)

FOREIGN PATENT DOCUMENTS

| | | |
|---|---|---|
| CN | 102292455 A | 12/2011 |
| CN | 103202812 A | 7/2013 |

(Continued)

OTHER PUBLICATIONS

10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.

(Continued)

*Primary Examiner* — David C Thomas
(74) *Attorney, Agent, or Firm* — Wilson Sonsini Goodrich & Rosati

(57) ABSTRACT

This disclosure provides methods and compositions for sample processing, particularly for sequencing applications. Included within this disclosure are bead compositions, such as diverse libraries of beads attached to large numbers of oligonucleotides containing barcodes. Often, the beads provides herein are degradable. For example, they may contain disulfide bonds that are susceptible to reducing agents. The methods provided herein include methods of making libraries of barcoded beads as well as methods of combining the beads with a sample, such as by using a microfluidic device.

28 Claims, 59 Drawing Sheets

Specification includes a Sequence Listing.

(56) References Cited

U.S. PATENT DOCUMENTS

| | | |
|---|---|---|
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,830,663 A | 11/1998 | Embleton et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |

(56) References Cited

U.S. PATENT DOCUMENTS

| | | |
|---|---|---|
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoj et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,119,167 B2 | 11/2018 | Srinivasan et al. |
| 10,137,449 B2 | 11/2018 | Bharadwaj et al. |
| 10,144,950 B2 | 12/2018 | Nolan |
| 10,150,117 B2 | 12/2018 | Bharadwaj et al. |
| 10,150,963 B2 | 12/2018 | Hindson et al. |
| 10,150,964 B2 | 12/2018 | Hindson et al. |
| 10,150,995 B1 | 12/2018 | Giresi et al. |
| 10,174,310 B2 | 1/2019 | Nolan |
| 10,208,343 B2 | 2/2019 | Hindson et al. |
| 10,221,436 B2 | 3/2019 | Hardenbol et al. |
| 10,221,442 B2 | 3/2019 | Hindson et al. |
| 10,227,648 B2 | 3/2019 | Hindson et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |

(56) References Cited

U.S. PATENT DOCUMENTS

| | | |
|---|---|---|
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1 | 7/2010 | Lee et al. |
| 2010/0210479 A1 | 8/2010 | Griffiths et al. |
| 2010/0216153 A1 | 8/2010 | Lapidus et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |

(56) References Cited

U.S. PATENT DOCUMENTS

| | | |
|---|---|---|
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0274117 A1 | 10/2013 | Church et al. |
| 2013/0296173 A1 | 11/2013 | Callow et al. |
| 2013/0343317 A1 | 12/2013 | Etemad et al. |
| 2014/0030350 A1 | 1/2014 | Ashrafi et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev et al. |
| 2014/0120529 A1 | 5/2014 | Andersen et al. |
| 2014/0155274 A1* | 6/2014 | Xie .................. C12Q 1/6853 506/2 |
| 2014/0155295 A1 | 6/2014 | Hindson et al. |
| 2014/0194323 A1 | 7/2014 | Gillevet et al. |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0031037 A1 | 1/2015 | Li et al. |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0211056 A1 | 7/2015 | Um et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0247182 A1 | 9/2015 | Faham et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0087050 A1 | 3/2018 | Zheng et al. |
| 2018/0088112 A1 | 3/2018 | Fan et al. |
| 2018/0094298 A1 | 4/2018 | Hindson et al. |
| 2018/0094312 A1 | 4/2018 | Hindson et al. |
| 2018/0094313 A1 | 4/2018 | Hindson |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0216162 A1 | 8/2018 | Belhocine et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0327839 A1 | 11/2018 | Hindson et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0346979 A1 | 12/2018 | Hindson et al. |
| 2018/0363029 A1 | 12/2018 | Hindson et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |

(56) References Cited

U.S. PATENT DOCUMENTS

| | | |
|---|---|---|
| 2019/0040464 A1 | 2/2019 | Giresi et al. |
| 2019/0085391 A1 | 3/2019 | Hindson et al. |

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| JP | 2012522517 A | 9/2012 |
| WO | WO-8402000 A1 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006071770 A2 | 7/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009048532 A2 | 4/2009 |
| WO | WO-2009061372 A1 | 5/2009 |
| WO | WO-2009085215 A1 | 7/2009 |
| WO | WO-2009147386 A1 | 12/2009 |
| WO | WO-2010004018 A2 | 1/2010 |
| WO | WO-2010009735 A2 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011106314 A2 | 9/2011 |
| WO | WO-2011140627 A1 | 11/2011 |
| WO | WO-2012012037 A1 | 1/2012 |
| WO | WO-2011140510 A3 | 3/2012 |
| WO | WO-2012047889 A2 | 4/2012 |
| WO | WO-2012048340 A2 | 4/2012 |
| WO | WO-2012048341 A2 | 4/2012 |
| WO | WO-2012061832 A1 | 5/2012 |
| WO | WO-2012083225 A2 | 6/2012 |
| WO | WO-2012087736 A1 | 6/2012 |
| WO | WO-2012106546 A2 | 8/2012 |
| WO | WO-2012112804 A2 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |

(56) References Cited

FOREIGN PATENT DOCUMENTS

| | | |
|---|---|---|
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |
| WO | WO-2014150931 A1 | 9/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015031691 A1 | 3/2015 |
| WO | WO-2015044428 A1 | 4/2015 |
| WO | WO-2015164212 A1 | 10/2015 |
| WO | WO-2015185067 A1 | 12/2015 |
| WO | WO-2015188839 A2 | 12/2015 |
| WO | WO-2016040476 A1 | 3/2016 |
| WO | WO-2016061517 A2 | 4/2016 |
| WO | WO-2016126871 A2 | 8/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017053905 A1 | 3/2017 |
| WO | WO-2017075265 A1 | 5/2017 |
| WO | WO-2017075294 A1 | 5/2017 |
| WO | WO-2017096158 A1 | 6/2017 |
| WO | WO-2017117358 A1 | 7/2017 |
| WO | WO-2017156336 A1 | 9/2017 |
| WO | WO-2018045186 A1 | 3/2018 |
| WO | WO-2018058073 A2 | 3/2018 |
| WO | WO-2018119301 A1 | 6/2018 |
| WO | WO-2018119447 A2 | 6/2018 |

OTHER PUBLICATIONS

Abate, et al. Beating Poisson encapsulation statistics using close-packed ordering. Lab Chip. Sep. 21, 2009;9(18):2628-31. doi: 10.1039/b909386a. Epub Jul. 8, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Ahern, "Biochemical, Reagents Kits Offer Scientists Good Return on Investment" The Scientist (1995) 9(15):1-7.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Biol., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna, S.L., et al., "Formation of dispersions using "flow focusing" in microchannels," Applied Physics Letters, vol. 82, No. 3, pp. 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB2886981354/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Ason et al. DNA sequence bias during Tn5 transposition. Journal of molecular biology 335.5 (2004): 1213-1225.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bjornsson et al., Intra-individual change over time in DNA methylation with familial clustering, JAMA, Jun. 25, 2008, vol. 299 No. 24, pp. 2877-2883.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLoS One, vol. 7:1-10, 2012.
Boyle, et al. "High-resolution genome-wide in vivo footprinting of diverse transcription factors in human cells", Genome Res. Mar. 2011;21(3):456-64.

(56) References Cited

OTHER PUBLICATIONS

Braeckmans et al., Scanning the Code. Modern Drug Discovery. 2003:28-32.
Bransky, et al. A microfluidic droplet generator based on a piezo-electric actuator. Lab Chip. Feb. 21, 2009;9(4):516-20. doi: 10.1039/b814810d. Epub Nov. 20, 2008.
Brenner, et al. In vitro cloning of complex mixtures of DNA on microbeads: physical separation of differentially expressed cDNAs. Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al., "Tranposition of native chromatin for fast and sensitive epigenomic profiling of open chromatin, DNA-binding proteins and nucleosome position", Nature Methods, 2013, 10(12): 1213-1218.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. 339.6121 (Feb. 15, 2013): 819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/720,085, filed Sep. 29, 2017.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/847,659, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Co-pending U.S. Appl. No. 15/875,899, filed Jan. 19, 2018.
Co-pending U.S. Appl. No. 15/887,711, filed Feb. 2, 2018.
Co-pending U.S. Appl. No. 15/887,947, filed Feb. 2, 2018.
Co-pending U.S. Appl. No. 15/933,299, filed Mar. 22, 2018.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.
Co-pending U.S. Appl. No. 16/000,803, filed Jun. 5, 2018.
Co-pending U.S. Appl. No. 16/045,474, filed Jul. 25, 2018.
Co-pending U.S. Appl. No. 16/052,431, filed Aug. 1, 2018.
Co-pending U.S. Appl. No. 16/056,231, filed Aug. 6, 2018.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.

(56) References Cited

OTHER PUBLICATIONS

Dekker, et al. Capturing chromosome conformation. Science. Feb. 15, 2002;295(5558):1306-11.
Demirci, et al. Single cell epitaxy by acoustic picolitre droplets. Lab Chip. Sep. 2007;7(9):1139-45. Epub Jul. 10, 2007.
Depristo et al. A framework for variation discovery and genotyping using next-generation DNA sequencing data. Nature Genet 43:491-498 (2011).
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77:75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology.1999; 17:1109-1111.
Fulton, et al. Advanced multiplexed analysis with the FlowMetrix system. Clin Chem. Sep. 1997;43(9):1749-56.
Gangadharan et al., DNA transposon Hermes insert into DNA in nucleosome-free regions in vivo, Proc nat Ad Sci, Dec. 21, 2010, vol. 107, No. 51, pp. 1966-1972.
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized self-replication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Green et al. Insertion site preference of Mu, Tn5, and Tn7 transposons. Mobile DNA 3.1 (2012): 3.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, X. et al. "CRISPR-Cas9 delivery to hard-to-transfect cells via membrane deformation" Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).

(56) References Cited

OTHER PUBLICATIONS

Hosono S, et al. Unbiased whole-genome amplification directly from clinical samples. Genome Res. May 2003; 13(5):954-64. Epub Apr. 14, 2003.
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to The University of Birmingham for the degree of Doctor of Philosophy. 2009.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Jung, et al. Micro machining of injection mold inserts for fluidic channel of polymeric biochips. Sensors. 2007; 7(8):1643-1654.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. 1999; 285:83-85.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly( ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioj, et al., "Counting Absolute Numbers of Molecules Using Unique Molecular Identifiers", Nature Methods 9, 72-74 (2012).
Klein, et al. Droplet barcoding for single-cell transcriptomics applied to embryonic stem cells. Cell. May 21, 2015;161(5):1187-201. doi: 10.1016/j.cell.2015.04.044.
Knapp, et al. Generating barcoded libraries for multiplex high-throughput sequencing. Methods Mol Biol. 2012;840:155-70. doi: 10.1007/978-1-61779-516-9_19.
Knight, et al. Subtle chromosomal rearrangements in children with unexplained mental retardation. Lancet. Nov. 13, 1999;354(9191):1676-81.
Kolodeziejczyk et al., "The technology and biology of single-cell RNA sequencing", Molecular Cell, vol. 58 (May 21, 2015).
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kutyavin, et al. Oligonucleotides containing 2-aminoadenine and 2-thiothymine act as selectively binding complementary agents. Biochemistry. Aug. 27, 1996;35(34):11170-6.
Kwok, et al, "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lander, et al. Initial sequencing and analysis of the human genome. Nature, 409 (Feb. 15, 2001): 860-921.
Lasken, et al. (1996) Archaebacterial DNA Polymerases Tightly Bind Uracil-containing DNA. The Journal of Biological Chemistry, 271(30):17692-17696 (Year: 1996).
Lee, et al. ACT-PRESTO: Rapid and consistent tissue clearing and labeling method for 3dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Highly multiplexed subcellular Rna sequencing in situ. Science. Mar. 21, 2014;343(6177):1360-3. doi: 10.1126/science.1250212. Epub Feb. 27, 2014."
Lee, J-H. et al. "Fluorescent in situ sequencing (FISSEQ) of RNA for gene expression profiling in intact cells and tissues" Nature Protocols (Feb. 12, 2015) 10(3):442-458.
Lennon; et al., "Lennon et al. A scalable, fully automated process for construction of sequence-ready barcoded libraries for 454. Genome Biology 11:R15 (2010)."

(56) References Cited

OTHER PUBLICATIONS

Li, et al. A single-cell-based platform for copy No. variation profiling through digital counting of amplified genomic DNA fragments. ACS Appl Mater Interfaces. Mar. 24, 2017. doi: 10.1021/acsami.7b03146. [Epub ahead of print].
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):543-7.
Macaulay; et al., "G&T-seq: parallel sequencing of single-cell genomes and transcriptomes. Nature Methods, 2015, p. 1-7."
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Man. Monolithic Structures for Integrated Microfluidic Analysis. PhD Thesis. 2001.
Marcus. Gene method offers diagnostic hope. The Wall Street Journal. Jul. 11, 2012.
Maricic T, et al. Optimization of 454 sequencing library preparation from small amounts of DNA permits sequence determination of both Dna strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-417. doi: 10.1002/elps.201200424.
Microfluidic ChipShop. Microfluidic product catalogue. Mar. 2005.
Microfluidic ChipShop. Microfluidic product catalogue. Oct. 2009.
Miller JC, et al. An improved zinc-finger nuclease architecture for highly specific genome editing. Nat. Biotechnol. 2007;25:778-785.
Miller-Stephenson Chemicals 157 FS Series catalog, www.miller-stephenon.com.

MiRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Narayanan, J. et al. "Determination of agarose gel pore size: Absorbance measurements vis a vis other techniques" Journal of Physics: Conference Series 28 (2006) 83-86 (Year: 2006).
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production of Monodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics.,13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP—seq: advantages and challenges of a maturing technology. Nature Reviews Genetics vol. 10, pp. 669-680 (2009).

(56) References Cited

OTHER PUBLICATIONS

Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013).
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. High-Throughput Single-Cell Labeling (HI-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sakaguchi, et al. (1996) Cautionary Note on the Use of dUMP-Containing PCR Primers with Pfu and VentR. Biotechniques, 21(3): 369-370 (Year: 1996).
Sander JD, et al. Selection-free zinc-finger-nuclease engineering by context-dependent assembly (CoDA). Nat. Methods. 2011;8:67-69.
Schirinzi et al., Combinatorial sequencing-by-hybridization: Analysis of the NF1 gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shah, "Fabrication of mono disperse thermosensitive microgels and gel capsules in micro fluidic devices", Soft Matter, 4:2303-2309 (2008).
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shaikh, et al. A modular microfluidic architecture for integrated biochemical analysis. Proc Natl Acad Sci U S A. Jul. 12, 2005;102(28):9745-50. Epub Jun. 28, 2005.
Shimkus, et al. A chemically cleavable biotinylated nucleotide: usefulness in the recovery of protein-DNA complexes from avidin affinity columns. Proc Natl Acad Sci U S A. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.

(56) References Cited

OTHER PUBLICATIONS

Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Simon, et al., "Using formaldehyde-assisted isolation of regulatory elements (FAIRE) to isolate active regulatory DNA", Nature Protocols, 2012, 7(2): 256-267.
Skerra. Phosphorothioate primers improve the amplification of DNA sequences by DNA polymerases with proofreading activity. Nucleic Acids Res. Jul. 25, 1992; 20(14):3551-4.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Spormann Laboratory, Polymerase Chain Reaction (PCR), Alfred Spormann Laboratory, 2009, 1-3. (Year: 2009).
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998).
Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
ThermoFisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1) 107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c51c00823a. Epub Dec. 2, 2015.
Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.

(56) References Cited

OTHER PUBLICATIONS

Xi, et al. New library construction method for single-cell genomes. PLoS One. Jul. 19, 2017;12(7):e0181163. doi: 10.1371/journal.pone. 0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Reverse transcriptase template switching: a SMART approach for full-length cDNA library construction. Biotechniques. Apr. 2001;30(4):892-7.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Hum• Antibodies Hybridomas. Jan. 1992; 3(1 ): 14-8.
Zong et al. Genome-Wide Detection of Single Nucleotide and Copy Number Variations of a Single Human Cell. Science 338(6114):1622-1626 (2012).
Anonymous: "TCEP=HCl" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCl_UG.pdf.
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Co-pending U.S. Appl. No. 16/138,448, filed Sep. 21, 2018.
Co-pending U.S. Appl. No. 16/144,832, filed Sep. 27, 2018.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Greenleaf, et al. Assaying the epigenome in limited numbers of cells. Methods. Jan. 15, 2015;72:51-6. doi: 10.1016/j.ymeth.2014. 10.010. Epub Oct. 22, 2014.
Hu et al., Shape Controllable Microgel Particles Prepared by Microfluidic Combining External Crosslinking, Biomicrofluidics 6:26502 (May 18, 2012).
Lebedev, A. et al. "Hot Start PCR with heat-activatable primers: a novel approach for improved PCR performance" NAR (2008) 36(20):E131-1.
McGinnis, et al. MULTI-seq: Scalable sample multiplexing for single-cell RNA sequencing using lipid-tagged indices. bioRxiv 387241; doi: https://doi.org/10.1101/387241.
Savva, et al. The structural basis of specific base-excision repair by uracil-DNA glycosylase. Nature. Feb. 9, 1995;373(6514):487-93.
Zhang, et al. One-step fabrication of supramolecular microcapsules from microfluidic droplets. Science. Feb. 10, 2012;335(6069):690-4. doi: 10.1126/science.1215416.
Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.
Co-pending U.S. Appl. No. 16/033,065, filed Jul. 11, 2018.
Co-pending U.S. Appl. No. 16/043,874, filed Jul. 24, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/170,980, filed Oct. 25, 2018.
Co-pending U.S. Appl. No. 16/206,168, filed Nov. 30, 2018.
Co-pending U.S. Appl. No. 16/212,441, filed Dec. 6, 2018.
Delehanty, et al. Peptides for specific intracellular delivery and targeting of nanoparticles: implications for developing nanoparticle-mediated drug delivery. Ther Deliv. Sep. 2010;1(3):411-33.
Epicentre., "EZ-Tn5TM Custom Transposome Construction Kits", http://www.epicentre.com, pp. 1-17, 2012.
"How many species of bacteria are there" (wisegeek.com; accessed Jan. 21, 2014).
"List of sequenced bacterial genomes" (Wikipedia.com; accessed Jan. 24, 2014).
Margulies 2005 Supplementary methods (Year: 2005).
Margulies et al. "Genome sequencing in microfabricated high-density picoliter reactors", Nature (2005) 437:376-380.
"Meyer, et al., From micrograms to picograms: quantitative PCR reduces the material demands of high-throughput sequencing, Nucleic Acids Research, 2008, vol. 36, No. 1, 6 pages".
Ullal et al. Cancer Cell Profiling by Barcoding Allows Multiplexed Protein Analysis in Fine-Needle Aspirates. Sci Transl Med. Jan. 15, 2014; 6(219): 219ra9.
Zhang, et al. Reconstruction of DNA sequencing by hybridization. Bioinformatics. Jan. 2003;19(1):14-21.
Thaxton, C.S. et al. "A Bio-Bar-Code Assay Based Upon Dithiothreitol Oligonucleotide Release" Anal Chem (2005) 77:8174-8178.
Co-pending U.S. Appl. No. 16/196,684, filed Nov. 20, 2018.
Jin, et al. Genome-wide detection of DNase I hypersensitive sites in single cells and FFPE tissue samples. Nature. Dec. 3, 2015;528(7580):142-6. doi: 10.1038/nature15740.
Anonymous: "Three Ways to Get Intimate with Epigenetic Marks". Oct. 24, 2012. Retrieved from Internet: https://epigenie.com/three-ways-to-get-intimate-with-epigenetic-marks/.
Co-pending U.S. Appl. No. 16/228,261, filed Dec. 20, 2018.
Co-pending U.S. Appl. No. 16/228,362, filed Dec. 20, 2018.
Co-pending U.S. Appl. No. 16/230,936, filed Dec. 21, 2018.
Co-pending U.S. Appl. No. 16/231,142, filed Dec. 21, 2018.
Co-pending U.S. Appl. No. 16/231,185, filed Dec. 21, 2018.
Co-pending U.S. Appl. No. 16/242,962, filed Jan. 8, 2019.
Co-pending U.S. Appl. No. 16/246,322, filed Jan. 11, 2019.
Co-pending U.S. Appl. No. 16/249,688, filed Jan. 16, 2019.

(56) References Cited

OTHER PUBLICATIONS

Meyer, et al. Targeted high-throughput sequencing of tagged nucleic acid samples. Nucleic Acids Res. 2007;35(15):e97.
AH006633.3 (Homo sapiens clone P1 and PAC max interactor 1 (MXI1) gene, complete cds, NCBI Reference Sequence, priority to Jun. 10, 2016, 5 pages) (Year:2016).
Ahern, H. The Scientist, vol. 20, pp. 20 and 22. Jul. (Year: 1995).
Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Bentley, et al. 2008. Supplementary Information. pp. 1-55 Nature. Nov. 6, 2008; 456(7218):53-9.
Cejas, P. et al. "Chromatin immunoprecipitation from fixed clinical tissues reveals tumor-specific enhancer profiles" Nature Med (2016) 22(6):685-691.
Co-pending U.S. Appl. No. 16/294,769, filed Mar. 6, 2019.
Epicenter, EZ-Tn5 Transposase, Epicenter, 2012, 1-5. (Year: 2012).
Fanielli, M. et al. "Pathology tissue-chromatin immunoprecipitation, coupled with high-throughput sequencing, allows the epigenetic profiling of patient samples" PNAS (2010) 107(50):21535-21540.
Hebenstreit. Methods, Challenges and Potentials of Single Cell RNA-seq. Biology (Basel). Nov. 16, 2012;1(3):658-67. doi: 10.3390/biology1030658.
Mali, et al. Barcoding cells using cell-surface programmable DNA-binding domains. Nat Methods. May 2013;10(5):403-6. doi: 10.1038/nmeth.2407. Epub Mar. 17, 2013.
Mignardi, M. et al. "Oligonucleotide gap-fill ligation for mutation detection and sequencing in situ" Nucl Acids Res (2015) 43(22):e151.
Pfeifer, et al. Bivalent cholesterol-based coupling of oligonucleotides to lipid membrane assemblies. J Am Chem Soc. Aug. 25, 2004;126(33):10224-5.
Co-pending U.S. Appl. No. 16/395,090, filed Apr. 25, 2019.

* cited by examiner

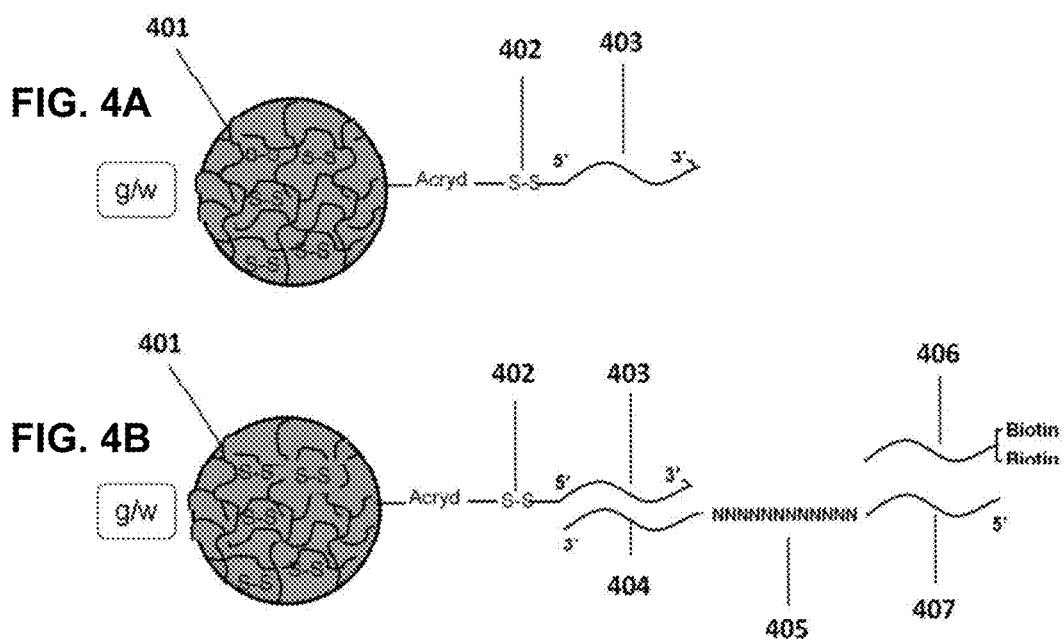

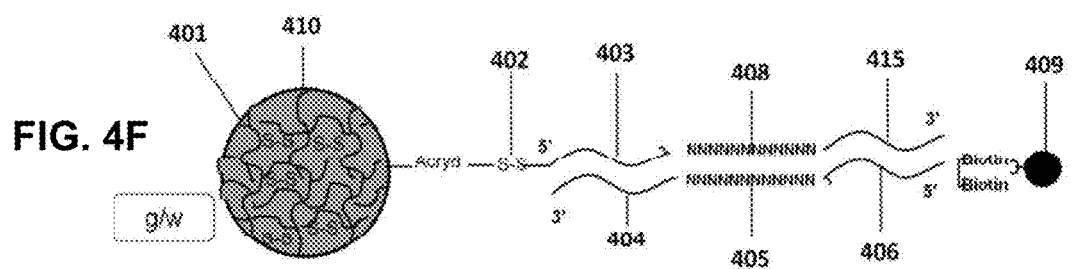
FIG. 4F
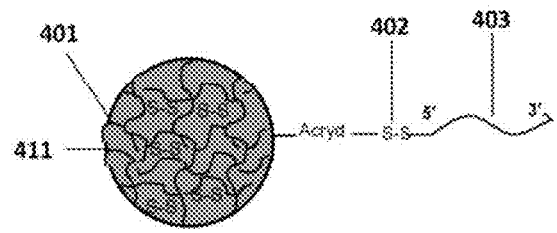
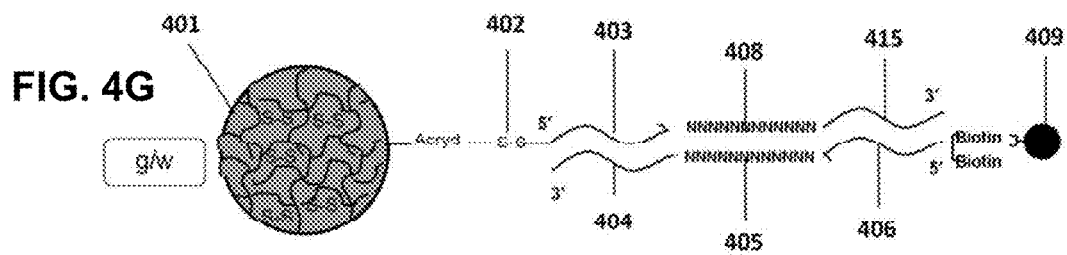
FIG. 4G

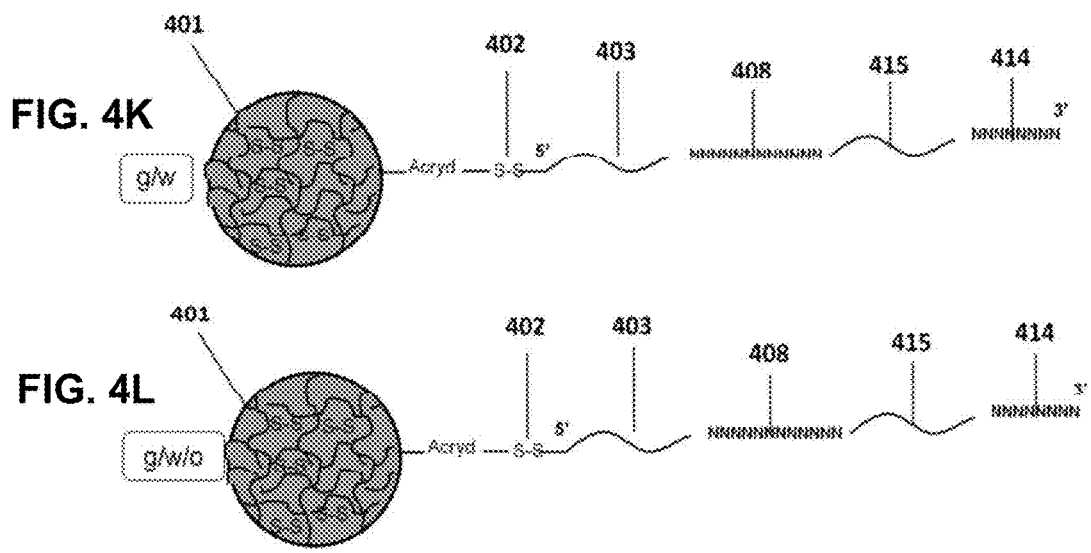

| FIG. 7A | FIG. 7B | FIG. 7C |
| Make (ssDNA) | Extend (dsDNA) | Denature (ssDNA) |
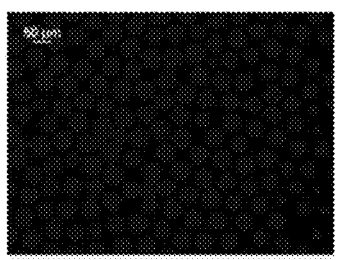 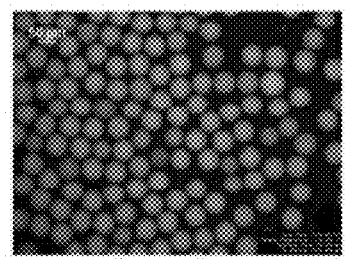 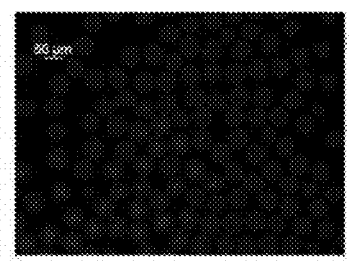

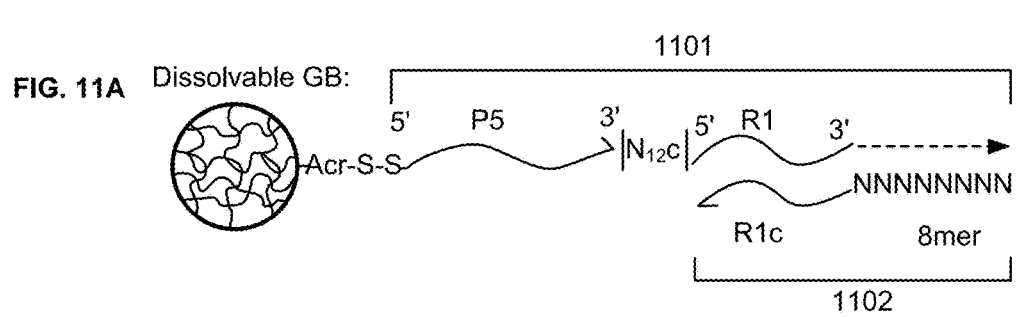
FIG. 11A
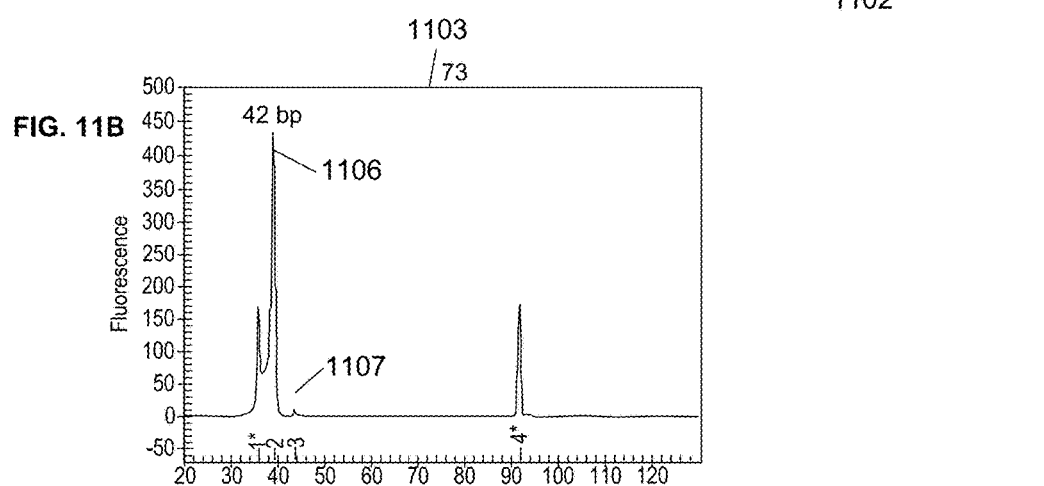
FIG. 11B
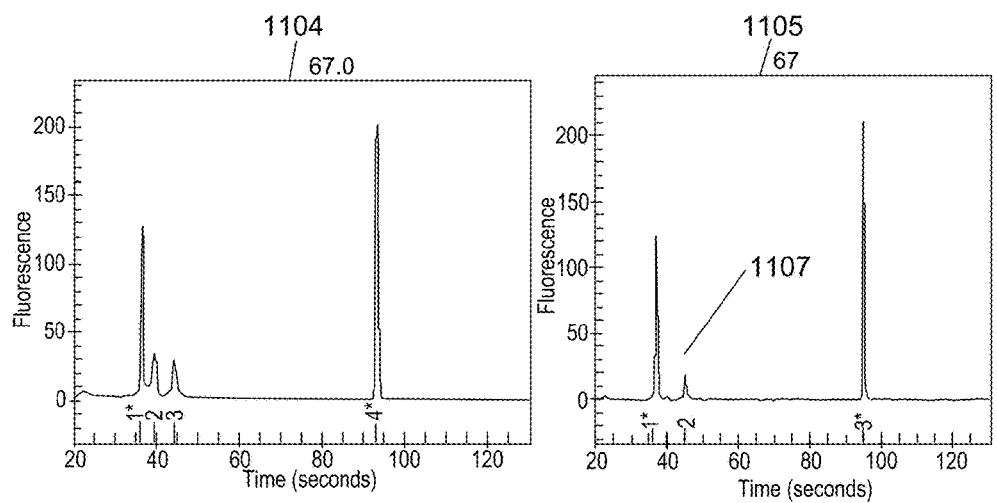

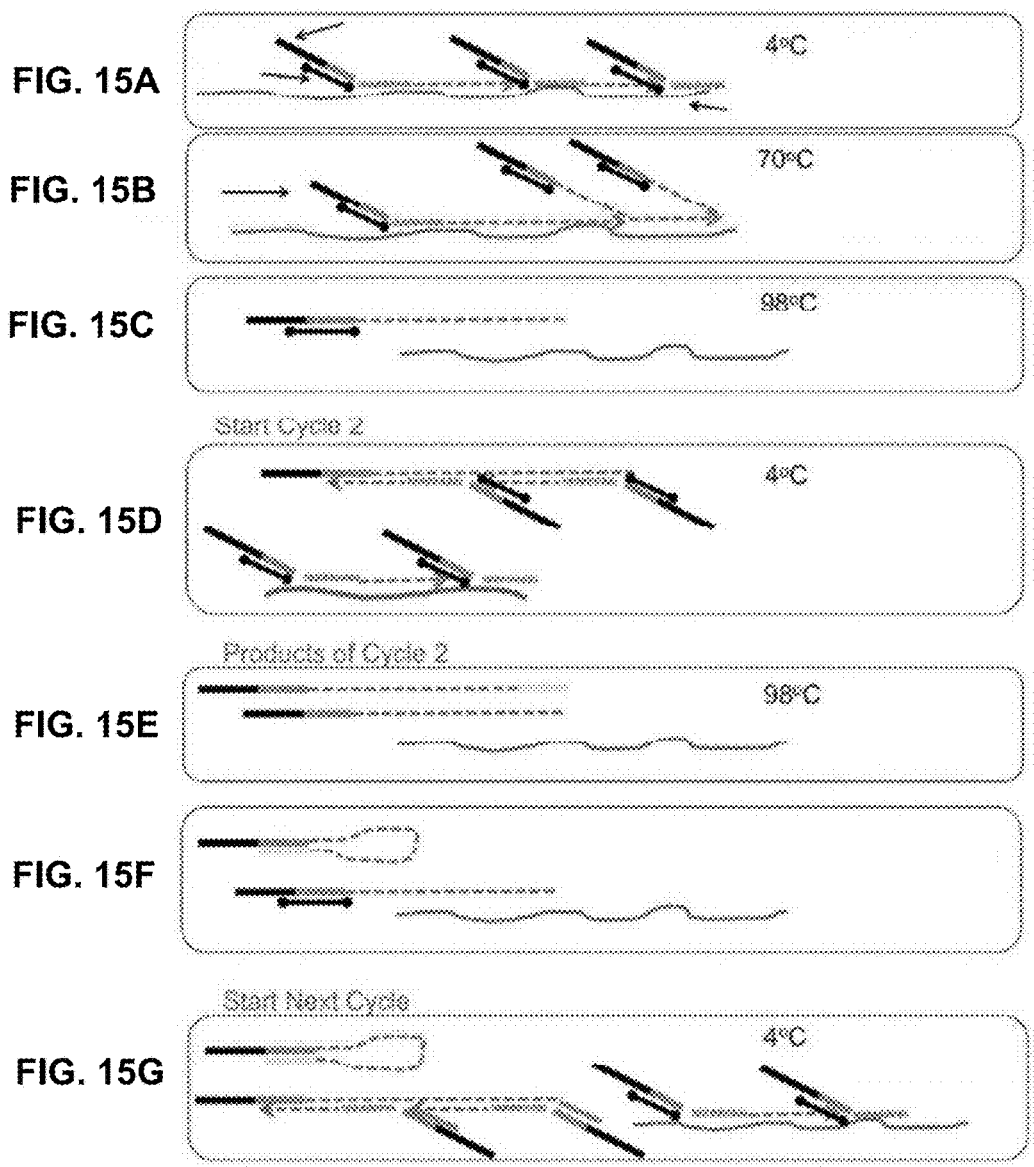

| Function | Name | Sequence 5'-3' | Mods |
|---|---|---|---|
| Primer for actual library production | P5_U | /5Acryd/iThioMC6-D/ AAG GAG ACG GCG ACC ACC GAG A | ["5' Acrydite", "iThioMC6-D", "Int deoxyUridine", "HPLC Purification"] |
| Reverse primer for sorting | S2-Bio-R1-rc | /52-Bio/ GCG TCG TGT AGG GAA AGA GTG T | ["3' Dual Biotin", "HPLC Purification"] |
| Limiting dilution template | R1-Barcode-P5_Template | GCG TCG TGT AGG GAA AGA GTG TNN NNN NNN NNN NGT NTA GAT CTC GGT GGT CGC CGT ATC ATT | Hand mixed, with native nucleotides |
| Template for adding 8-mer random primer | R1-Partial-8Nmer-rc | NNN NNN NNA GAT CGG AAG AGC GTC GTG TAG GGA AAG AGT GT | Hand mixed, with native nucleotides, no 3'blocker needed |

FIG. 19

| Gel Bead Aliquot | Final vol (uL) | Concentration of mag beads mg/mL | Incubation time (hr) | Selective Deposition | Recovery (Y/N) |
| --- | --- | --- | --- | --- | --- |
| 1 | 100 | 100 | 24 | Yes | No |
| 2 | 100 | 80 | 24 | Yes | No |
| 3 | 100 | 60 | 24 | Yes | Yes |
| 4 | 100 | 40 | 24 | Yes | Yes |
| 5 | 100 | 20 | 24 | No | No |
| 6 | 100 | 10 | 24 | No | No |

FIG. 20

| Metric | Description | Value | Target Value |
|---|---|---|---|
| Q40 Error | Error rate across all q40 positions | 0.002 | <=0.02 |
| Unmapped fraction | Fraction of reads with both ends unmapped | 0.996 | <=0.04 |
| Median insert size | Median insert size | 399 | [200;400] |
| IQR insert size | Interquartile range of insert size | 413 | <=250 |
| Zero coverage fraction | Fraction of genome with zero coverage | 0.9242 | <=0.01 |

FIG. 21

| Metric | Description | Value | Target Value |
|---|---|---|---|
| Q40 Error | Error rate across all q40 positions | 0.001 | <=0.02 |
| Unmapped fraction | Fraction of reads with both ends unmapped | 0.03 | <=0.04 |
| Median insert size | Median insert size | 310 | [200:400] |
| IQR insert size | Interquartile range of insert size | 209 | <=250 |
| Zero coverage fraction | Fraction of genome with zero coverage | 0.0093 | <=0.01 |

FIG. 22

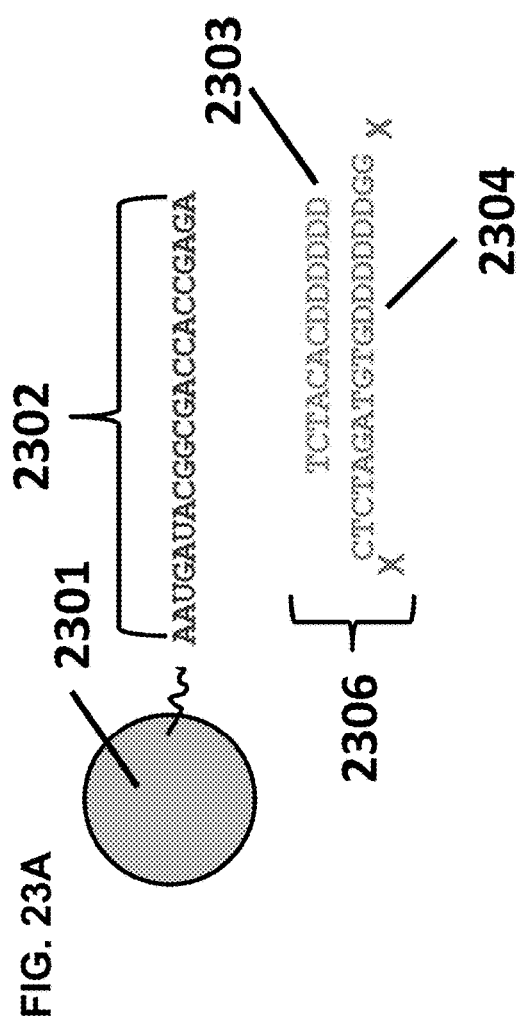
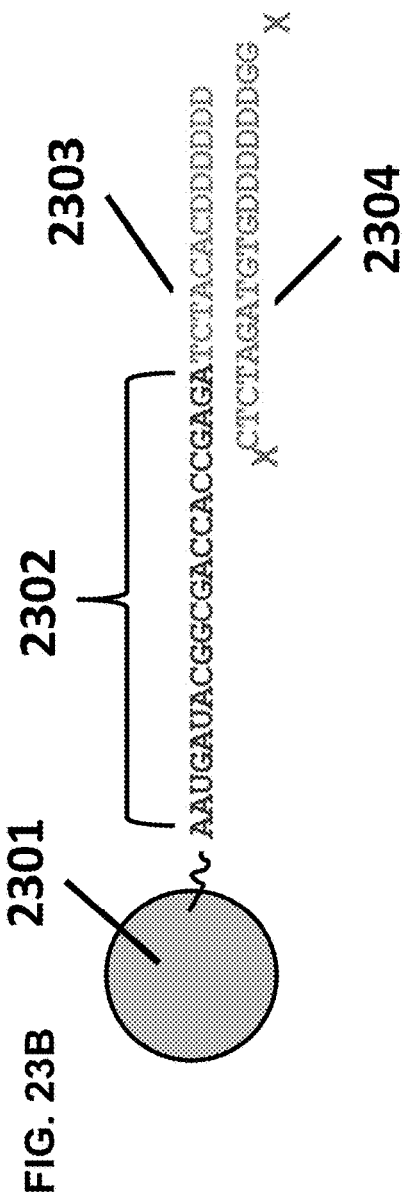
FIG. 23A
FIG. 23B

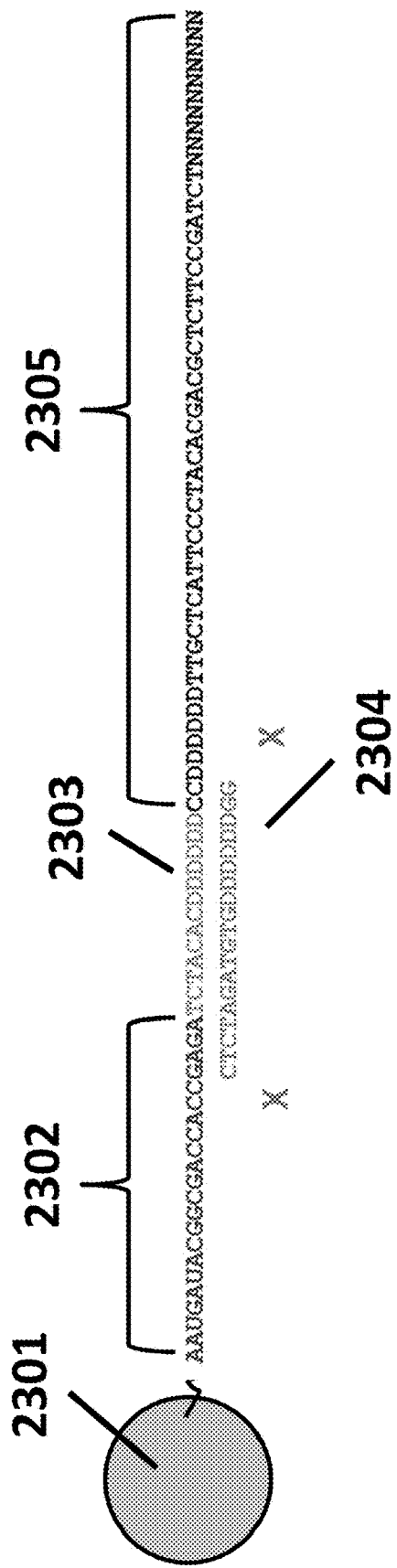

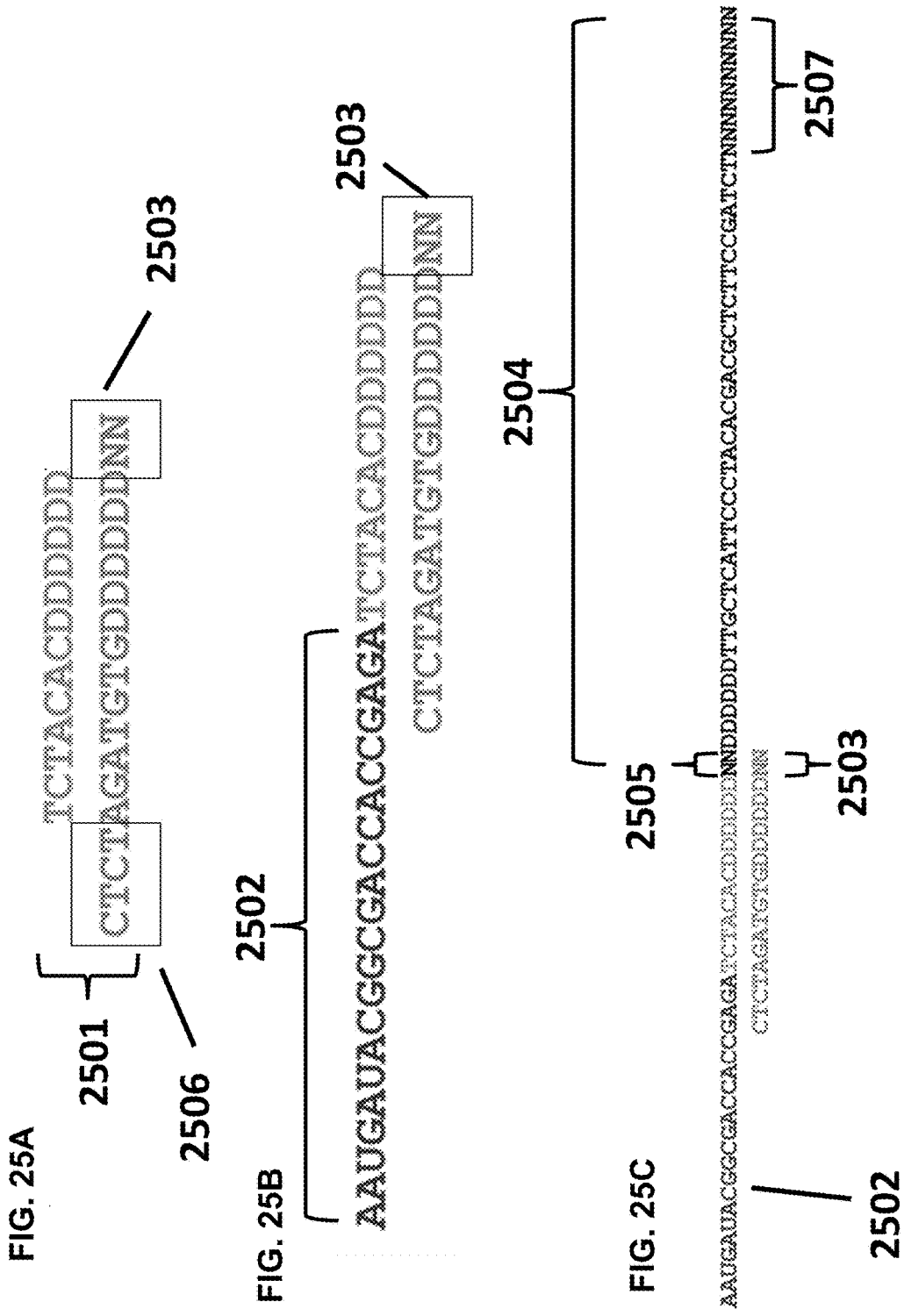

2601
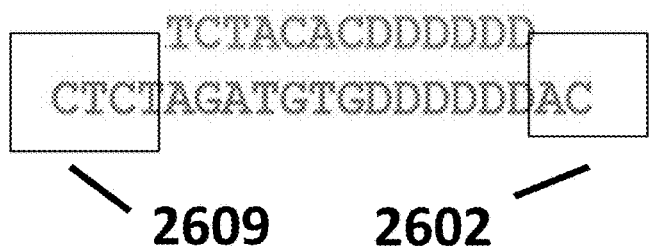
2609  2602
2603
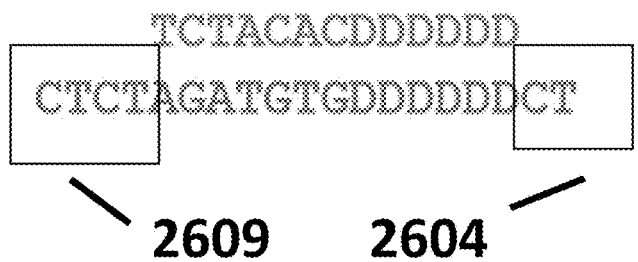
2609  2604
2605
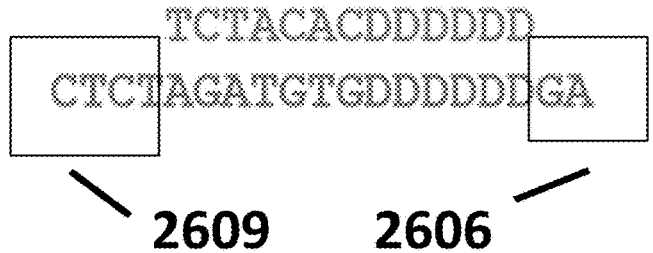
2609  2606
2607
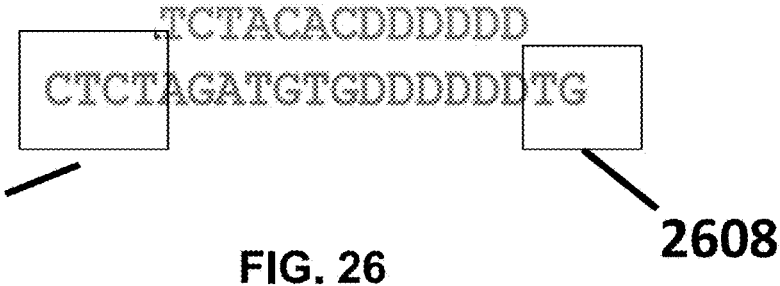
2609  2608
FIG. 26

P₅ monomer

Multi-P₅ monomer

Multi-P₅ crosslinker

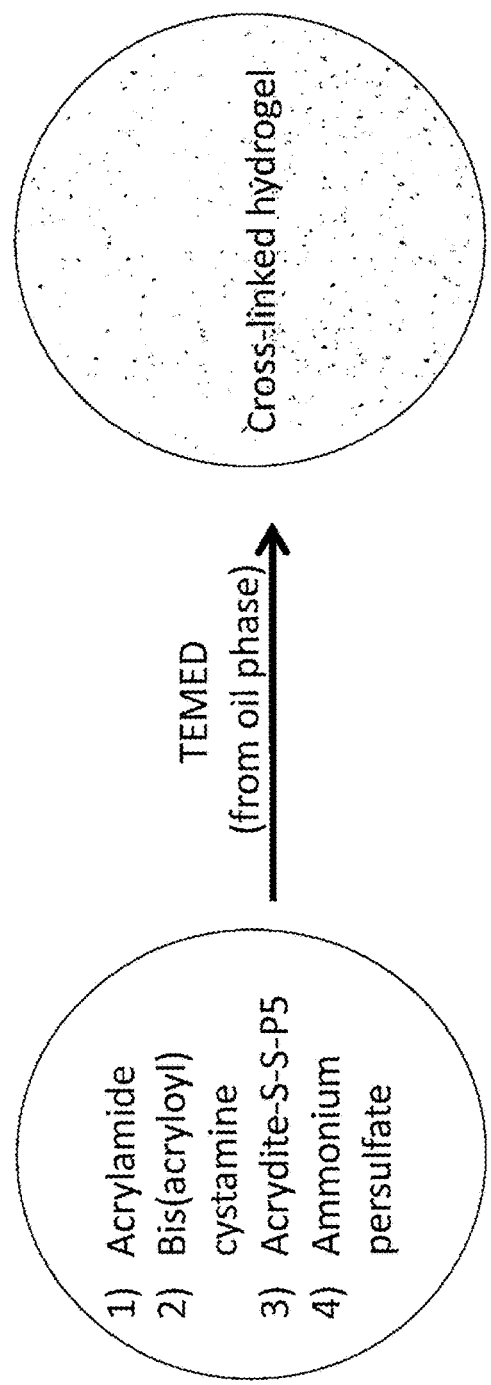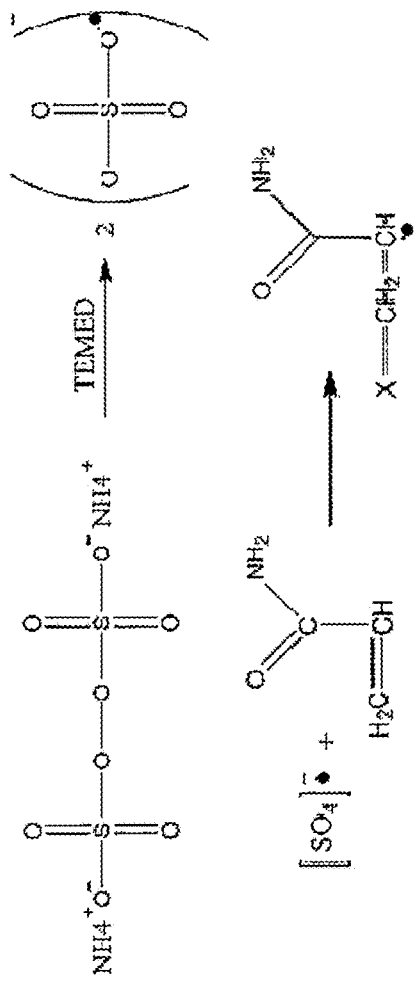
FIG. 30A

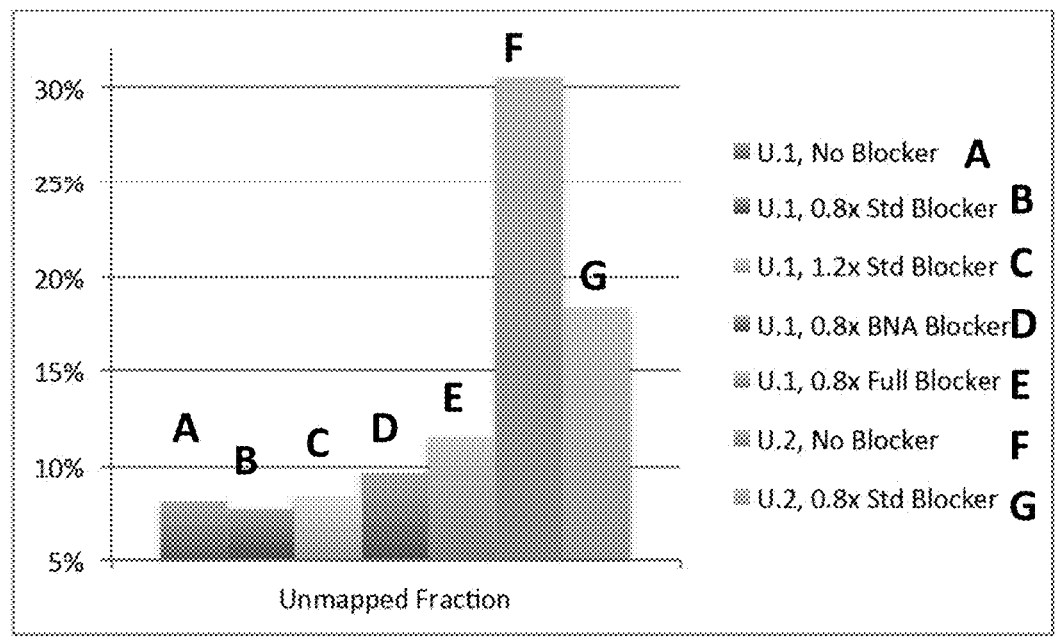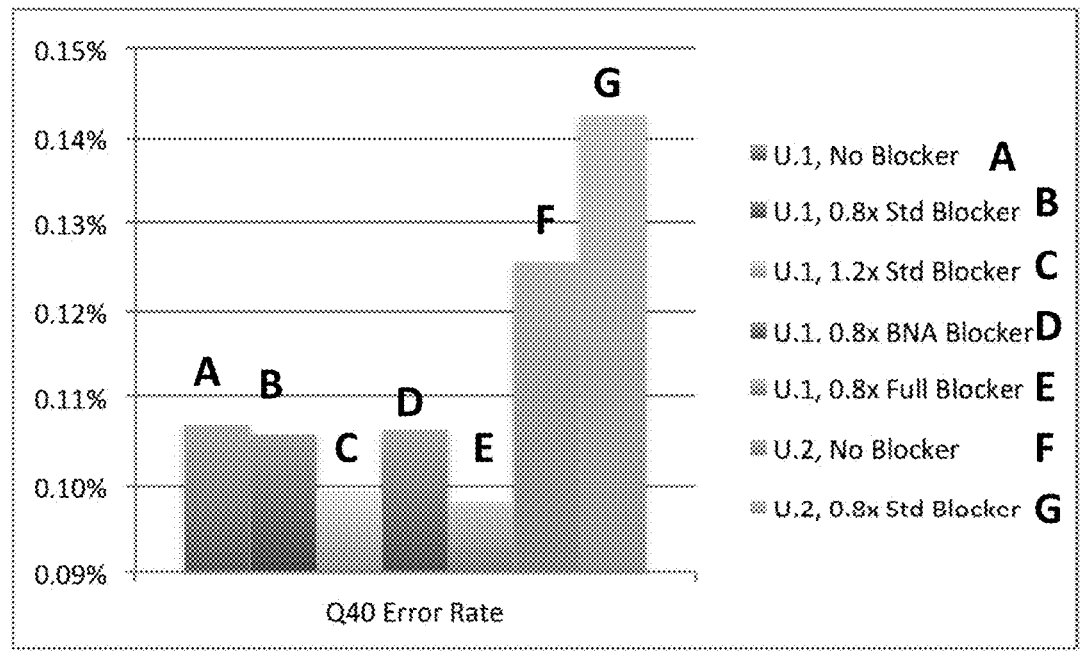
FIG. 33D

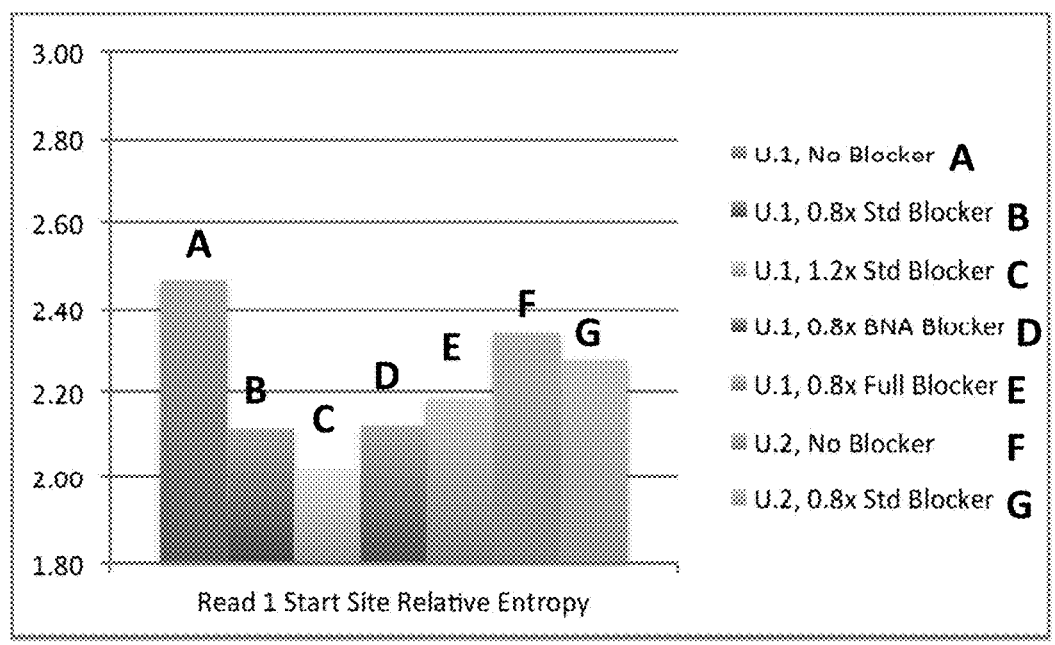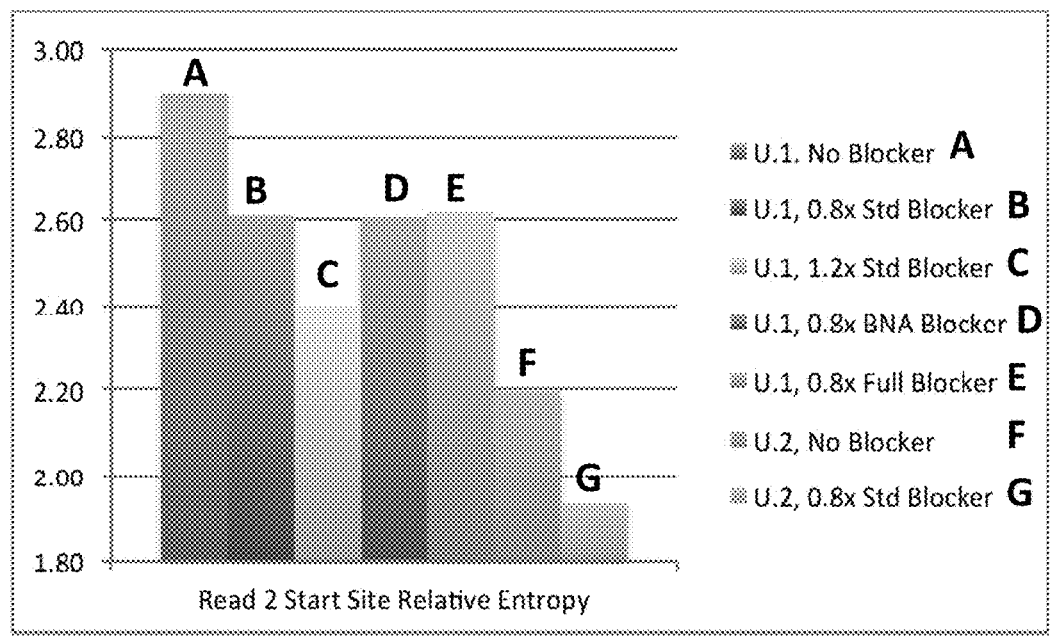
FIG. 33E

1: 50 pmoles P5-acrydite
2: 25 bp ladder
3-5: TCEP:GB = 2.5 billion
6-8: TCEP:GB = 10.0 billion 9-11: TCEP:GB = 0
3,6,9: P5:GB = 50 million
4,7,10: P5:GB = 500 million
5,8,11: P5:GB = 5 billion 1: 50 bp ladder
2: FCBC:GB = 400 million
3: FCBC:GB = 1.6 billion
4: Acrydite Polymerization Chemistry Bright beads: Acrydite Polymerization Chemistry (Functionalization During Gel Bead Production)

Dim beads: Thiol-Disulfide Exchange Chemistry (Functionalization Post-Production of Gel Beads)

METHODS AND SYSTEMS FOR PROCESSING POLYNUCLEOTIDES

CROSS-REFERENCE

This application is a continuation-in-part of U.S. application Ser. No. 16/000,803, filed Jun. 5, 2018, which is a continuation of U.S. application Ser. No. 15/850,241, filed Dec. 21, 2017, which is a continuation of U.S. patent application Ser. No. 15/588,519, filed May 5, 2017, now U.S. Pat. No. 9,856,530, which is a continuation of U.S. patent application Ser. No. 15/376,582, filed Dec. 12, 2016, now U.S. Pat. No. 9,701,998, which is a continuation-in-part of U.S. patent application Ser. No. 14/104,650, filed on Dec. 12, 2013, now U.S. Pat. No. 9,567,631, which claims priority to U.S. Provisional Application No. 61/737,374, filed on Dec. 14, 2012; U.S. patent application Ser. No. 15/376,582 is also a continuation-in-part of U.S. patent application Ser. No. 14/250,701, filed on Apr. 11, 2014, which is a continuation of U.S. patent application Ser. No. 14/175,973, filed on Feb. 7, 2014, now U.S. Pat. No. 9,388,465, which claims priority to U.S. Provisional Application No. 61/844,804, filed on Jul. 10, 2013, U.S. Provisional Application No. 61/840,403, filed on Jun. 27, 2013, U.S. Provisional Application No. 61/800,223, filed on Mar. 15, 2013, and U.S. Provisional Application No. 61/762,435, filed on Feb. 8, 2013, each of which is entirely incorporated herein by reference for all purposes. This application is also a continuation-in-part of U.S. application Ser. No. 14/316,447, filed on Jun. 26, 2014, which is a continuation-in-part of U.S. patent application Ser. No. 13/966,150, filed on Aug. 13, 2013, which claims priority to U.S. Provisional Application No. 61/844,804, filed on Jul. 10, 2013, U.S. Provisional Application No. 61/840,403, filed on Jun. 27, 2013, U.S. Provisional Application No. 61/800,223, filed on Mar. 15, 2013, U.S. Provisional Application No. 61/762,435, filed on Feb. 8, 2013, U.S. Provisional Application No. 61/737,374, filed on Dec. 14, 2012, U.S. Provisional Application No. 61/683,192, filed on Aug. 14, 2012; and a continuation-in-part of PCT International Patent Application No. PCT/US13/54797, filed on Aug. 13, 2013, which claims priority to U.S. Provisional Patent Application No. 61/683,192, filed on Aug. 14, 2012; U.S. Provisional Patent Application No. 61/737,374, filed on Dec. 14, 2012; U.S. Provisional Patent Application No. 61/762,435, filed on Feb. 8, 2013; U.S. Provisional Patent Application No. 61/800,223, filed on Mar. 15, 2013; U.S. Provisional Patent Application No. 61/840,403 filed on Jun. 27, 2013; and U.S. Provisional Patent Application No. 61/844,804 filed on Jul. 10, 2013, which applications are incorporated herein by reference in their entireties for all purposes. U.S. application Ser. No. 14/316,447, filed on Jun. 26, 2014, also claims the benefit of U.S. Provisional Patent Application No. 61/896,060 filed on Oct. 26, 2013; U.S. Provisional Patent Application No. 61/909,974 filed on Nov. 27, 2013; U.S. Provisional Patent Application No. 61/937,344 filed on Feb. 7, 2014; U.S. Provisional Patent Application No. 61/940,318 filed on Feb. 14, 2014; and U.S. Provisional Patent Application No. 61/991,018, filed on May 9, 2014, which applications are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Aug. 30, 2018, is named 43487703313SL.txt and is 12 kilobytes in size.

BACKGROUND

Genomic sequencing can be used to obtain information in a wide variety of biomedical contexts, including diagnostics, prognostics, biotechnology, and forensic biology. Sequencing may involve basic methods including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, HeliScope single molecule sequencing, SMRT® sequencing, and others. For most sequencing applications, a sample such as a nucleic acid sample is processed prior to introduction to a sequencing machine. A sample may be processed, for example, by amplification or by attaching a unique identifier. Often unique identifiers are used to identify the origin of a particular sample.

SUMMARY

The present disclosure generally provides methods, compositions, devices, and kits for the generation of beads with covalently attached polynucleotides. Such beads may be used for any suitable application. The present disclosure further provides methods, compositions, devices, and kits for polynucleotide barcoding.

In an aspect, the present disclosure provides a method for polynucleotide barcoding, comprising: (a) in a first set of partitions, attaching a first set of nucleic acid barcode molecules comprising barcode sequences to polynucleotides to provide a first set of barcoded polynucleotides; (b) pooling contents of said first set of partitions; (c) partitioning at least a portion of said contents from (b) into a second set of partitions different than said first set of partitions; and (d) in said second set of partitions, attaching a second set of nucleic acid barcode molecules comprising barcode sequences to said first set of barcoded polynucleotides to provide a second set of barcoded polynucleotides.

In some embodiments, a subset of barcoded polynucleotides of said first set of barcoded polynucleotides have identical barcode sequences. In some embodiments, at least a subset of barcoded polynucleotides of said second set of barcoded polynucleotides have different barcode sequences.

In some embodiments, said polynucleotides are attached to beads.

In some embodiments, said polynucleotides are cellular polynucleotides.

In some embodiments, said first set of partitions are a first set of wells and said second set of partitions are a second set of wells. In some embodiments, said first set of partitions are a first set of droplets and said second set of partitions are a second set of droplets.

In some embodiments, said first set of nucleic acid barcode molecules or said second set of nucleic acid barcode molecules are attached to said polynucleotides by a nucleic acid reaction. In some embodiments, said first set of nucleic acid barcode molecules or said second set of nucleic acid barcode molecules are attached to said polynucleotides by a nucleic acid primer extension reaction. In some embodiments, said first set of nucleic acid barcode molecules or said second set of nucleic acid barcode molecules are attached to said polynucleotides by a nucleic acid amplification reaction. In some embodiments, said first set of nucleic acid barcode molecules or said second set of nucleic acid barcode molecules are attached to said polynucleotides by ligation.

In some embodiments, said first set of barcoded polynucleotides or said second set of barcoded polynucleotides are coupled to a plurality of beads. In some embodiments, said nucleic acid barcode molecules are releasable from said plurality of beads. In some embodiments, said plurality of beads are a plurality of gel beads. In some embodiments, each gel bead of said plurality of gel beads is dissolvable or disruptable.

In some embodiments, each nucleic acid barcode molecule of said first set of nucleic acid barcode molecules or said second set of nucleic acid barcode molecules further comprises a primer sequence. In some embodiments, said primer sequence is a targeted primer sequence or a random primer sequence. In some embodiments, each nucleic acid barcode molecule of said first set of nucleic acid barcode molecules or said second set of nucleic acid barcode molecules further comprises a random N-mer.

In some embodiments, said barcode sequences of said first set of nucleic acid barcode molecules or said barcode sequences of said second set of nucleic acid barcode molecules are greater than 4 nucleic acid bases in length. In some embodiments, said barcode sequences of said first set of nucleic acid barcode molecules or said barcode sequences of said second set of nucleic acid barcode molecules are 4 to 20 nucleic acid bases in length. In some embodiments, each barcoded polynucleotide of said second set of barcoded polynucleotides comprises a barcode sequence that is at least 15 nucleic acid bases in length.

In some embodiments, said second set of barcoded polynucleotides comprises at least 100,000 different barcode sequences. In some embodiments, said second set of barcoded polynucleotides comprises at least 1,000,000 different barcode sequences. In some embodiments, said second set of barcoded polynucleotides comprises at least 10,000,000 different barcode sequences.

In some embodiments, the method further comprises: (e) pooling contents of said second set of partitions; (f) partitioning at least a portion of said contents from (e) into a third set of partitions different than said first set of partitions and said second set of partitions; and (g) in said third set of partitions, attaching a third set of nucleic acid barcode molecules comprising barcode sequences to said second set of barcoded polynucleotides to provide a third set of barcoded polynucleotides. In some embodiments, the method further comprises: (h) pooling contents of said second third of partitions; (i) partitioning at least a portion of said contents from (h) into a fourth set of partitions different than said first set of partitions, said second set of partitions, and said third set of partitions; and (j) in said fourth set of partitions, attaching a fourth set of nucleic acid barcode molecules comprising barcode sequences to said third set of barcoded polynucleotides to provide a fourth set of barcoded polynucleotides.

In some embodiments, said first set of nucleic acid barcode molecules are attached to said polynucleotides by a nucleic acid primer extension reaction, wherein said second set of nucleic acid barcode molecules are attached to said first set of barcoded polynucleotides by ligation, wherein said third set of nucleic acid barcode molecules are attached to said second set of barcoded polynucleotides by ligation, and wherein said fourth set of nucleic acid barcode molecules are attached to said third set of barcoded polynucleotides by a nucleic acid amplification reaction.

An aspect of the disclosure provides a method of barcoding sample materials. A first partition comprising a plurality of nucleic acid barcode molecules associated therewith may be provided and the nucleic acid barcode molecules can comprise the same nucleic acid barcode sequence. The first partition may be co-partitioned with components of a sample material into a second partition and the barcode molecules can then be released from the first partition into the second partition. The released barcode molecules can be attached to one or more of the components of the sample material or fragments thereof within the second partition. In some cases, the first partition may comprise at least 1,000 barcode molecules, at least 10,000 barcode molecules, at least 100,000 barcode molecules, or at least 1,000,000 barcode molecules associated therewith having the same barcode sequence. Moreover, in some examples, the first partition may be a bead, a microcapsule, or a droplet. In some cases, the first partition may comprise a bead (e.g., a gel bead) and the barcode molecules may be releasably coupled to the bead. Moreover, the second partition may comprise a droplet and/or may comprise no more than one first partition.

In some cases, the co-partitioning of the first partition and the components of the sample material into the second partition may comprise combining a first aqueous fluid comprising beads with a second aqueous fluid comprising the sample components in a droplet within an immiscible fluid. Moreover, the barcode molecules may be released from the first partition by degrading the first partition. In cases where the first partition is a bead, the barcode molecules may be released in the second partition by degrading the bead and/or cleaving a chemical linkage between the barcode molecules and the bead. In some cases, at least one of crosslinking of the bead and a linkage between the bead and the barcode molecules may comprise a disulfide linkage. In such cases, the barcode molecules may be released from the bead by exposing the bead to a reducing agent (e.g., dithiothreitol (DTT) or tris(2-carboxyethyl)phosphine (TCEP)).

The sample materials may comprise one or more template nucleic acid molecules and the barcode molecules may be attached to one or more fragments of the template nucleic acid molecules. In some cases, the barcode molecules may comprise a primer sequence complementary to at least a portion of the template nucleic acid molecules and the barcode molecules may be attached to the template nucleic acid molecule or fragments thereof by extending the barcode molecules to replicate at least a portion of the template nucleic acid molecules. Moreover, the sample materials may comprise the contents of a single cell, such as, for example, a cancer cell or a bacterial cell (e.g., a bacterial cell isolated from a human microbiome sample).

Furthermore, a plurality of first partitions comprising a plurality of different nucleic acid barcode sequences may be provided. Each of the first partitions can include a plurality of at least 1000 nucleic acid barcode molecules having the same nucleic acid barcode sequence associated therewith. The first partitions may be co-partitioned with components of the sample material into a plurality of second partitions. The nucleic acid barcode molecules from the first partitions may then be released into the second partitions. The released nucleic acid barcode molecules can then be attached to the components of the sample material or fragments thereof within the second partitions. In some cases, the plurality of different nucleic acid barcode sequences may comprise at least about 1,000 different barcode sequences, at least about 10,000 different barcode sequences, at least about 100,000 different barcode sequences, or at least about 500,000 different barcode sequences. Additionally, in some examples, a subset of the second partitions may comprise the same nucleic acid barcode sequence. For example, at least about 1%, at least about 2%, or at least about 5% of the second partitions may comprise the same nucleic acid barcode sequence. In addition, in some cases, at least 50% of the second partitions, at least 70% of the second partitions, or at least 90% of the second partitions may contain no more than one first partition. In some cases, at least 50% of the second partitions, at least 70% of the second partitions, or at least 90% of the second partitions may contain exactly one first partition.

Fragments of the components of the sample material may include one or more fragments of one or more template nucleic acid sequences. The fragments of the template nucleic acid sequences may be sequenced and characterized based at least in part upon a nucleic acid barcode sequence attached thereto. In some cases, the fragments of the template nucleic acid sequences may be characterized by mapping a fragment of an individual template nucleic acid sequence of the template nucleic acid sequences to an individual template nucleic acid sequence of the template nucleic acid sequences or a genome from which the individual template nucleic acid sequence was derived. In some cases, the fragments of the template nucleic acid sequence may be characterized by at least identifying an individual nucleic acid barcode sequence of the different nucleic acid barcode sequences and identifying a sequence of an individual fragment of the fragments of the template nucleic acid sequences attached to the individual nucleic acid barcode sequence.

An additional aspect of the disclosure provides a method of barcoding sample materials. A plurality of first partitions may be provided that comprise a plurality of different nucleic acid barcode sequences. Each of the first partitions may comprise a plurality of nucleic acid barcode molecules having the same nucleic acid barcode sequence associated therewith. The first partitions may by co-partitioned with components of a sample material into a plurality of second partitions. The barcode molecules can be released from the first partitions into the second partitions. The released barcode molecules can then be attached to the components of the sample material within the second partitions.

A further aspect of the disclosure provides a method of barcoding sample materials. An activatable nucleic acid barcode sequence may be provided and partitioned with one or more components of a sample material into a first partition. The activatable nucleic acid barcode sequence may be activated to produce an active nucleic acid barcode sequence in the first partition. The active nucleic acid barcode sequence can be attached to the one or more components of the sample material. In some cases, the activatable nucleic acid barcode sequence may be activated by releasing the activatable nucleic acid barcode sequence from a second partition within the first partition. In some cases, the activatable nucleic acid barcode sequence may be activated by removing a removable protecting group from the activatable nucleic acid barcode sequence.

An additional aspect of the disclosure provides a composition comprising a first partition that comprises one or more sample components and a second partition that is contained within the first partition. The second partition can have a plurality of oligonucleotides releasably associated therewith and the oligonucleotides may comprise a common barcode sequence. In some cases, the first partition may comprise an aqueous droplet in an emulsion and/or the second partition may comprise a microcapsule or bead. In some cases, the second partition may comprise a degradable bead that can be a photodegradable bead, a chemically degradable bead, and/or a thermally degradable bead. The degradable bead may comprise a chemically cleavable cross-linking such as, for example, disulfide cross-linking. Moreover, in some cases, the oligonucleotides may be releasably associated with the second partition by a cleavable linkage. The cleavable linkage may comprise, for example, a chemically cleavable linkage, a photocleavable linkage, and/or a thermally cleavable linkage. In some cases, the cleavable linkage is a disulfide linkage. Furthermore, the sample components may comprise, for example, nucleic acids (e.g., genomic nucleic acid such as genomic DNA) or fragments thereof. The nucleic acids can comprise nucleic acid fragments that can have a length of between about 1 kb and about 100 kb, a length of between about 5 kb and about 50 kb, or a length of between about 10 kb and about 30 kb.

In some cases, the composition comprises a plurality of first partitions and a plurality of different second partitions. Each of the different second partitions can be disposed within a separate first partition and may comprise a plurality of oligonucleotides releasably associated therewith. The oligonucleotides associated with each second partition can comprise a common barcode sequence and the oligonucleotides associated with different second partitions can comprise different barcode sequences. In some cases, the different second partitions may comprise at least 1,000 different second partitions, at least 10,000 different second partitions, at least 100,000 different second partitions, or at least 500,000 different second partitions.

An additional aspect of the disclosure provides a method that comprises combining a sample of nucleic acids with a library of barcoded beads to form a mixture. The mixture can be partitioned into a plurality of partitions such that at least a subset of the partitions comprises at most one barcoded bead. Within the partitions, barcodes can be released from the barcoded beads. In some cases, the barcodes may be pre-synthesized with known sequences and/or may comprise a plurality of random N-mers. The random N-mers may be hybridized to the sample of nucleic acids in order to perform, for example, a nucleic acid amplification reaction within the partitions. In some cases, the barcoded beads may be capable of being dissolved by a reducing agent and may comprise disulfide bonds. Moreover, in some cases, the sample nucleic acids may be genomic DNA that may or may not be fragmented prior to being combined with the barcoded beads. In some cases, barcodes may be released from the barcoded beads by the action of a reducing agent. In some cases, the barcoded beads may comprise a matrix that is crosslinked with disulfide bonds and barcodes may be released from the barcoded beads by the action of a reducing agent that dissolves the barcoded beads. In some cases, barcodes may be released from the barcoded beads by heating the partitions.

In some cases, the sample of nucleic acids may be combined with the library of barcoded beads and/or the mixture of the two may be partitioned into a plurality of partitions using a microfluidic device. In some examples, the partitions may be aqueous droplets within a water-in-oil emulsion. Partitioning of the mixture into aqueous droplets within a water-in-oil emulsion may be completed using a microfluidic device.

A microfluidic device may be a droplet generator and, in some cases, may comprise a first input channel and a second input channel that meet at a junction that is fluidly connected to an output channel. The sample of nucleic acids can be introduced into the first input channel and the library of barcoded beads can be introduced to the second input channel to generate the mixture of the sample nucleic acids and the library of barcoded beads in the output channel. In some cases, a reducing agent may also be introduced to either or both of the first input channel and second input channel. Moreover, the first input channel and the second input channel may form a substantially perpendicular angle between one another.

In some cases, the output channel may be fluidly connected to a third input channel at a junction. Oil can be introduced into the third input channel such that aqueous droplets within a water-in-oil emulsion and that comprise barcoded beads are formed. The droplets may comprise on average, for example, at most ten barcoded beads, at most seven barcoded beads, at most five barcoded beads, at most three barcoded beads, at most two barcoded beads, or at most one barcoded bead. Moreover, the microfluidic device may comprise a fourth input channel that intersects the third input channel and the output channel at a junction. In some cases, oil may also be provided to the fourth input channel. In some cases, the microfluidic device may include an additional input channel that intersects the first input channel, the second input channel, or the junction of the first input channel and the second input channel. In some cases, a reducing agent may be introduced into the additional input channel.

An additional aspect of the disclosure provides a composition comprising a bead that is covalently linked to a plurality of oligonucleotides that comprise an identical barcode sequence and a variable domain. In some cases, the oligonucleotides may also comprise a primer binding site and/or a universal primer. Additionally, the identical barcode sequence may be between about 6 nucleotides and about 20 nucleotides in length. Moreover, the oligonucleotides may be covalently linked to the bead by disulfide linkages and/or the bead may comprise a cystamine or a modified cystamine. In some cases, the bead may be capable of being substantially dissolved by a reducing agent. Furthermore, in some cases, the bead may comprise at least about 1,000,000 oligonucleotides comprising an identical barcode sequence. In some cases, at least about 30% of the oligonucleotides may comprise variable domains with different sequences. In some cases, the variable domain may be a random N-mer. In some cases, the bead may be covalently linked to the oligonucleotides through a cleavable linkage such as, for example, a chemically cleavable linkage, a photocleavable linkage, and a thermally cleavable linkage.

A further aspect of the disclosure provides a composition comprising a bead that may comprise a plurality of more than 1,000,000 oligonucleotides, where each of the oligonucleotides comprises a constant region and a variable region. The bead can be capable of being substantially dissolved with a reducing agent. In some cases, each of the oligonucleotides may comprise an identical constant region. In some cases, at least 25% of the oligonucleotides may have an identical constant region. In some cases, the constant region may be a barcode sequence. In some cases, at least 25% of the oligonucleotides may have a variable region comprising a different sequence. A further aspect of the disclosure provides a library comprising at least about 1,000,000 beads that each comprise a plurality of more than 1,000,000 oligonucleotides that comprise a constant region and a variable region. In some cases, at least about 25% of the beads comprise oligonucleotides with different nucleotide sequences.

An additional aspect of the disclosure provides a composition comprising a plurality of beads where each of the beads comprises a plurality of oligonucleotides releasably coupled thereto. The oligonucleotides associated with an individual bead may comprise a common barcode domain and a variable domain. The common barcode domain can be different between two or more of the beads. In some cases, the beads may comprise at least about 10,000 different barcode domains coupled to different beads. In some cases, each of the beads may comprise at least about 1,000,000 oligonucleotides releasably coupled thereto.

A further aspect of the disclosure provides a method of generating functionalized beads. A plurality of polymers or monomers may be mixed with one or more oligonucleotides. The polymers or monomers can be crosslinked such that disulfide bonds form between the polymers or monomers, thereby forming hardened beads. Moreover, covalent linkages can be caused to form between the oligonucleotides and the polymers or monomers. In some cases, the polymers or monomers may comprise acrylamide. In some cases, the polymers and monomers may be crosslinked to form hardened beads and covalent linkages can be caused to form between the oligonucleotides and the polymers or monomers either contemporaneously or sequentially. Moreover, in some cases, the oligonucleotides may comprise a primer (e.g., a universal primer, a sequencing primer) that may be linked to an acrydite moiety.

Additionally, one or more additional oligonucleotides may be attached to the oligonucleotides. The additional oligonucleotides may be a barcode sequence and, thus, upon attachment to the oligonucleotides, barcoded beads can be formed. In some cases, the barcode sequence may be between about 6 nucleotides and about 20 nucleotides in length.

In some cases, functionalized beads may be combined with a plurality of first additional oligonucleotides to create a mixture. The mixture may be partitioned into a plurality of partitions such that, on average, each partition comprises no more than one of the first additional oligonucleotides. In some cases, the partitions may be aqueous droplets within a water-in-oil emulsion and/or may be generated by a microfluidic device. In some cases, the partitions are generated by a bulk emulsification process. Moreover, the first additional oligonucleotides can be amplified within the partitions to produce beads comprising amplified first oligonucleotides. In some cases, a capture primer may be used during amplification and the capture primer may be attached to a capture moiety such as, for example, biotin, streptavidin or glutathione-S-transferase (GST). Following amplification, the contents of the partitions can be pooled into a common vessel. The beads comprising amplified first oligonucleotides can be separated from the contents of the partitions. In some cases, a probe may be hybridized to the amplified first oligonucleotides. The probe may comprise a capture moiety.

Furthermore, one or more second additional oligonucleotides can be attached to the amplified first oligonucleotides. In some cases, the second additional oligonucleotides may comprise a random N-mer sequence and/or a pseudo random N-mer sequence. In some cases, the second additional oligonucleotides may comprise a primer binding site that can comprise a universal sequence portion. In some cases, the primer binding site may comprise uracil containing nucleotide. Moreover, the universal sequence portion can be compatible with a sequencing device and/or may comprise a subsection of uracil containing nucleotides.

An additional aspect of the disclosure provides a method of preparing a barcode library. A plurality of separate first bead populations can be provided and a first oligonucleotide comprising a first barcode sequence segment can be attached to the separate first bead populations, such that each separate first bead population comprises a different first barcode sequence segment attached thereto. The separate bead populations can then be pooled to provide a first pooled bead population. The first pooled bead population can then be separated into a plurality of second bead populations. A second oligonucleotide comprising a second barcode sequence segment may be attached to the first oligonucleotide attached to the second bead populations, such that each of the separate second bead populations comprises a different second barcode sequence segment. The separate second bead populations can then be pooled to provide a second pooled bead population that comprises a barcode library.

In some cases, the first barcode sequence segments and the second barcode sequence segments may be independently selected from a first set of barcode sequence segments. Additionally, the first barcode sequence segments and the second barcode sequence segments may independently comprise at least 4 nucleotides in length, at least 6 nucleotides in length, or at least 10 nucleotides in length. In some cases, the first barcode sequence segments and the second barcode sequence segments may independently include from about 4 nucleotides in length to about 20 nucleotides in length. Moreover, in some cases, the first bead populations may comprise at least 100 different first barcode sequence segments or at least 1,000 different first barcode sequence segments. Furthermore, in some cases, at least 1,000,000 first oligonucleotide molecules may be attached to each bead in each of the separate first bead populations. In some cases, the second bead populations may comprise at least 100 different second barcode sequence segments or at least 1,000 different second barcode sequence segments. In some cases, at least 1,000,000 second oligonucleotide molecules may be attached to each bead in each of the second bead populations.

Further, in some cases, at least one of the first oligonucleotide and the second oligonucleotide may comprise a functional sequence such as, for example, a primer sequence, a primer annealing sequence, an attachment sequence, and a sequencing primer sequence. In some cases, at least one of the first oligonucleotide and the second oligonucleotide may comprise a sequence segment that comprises one or more of a uracil containing nucleotide and a non-native nucleotide.

In some cases, the first oligonucleotide may be attached to the separate first bead populations by providing a splint sequence that is in part complementary to at least a portion of the first oligonucleotide and in part complementary to at least a portion of an oligonucleotide attached to the separate first bead populations. In some cases, the first oligonucleotide may be attached to the separate first bead populations such that it is releasably attached to the separate first bead populations. For example, the first oligonucleotide may be attached to the separate first bead populations through a cleavable linkage. In some cases, the first oligonucleotide may be attached to the separate first bead populations either directly or indirectly.

Additionally, in some cases, the second oligonucleotide may be attached to the first oligonucleotide by ligation. In some cases, the second oligonucleotide may be attached to the first oligonucleotide by providing a splint sequence that is in part complementary to at least a portion of the first oligonucleotide and in part complementary to at least a portion of the second oligonucleotide. In some cases, the splint sequence may provides a first overhang sequence when hybridized to the first oligonucleotide, and the second barcode sequence segment may comprise a second overhang sequence complementary to the first overhang sequence. In some cases, the first overhang sequence and the second overhang sequences may be from about 2 nucleotides in length to about 6 nucleotides in length. Furthermore, in some cases, the first overhang sequence may comprise a plurality of different overhang sequences, and the second oligonucleotides may comprise a plurality of different second overhang sequences complementary to the plurality of different first overhang sequences.

Moreover, the separate first bead populations may comprise degradable beads, such as, for example, chemically degradable beads, photodegradable beads, and/or thermally degradable beads. In some cases, the separate first bead populations may comprise beads that comprise chemically reducible cross-linkers such, as for example, chemically reducible cross-linkers that comprise disulfide linkages.

In some cases, a third oligonucleotide may be attached to the second oligonucleotide attached to the first oligonucleotide. The third oligonucleotide may comprise a functional sequence that may be a primer sequence (e.g., a universal primer sequence, a targeted primer sequence, or a random sequence) and/or may be a random N-mer sequence. In cases where the third oligonucleotide comprises a random N-mer sequence, the random N-mer sequence may be from about 5 nucleotides in length to about 25 nucleotides in length.

An additional aspect of the disclosure provides a method of preparing a barcode library. A first pooled bead population comprising a plurality of different first bead populations may be provided, where each different first bead population comprises a different first oligonucleotide attached thereto. Each different first oligonucleotide may comprise a different first barcode sequence segment. The first pooled bead population may be separated into a plurality of second bead populations. A second oligonucleotide comprising a second barcode sequence segment may be attached to the first oligonucleotide already attached to the second bead populations, where each second bead population comprises a different second barcode sequence segment. The second bead populations can be pooled to provide a second pooled bead population comprising a barcode library.

In some cases, the first oligonucleotide may be releasably attached to the beads in the first pooled bead population. In some cases, the first oligonucleotide may be attached to the beads in the first pooled bead population through a cleavable linkage. In some cases, the beads in the first pooled population may each comprise at least 1,000,000 first oligonucleotides attached thereto. In some cases, the first pooled bead population may comprise at least 10 different first bead populations, at least 100 different first bead populations, or at least 500 different first bead populations.

A further aspect of the disclosure provides a barcode library comprising a plurality of different oligonucleotides. Each different oligonucleotide may comprise a first barcode sequence segment selected from a first set of barcode sequence segments; a second barcode sequence segment selected from a second set of barcode sequence segments; and a linking sequence joining the first barcode sequence segment and the second barcode sequence segment. The linking sequence can be from about 2 nucleotides in length to about 6 nucleotides in length and may be selected from a set of linking sequences. In some cases, the set of linking sequences includes from about 2 different linking sequences to about 50 different linking sequences. In some cases, the first set of barcode sequence segments and the second set of barcode sequence segments are the same.

An additional aspect of the disclosure provides a method of amplifying a template nucleic acid sequence. A template nucleic acid sequence and a bead comprising a plurality of releasably attached oligonucleotides may be co-partitioned into a partition. The oligonucleotides may comprise a primer sequence complementary to one or more regions of the template nucleic acid sequence and may comprise a common sequence. The primer sequence can be annealed to the template nucleic acid sequence and the primer sequence can be extended to produce one or more first copies of at least a portion of the template nucleic acid sequence, where the one or more first copies comprising the primer sequence and the common sequence.

In some cases, the primer sequence may comprise a variable primer sequence (e.g., a random N-mer) and/or may comprise a targeted primer sequence. In some cases, the partition may comprise a droplet in an emulsion. Prior to annealing the primer sequence to the template nucleic acid sequence, the oligonucleotides may be released from the bead into the partition. In some examples, a polymerase enzyme (e.g., an exonuclease deficient polymerase enzyme) may be provided in the partition. Moreover, extension of the primer sequence may comprise extending the primer sequence using a strand displacing polymerase enzyme (e.g., a thermostable strand displacing polymerase enzyme having, for example, substantially no exonuclease activity). Furthermore, the oligonucleotides may be exonuclease resistant. For example, the oligonucleotides may comprise one or more phosphorothioate linkages. In some cases, the phosphorothioate linkages may comprise a phosphorothioate linkage at a terminal internucleotide linkage in the oligonucleotides.

Additionally, one or more variable primer sequences may be annealed to the first copies and extended to produce one or more second copies from the first copies, such that the second copies comprise the one or more variable primer sequences and the common sequence. In some cases, the second copies may comprise a sequence complementary to at least a portion of an individual first copy of the first copies and a sequence complementary to an individual variable sequence of the one or more variable primer sequences. In some cases, the second copies may preferentially form a hairpin molecule under annealing conditions. Moreover, in some cases, the oligonucleotides may comprise a sequence segment that is not copied during the extension of the variable primer sequences. The sequence segment that is not copied may comprise, for example, one or more uracil containing nucleotides. In addition, any steps of the method may be repeated to produce amplified nucleic acids.

A further aspect of the disclosure provides a method of amplifying a plurality of different nucleic acids. Different nucleic acids may be partitioned into separate first partitions, where each first partition comprises a second partition having a plurality of oligonucleotides releasably associated therewith. The plurality of oligonucleotides associated with a given second partition may comprise a variable primer sequence and a barcode sequence, with the oligonucleotides associated with different second partitions comprising different barcode sequences. The oligonucleotides associated with the plurality of second partitions can be released into the first partitions. The variable primer sequences in the first partitions can be released to nucleic acids within the first partitions and extended to produce one or more copies of at least a portion of the nucleic acids within the first partitions, such that the copies comprise the oligonucleotides and associated barcode sequences released into the first partitions. In some cases, the first partitions may comprise droplets in an emulsion and the second partitions may comprise beads. In some cases, each bead may comprise more than 100,000 oligonucleotides associated therewith or more than 1,000,000 oligonucleotides associated therewith.

In some cases, the second partitions may comprise at least 1,000 different barcode sequences, at least 10,000 different barcode sequences, or at least 100,000 different barcode sequences.

An additional aspect of the disclosure provides a method of whole genome amplification. A random primer may be hybridized to a genomic nucleic acid. The random primer may be attached to a universal nucleic acid sequence and a nucleic acid barcode sequence, where the universal nucleic acid sequence may comprise one or more uracil containing nucleotides. The random primer may be extended to form an amplified product and the amplified product may be exposed to conditions suitable to cause the amplified product to undergo an intramolecular hybridization reaction that forms a partial hairpin molecule. In some cases, the random primer may be a random N-mer sequence. In some cases, the universal nucleic acid sequence may comprise a segment of at least 10 nucleotides that do not comprise uracil. Moreover, the method may be performed in the presence of an oligonucleotide blocker. The oligonucleotide blocker may be capable of hybridizing to at least a portion of the universal nucleic acid sequence and/or may comprise a C3 spacer (/3SpC3/), a Dideoxy-C (/3ddC/), or a 3' phosphate.

An additional aspect of the disclosure provides a method of amplifying nucleic acids. A genomic component may be fragmented into a plurality of first fragments. The first fragments may be co-partitioned with a plurality of oligonucleotides into a plurality of partitions. The oligonucleotides in each of the partitions may comprise a primer sequence and a common sequence. The primer sequences in each partition may be annealed to a plurality of different regions of the first fragments within each partition and the primer sequences extended along the first fragments to produce amplified first fragments within each partition. In some cases, the amplified first fragments within the partitions may comprise at least 1× coverage of the genomic component, at least 2× coverage of the genomic component, or at least 10× coverage of the genomic component. In some cases, the genomic component may comprise a chromosome. In some cases, the genomic component may comprise a whole genome of an organism.

A further aspect of the disclosure provides a method of characterizing a nucleic acid segment. A nucleic acid segment may be co-partitioned with a bead comprising a comprising a plurality of oligonucleotides that comprise a common nucleic acid barcode sequence into a partition. The oligonucleotides may be attached to fragments of the nucleic acid segment or to copies of portions of the nucleic acid segment, such that the common nucleic acid barcode sequence is attached to the fragments of the nucleic acid segment or the copies of the portions of the nucleic acid segment. The fragments of the nucleic acid segment or the copies of the portions of the nucleic acid segment and attached common nucleic acid barcode sequence can be sequenced and the fragments of the nucleic acid segment or the copies of the nucleic acid segment can be characterized as being linked within the nucleic acid segment based at least in part, upon a their attachment to the common nucleic acid barcode sequence. The nucleic acid segment and the bead, for example, may be co-partitioned into a droplet in an emulsion or may be co-partitioned into a microcapsule. In some cases, the fragments of the nucleic acid segment may comprise overlapping fragments of the nucleic acid segment. In some cases, the fragments of the nucleic acid segment may comprise greater than 2× coverage of the nucleic acid segment or greater than 10× coverage of the nucleic acid segment.

Moreover, in some cases, the oligonucleotides may be releasably attached to the bead. For example, the oligonucleotides may be releasable from the bead upon the application of a stimulus (e.g., a thermal stimulus, a photo stimulus, a chemical stimulus, etc.) to the bead. In some cases, the application of the stimulus may result in the cleavage of a linkage between the oligonucleotides and the bead and/or may result in the degradation of the bead, such that the oligonucleotides are released from the bead. Furthermore, the bead may comprise at least about 10,000 oligonucleotides attached thereto, at least about 100,000 oligonucleotides attached thereto, at least about 1,000,000 oligonucleotides attached thereto, at least about 10,000,000 oligonucleotides attached thereto, or at least about 100,000,000 oligonucleotides attached thereto. Additionally, in some cases, the oligonucleotides may comprise one or more functional sequences, such as, for example, a primer sequence, a primer annealing sequence, or an immobilization sequence. In some cases, the fragments of the nucleic acid segment or the copies of the portions of the nucleic acid segment and attached common nucleic acid barcode sequence may be sequenced via a sequencing by synthesis process.

Further, in some cases, the oligonucleotides may comprise a primer sequence capable of annealing with a portion of the nucleic acid segment or a complement thereof. The primer sequence can be extended to replicate at least a portion of the nucleic acid segment or complement thereof, to produce a copy of a portion of the nucleic acid segment or complement thereof that comprises the common nucleic acid barcode sequence. In some cases, the oligonucleotides may comprise at least a first sequencing primer sequence.

In some cases, a plurality of nucleic acid segments may be co-partitioned with a plurality of different beads into a plurality of separate partitions, such that each partition of a plurality of different partitions of the separate partitions contains a single bead. Each bead may comprise a plurality of oligonucleotides that comprise a common barcode sequence attached thereto, where the different beads comprises a plurality of different barcode sequences. Barcode sequences in each partition may be attached to fragments of the nucleic acid segments or to copies of portions of the nucleic acid segments within the separate partitions. The fragments or copies can then be pooled from the separate partitions and the fragments or copies and any associated barcode sequences may be sequenced to provide sequenced fragments or sequenced copies. The sequenced fragments or sequenced copies may be characterized as deriving from a common nucleic acid segment, based in part upon the sequenced fragments or sequenced copies comprising a common barcode sequence. In some cases, the nucleic acid segments may comprise fragments of at least a portion of a genome. In such cases, sequences may be assembled from the sequenced fragments or sequenced copies to provide a contiguous sequence of the at least a portion of the genome. Assembly of the sequences from the sequenced fragments or sequenced copies may be based in part upon each of a nucleotide sequence of the sequenced fragments or sequenced copies and the sequenced fragments or sequenced copies comprising a common barcode sequence. Moreover, in some cases, the fragments of the nucleic acid segments or the copies of the portions of the nucleic acid segments may be characterized based in part upon each of a nucleotide sequence of the fragments of the nucleic acid segments or the copies of the portions of the nucleic acid segments and the sequenced fragments or sequenced copies comprising a common barcode sequence.

In some cases, the different beads may comprise at least 1,000 different barcode sequences, at least 10,000 different barcode sequences, at least 100,000 different barcode sequences, or at least 1,000,000 different barcode sequences. In some cases, two or more partitions of the separate partitions may comprise beads that comprise the same barcode sequence. In some cases, at least 1% of the separate partitions comprise beads having the same barcode sequence.

An additional aspect of the disclosure provides a method of characterizing a target nucleic acid. First fragments of a target nucleic acid may be partitioned into a plurality of droplets, where each droplet comprises a bead having a plurality of oligonucleotides attached thereto. The oligonucleotides attached to a given bead can comprise a common barcode sequence. The common barcode sequence can be attached to second fragments of the first fragments and the droplets can be pooled. The second fragments and attached barcode sequences can sequenced and the second fragments can be mapped to one or more of the first fragments based, at least in part, upon the second fragments comprising a common barcode sequence.

An additional aspect of the disclosure provides a method of sequencing nucleic acids. A plurality of target nucleic acid sequences may be provided and separated into a plurality of separate partitions. Each partition of the separate partitions may comprise one or more target nucleic acid sequences and a bead comprising a plurality of oligonucleotides attached thereto. The oligonucleotides attached to a given bead may comprise a common barcode sequence. The oligonucleotides may be attached to fragments of the one or more target nucleic acid sequences or to copies of portions of the one or more target nucleic acid sequences within a partition, thereby attaching the common barcode sequence to the fragments of the one or more target nucleic acid sequences or the copies of the portions of the one or more target nucleic acid sequences. The separate partitions can be pooled and the fragments of the one or more target nucleic acid sequences or the copies of the portions of the one or more target nucleic acid sequences and attached barcode sequences can be sequenced to provide barcoded fragment sequences or barcoded copy sequences. In some cases, the barcoded fragment sequences or barcoded copy sequences can be assembled into one or more contiguous nucleic acid sequences based, in part, upon a barcode portion of the barcoded fragment sequences or barcoded copy sequences.

An additional aspect of the disclosure provides a method of characterizing a nucleic acid segment. A nucleic acid segment may be co-partitioned with a bead comprising a plurality of oligonucleotides that comprise a common nucleic acid barcode sequence, into a first droplet. The oligonucleotides may be attached to fragments of the nucleic acid segment or to copies of portions of the nucleic acid segment, thereby attaching the common nucleic acid barcode sequence to the fragments of the nucleic acid segment or to the copies of the portions of the nucleic acid segment. The fragments of the nucleic acid segment or the copies of the portions of the nucleic acid segment and attached common nucleic acid barcode sequence can be sequenced to provide a plurality of barcoded fragment sequences or barcoded copy sequences. The barcoded fragment sequences or barcoded copy sequences can be assembled into one or more contiguous nucleic acid sequences based at least in part on the common nucleic acid barcode sequence. In some cases, the barcoded fragment sequences or barcoded copy sequences may be assembled based in part upon a nucleic acid sequence of non-barcode portion of the barcoded fragment sequences or barcoded copy sequences.

An additional aspect of the disclosure provides a method of sequencing nucleic acids. A plurality of target nucleic acid sequences may be provided and the target nucleic acid sequences separated into a plurality of separate partitions. Each partition of the separate partitions may comprise one or more target nucleic acid sequences and a plurality of oligonucleotides. The oligonucleotides in a given partition may comprise a common barcode sequence and the plurality of separate partitions may comprise at least 10,000 different barcode sequences. The common barcode sequence in each partition may be attached to fragments of the one or more target nucleic acid sequences or to copies of portions of the one or more target nucleic acid sequences within the partition. The separate partitions can be pooled and the fragments of the one or more target nucleic acid sequences or the copies of the portions of the one or more target nucleic acid sequences and attached barcode sequences can be sequenced. In some cases, the separate partitions may comprise at least 100,000 different barcode sequences.

INCORPORATION BY REFERENCE

All publications, patents, and patent applications mentioned in this specification are herein incorporated by reference in their entireties for all purposes and to the same extent as if each individual publication, patent, or patent application was specifically and individually indicated to be incorporated by reference.

BRIEF DESCRIPTION OF THE DRAWINGS

FIGS. 7A-7C provide fluorescent images of beads attached to DNA.

FIG. 11A provides a schematic of a functionalized bead. FIGS. 11B-11D provide graphic depictions of the presence of barcode oligonucleotides and primer-dimer pairs when beads are prepared using different conditions.

FIGS. 15A-15G are diagrams of steps used in the partial hairpin amplification for sequencing (PHASE) process.

FIG. 19 is a table providing example sequences for Illumina sequencers. FIG. 19 discloses SEQ ID NOS 4 and 7-9, respectively, in order of appearance.

FIG. 20 is a table providing a list of example capture moiety concentrations used to label beads.

FIG. 21 is a table providing a list of sequencing metrics obtained using primers comprising thymine containing nucleotides.

FIG. 22 is a table providing a list of sequencing metrics obtained using primers comprising uracil containing nucleotides.

FIGS. 23A-23D are schematics illustrating the use of an example ligation-based combinatorial approach to make barcoded beads. FIGS. 23A-23D disclose SEQ ID NOS 4, 10, 11, 12, 11, 13, 11 and 13, respectively, in order of appearance.

FIGS. 24A-24B are schematics illustrating an example use of spacer bases in a ligation-based combinatorial approach to make barcoded beads. FIGS. 24A-24B disclose SEQ ID NOS 14, 14, 14 and 14-16, respectively, in order of appearance.

FIGS. 25A-25C are schematics illustrating the use of an example ligation-based combinatorial approach to make barcoded beads. FIGS. 25A-25C disclose SEQ ID NOS 10, 17, 12, 17, 18 and 17, respectively, in order of appearance.

FIG. 26 is a schematic illustrating example nucleic acids used in an example ligation-based combinatorial approach to make barcoded beads. FIG. 26 discloses SEQ ID NOS 10, 19, 10, 20, 10, 21, 10 and 22, respectively, in order of appearance.

FIGS. 30A-30C are structural depictions of an example method that can be used to generate beads.

FIGS. 33B-33E are graphic depictions of data corresponding to example amplification reaction experiments described in Example 16.

DETAILED DESCRIPTION

I. General Overview

Figure 1A:
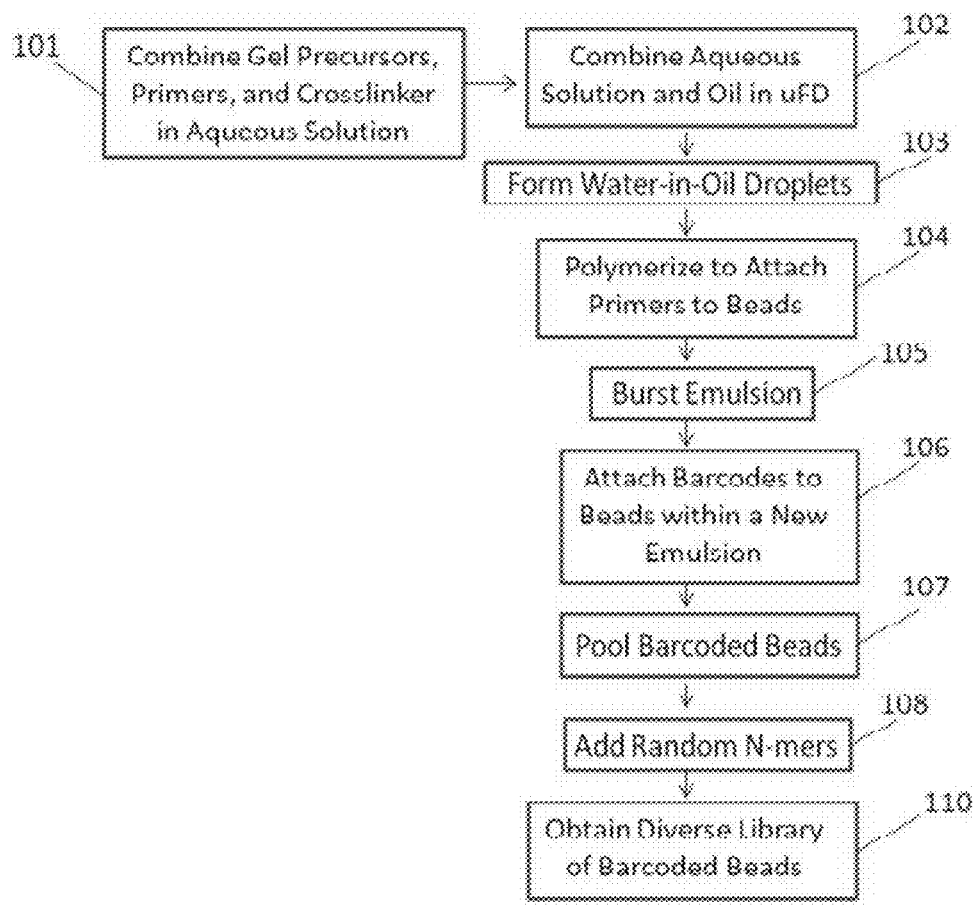
FIG. 1A is a flow diagram for making barcoded beads.

This disclosure provides methods, systems and compositions useful in the processing of sample materials through the controlled delivery of reagents to subsets of sample components, followed by analysis of those sample components employing, in part, the delivered reagents. In many cases, the methods and compositions are employed for sample processing, particularly for nucleic acid analysis applications, generally, and nucleic acid sequencing applications, in particular. Included within this disclosure are bead compositions that include diverse sets of reagents, such as diverse libraries of beads attached to large numbers of oligonucleotides containing barcode sequences, and methods of making and using the same.

Methods of making beads can generally include, e.g. combining bead precursors (such as monomers or polymers), primers, and cross-linkers in an aqueous solution, combining said aqueous solution with an oil phase, sometimes using a microfluidic device or droplet generator, and causing water-in-oil droplets to form. In some cases, a catalyst, such as an accelerator and/or an initiator, may be added before or after droplet formation. In some cases, initiation may be achieved by the addition of energy, such as for example via the addition of heat or light (e.g., UV light). A polymerization reaction in the droplet can occur to generate a bead, in some cases covalently linked to one or more copies of an oligonucleotide (e.g., primer). Additional sequences can be attached to the functionalized beads using a variety of methods. In some cases, the functionalized beads are combined with a template oligonucleotide (e.g., containing a barcode) and partitioned such that on average one or fewer template oligonucleotides occupy the same partition as a functionalized bead. While the partitions may be any of a variety of different types of partitions, e.g., wells, microwells, tubes, vials, microcapsules, etc., in preferred aspects, the partitions may be droplets (e.g., aqueous droplets) within an emulsion. The oligonucleotide (e.g., barcode) sequences can be attached to the beads within the partition by a reaction such as a primer extension reaction, ligation reaction, or other methods. For example, in some cases, beads functionalized with primers are combined with template barcode oligonucleotides that comprise a binding site for the primer, enabling the primer to be extended on the bead. After multiple rounds of amplification, copies of the single barcode sequence are attached to the multiple primers attached to the bead. After attachment of the barcode sequences to the beads, the emulsion can be broken and the barcoded beads (or beads linked to another type of amplified product) can be separated from beads without amplified barcodes. Additional sequences, such as a random sequence (e.g., a random N-mer) or a targeted sequence, can then be added to the bead-bound barcode sequences, using, for example, primer extension methods or other amplification reactions. This process can generate a large and diverse library of barcoded beads.

FIG. 1A illustrates an example method for generating a barcoded bead. First, gel precursors (e.g., linear polymers and/or monomers), cross-linkers, and primers may be combined in an aqueous solution, 101. Next, in a microfluidic device, the aqueous solution can then be combined with an oil phase, 102. Combining the oil phase and aqueous solution can cause water-in-oil droplets to form, 103. Within water-in-oil droplets, polymerization of the gel precursors occurs to form beads comprising multiple copies of a primer, 104. Following generation of a primer-containing bead, the emulsion may be broken, 105 and the beads recovered. The recovered beads may be separated from unreacted components, via, for example, washing and introduced to any suitable solvent (e.g., an aqueous solvent, a non-aqueous solvent). In some cases, the primer-containing beads may then be combined (e.g., via limiting dilution methods) with template barcode sequences in droplets of another emulsion, such that each droplet comprises on average at least one bead and on average one or less molecules of a template barcode sequence. The template barcode sequence may be clonally amplified, using the primer attached to the bead, resulting in attachment to the bead of multiple copies of a barcode sequence complementary to the template, 106. The barcoded beads may then be pooled into a population of beads either containing barcodes or not containing barcodes, 107. The barcoded beads may then be isolated by, for example, an enrichment step. The barcode molecules may also be provided with additional functional sequence components for exploitation in subsequent processing. For example, primer sequences may be incorporated into the same oligonucleotides that include the barcode sequence segments, to enable the use of the barcode containing oligonucleotides to function as extension primers for duplicating sample nucleic acids, or as priming sites for subsequent sequencing or amplification reactions. In one example, random N-mer sequences may then be added to the barcoded beads, 108, via primer extension or other amplification reaction and a diverse library of barcoded beads, 110, may thereby be obtained, where such random n-mer sequences can provide a universal primer sequence. Likewise, functional sequences may include immobilization sequences for immobilizing barcode containing sequences onto surfaces, e.g., for sequencing applications. For ease of discussion, a number of specific functional sequences are described below, such as P5, P7, R1, R2, sample indexes, random Nmers, etc., and partial sequences for these, as well as complements of any of the foregoing. However, it will be appreciated that these descriptions are for purposes of discussion, and any of the various functional sequences included within the barcode containing oligonucleotides may be substituted for these specific sequences, including without limitation, different attachment sequences, different sequencing primer regions, different n-mer regions (targeted and random), as well as sequences having different functions, e.g., secondary structure forming, e.g., hairpins or other structures, probe sequences, e.g., to allow interrogation of the presence or absence of the oligonucleotides or to allow pull down of resulting amplicons, or any of a variety of other functional sequences.

Also included within this disclosure are methods of sample preparation for nucleic acid analysis, and particularly for sequencing applications. Sample preparation can generally include, e.g. obtaining a sample comprising sample nucleic acid from a source, optionally further processing the sample, combining the sample nucleic acid with barcoded beads, and forming emulsions containing fluidic droplets comprising the sample nucleic acid and the barcoded beads. Droplets may be generated, for example, with the aid of a microfluidic device and/or via any suitable emulsification method. The fluidic droplets can also comprise agents capable of dissolving, degrading, or otherwise disrupting the barcoded beads, and/or disrupting the linkage to attached sequences, thereby releasing the attached barcode sequences from the bead. The barcode sequences may be released either by degrading the bead, detaching the oligonucleotides from the bead such as by a cleavage reaction, or a combination of both. By amplifying (e.g., via amplification methods described herein) the sample nucleic acid in the fluidic droplets, for example, the free barcode sequences can be attached to the sample nucleic acid. The emulsion comprising the fluidic droplets can then be broken and, if desired, additional sequences (e.g., sequences that aid in particular sequencing methods, additional barcode sequences, etc.) can then be added to the barcoded sample nucleic acid using, for example, additional amplification methods. Sequencing can then be performed on the barcoded, amplified sample nucleic acid and one or more sequencing algorithms applied to interpret the sequencing data. As used herein, the sample nucleic acids may include any of a wide variety of nucleic acids, including, e.g., DNA and RNA, and specifically including for example, genomic DNA, cDNA, mRNA total RNA, and cDNA created from a mRNA or total RNA transcript.

Figure 1B:
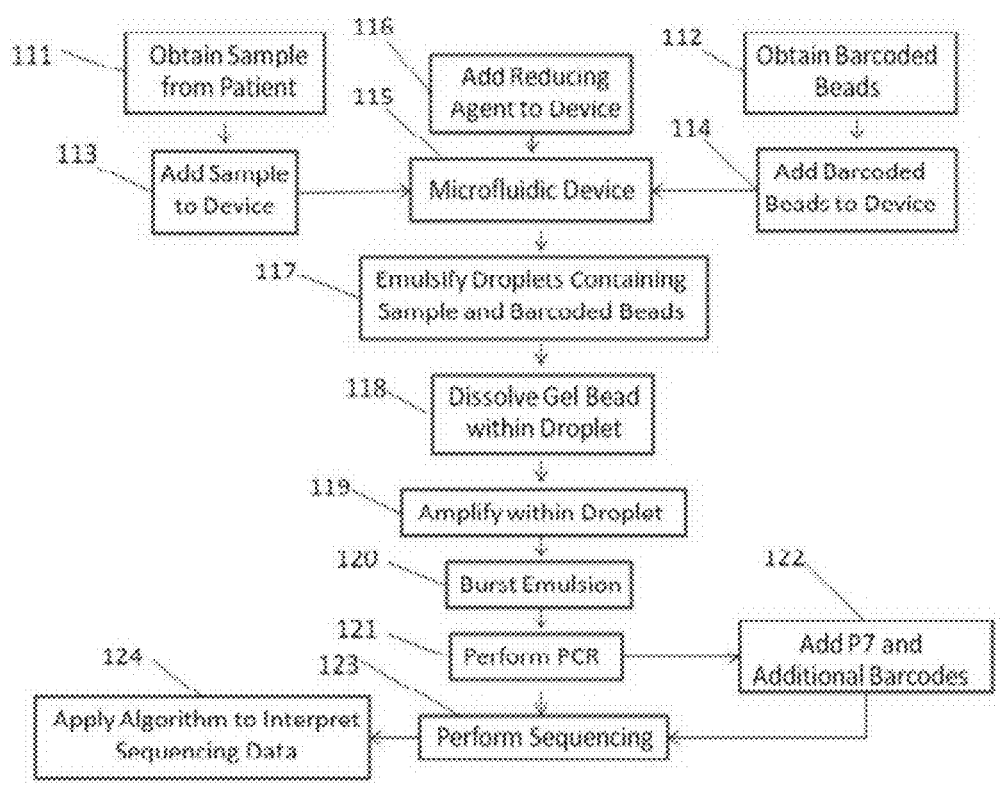
FIG. 1B is a flow diagram for processing a sample for sequencing.

FIG. 1B illustrates an example method for barcoding and subsequently sequencing a sample nucleic acid. First, a sample comprising nucleic acid may be obtained from a source, 111, and a set of barcoded beads may be obtained, e.g., as described herein, 112. The beads are preferably linked to oligonucleotides containing one or more barcode sequences, as well as a primer, such as a random N-mer or other primer. Preferably, the barcode sequences are releasable from the barcoded beads, e.g., through cleavage of a linkage between the barcode and the bead or through degradation of the underlying bead to release the barcode, or a combination of the two. For example, in certain preferred aspects, the barcoded beads can be degraded or dissolved by an agent, such as a reducing agent to release the barcode sequences. In this example, the sample comprising nucleic acid, 113, barcoded beads, 114, and e.g., a reducing agent, 116, are combined and subject to partitioning. By way of example, such partitioning may involve introducing the components to a droplet generation system, such as a microfluidic device, 115. With the aid of the microfluidic device 115, a water-in-oil emulsion 117 may be formed, wherein the emulsion contains aqueous droplets that contain sample nucleic acid, reducing agent, and barcoded beads, 117. The reducing agent may dissolve or degrade the barcoded beads, thereby releasing the oligonucleotides with the barcodes and random N-mers from the beads within the droplets, 118. The random N-mers may then prime different regions of the sample nucleic acid, resulting in amplified copies of the sample after amplification, wherein each copy is tagged with a barcode sequence, 119. Preferably, each droplet contains a set of oligonucleotides that contain identical barcode sequences and different random N-mer sequences. Subsequently, the emulsion is broken, 120 and additional sequences (e.g., sequences that aid in particular sequencing methods, additional barcodes, etc.) may be added, 122, via, for example, amplification methods (e.g., PCR). Sequencing may then be performed, 123, and an algorithm applied to interpret the sequencing data, 124. Sequencing algorithms are generally capable, for example, of performing analysis of barcodes to align sequencing reads and/or identify the sample from which a particular sequence read belongs.

The methods and compositions of this disclosure may be used with any suitable digital processor. The digital processor may be programmed, for example, to operate any component of a device and/or execute methods described herein. In some embodiments, bead formation may be executed with the aid of a digital processor in communication with a droplet generator. The digital processor may control the speed at which droplets are formed or control the total number of droplets that are generated. In some embodiments, attaching barcode sequences to sample nucleic acid may be completed with the aid of a microfluidic device and a digital processor in communication with the microfluidic device. In some cases, the digital processor may control the amount of sample and/or beads provided to the channels of the microfluidic device, the flow rates of materials within the channels, and the rate at which droplets comprising barcode sequences and sample nucleic acid are generated.

The methods and compositions of this disclosure may be useful for a variety of different molecular biology applications including, but not limited to, nucleic acid sequencing, protein sequencing, nucleic acid quantification, sequencing optimization, detecting gene expression, quantifying gene expression, epigenetic applications, and single-cell analysis of genomic or expressed markers. Moreover, the methods and compositions of this disclosure have numerous medical applications including identification, detection, diagnosis, treatment, staging of, or risk prediction of various genetic and non-genetic diseases and disorders including cancer.

II. Partitioning of Polynucleotides

As described throughout the disclosure, certain methods, systems, and compositions of the disclosure may utilize partitioning of polynucleotides into separate partitions (e.g., microwells, droplets of an emulsion). These partitions may be used to contain polynucleotides for further processing, such as, for example, cutting, ligating, and/or barcoding.

Any number of devices, systems or containers may be used to hold, support or contain partitions of polynucleotides and their fragments. In some cases, partitions are formed from droplets, emulsions, or spots on a substrate. Weizmann et al. (Nature Methods, 2006, Vol. 3 No. 7 pages 545-550). Suitable methods for forming emulsions, which can be used as partitions or to generate microcapsules, include the methods described in Weitz et al. (U.S. Pub. No. 2012/0211084). Partitions may also be formed through the use of wells, microwells, multi-well plates, and microwell arrays. Partitioning may be performed using piezoelectric droplet generation (e.g., Bransky et al., *Lab on a Chip,* 2009, 9, 516-520). Partitioning may be performed using surface acoustic waves (e.g., Demirci and Montesano, *Lab on a Chip,* 2007, 7, 1139-1145).

Each partition may also contain, or be contained within any other suitable partition. For example, a well, microwell, hole, a surface of a bead, or a tube may comprise a droplet (e.g., a droplet in an emulsion), a continuous phase in an emulsion, a spot, a capsule, or any other suitable partition. A droplet may comprise a capsule, bead, or another droplet. A capsule may comprise a droplet, bead, or another capsule. These descriptions are merely illustrative, and all suitable combinations and pluralities are also envisioned. For example, any suitable partition may comprise a plurality of the same or different partitions. In one example, a well or microwell comprises a plurality of droplets and a plurality of capsules. In another example, a capsule comprises a plurality of capsules and a plurality of droplets. All combinations of partitions are envisioned. Table 1 shows non-limiting examples of partitions that may be combined with each other.

TABLE 1

Examples of partitions that may be combined with each other.

|  | Well | Spot | Droplet | Capsule |
|---|---|---|---|---|
| Well | Well inside well | Spot inside well | Droplet inside well | Capsule inside well |
| Spot | Spot inside well | Spot inside spot | Droplet inside spot | Capsule inside spot |
| Droplet | Droplet inside well | Droplet inside spot | Droplet inside droplet | Droplet inside capsule<br>Capsule inside droplet |
| Capsule | Capsule inside well | Capsule inside spot<br>Spot inside capsule | Capsule inside droplet<br>Droplet inside capsule | Capsule inside capsule |
| Surface of a Bead | Bead inside well | Spot on bead<br>Bead inside spot | Bead inside droplet | Bead inside capsule |

Any partition described herein may comprise multiple partitions. For example, a partition may comprise 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. A partition may comprise at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, a partition may comprise less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, each partition may comprise 2-50, 2-20, 2-10, or 2-5 partitions.

The number of partitions employed may vary depending on the application. For example, the number of partitions may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000, or more. The number of partitions may be at least about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 000, 10000000, 20000000, or more. The number of partitions may be less than about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 000, 10000000, 20000000. The number of partitions may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

Such partitions may be pre-loaded with reagents to perform a particular reaction. For example, a capsule containing one or more reagents may be placed within a microwell. After adding a polynucleotide sample to the well, the capsule may be made to release its contents. The contents of the capsule may include, for example, restriction enzymes, ligases, barcodes, and adapters for processing the polynucleotide sample placed in the microwell.

In some cases, such partitions may be droplets of an emulsion. For example, a droplet of an emulsion may be an aqueous droplet in an oil phase. The droplet may comprise, for example, one or more reagents (e.g., restriction enzymes, ligases, polymerases, reagents necessary for nucleic acid amplification (e.g., primers, DNA polymerases, dNTPs, buffers)), a polynucleotide sample, and a barcode sequence. In some cases, the barcode sequence, polynucleotide sample, or any reagent may be associated with a solid surface within a droplet. In some cases, the solid surface is a bead. In some cases, the bead is a gel bead (see e.g., Agresti et al., U.S. Patent Publication No. 2010/0136544). In some cases the droplet is hardened into a gel bead (e.g., via polymerization).

A species may be contained within a droplet in an emulsion containing, for example, a first phase (e.g., oil or water) forming the droplet and a second (continuous) phase (e.g., water or oil). An emulsion may be a single emulsion, for example, a water-in-oil or an oil-in-water emulsion. An emulsion may be a double emulsion, for example a water-in-oil-in-water or an oil-in-water-in-oil emulsion. Higher-order emulsions are also possible. The emulsion may be held in any suitable container, including any suitable partition described in this disclosure.

In some cases, droplets in an emulsion comprise other partitions. A droplet in an emulsion may comprise any suitable partition including, for example, another droplet (e.g., a droplet in an emulsion), a capsule, a bead, and the like. Each partition may be present as a single partition or a plurality of partitions, and each partition may comprise the same species or different species.

In one example, a droplet in an emulsion comprises a capsule comprising reagents for sample processing. As described elsewhere in this disclosure, a capsule may contain one or more capsules, or other partitions. A sample comprising an analyte to be processed is contained within the droplet. A stimulus is applied to cause release of the contents of the capsule into the droplet, resulting in contact between the reagents and the analyte to be processed. The droplet is incubated under appropriate conditions for the processing of the analyte. Processed analyte may then be recovered. While this example describes an embodiment where a reagent is in a capsule and an analyte is in the droplet, the opposite configuration—i.e., reagent in the droplet and analyte in the capsule—is also possible.

The droplets in an emulsion may be of uniform size or heterogeneous size. In some cases, the diameter of a droplet in an emulsion may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm A droplet may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400

µm, 500 µm, 600 µm, 700 µm, 800 µm, 900 µm, or 1 mm. In some cases, a droplet may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 150 µm to 200 µm, 150 µm to 300 µm, or 150 µm to 400 µm.

Droplets in an emulsion also may have a particular density. In some cases, the droplets are less dense than an aqueous fluid (e.g., water); in some cases, the droplets are denser than an aqueous fluid. In some cases, the droplets are less dense than a non-aqueous fluid (e.g., oil); in some cases, the droplets are denser than a non-aqueous fluid. Droplets may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Droplets may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, droplet densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

Polynucleotides may be partitioned using a variety of methods. For example, polynucleotides may be diluted and dispensed across a plurality of partitions. A terminal dilution of a medium comprising polynucleotides may be performed such that the number of partitions or wells exceeds the number of polynucleotides. The ratio of the number of polynucleotides to the number of partitions may range from about 0.1-10, 0.5-10, 1-10, 2-10, 10-100, 100-1000, or more. The ratio of the number of polynucleotides to the number of partitions may be about 0.1, 0.5, 1, 2, 4, 8, 10, 20, 50, 100, or 1000. The ratio of the number of polynucleotides to the number of partitions may be at least about 0.1, 0.5, 1, 2, 4, 8, 10, 20, 50, 100, or 1000. The ratio of the number of polynucleotides to the number of partitions may be less than about 0.1, 0.5, 1, 2, 4, 8, 10, 20, 50, 100, or 1000.

The number of partitions employed may vary depending on the application. For example, the number of partitions may be about 5, 10, 50, 100, 250, 500, 750, 1000, 1500, 2000, 2500, 5000, 7500, or 10,000, or more. The number of partitions may be at least about 5, 10, 50, 100, 250, 500, 750, 1000, 1500, 2000, 2500, 5000, 7500, or 10,000, or more.

The number of partitions may be less than about 5, 10, 50, 100, 250, 500, 750, 1000, 1500, 2000, 2500, 5000, 7500, or 10,000.

The volume of the partitions may vary depending on the application. For example, the volume of the partitions may be about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, or 5 nL. The volume of the partitions may be at least about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, or 5 nL. The volume of the partitions may be less than about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, or 5 nL.

Species may also be partitioned at a particular density. For example, species may be partitioned so that each partition contains about 1, 5, 10, 50, 100, 1000, 10000, 100000, or 1000000 species per partition. Species may be partitioned so that each partition contains at least about 1, 5, 10, 50, 100, 1000, 10000, 100000, 1000000 or more species per partition. Species may be partitioned so that each partition contains less than about 1, 5, 10, 50, 100, 1000, 10000, 100000, or 1000000 species per partition. Species may be partitioned such that each partition contains about 1-5, 5-10, 10-50, 50-100, 100-1000, 1000-10000, 10000-100000, or 100000-1000000 species per partition.

Species may be partitioned such that at least one partition comprises a species that is unique within that partition. This may be true for about 1%, 5%, 10%, 20%, 30%, 40%, 50%, 60%, 70%, 80%, 90%, or more of the partitions. This may be true for at least about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, or 90% of the partitions.

Particular polynucleotides may also be targeted to specific partitions. For example, in some cases, a capture reagent such as an oligonucleotide probe may be immobilized in a partition to capture specific polynucleotides through hybridization.

Polynucleotides may also be partitioned at a particular density. For example, polynucleotides may be partitioned such that each partition contains about 1-5, 5-10, 10-50, 50-100, 100-1000, 1000-10000, 10000-100000, or 100000-1000000 polynucleotides per partition. Polynucleotides may be partitioned so that each partition contains about 1, 5, 10, 50, 100, 1000, 10000, 100000, 1000000 or more polynucleotides per partition. Polynucleotides may be partitioned so that each partition contains less than about 1, 5, 10, 50, 100, 1000, 10000, 100000, or 1000000 polynucleotides per partition. Polynucleotides may be partitioned so that each partition contains at least about 1, 5, 10, 50, 100, 1000, 10000, 100000, or 1000000 polynucleotides per partition.

Polynucleotides may be partitioned such that at least one partition comprises a polynucleotide sequence with a unique sequence compared to all other polynucleotide sequences contained within the same partition. This may be true for about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, 90%, or more of the partitions. This may be true for more than about 1%, 5%, 10%, 20%, 30%, 40%, 50%, 60%, 70%, 80%, 90%, or more of the partitions.

III. Beads or Particles

The methods, compositions, devices, and kits of this disclosure may be used with any suitable bead or particle, including gel beads and other types of beads. Beads may serve as a carrier for reagents that are to be delivered in accordance with the methods described herein. In particular, these beads may provide a surface to which reagents are releasably attached, or a volume in which reagents are entrained or otherwise releasably partitioned. These reagents may then be delivered in accordance with a desired method, for example, in the controlled delivery of reagents into discrete partitions. A wide variety of different reagents or reagent types may be associated with the beads, where one may desire to deliver such reagents to a partition. Non-limiting examples of such reagents include, e.g., enzymes, polypeptides, antibodies or antibody fragments, labeling reagents, e.g., dyes, fluorophores, chromophores, etc., nucleic acids, polynucleotides, oligonucleotides, and any combination of two or more of the foregoing. In some cases, the beads may provide a surface upon which to synthesize or attach oligonucleotide sequences. Various entities including oligonucleotides, barcode sequences, primers, crosslinkers and the like may be associated with the outer surface of a bead. In the case of porous beads, an entity may be associated with both the outer and inner surfaces of a bead. The entities may be attached directly to the surface of a bead (e.g., via a covalent bond, ionic bond, van der Waals interactions, etc.), may be attached to other oligonucleotide sequences attached to the surface of a bead (e.g. adaptor or primers), may be diffused throughout the interior of a bead and/or may be combined with a bead in a partition (e.g. fluidic droplet). In preferred embodiments, the oligonucleotides are covalently attached to sites within the polymeric matrix of the bead and are therefore present within the interior and exterior of the bead. In some cases, an entity such as a cell or nucleic acid is encapsulated within a bead. Other entities including amplification reagents (e.g., PCR reagents, primers) may also be diffused throughout the bead or chemically-linked within the interior (e.g., via pores, covalent attachment to polymeric matrix) of a bead.

Beads may serve to localize entities or samples. In some embodiments, entities (e.g. oligonucleotides, barcode sequences, primers, crosslinkers, adaptors and the like) may be associated with the outer and/or an inner surface of the bead. In some cases, entities may be located throughout the bead. In some cases, the entities may be associated with the entire surface of a bead or with at least half the surface of the bead.

Beads may serve as a support on which to synthesize oligonucleotide sequences. In some embodiments, synthesis of an oligonucleotide may comprise a ligation step. In some cases, synthesis of an oligonucleotide may comprise ligating two smaller oligonucleotides together. In some cases, a primer extension or other amplification reaction may be used to synthesize an oligonucleotide on a bead via a primer attached to the bead. In such cases, a primer attached to the bead may hybridize to a primer binding site of an oligonucleotide that also contains a template nucleotide sequence. The primer can then be extended by an primer extension reaction or other amplification reaction, and an oligonucleotide complementary to the template oligonucleotide can thereby be attached to the bead. In some cases, a set of identical oligonucleotides associated with a bead may be ligated to a set of diverse oligonucleotides, such that each identical oligonucleotide is attached to a different member of the diverse set of oligonucleotides. In other cases, a set of diverse oligonucleotides associated with a bead may be ligated to a set of identical oligonucleotides.

Bead Characteristics

The methods, compositions, devices, and kits of this disclosure may be used with any suitable bead. In some embodiments, a bead may be porous, non-porous, solid, semi-solid, semi-fluidic, or fluidic. In some embodiments, a bead may be dissolvable, disruptable, or degradable. In some cases, a bead may not be degradable. In some embodiments, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the beads are silica beads. In some cases, the beads are rigid. In some cases, the beads may be flexible.

In some embodiments, the bead may contain molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor comprises one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

A bead may comprise natural and/or synthetic materials, including natural and synthetic polymers. Examples of natural polymers include proteins and sugars such as deoxyribonucleic acid, rubber, cellulose, starch (e.g. amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and combinations (e.g., co-polymers) thereof. Beads may also be formed from materials other than polymers, including lipids, micelles, ceramics, glass-ceramics, material composites, metals, other inorganic materials, and others.

In some cases, a chemical cross-linker may be a precursor used to cross-link monomers during polymerization of the monomers and/or may be used to functionalize a bead with a species. In some cases, polymers may be further polymerized with a cross-linker species or other type of monomer to generate a further polymeric network. Non-limiting examples of chemical cross-linkers (also referred to as a "crosslinker" or a "crosslinker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilance, N,N'diallyltartardiamide (DATD), N,N'-Bis(acryloyl)cystamine (BAC), or homologs thereof. In some cases, the crosslinker used in the present disclosure contains cystamine.

Crosslinking may be permanent or reversible, depending upon the particular crosslinker used. Reversible crosslinking may allow for the polymer to linearize or dissociate under appropriate conditions. In some cases, reversible crosslinking may also allow for reversible attachment of a material bound to the surface of a bead. In some cases, a cross-linker may form disulfide linkages. In some cases, the chemical cross-linker forming disulfide linkages may be cystamine or a modified cystamine. In some embodiments, disulfide linkages may be formed between molecular precursor units (e.g. monomers, oligomers, or linear polymers). In some embodiments, disulfide linkages may be may be formed between molecular precursor units (e.g. monomers, oligomers, or linear polymers) or precursors incorporated into a bead and oligonucleotides.

Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In at least one alternative example, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some embodiments, the bead may comprise covalent or ionic bonds between polymeric precursors (e.g. monomers, oligomers, linear polymers), oligonucleotides, primers, and other entities. In some cases, the covalent bonds comprise carbon-carbon bonds or thioether bonds.

In some cases, a bead may comprise an acrydite moiety, which in certain aspects may be used to attach one or more species (e.g., barcode sequence, primer, other oligonucleotide) to the bead. In some cases, an acrydite moiety can refer to an acrydite analogue generated from the reaction of acrydite with one or more species, such as, for example, the reaction of acrydite with other monomers and cross-linkers during a polymerization reaction. Acrydite moieties may be modified to form chemical bonds with a species to be attached, such as an oligonucleotide (e.g., barcode sequence, primer, other oligonucleotide). For example, acrydite moieties may be modified with thiol groups capable of forming a, disulfide bond or may be modified with groups already comprising a disulfide bond. The thiol or disulfide (via disulfide exchange) may be used as an anchor point for a species to be attached or another part of the acrydite moiety may be used for attachment. In some cases, attachment is reversible, such that when the disulfide bond is broken (e.g., in the presence of a reducing agent), the agent is released from the bead. In other cases, an acrydite moiety comprises a reactive hydroxyl group that may be used for attachment.

Functionalization of beads for attachment of other species, e.g., nucleic acids, may be achieved through a wide range of different approaches, including activation of chemical groups within a polymer, incorporation of active or activatable functional groups in the polymer structure, or attachment at the pre-polymer or monomer stage in bead production.

For example, in some examples, precursors (e.g., monomers, cross-linkers) that are polymerized to form a bead may comprise acrydite moieties, such that when a bead is generated, the bead also comprises acrydite moieties. Often, the acrydite moieties are attached to an oligonucleotide sequence, such as a primer (e.g., a primer for one or more of amplifying target nucleic acids and/or sequencing target nucleic acids barcode sequence, binding sequence, or the like)) that is desired to be incorporated into the bead. In some cases, the primer comprises a P5 sequence. For example, acrylamide precursors (e.g., cross-linkers, monomers) may comprise acrydite moieties such that when they are polymerized to form a bead, the bead also comprises acrydite moieties.

Figure 29A:
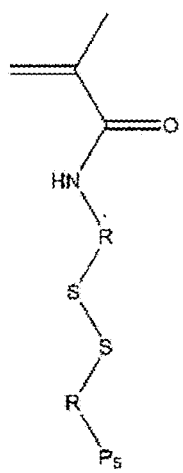
FIGS. 29A-29C are structural depictions of example monomers and cross-linkers that can be polymerized to generate beads.
Figure 29B:
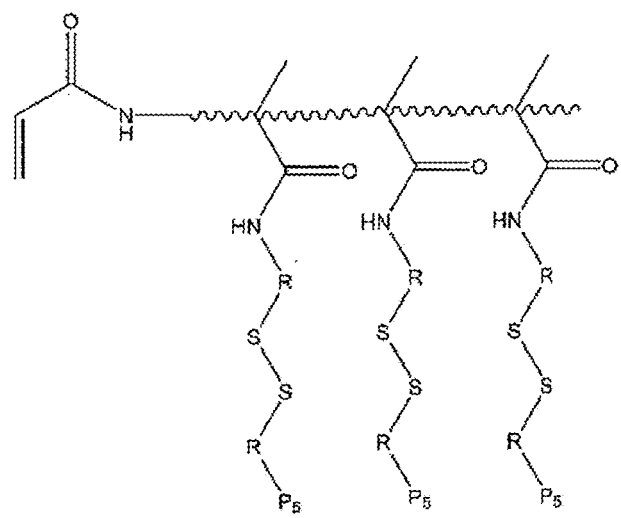
Figure 29C:
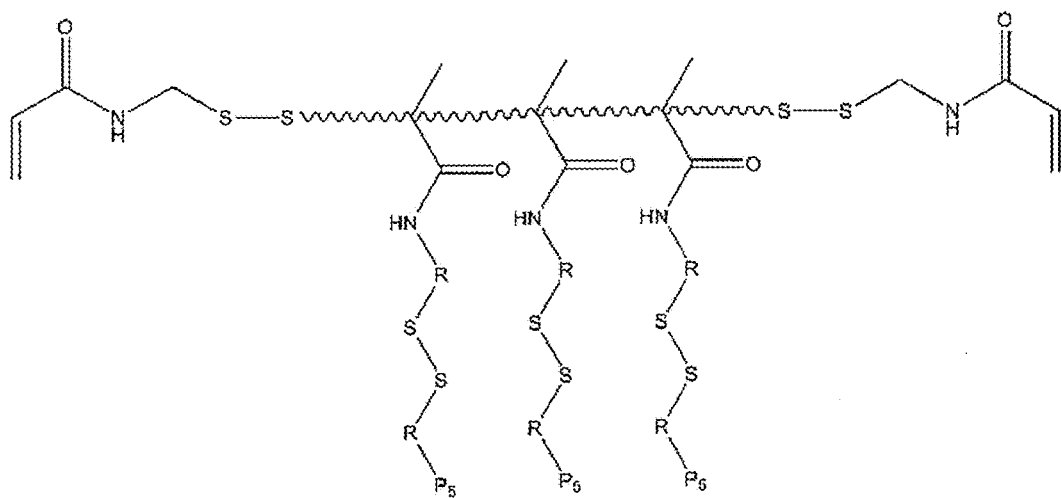

In some cases, precursors such as monomers and cross-linkers may comprise, for example, a single oligonucleotide (e.g., such as a primer or other sequence) or other species. FIG. 29A depicts an example monomer comprising an acrydite moiety and single P5 sequence linked to the acrydite moiety via a disulfide bond. In some cases, precursors such as monomers and cross-linkers may comprise multiple oligonucleotides, other sequences, or other species. FIG. 29B depicts an example monomer comprising multiple acrydite moieties each linked to a P5 primer via a disulfide bond. Moreover, FIG. 29C depicts an example cross-linker comprising multiple acrydite moieties each linked to a P5 species via a disulfide bond. The inclusion of multiple acrydite moieties or other linker species in each precursor may improve loading of a linked species (e.g., an oligonucleotide) into beads generated from the precursors because each precursor can comprise multiple copies of a species to be loaded.

Figure 31:
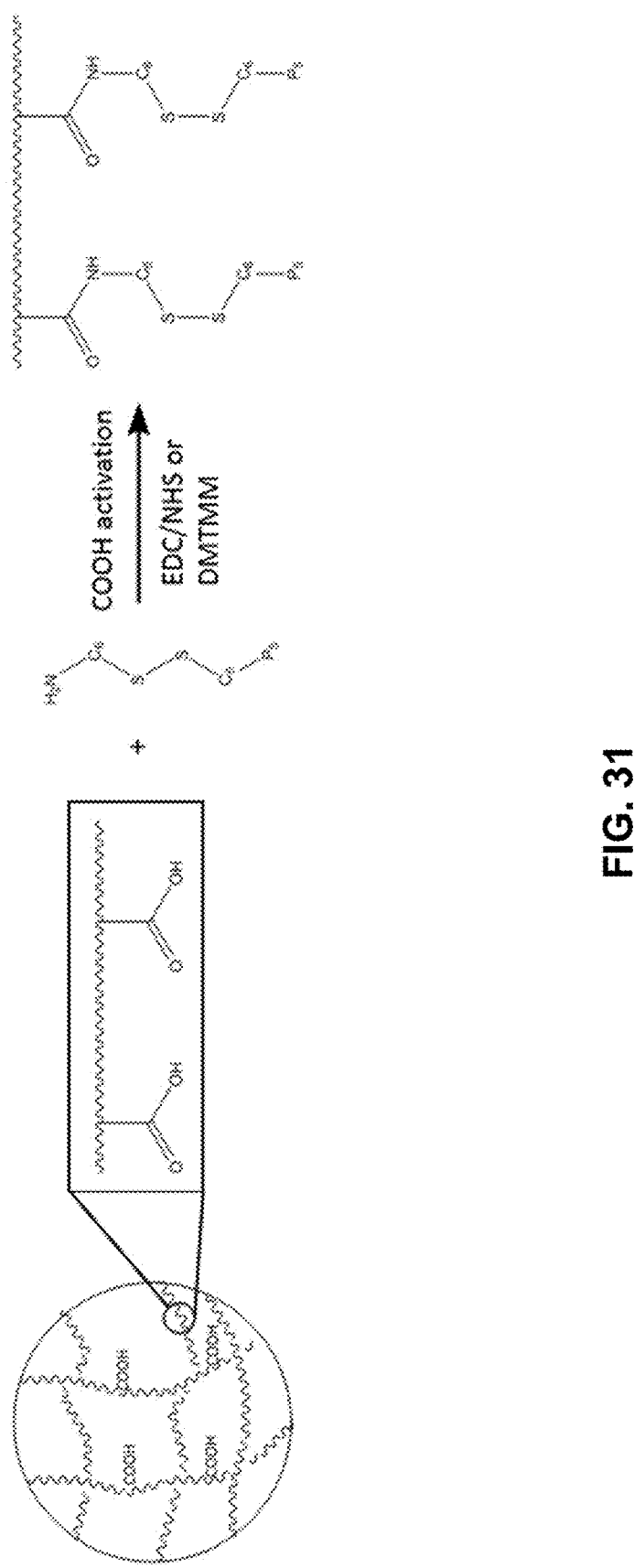
FIG. 31 is a schematic depiction of example beads comprising functional groups that can be used to attach species to the beads.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group, as shown in FIG. 31. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM) as shown in FIG. 31) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

An example species comprising an amine group linked to a P5 primer via a disulfide bond (e.g., $H_2N-C_6-S-S-C_6-P_5$) is shown in FIG. 31. COOH functional groups of a gel bead can be activated with EDC/NHS or DMTMM to generate an amine reactive species at one or more of the COOH sites. The amine group of the species $H_2N-C_6-S-S-C_6-P_5$ moiety can then react with the activated carboxylic acid such that the moiety and attached P5 oligonucleotide becomes covalently linked to the bead as shown in FIG. 31. Unreacted COOH species can be converted to other species such that they are blocked.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange)) such that the species can be linked to the beads (e.g., via a generated disulfide bond). In some cases, though, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as, for example, N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than about 10000, 100000, 1000000, 10000000, 100000000, 1000000000, 10000000000, or 100000000000) of reducing agent may be used for reduction. Controlling the number of disulfide linkages that are reduced to free thiols may be useful in ensuring bead structural integrity during functionalization. In some cases, optically-active agents, such as fluorescent dyes may be may be coupled to beads via free thiol groups of the beads and used to quantify the number of free thiols present in a bead and/or track a bead.

Figure 35A:
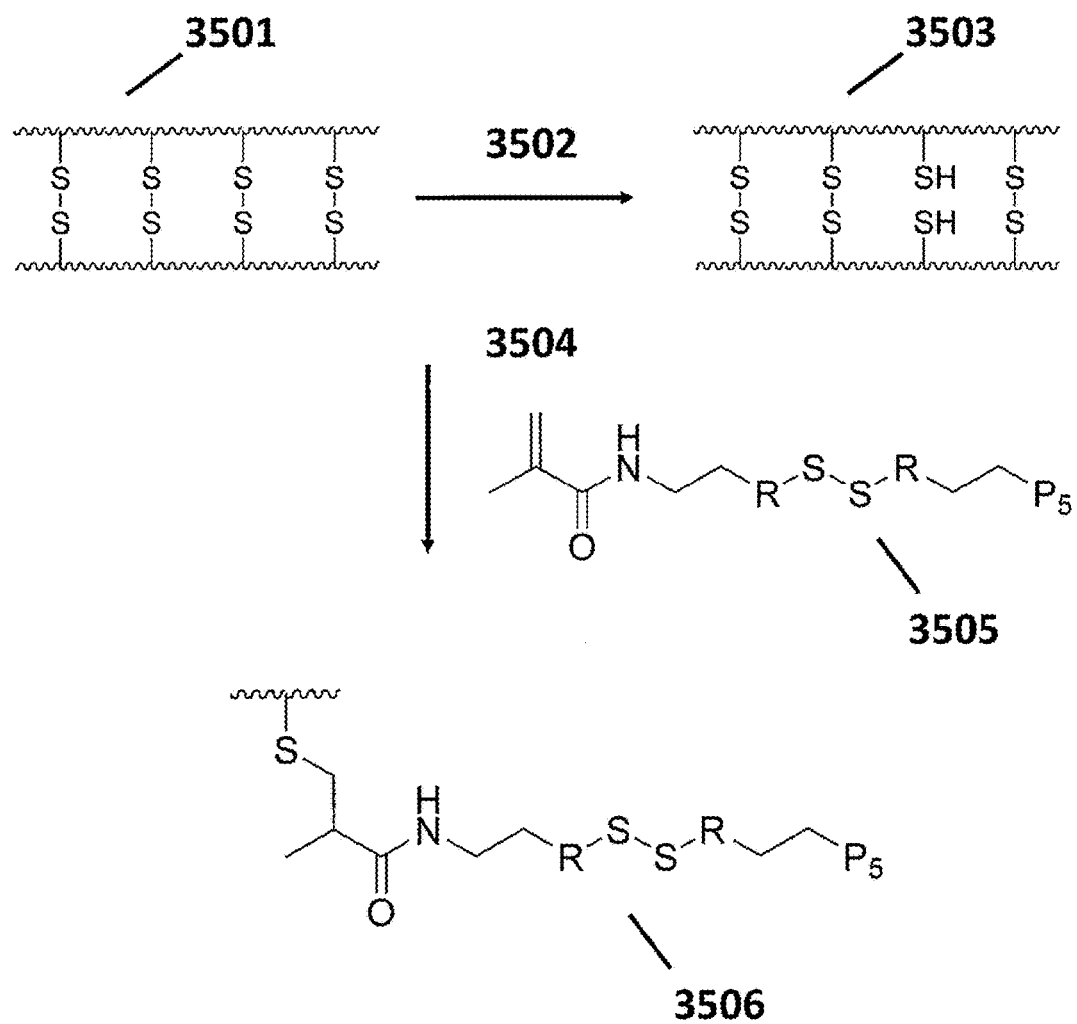
FIGS. 35A-35B are schematics of example methods for functionalizing beads.

An example scheme for functionalizing gel beads comprising disulfide linkages is shown in FIG. 35A. As shown, beads 3501 (e.g., gel beads) comprising disulfide linkages can be generated using, for example, any of the methods described herein. Upon action of a reducing agent 3502 (e.g., DTT, TCEP, or any other reducing agent described herein) at a concentration not suitable for bead degradation, some of the gel bead 3501 disulfide linkages can be reduced to free thiols to generate beads 3503 comprising free thiol groups. Upon removal of the reducing agent (e.g., via washing) 3504, beads 3503 can be reacted with an acrydite-S—S-species moiety 3505 comprising a species to be loaded (e.g., P5 oligonucleotide shown, but the species may be another type of polynucleotide such as, for, example, an oligonucleotide comprising P5, a barcode sequence, R1, and a random N-mer) linked to the acrydite via a disulfide bond. Moiety 3505 can couple with the gel beads 3503 via Michael addition chemistry to generate beads 3506 comprising moiety 3505. The generated beads 3506 can then be purified (e.g., via washing) by removing unwanted (e.g., non-attached) species.

Figure 35B:
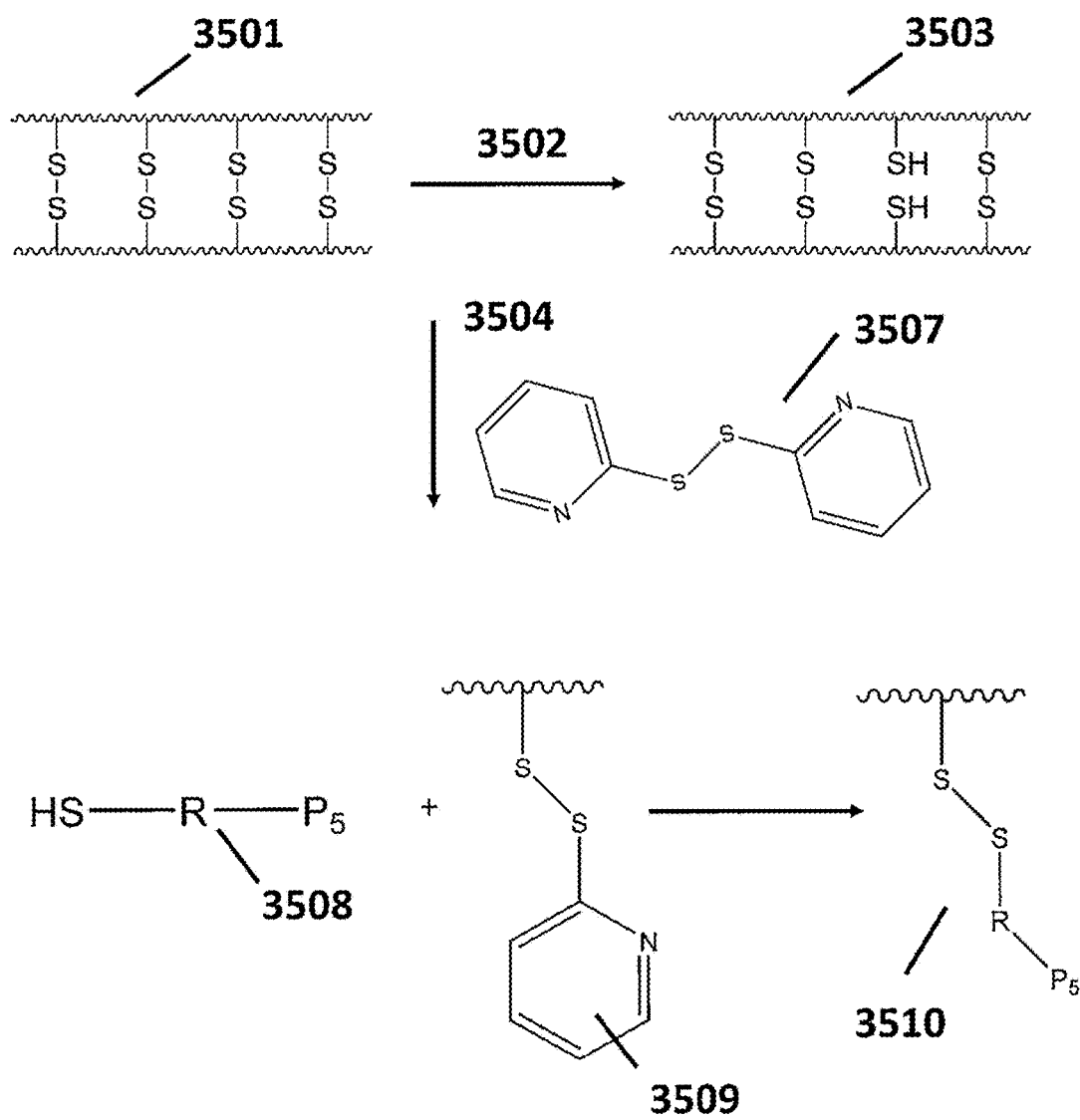

Another example scheme for functionalizing gel beads comprising disulfide linkages is shown in FIG. 35B. As shown, beads 3501 (e.g., gel beads) comprising disulfide linkages can be generated using, for example, any of the methods described herein. Upon action of a reducing agent 3502 (e.g., DTT, TCEP, or any other reducing agent described herein) at a concentration not suitable for bead degradation, some of the gel beads 3501 disulfide linkages can be reduced to free thiols to generate beads 3503 comprising free thiol groups. Upon removal of the reducing agent (e.g., via washing) 3504, beads 3503 can be reacted with 2,2'-Dithiopyridine 3507 to generate gel beads 3509 linked to a pyridine moiety via a disulfide bond. As an alternative to 2,2'-Dithiopyridine, other similar species, such as 4,4'-Dithiopyridine or 5,5'-dithiobis-(2-nitrobenzoic acid) (e.g., DTNB or Ellman's Reagent) may be used. 2,2'-Dithiopyridine 3507 can couple with the gel beads 3503 via disulfide exchange to generate beads 3509 comprising a pyridine moiety linked to the beads 3509 via a disulfide bond. Gel beads 3509 can then be separated from unreacted species (e.g., via washing).

The purified gel beads 3509 can then be reacted with a moiety 3508 comprising a species of interest (e.g., a P5 oligonucleotide as shown) to be coupled to the gel beads and a free thiol group. In some cases, moiety 3508 may be generated from another species comprising a disulfide bond, such that when the disulfide bond is reduced (e.g., via the action of a reducing agent such as DTT, TCEP, etc.), moiety 3508 with a free thiol group is obtained. Moiety 3508 can participate in thiol-disulfide exchange with the pyridine group of beads 3509 to generate gel beads 3510 comprising moiety 3508. The pyridine group is generally a good leaving group, which can permit effective thiol-disulfide exchange with the free thiol of moiety 3508. The generated beads 3510 can then be purified (e.g., via washing) by removing unwanted species.

In some cases, addition of moieties to a gel bead after gel bead formation may be advantageous. For example, addition of a species after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in species (e.g., a primer, a P5 primer) infiltration into the bead during subsequent functionalization of the bead with the species. Post-production functionalization may also be useful in controlling loading ratios of species in beads, such that, for example, the variability in loading ratio is minimized. Also, species loading may be performed in a batch process such that a plurality of beads can be functionalized with the species in a single batch.

In some cases, acrydite moieties linked to precursors, another species linked to a precursor, or a precursor itself comprise a labile bond, such as, for example, chemically, thermally, or photo-sensitive bonds e.g., disulfide bonds, UV sensitive bonds, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule. Moreover, the addition of multiple types of labile bonds to a gel bead may result in the generation of a bead capable of responding to varied stimuli. Each type of labile bond may be sensitive to an associated stimulus (e.g., chemical stimulus, light, temperature, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both. In general, the barcodes that are releasable as described herein, may generally be referred to as being activatable, in that they are available for reaction once released. Thus, for example, an activatable barcode may be activated by releasing the barcode from a bead (or other suitable type of partition described herein). As will be appreciated, other activatable configurations are also envisioned in the context of the described methods and systems. In particular, reagents may be provided releasably attached to beads, or otherwise disposed in partitions, with associated activatable groups, such that once delivered to the desired set of reagents, e.g., through co-partitioning, the activatable group may be reacted with the desired reagents. Such activatable groups include caging groups, removable blocking or protecting groups, e.g., photolabile groups, heat labile groups, or chemically removable groups.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

A bead may be linked to a varied number of acrydite moieties. For example, a bead may comprise about 1, 10, 100, 1000, 10000, 100000, 1000000, 10000000, 100000000, 1000000000, or 10000000000 acrydite moieties linked to the beads. In other examples, a bead may comprise at least 1, 10, 100, 1000, 10000, 100000, 1000000, 10000000, 100000000, 1000000000, or 10000000000 acrydite moieties linked to the beads. For example, a bead may comprise about 1, 10, 100, 1000, 10000, 100000, 1000000, 10000000, 100000000, 1000000000, or 10000000000 oligonucleotides covalently linked to the beads, such as via an acrydite moiety. In other examples, a bead may comprise at least 1, 10, 100, 1000, 10000, 100000, 1000000, 10000000, 100000000, 1000000000, or 10000000000 oligonucleotides covalently linked to the beads, such as via an acrydite moiety.

Species that do not participate in polymerization may also be encapsulated in beads during bead generation (e.g., during polymerization of precursors). Such species may be entered into polymerization reaction mixtures such that generated beads comprise the species upon bead formation. In some cases, such species may be added to the gel beads after formation. Such species may include, for example, oligonucleotides, species necessary for a nucleic acid amplification reaction (e.g., primers, polymerases, dNTPs, co-factors (e.g., ionic co-factors)) including those described herein, species necessary for enzymatic reactions (e.g., enzymes, co-factors, substrates), or species necessary for a nucleic acid modification reaction such as polymerization, ligation, or digestion. Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead.

Beads may be of uniform size or heterogeneous size. In some cases, the diameter of a bead may be about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, or 1 mm. In some cases, a bead may have a diameter of at least about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, 1 mm, or more. In some cases, a bead may have a diameter of less than about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, or 1 mm. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain preferred aspects, the beads are provided as a population of beads having a relatively monodisperse size distribution. As will be appreciated, in some applications, where it is desirable to provide relatively consistent amounts of reagents within partitions, maintaining relatively consistent bead characteristics, such as size, contributes to that overall consistency. In particular, the beads described herein may have size distributions that have a coefficient of variation in their cross-sectional dimensions of less than 50%, less than 40%, less than 30%, less than 20%, and in some cases less than 15%, less than 10%, or even less than 5%.

Beads may be of a regular shape or an irregular shape. Examples of bead shapes include spherical, non-spherical, oval, oblong, amorphous, circular, cylindrical, and homologs thereof.

Degradable Beads

In addition to, or as an alternative to the cleavable linkages between the beads and the associated molecules, e.g., barcode containing oligonucleotides, described above, the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental changes, such as, for example, temperature, or pH. For example, a gel bead may be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid species) may result in release of the species from the bead.

A degradable bead may comprise one or more species with a labile bond such that when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond is broken and the bead is degraded. For example, a polyacrylamide gel bead may comprise cystamine crosslinkers. Upon exposure of the bead to a reducing agent, the disulfide bonds of the cystamine are broken and the bead is degraded.

A degradable bead may be useful in more quickly releasing an attached species (e.g., an oligonucleotide, a barcode sequence) from the bead when the appropriate stimulus is applied to the bead. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

A degradable bead may be introduced into a partition, such as a droplet of an emulsion or a well, such that the bead degrades within the partition and any associated species are released within the droplet when the appropriate stimulus is applied. The free species may interact with other species. For example, a polyacrylamide bead comprising cystamine and linked, via a disulfide bond, to a barcode sequence, may be combined with a reducing agent within a droplet of a water-in-oil emulsion. Within the droplet, the reducing agent breaks the various disulfide bonds resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

As will be appreciated, where degradable beads are provided, it may be desirable to avoid exposing such beads to the stimulus or stimuli that cause such degradation prior to the desired time, in order to avoid premature bead degradation and issues that arise from such degradation, including for example poor flow characteristics, clumping and aggregation. By way of example, where beads comprise reducible cross-linking groups, such as disulfide groups, it will be desirable to avoid contacting such beads with reducing agents, e.g., DTT or other disulfide cleaving reagents. In such cases, treatments to the beads described herein will, in some cases be provided to be free of reducing agents, such as DTT. Because reducing agents are often provided in commercial enzyme preparations, it is often desirable to provide reducing agent free (or DTT free) enzyme preparations in treating the beads described herein. Examples of such enzymes include, e.g., polymerase enzyme preparations, ligase enzyme preparations, as well as many other enzyme preparations that may be used to treat the beads described herein. By "reducing agent free" or "DTT free" preparations means that the preparation will have less than $\frac{1}{10}$th, less than $\frac{1}{50}^{th}$, and even less than $\frac{1}{100}^{th}$ of the lower ranges for such materials used in degrading the beads. For example, for DTT, the reducing agent free preparation will typically have less than 0.01 mM, 0.005 mM, 0.001 mM DTT, 0.0005 mM DTT, or even less than 0.0001 mM DTT or less. In many cases, the amount of DTT will be undetectable.

Methods for Degrading Beads

In some cases, a stimulus may be used to trigger degrading of the bead, which may result in the release of contents from the bead. Generally, a stimulus may cause degradation of the bead structure, such as degradation of the covalent bonds or other types of physical interaction. These stimuli may be useful in inducing a bead to degrade and/or to release its contents. Examples of stimuli that may be used include chemical stimuli, thermal stimuli, light stimuli and any combination thereof, as described more fully below.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degrading the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

The methods, compositions, devices, and kits of this disclosure may be used with any suitable agent to degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at 0.1 mM, 0.5 mM, 1 mM, 5 mM, or 10 mM. The reducing agent may be present at more than 0.1 mM, 0.5 mM, 1 mM, 5 mM, 10 mM, or more. The reducing agent may be present at less than 0.1 mM, 0.5 mM, 1 mM, 5 mM, or 10 mM.

Timing of Degrading Step

Beads may be degraded to release contents attached to and contained within the bead. This degrading step may occur simultaneously as the sample is combined with the bead. This degrading step may occur simultaneously when the sample is combined with the bead within a fluidic droplet that may be formed in a microfluidic device. This degrading step may occur after the sample is combined with the bead within a fluidic droplet that may be formed in a microfluidic device. As will be appreciated, in many applications, the degrading step may not occur.

The reducing agent may be combined with the sample and then with the bead. In some cases, the reducing agent may be introduced to a microfluidic device as the same time as the sample. In some cases, the reducing agent may be introduced to a microfluidic device after the sample is introduced. In some cases, the sample may be mixed with the reducing agent in a microfluidic device and then contacted with the gel bead in the microfluidic device. In some embodiments, the sample may be pre-mixed with the reducing agent and then added to the device and contacted with the gel bead.

A degradable bead may degrade instantaneously upon application of the appropriate stimuli. In other cases, degradation of the bead may occur over time. For example, a bead may degrade upon application of an appropriate stimulus instantaneously or within about 0, 0.01, 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15 or 20 minutes. In other examples, a bead may degrade upon application of a proper stimulus instantaneously or within at most about 0, 0.01, 0.1, 0.5, 1, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 11, 12, 13, 14, 15 or 20 minutes.

Beads may also be degraded at different times, relative to combining with a sample. For example, the bead may be combined with the sample and subsequently degraded at a point later in time. The time between combining the sample with the bead and subsequently degrading the bead may be about 0.0001, 0.001, 0.01, 1, 10, 30, 60, 300, 600, 1800, 3600, 18000, 36000, 86400, 172800, 432000, or 864000 seconds. The time between combining the sample with the bead and subsequently degrading the bead may be more than about 0.0001, 0.001, 0.01, 1, 10, 30, 60, 300, 600, 1800, 3600, 18000, 36000, 86400, 172800, 432000, 864000 seconds or more. The time between combining the sample with the bead and subsequently degrading the bead may be less than about 0.0001, 0.001, 0.01, 1, 10, 30, 60, 300, 600, 1800, 3600, 18000, 36000, 86400, 172800, 432000, or 864000 seconds.

Preparing Beads Pre-functionalized with Oligonucleotides

The beads described herein may be produced using a variety of methods. In some cases, beads may be formed from a liquid containing molecular precursors (e.g. linear polymers, monomers, cross-linkers). The liquid is then subjected to a polymerization reaction, and thereby hardens or gels into a bead (or gel bead). The liquid may also contain entities such as oligonucleotides that become incorporated into the bead during polymerization. This incorporation may be via covalent or non-covalent association with the bead. For example, in some cases, the oligonucleotides may be entrained within a bead during formation. Alternatively, they may be coupled to the bead or the bead framework either during formation or following formation. Often, the oligonucleotides are connected to an acrydite moiety that becomes cross-linked to the bead during the polymerization process. In some cases, the oligonucleotides are attached to the acrydite moiety by a disulfide linkage. As a result, a composition comprising a bead-acrydite-S—S-oligonucleotide linkage is formed. FIG. 4A is an exemplary diagram of a bead functionalized with an acrydite-linked primer.

In one exemplary process, functionalized beads may be generated by mixing a plurality of polymers and/or monomers with one or more oligonucleotides, such as, for example, one or more oligonucleotides that comprises a primer (e.g., a universal primer, a sequencing primer). The polymers and/or monomers may comprise acrylamide and may be crosslinked such that disulfide bonds form between the polymers and/or monomers, resulting in the formation of hardened beads. The oligonucleotides may be covalently linked to the plurality of polymers and/or monomers during the formation of the hardened beads (e.g., contemporaneously) or may be covalently linked to the plurality of polymers and/or monomers after the formation of the hardened beads (e.g., sequentially). In some cases, the oligonucleotides may be linked to the beads via an acrydite moiety.

In most cases, a population of beads is pre-functionalized with the identical oligonucleotide such as a universal primer or primer binding site. In some cases, the beads in a population of beads are pre-functionalized with multiple different oligonucleotides. These oligonucleotides may optionally include any of a variety of different functional sequences, e.g., for use in subsequent processing or application of the beads. Functional sequences may include, e.g., primer sequences, such as targeted primer sequences, universal primer sequences, e.g., primer sequences that are sufficiently short to be able to hybridize to and prime extension from large numbers of different locations on a sample nucleic acid, or random primer sequences, attachment or immobilization sequences, ligation sequences, hairpin sequences, tagging sequences, e.g., barcodes or sample index sequences, or any of a variety of other nucleotide sequences.

By way of example, in some cases, the universal primer (e.g., P5 or other suitable primer) may be used as a primer on each bead, to attach additional content (e.g., barcodes, random N-mers, other functional sequences) to the bead. In some cases, the universal primer (e.g., P5) may also be compatible with a sequencing device, and may later enable attachment of a desired strand to a flow cell within the sequencing device. For example, such attachment or immobilization sequences may provide a complementary sequence to oligonucleotides that are tethered to the surface of a flow cell in a sequencing device, to allow immobilization of the sequences to that surface for sequencing. Alternatively, such attachments sequences may additionally be provided within, or added to the oligonucleotide sequences attached to the beads. In some cases, the beads and their attached species may be provided to be compatible with subsequent analytical process, such as sequencing devices or systems. In some cases, more than one primer may be attached to a bead and more than one primer may contain a universal sequence, in order to, for example, allow for differential processing of the oligonucleotide as well as any additional sequences that are coupled to that sequence, in different sequential or parallel processing steps, e.g., a first primer for amplification of a target sequence, with a second primer for sequencing the amplified product. For example, in some cases, the oligonucleotides attached to the beads will comprise a first primer sequence for conducting a first amplification or replication process, e.g., extending the primer along a target nucleic acid sequence, in order to generate an amplified barcoded target sequence(s). By also including a sequencing primer within the oligonucleotides, the resulting amplified target sequences will include such primers, and be readily transferred to a sequencing system. For example, in some cases, e.g., where one wishes to sequence the amplified targets using, e.g., an Illumina sequencing system, an R1 primer or primer binding site may also be attached to the bead.

Entities incorporated into the beads may include oligonucleotides having any of a variety of functional sequences as described above. For example, these oligonucleotides may include any one or more of P5, R1, and R2 sequences, non cleavable 5'acrydite-P5, a cleavable 5' acrydite-SS-P5, R1c, sequencing primer, read primer, universal primer, P5_U, a universal read primer, and/or binding sites for any of these primers. In some cases, a primer may contain one or more modified nucleotides nucleotide analogues, or nucleotide mimics. For example, in some cases, the oligonucleotides may include peptide nucleic acids (PNAs), locked nucleic acid (LNA) nucleotides, or the like. In some cases, these oligonucleotides may additionally or alternatively include nucleotides or analogues that may be processed differently, in order to allow differential processing at different steps of their application. For example, in some cases one or more of the functional sequences may include a nucleotide or analogue that is not processed by a particular polymerase enzyme, thus being uncopied in a process step utilizing that enzyme. For example, e.g., in some cases, one or more of the functional sequence components of the oligonucleotides will include, e.g., a uracil containing nucleotide, a nucleotide containing a non-native base, a blocker oligonucleotide, a blocked 3' end, 3'ddCTP. FIG. 19 provides additional examples. As will be appreciated, sequences of any of these entities may function as primers or primer binding sites depending on the particular application.

Polymerization may occur spontaneously. In some cases, polymerization may be initiated by an initiator and/or an accelerator, by electromagnetic radiation, by temperature changes (e.g., addition or removal of heat), by pH changes, by other methods, and combinations thereof. An initiator may refer to a species capable of initiating a polymerization reaction by activating (e.g., via the generation of free radicals) one or more precursors used in the polymerization reaction. An accelerator may refer to a species capable of accelerating the rate at which a polymerization reaction occurs. In some cases, an accelerator may speed up the activation of an initiator (e.g., via the generation of free radicals) used to then activate monomers (e.g., via the generation of free radicals) and, thus, initiate a polymerization reaction. In some cases, faster activation of an initiator can give rise to faster polymerization rates. In some cases, though, acceleration may also be achieved via non-chemical means such as thermal (e.g., addition and removal of heat) means, various types of radiative means (e.g., visible light, UV light, etc.), or any other suitable means. To create droplets containing molecular precursors, which may then polymerize to form hardened beads, an emulsion technique may be employed. For example, molecular precursors may be added to an aqueous solution. The aqueous solution may then be emulsified with an oil (e.g., by agitation, microfluidic droplet generator, or other method). The molecular precursors may then be polymerized in the emulsified droplets to form the beads.

An emulsion may be prepared, for example, by any suitable method, including methods known in the art, such as bulk shaking, bulk agitation, flow focusing, and microsieve (See e.g., Weizmann et al., Nature Methods, 2006, 3(7):545-550; Weitz et al. U.S. Pub. No. 2012/0211084). In some cases, an emulsion may be prepared using a microfluidic device. In some cases, water-in-oil emulsions may be used. These emulsions may incorporate fluorosurfactants such as Krytox FSH with a PEG-containing compound such as bis krytox peg (BKP). In some cases, oil-in-water emulsions may be used. In some cases, polydisperse emulsions may be formed. In some cases, monodisperse emulsions may be formed. In some cases, monodisperse emulsions may be formed in a microfluidic flow focusing device. (Gartecki et al., Applied Physics Letters, 2004, 85(13):2649-2651).

In at least one example, a microfluidic device for making the beads may contain channel segments that intersect at a single cross intersection that combines two or more streams of immiscible fluids, such as an aqueous solution containing molecular precursors and an oil. Combining two immiscible fluids at a single cross intersection may cause fluidic droplets to form. The size of the fluidic droplets formed may depend upon the flow rate of the fluid streams entering the fluidic cross, the properties of the two fluids, and the size of the microfluidic channels. Initiating polymerization after formation of fluidic droplets exiting the fluidic cross may cause hardened beads to form from the fluidic droplets. Examples of microfluidic devices, channel networks and systems for generating droplets, both for bead formation and for partitioning beads into discrete droplets as discussed elsewhere herein, are described for example in U.S. Provisional Patent Application No. 61/977,804, filed Apr. 4, 2014, and incorporated herein by reference in its entirety for all purposes.

To manipulate when individual molecular precursors, oligomers, or polymers begin to polymerize to form a hardened bead, an initiator and/or accelerator may be added at different points in the bead formation process. An accelerator may be an agent which may initiate the polymerization process (e.g., in some cases, via activation of a polymerization initiator) and thus may reduce the time for a bead to harden. In some cases, a single accelerator or a plurality of accelerators may be used for polymerization. Careful tuning of acceleration can be important in achieving suitable polymerization reactions. For example, if acceleration is too fast, weight and excessive chain transfer events may cause poor gel structure and low loading of any desired species. If acceleration is too slow, high molecular weight polymers can generate trapped activation sites (e.g., free radicals) due to polymer entanglement and high viscosities. High viscosities can impede diffusion of species intended for bead loading, resulting in low to no loading of the species. Tuning of accelerator action can be achieved, for example, by selecting an appropriate accelerator, an appropriate combination of accelerators, or by selecting the appropriate accelerator(s) and any stimulus (e.g., heat, electromagnetic radiation (e.g., light, UV light), another chemical species, etc.) capable of modulating accelerator action. Tuning of initiator action may also be achieved in analogous fashion.

Figure 32:
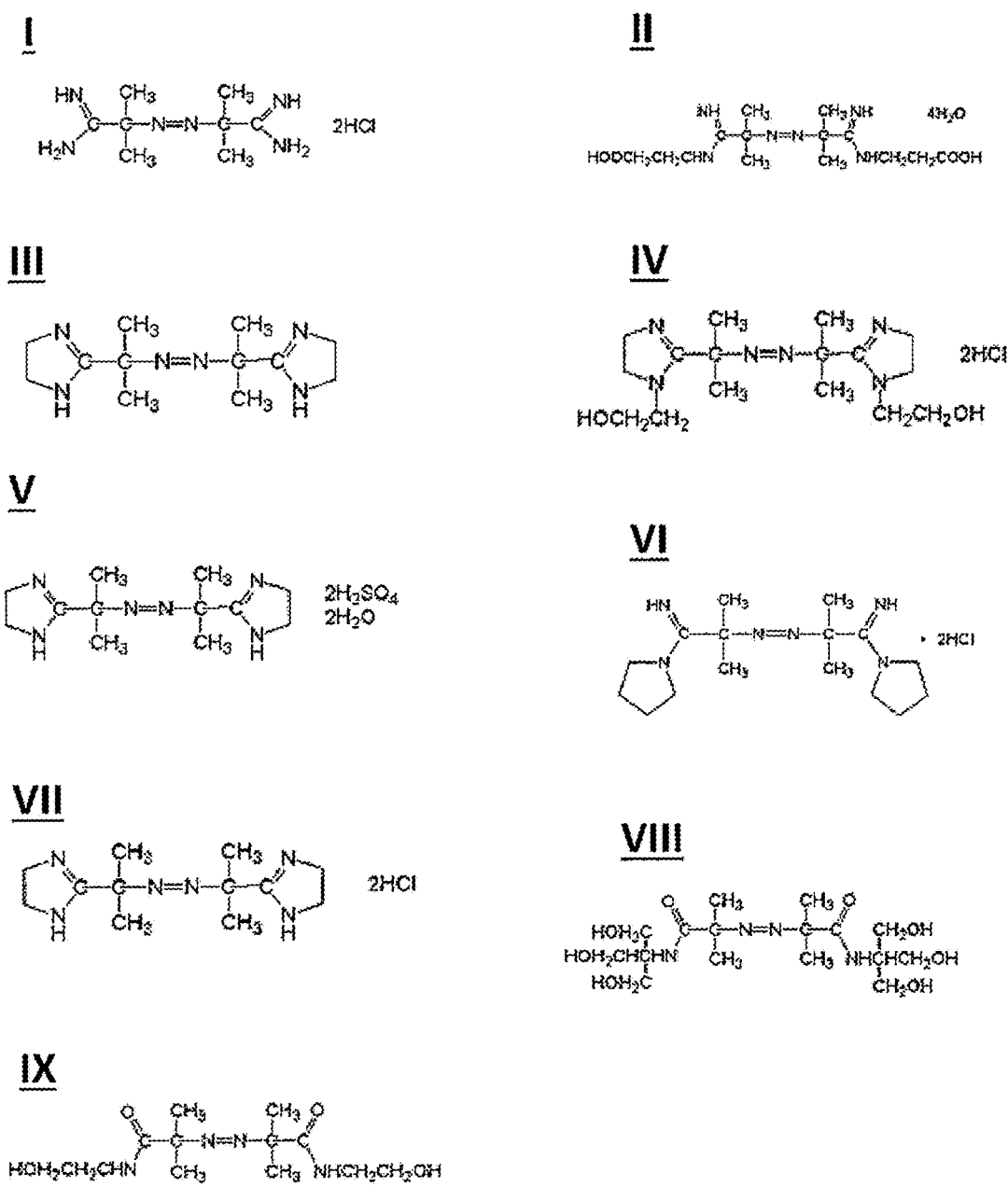
FIG. 32 provides structural depictions of example initiators that may be used during a polymerization reaction.

An accelerator may be water-soluble, oil-soluble, or may be both water-soluble and oil-soluble. For example, an accelerator may be tetramethylethylenediamine (TMEDA or TEMED), dimethylethylenediamine, N,N, N,'N'-tetramethylmethanediamine, N,N'-dimorpholinomethane, or N,N,N', N'-Tetrakis(2-Hydroxypropyl)ethylenediamine. For example, an initiator may be ammonium persulfate (APS), calcium ions, or any of the compounds (I-IX) shown in FIG. 32. The compounds (I-IX) shown in FIG. 32 can function as water-soluble azo-based initiators. Azo-based initiators may be used in the absence of TEMED and APS and can function as thermal based initiators. A thermal based initiator can activate species (e.g., via the generation of free radicals) thermally and, thus, the rate of initiator action can be tuned by temperature and/or the concentration of the initiator. A polymerization accelerator or initiator may include functional groups including phosphonate, sulfonate, carboxylate, hydroxyl, albumin binding moieties, N-vinyl groups, and phospholipids. A polymerization accelerator or initiator may be a low molecular weight monomeric-compound. An accelerator or initiator may be a) added to the oil prior to droplet generation, b) added in the line after droplet generation, c) added to the outlet reservoir after droplet generation, or d) combinations thereof.

Polymerization may also be initiated by electromagnetic radiation. Certain types of monomers, oligomers, or polymers may contain light-sensitive properties. Thus, polymerization may be initiated by exposing such monomers, oligomers, or polymers to UV light, visible light, UV light combined with a sensitizer, visible light combined with a sensitizer, or combinations thereof. An example of a sensitizer may be riboflavin.

The time for a bead to completely polymerize or harden may vary depending on the size of the bead, whether an accelerator may be added, when an accelerator may be added, the type of initiator, when electromagnetic radiation may be applied, the temperature of solution, the polymer composition, the polymer concentration, and other relevant parameters. For example, polymerization may be complete after about 5, 6, 7, 8, 9, 10, 11, 12, 13, 14, 15, 16, 17, 18, 19, or 20 minutes. Polymerization may be complete after more than about 5, 6, 7, 8, 9, 10, 11, 12, 13, 14, 15, 16, 17, 18, 19, 20 minutes or more. Polymerization may be complete in less than about 5, 6, 7, 8, 9, 10, 11, 12, 13, 14, 15, 16, 17, 18, 19, or 20 minutes.

Beads may be recovered from emulsions (e.g. gel-water-oil) by continuous phase exchange. Excess aqueous fluid may be added to the emulsion (e.g. gel-water-oil) and the hardened beads may be subjected to sedimentation, wherein the beads may be aggregated and the supernatant containing excess oil may be removed. This process of adding excess aqueous fluid followed by sedimentation and removal of excess oil may be repeated until beads are suspended in a given purity of aqueous buffer, with respect to the continuous phase oil. The purity of aqueous buffer may be about 80%, 90%, 95%, 96%, 97%, 98%, or 99% (v/v). The purity of aqueous buffer may be more than about 80%, 90%, 95%, 96%, 97%, 98%, 99% or more (v/v). The purity of aqueous buffer may be less than about 80%, 90%, 95%, 96%, 97%, 98%, or 99% (v/v). The sedimentation step may be repeated about 2, 3, 4, or 5 times. The sedimentation step may be repeated more than about 2, 3, 4, 5 times or more. The sedimentation step may be repeated less than about 2, 3, 4, or 5 times. In some cases, sedimentation and removal of the supernatant may also remove un-reacted starting materials.

Examples of droplet generators may include single flow focuser, parallel flow focuser, and microsieve membrane, such as those used by Nanomi B. V., and others. Preferably, a microfluidic device is used to generate the droplets.

Figure 30B:
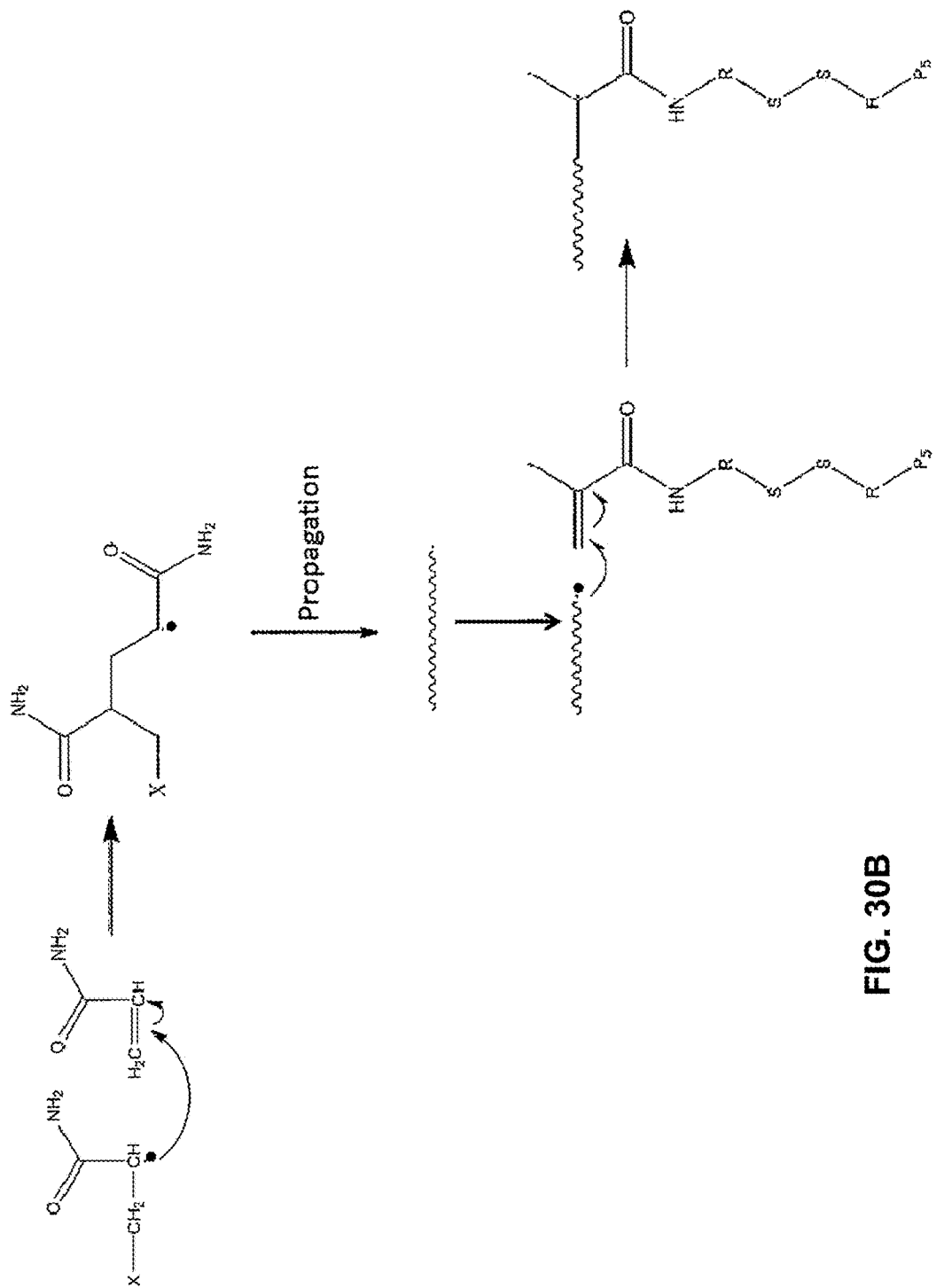
Figure 30C:
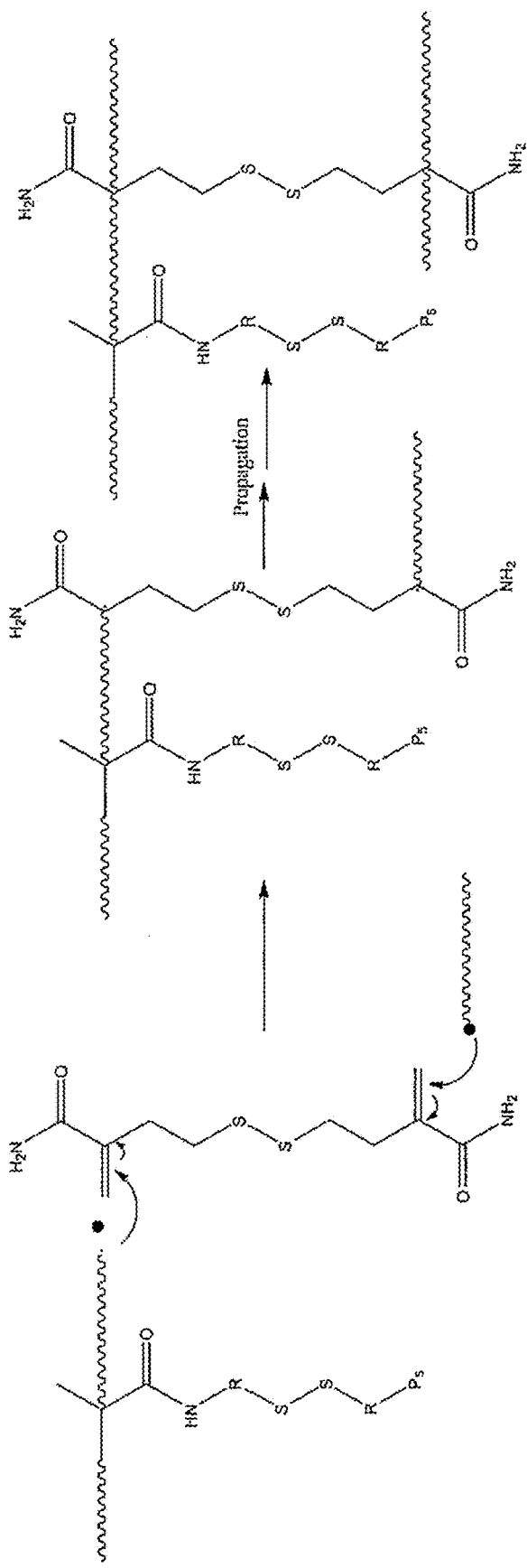

An example emulsion based scheme for generating gel beads pre-functionalized with an acrydite moiety linked to a P5 primer via a disulfide bond is depicted in FIGS. 30A-30C. As shown in FIG. 30A, acrylamide, bis(acryloyl) cystamine, acrydite-S—S-P5 moieties, and ammonium persulfate are combined into a droplets of an emulsion. TEMED can be added to the emulsion oil phase and can diffuse into the droplets to initiate the polymerization reaction. As shown in FIG. 30A, TEMED action on ammonium persulfate results in the generation of $SO_4$ free radicals that can then activate the carbon-carbon double bond of the acrylamide via generation of a free radical at one of the carbons of the carbon-carbon double bond.

As shown in FIG. 30B, activated acrylamide can react with non-activated acrylamide (again, at its carbon-carbon double bond) to begin polymerization. Each product generated can again be activated via the formation of a free radical resulting in polymer propagation. Moreover, both the bis (acryloyl)cystamine cross-linker and acrydite-S—S-P5 moieties comprise carbon-carbon double bonds that can react with activated species and the products themselves can then become activated. The inclusion of the bis(acryloyl)cystamine cross-linker into the polymerization reaction can result in cross-linking of polymer chains that are generated as shown in FIG. 30C. Thus, a hydrogel polymer network comprising acrydite-S—S-P5 moieties linked to polymer backbones can be generated, as depicted in FIG. 30C. The polymerization reaction can continue until it terminates. Upon reaction termination, continuous phase exchange or other suitable method can be used to break the emulsion and obtain gel beads comprising a cross-linked hydrogel (shown schematically in FIG. 30A) coupled to the acrydite-S—S-P5 moieties.

Barcode and Random N-mers (Introduction)

Certain applications, for example polynucleotide sequencing, may rely on unique identifiers ("barcodes") to identify a sequence and, for example, to assemble a larger sequence from sequenced fragments. Therefore, it may be desirable to add barcodes to polynucleotide fragments before sequencing. In the case of nucleic acid applications, such barcodes are typically comprised of a relatively short sequence of nucleotides attached to a sample sequence, where the barcode sequence is either known, or identifiable by its location or sequence elements. In some cases, a unique identifier may be useful for sample indexing. In some cases, though, barcodes may also be useful in other contexts. For example, a barcode may serve to track samples throughout processing (e.g., location of sample in a lab, location of sample in plurality of reaction vessels, etc.); provide manufacturing information; track barcode performance over time (e.g., from barcode manufacturing to use) and in the field; track barcode lot performance over time in the field; provide product information during sequencing and perhaps trigger automated protocols (e.g., automated protocols initiated and executed with the aid of a computer) when a barcode associated with the product is read during sequencing; track and troubleshoot problematic barcode sequences or product lots; serve as a molecular trigger in a reaction involving the barcode, and combinations thereof. In particularly preferred aspects, and as alluded to above, barcode sequence segments as described herein, can be used to provide linkage information as between two discrete determined nucleic acid sequences. This linkage information may include, for example, linkage to a common sample, a common reaction vessel, e.g., a well or partition, or even a common starting nucleic acid molecule. In particular, by attaching common barcodes to a specific sample component, or subset of sample components within a given reaction volume, one can attribute the resulting sequences bearing that barcode to that reaction volume. In turn, where the sample is allocated to that reaction volume based upon its sample of origin, the processing steps to which it is subsequently exposed, or on an individual molecule basis, one can better identify the resulting sequences as having originated from that reaction volume.

Barcodes may be generated from a variety of different formats, including bulk synthesized polynucleotide barcodes, randomly synthesized barcode sequences, microarray based barcode synthesis, native nucleotides, partial complement with N-mer, random N-mer, pseudo random N-mer, or combinations thereof. Synthesis of barcodes is described herein, as well as in, for example, in U.S. patent application Ser. No. 14/175,973, filed Feb. 7, 2014, the full disclosure of which is hereby incorporated herein by reference in its entirety for all purposes.

As described above, oligonucleotides incorporating barcode sequence segments, which function as a unique identifier, may also include additional sequence segments. Such additional sequence segments may include functional sequences, such as primer sequences, primer annealing site sequences, immobilization sequences, or other recognition or binding sequences useful for subsequent processing, e.g., a sequencing primer or primer binding site for use in sequencing of samples to which the barcode containing oligonucleotide is attached. Further, as used herein, the reference to specific functional sequences as being included within the barcode containing sequences also envisioned the inclusion of the complements to any such sequences, such that upon complementary replication will yield the specific described sequence.

In some examples, barcodes or partial barcodes may be generated from oligonucleotides obtained from or suitable for use in an oligonucleotide array, such as a microarray or bead array. In such cases, oligonucleotides of a microarray may be cleaved, (e.g., using cleavable linkages or moieties that anchor the oligonucleotides to the array (such as photocleavable, chemically cleavable, or otherwise cleavable linkages)) such that the free oligonucleotides are capable of serving as barcodes or partial barcodes. In some cases, barcodes or partial barcodes are obtained from arrays are of known sequence. The use of known sequences, including those obtained from an array, for example, may be beneficial in avoiding sequencing errors associated with barcodes of unknown sequence. A microarray may provide at least about 10,000,000, at least about 1,000,000, at least about 900,000, at least about 800,000, at least about 700,000, at least about 600,000, at least about 500,000, at least about 400,000, at least about 300,000, at least about 200,000, at least about 100,000, at least about 50,000, at least about 10,000, at least about 1,000, at least about 100, or at least about 10 different sequences that may be used as barcodes or partial barcodes.

The beads provided herein may be attached to oligonucleotide sequences that may behave as unique identifiers (e.g., barcodes). Often, a population of beads provided herein contains a diverse library of barcodes, wherein each bead is attached to multiple copies of a single barcode sequence. In some cases, the barcode sequences are pre-synthesized and/or designed with known sequences. In some cases, each bead within the library is attached to a unique barcode sequence. In some cases, a plurality of beads will have the same barcode sequence attached to them. For example, in some cases about 1%, 2%, 3%, 4%, 5%, 10%, 20%, 25%, 30%, 50%, 75%, 80%, 90%, 95%, or 100% of the beads in a library are attached to a barcode sequence that is identical to a barcode sequence attached to a different bead in the library. Sometimes, about 1%, 2%, 3%, 4%, 5%, 10%, 20%, 25%, or 30% of the beads are attached to the same barcode sequence.

The length of a barcode sequence may be any suitable length, depending on the application. In some cases, a barcode sequence may be about 2 to about 500 nucleotides in length, about 2 to about 100 nucleotides in length, about 2 to about 50 nucleotides in length, about 2 to about 20 nucleotides in length, about 6 to about 20 nucleotides in length, or about 4 to 16 nucleotides in length. In some cases, a barcode sequence is about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some cases, a barcode sequence is greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some cases, a barcode sequence is less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length.

The barcodes may be loaded into beads so that one or more barcodes are introduced into a particular bead. In some cases, each bead may contain the same set of barcodes. In other cases, each bead may contain different sets of barcodes. In other cases, each bead may comprise a set of identical barcodes. In other cases, each bead may comprise a set of different barcodes.

The beads provided herein may be attached to oligonucleotide sequences that are random, pseudo-random, or targeted N-mers capable of priming a sample (e.g., genomic sample) in a downstream process. In some cases, the same n-mer sequences will be present on the oligonucleotides attached to a single bead or bead population. This may be the case for targeted priming methods, e.g., where primers are selected to target certain sequence segments within a larger target sequence. In other cases, each bead within a population of beads herein is attached to a large and diverse number of N-mer sequences to, among other things, diversify the sampling of these primers against template molecules, as such random n-mer sequences will randomly prime against different portions of the sample nucleic acids.

The length of an N-mer may vary. In some cases, an N-mer (e.g., a random N-mer, a pseudo-random N-mer, or a targeted N-mer) may be between about 2 and about 100 nucleotides in length, between about 2 and about 50 nucleotides in length, between about 2 and about 20 nucleotides in length, between about 5 and about 25 nucleotides in length, or between about 5 and about 15 nucleotides in length. In some cases, an N-mer (e.g., a random N-mer, a pseudo-random N-mer, or a targeted N-mer) may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, or 500 nucleotides in length. In some cases, an N-mer (e.g., a random N-mer, a pseudo-random N-mer, or targeted a N-mer) may be greater than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, 1000, 5000, or 10000 nucleotides in length. In some cases, an N-mer (e.g., a random N-mer, a pseudo-random N-mer, or a targeted N-mer) may be less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 85, 90, 95, 100, 150, 200, 250, 300, 400, 500, 750, or 1000 nucleotides in length.

N-mers (including random N-mers) can be engineered for priming a specific sample type. For example, N-mers of different lengths may be generated for different types of sample nucleic acids or different regions of a sample nucleic acid, such that each N-mer length corresponds to each different type of sample nucleic acid or each different region of a sample nucleic acid. For example, an N-mer of one length may be generated for sample nucleic acid originating from the genome of one species (e.g., for example, a human genome) and an N-mer of another length may be generated for a sample nucleic acid originating from another species (e.g., for example, a yeast genome). In another example, an N-mer of one length may be generated for sample nucleic acid comprising a particular sequence region of a genome and an N-mer of another length may be generated for a sample nucleic acid comprising another sequence region of the genome. Moreover, in addition or as an alternative to N-mer length, the base composition of the N-mer (e.g., GC content of the N-mer) may also be engineered to correspond to a particular type or region of a sample nucleic acid. Base content may vary in a particular type of sample nucleic acid or in a particular region of a sample nucleic acid, for example, and, thus, N-mers of different base content may be useful for priming different sample types of nucleic acid or different regions of a sample nucleic acid.

Populations of beads described elsewhere herein can be generated with an N-mer engineered for a particular sample type or particular sample sequence region. In some cases, a mixed population of beads (e.g., a mixture of beads comprising an N-mer engineered for one sample type or sequence region and beads comprising another N-mer engineered for another sample type or sequence region) with respect to N-mer length and content may be generated. In some cases, a population of beads may be generated, where one or more of the beads can comprise a mixed population of N-mers engineered for a plurality of sample types or sequence regions.

As noted previously, in some cases, the N-mers, whether random or targeted, may comprise nucleotide analogues, mimics, or non-native nucleotides, in order to provide primers that have improved performance in subsequent processing steps. For example, in some cases, it may be desirable to provide N-mer primers that have different melting/annealing profiles when subjected to thermal cycling, e.g., during amplification, in order to enhance the relative priming efficiency of the n-mer sequence. In some cases, nucleotide analogues or non-native nucleotides may be incorporated into the N-mer primer sequences in order to alter the melting temperature profile of the primer sequence as compared to a corresponding primer that includes native nucleotides. In certain cases, the primer sequences, such as the N-mer sequences described herein, may include modified nucleotides or nucleotide analogues, e.g., LNA bases, at one or more positions within the sequence, in order to provide elevated temperature stability for the primers when hybridized to a template sequence, as well as provide generally enhanced duplex stability. In some cases, LNA nucleotides are used in place of the A or T bases in primer synthesis to replace those weaker binding bases with tighter binding LNA analogues. By providing enhanced hybridizing primer sequences, one may generate higher efficiency amplification processes using such primers, as well as be able to operate within different temperature regimes.

Other modifications may also be provided to the oligonucleotides described above. For example, in some cases, the oligonucleotides may be provided with protected termini or other regions, in order to prevent or reduce any degradation of the oligonucleotides, e.g., through any present exonuclease activity. In one example, the oligonucleotides may be provided with one or more phosphorothioate nucleotide analogue at one or more positions within the oligonucleotide sequence, e.g., adjacent or proximal to the 3' and/or 5' terminal position. These phosphorothioate nucleotides typically provide a sulfur group in place of the non-linking oxygen in an internucleotide linkage within the oligonucleotide to reduce or eliminate nuclease activity on the oligonucleotides, including, e.g., 3'-5' and/or 5'-3' exonucleases. In general, phosphorothioate analogues are useful in imparting exo and/or endonuclease resistance to oligonucleotides that include them, including providing protection against, e.g., 3'-5' and/or 5'-3' exonuclease digestion of the oligonucleotides. Accordingly, in some aspects, these one or more phosphorothioate linkages will be in one or more of the last 5 to 10 internucleotide linkages at either the 3' or the 5' terminus of the oligonucleotides, and preferably include one or more of the last 3' or 5' terminal internucleotide linkage and second to last 5' terminal internucleotide linkage, in order to provide protection against 3'-5' or 5'-3' exonuclease activity. Other positions within the oligonucleotides may also be provided with phosphorothiate linkages as well. In addition to providing such protection on the oligonucleotides that comprise the barcode sequences (and any associated functional sequences), the above described modifications are also useful in the context of the blocker sequences described herein, e.g., incorporating phosphorothioate analogues within the blocker sequences, e.g., adjacent or proximal to the 3' and/or 5' terminal position as well as potentially other positions within the oligonucleotides.

Attaching Content to Pre-functionalized Beads

A variety of content may be attached to the beads described herein, including beads functionalized with oligonucleotides. Often, oligonucleotides are attached, particularly oligonucleotides with desired sequences (e.g., barcodes, random N-mers). In many of the methods provided herein, the oligonucleotides are attached to the beads through a primer extension reaction. Beads pre-functionalized with primer can be contacted with oligonucleotide template. Amplification reactions may then be performed so that the primer is extended such that a copy of the complement of the oligonucleotide template is attached to the primer. Other methods of attachment are also possible such as ligation reactions.

In some cases, oligonucleotides with different sequences (or the same sequences) are attached to the beads in separate steps. For example, in some cases, barcodes with unique sequences are attached to beads such that each bead has multiple copies of a first barcode sequence on it. In a second step, the beads can be further functionalized with a second sequence. The combination of first and second sequences may serve as a unique barcode, or unique identifier, attached to a bead. The process may be continued to add additional sequences that behave as barcode sequences (in some cases, greater than 1, 2, 3, 4, 5, 6, 7, 8, 9, or 10 barcode sequences are sequentially added to each bead). The beads may also be further functionalized random N-mers that can, for example, act as a random primer for downstream whole genome amplification reactions.

Figure 4C:
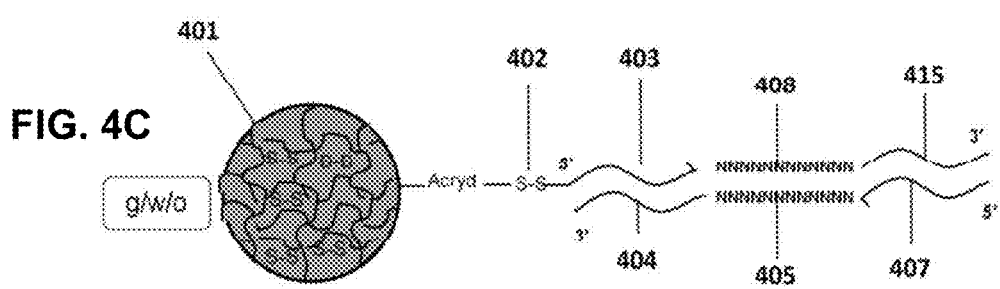
FIGS. 4A-4N are diagrams for attaching sequences to beads. "g/w" means gel-in-water; "g/w/o" means gel-in-water-in-oil.

In some cases, after functionalization with a certain oligonucleotide sequence (e.g., barcode sequence), the beads may be pooled and then contacted with a large population of random Nmers that are then attached to the beads. In some cases, particularly when the beads are pooled prior to the attachment of the random Nmers, each bead has one barcode sequence attached to it, (often as multiple copies), but many different random Nmer sequences attached to it. FIGS. 4A-4N provide a step-by-step depiction of one example method, an example limiting dilution method, for attaching oligonucleotides, such as barcodes and Nmers, to beads.

Limiting dilution may be used to attach oligonucleotides to beads, such that the beads, on average, are attached to no more than one unique oligonucleotide sequence such as a barcode. Often, the beads in this process are already functionalized with a certain oligonucleotide, such as primers. For example, beads functionalized with primers (e.g., such as universal primers) and a plurality of template oligonucleotides may be combined, often at a high ratio of beads: template oligonucleotides, to generate a mixture of beads and template oligonucleotides. The mixture may then be partitioned into a plurality of partitions (e.g., aqueous droplets within a water-in-oil emulsion), such as by a bulk emulsification process, emulsions within plates, or by a microfluidic device, such as, for example, a microfluidic droplet generator. In some cases, the mixture can be partitioned into a plurality of partitions such that, on average, each partition comprises no more than one template oligonucleotide.

Moreover, the template oligonucleotides can be amplified (e.g., via primer extension reactions) within the partitions via the primers attached to the beads. Amplification can result in the generation of beads comprising amplified template oligonucleotides. Following amplification, the contents of the partitions may be pooled into a common vessel (e.g., a tube, a well, etc.). The beads comprising the amplified template oligonucleotides may then be separated from the other contents of the partitions (including beads that do not comprise amplified template oligonucleotides) by any suitable method including, for example, centrifugation and magnetic separation, with or without the aid of a capture moiety as described elsewhere herein.

Beads comprising amplified template oligonucleotides may be combined with additional template oligonucleotides to generate a bulk mixture comprising the beads and the additional template oligonucleotides. The additional template oligonucleotides may comprise a sequence that is at least partially complementary to the amplified template oligonucleotides on the beads, such that the additional template oligonucleotide hybridizes to the amplified template oligonucleotides. The amplified template oligonucleotides can then be extended via the hybridized additional template oligonucleotides in an amplification reaction, such that the complements of the additional template oligonucleotides are attached to the amplified template oligonucleotides. The cycle of binding additional template oligonucleotides to amplified oligonucleotides, followed by extension of the amplified oligonucleotides in an amplification reaction, can be repeated for any desired number of additional oligonucleotides that are to be added to the bead.

The oligonucleotides attached to the amplified template oligonucleotides may comprise, for example, one or more of a random N-mer sequence, a pseudo random N-mer sequence, or a primer binding site (e.g., a universal sequence portion, such as a universal sequence portion that is compatible with a sequencing device). Any of these sequences or any other sequence attached to a bead may comprise at least a subsection of uracil containing nucleotides, as described elsewhere herein.

An example of a limiting dilution method for attaching a barcode sequence and a random N-mer to beads is shown in FIGS. 4A-4N. As shown in FIG. 4A, beads 401, (e.g., disulfide cross-linked polyacrylamide gel beads) are pre-functionalized with a first primer 403. The first primer 403 may be, for example, coupled to the beads via a disulfide linkage 402 with an acrydite moiety bound to the surface of the beads 401. In some cases, though, first primer 403 may be coupled to a bead via an acrydite moiety, without a disulfide linkage 402. The first primer 403 may be a universal primer for priming template sequences of oligonucleotides to be attached to the beads and/or may be a primer binding site (e.g., P5) for use in sequencing an oligonucleotide that comprises first primer 403.

The first primer 403 functionalized beads 401 can then be mixed in an aqueous solution with template oligonucleotides (e.g., oligonucleotides comprising a first primer binding site 404 (e.g., P5c), a template barcode sequence 405, and a template primer binding site 407 (e.g., R1c)) and reagents necessary for nucleic acid amplification (e.g., dNTPs, polymerase, co-factors, etc.) as shown in FIG. 4B. The aqueous mixture may also comprise a capture primer 406 (e.g., sometimes referred to as a read primer) linked to a capture moiety (e.g., biotin), identical in sequence to the template primer binding site 407 of the template oligonucleotide.

The aqueous mixture is then emulsified in a water/oil emulsion to generate aqueous droplets (e.g., the droplets comprising one or more beads 401, a template oligonucleotide, reagents necessary for nucleic amplification, and, if desired, any capture primers 406) in a continuous oil phase. In general, the droplets comprise, on average, at most one template oligonucleotide per droplet. As shown in FIGS. 4B and 4C, a first round of thermocycling of the droplets results in priming of the template oligonucleotides at primer binding site 404 by first primer 403 and extension of first primer 403 such that oligonucleotides complementary to the template oligonucleotide sequences are attached to the gel beads at first primer 403. The complementary oligonucleotides comprises first primer 403, a barcode sequence 408 (e.g., complementary to template barcode sequence 405), and a capture primer binding site 415 complementary to both template primer binding site 407 and capture primer 406. Capture primer binding site 415 may also be used as a read primer binding site (e.g., R1) during sequencing of the complementary oligonucleotide.

Figure 4D:
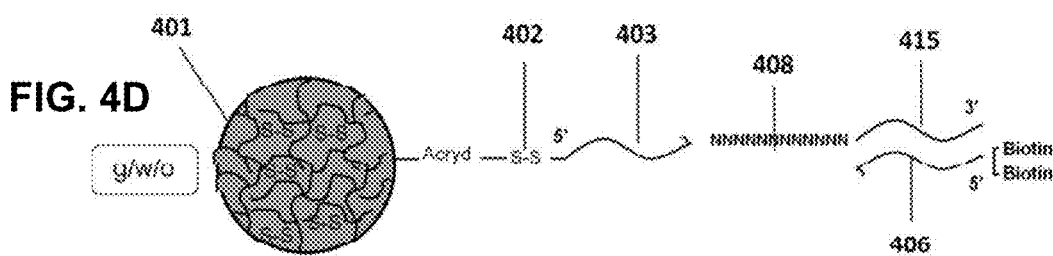
Figure 4E:
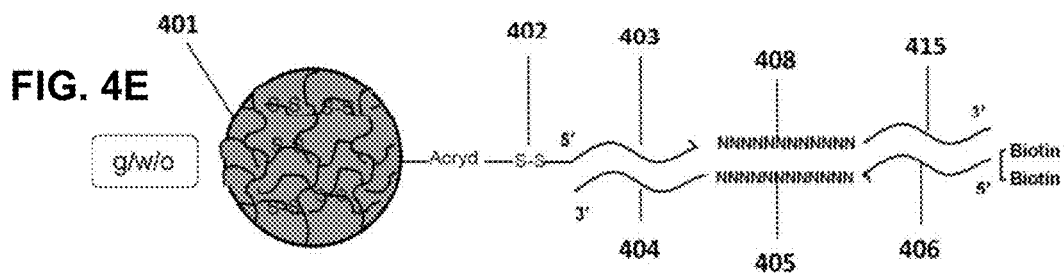

As shown in FIG. 4D, capture primer 406 can bind to capture primer binding site 415 during the next round of thermocycling. Capture primer 406, comprising a capture moiety (e.g., biotin) at its 5' end, can then be extended to generate additional template oligonucleotides (e.g., comprising sequences 404, 405, and 406), as shown in FIG. 4E. Thermocyling may continue for a desired number of cycles (e.g., at least about 1, 5, 10, 15, 20, 25, 30, 35, 40, 45, 50 or more cycles) up until all first primer 403 sites of beads 401 are linked to a barcode sequence 408 and a capture primer binding site 415. Because each droplet generally comprises one or zero template oligonucleotides to start, each droplet will generally comprise beads attached to multiple copies of a sequence complementary to the template oligonucleotide or no copies of a sequence complementary to the template oligonucleotide. At the conclusion of thermocycling, the oligonucleotide products attached to the beads are hybridized to template oligonucleotides also comprising the capture moiety (e.g., biotin), as shown in FIG. 4E.

Figure 4H:
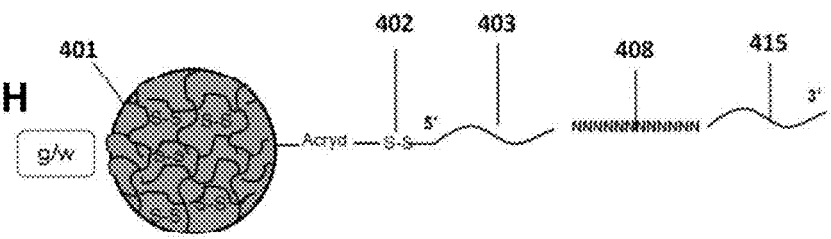

The emulsion may then be broken via any suitable means and the released beads can be pooled into a common vessel. Using a capture bead (or other device, including capture devices described herein) 409 linked to a moiety (e.g., streptavidin) capable of binding with the capture moiety of capture primer 406, positive beads (e.g., beads comprising sequences 403, 408, and 415) may be enriched from negative beads (e.g., beads not comprising sequences 403, 408, and 415) by interaction of the capture bead with the capture moiety, as shown in FIGS. 4F and 4G. In cases where capture beads are used, the beads may be magnetic, such that a magnet may be used for enrichment. As an alternative, centrifugation may be used for enrichment. Upon enrichment of the positive beads, the hybridized template oligonucleotides comprising the capture moiety and linked to the capture bead may be denatured from the bead-bound oligonucleotide via heat or chemical means, including chemical means described herein, as shown in FIG. 4H. Denatured oligonucleotides (e.g., oligonucleotides comprising sequences 404, 405 and 406) may then be separated from the positive beads via the capture beads attached to the denatured oligonucleotides. As shown in FIG. 4H, beads comprising sequences 403, 408, and 415 are obtained. As an alternative to capture beads, positive beads may also be sorted from positive beads via flow cytometry by including, for example, an optically active dye in partitions capable of binding to beads or species coupled to beads.

Figure 4I:
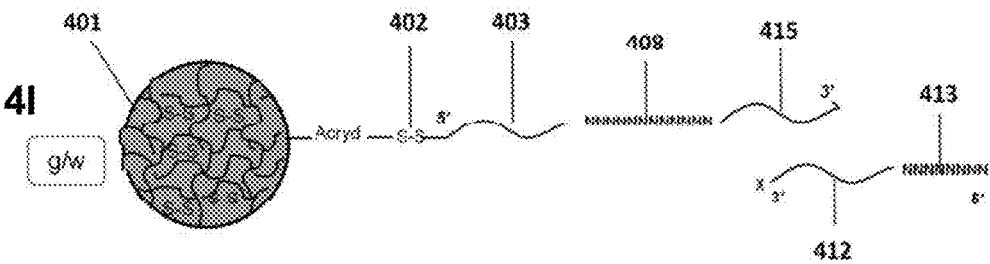
Figure 4J:
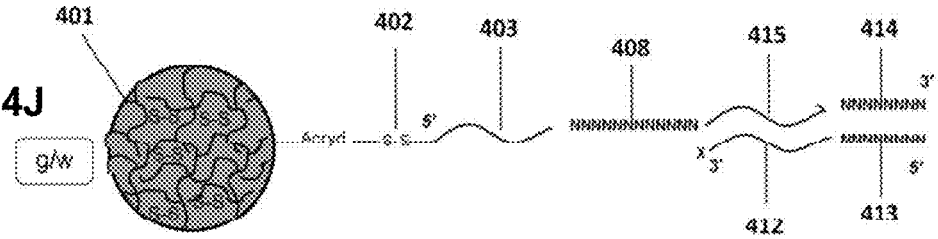
Figure 4M:
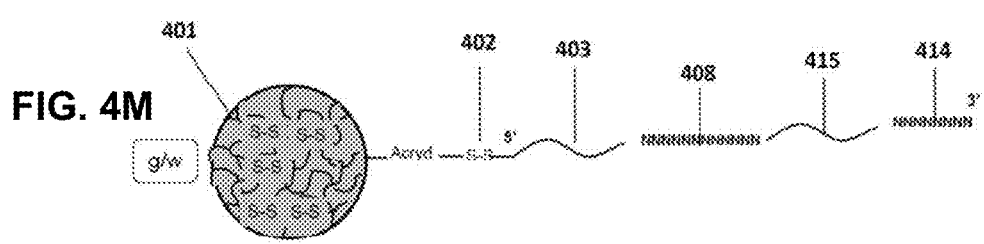
Figure 4N:
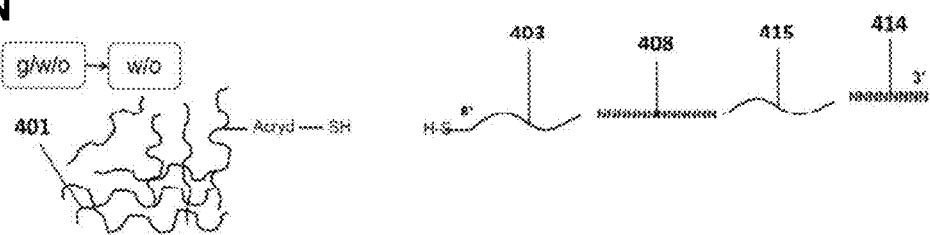

In bulk aqueous fluid, the beads comprising sequences 403, 408, and 415 can then be combined with template random sequences (e.g., random N-mers) 413 each linked to a sequence 412 complementary to capture primer binding site 415, as shown in FIG. 4I. As shown in FIG. 4J, capture primer binding site 415 can prime oligonucleotides comprising template random sequences 413 at sequence 412 upon heating. Following priming, capture primer binding site 415 can be extended (e.g., via polymerase) to link capture primer binding site 415 with a random sequence 414 that is complementary to template random sequence 413. Oligonucleotides comprising template random sequences 413 and sequence 412 can be denatured from the bead using heat or chemical means, including chemical means described herein. Centrifugation and washing of the beads, for example, may be used to separate the beads from denatured oligonucleotides. Following removal of the denatured oligonucleotides, beads comprising a barcode sequence 408 and a random sequence 414 are obtained, as shown in FIGS. 4K, 4L, and 4M. Because the attachment of random sequence 414 was done in bulk, each bead that comprises multiple copies of a unique barcode sequence 408, also comprises various random sequences 414.

To release bead-bound oligonucleotides from the beads, stimuli described elsewhere herein, such as, for example, a reducing agent, may be used. As shown in FIG. 4N, contact of a bead comprising disulfide bonds and linkages to oligonucleotides via disulfide bonds with a reducing agent degrades both the bead and the disulfide linkages freeing the oligonucleotide from the bead. Contact with a reducing agent may be completed, for example, in another partition (e.g., a droplet of another emulsion), such that, upon oligonucleotide release from the bead, each droplet generally comprises free oligonucleotides all comprising the same barcode sequence 408, yet various random sequences 414. Via random sequence 414 acting as a random primer, free oligonucleotides may be used to barcode different regions of a sample nucleic acid also in the partition. Amplification or ligation schemes, including those described herein, may be used to complete attachment of barcodes to the sample nucleic acid.

With limiting dilution, the partitions (e.g., droplets) may contain on average at most one oligonucleotide sequence per partition. This frequency of distribution at a given sequence-bead dilution follows Poisson distribution. Thus, in some cases, about 6%, 10%, 18%, 20%, 30%, 36%, 40%, or 50% of the droplets or partitions may comprise one or fewer oligonucleotide sequences. In some cases, more than about 6%, 10%, 18%, 20%, 30%, 36%, 40%, 50%, 60%, 70%, 75%, 80%, 85%, 90%, 95%, 96%, 97%, 98%, 99%, 99.1%, 99.2%, 99.3%, 99.4%, 99.5%, 99.6%, 99.7%, 99.8%, 99.9%, or more of the droplets may comprise one or fewer oligonucleotide sequences. In other cases, less than about 6%, 10%, 18%, 20%, 30%, 36%, 40%, or 50% of the droplets may comprise one or fewer oligonucleotide sequences.

In some cases, limiting dilution steps may be repeated, prior to the addition of a random N-mer sequence in order to increase the number of positive beads with copies of barcodes. For example, a limiting dilution could be prepared such that a desired fraction (e.g., 1/10 to 1/3) of emulsion droplets comprises a template for amplification. Positive beads could be generated via amplification of the template (as depicted in FIGS. 4A-4N) such that positives generally comprise no more primer for amplification (e.g., all P5 primer sites have been extended). The emulsion droplets can then be broken, and subsequently re-emulsified with fresh template at limiting dilution for a second round of amplification. Positive beads generated in the first round of amplification generally would not participate in further amplification because their priming sites would already be occupied. The process of amplification followed by re-emulsification can be repeated for a suitable number of steps, until the desired fraction of positive beads is obtained.

In some cases, negative beads obtained during sorting after a limiting dilution functionalization may be recovered and further processed to generate additional positive beads. For example, negative beads may be dispensed into wells of a plate (e.g., a 384 well plate) after recovery such that each well generally comprises 1 bead. In some cases, dispensing may be achieved with the aid of flow cytometry (e.g., a flow cytometer directs each negative bead into a well during sorting—an example flow cytometer being a BD FACS Jazz) or via a dispensing device, such as for example, a robotic dispensing device. Each well can also comprise a template barcode sequence and the process depicted in FIGS. 4A-4N repeated, except that each well partitions each bead, rather than a fluidic droplet. Because each well comprises template and a bead, each well can produce a positive bead. The beads can then be pooled from each well and additional sequences (e.g., a random N-mer sequence) can be added in bulk as described elsewhere herein.

The barcodes may be loaded into the beads at an expected or predicted ratio of barcodes per bead to be barcoded. In some cases, the barcodes are loaded such that a ratio of about 0.0001, 0.001, 0.1, 1, 2, 3, 4, 5, 6, 7, 8, 9, 10, 20, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 barcodes are loaded per bead. In some cases, the barcodes are loaded such that a ratio of more than 0.0001, 0.001, 0.1, 1, 2, 3, 4, 5, 6, 7, 8, 9, 10, 20, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more barcodes are loaded per bead. In some cases, the barcodes are loaded such that a ratio of less than about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.1, 0.2, 0.3, 0.4, 0.5, 0.6, 0.7, 0.8, 0.9, 1, 2, 3, 4, 5, 6, 7, 8, 9, 10, 20, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 barcodes are loaded per bead.

Beads, including those described herein (e.g., substantially dissolvable beads, in some cases, substantially dissolvable by a reducing agent), may be covalently or non-covalently linked to a plurality of oligonucleotides, wherein at least a subset of the oligonucleotides comprises a constant region or domain (e.g., a barcode sequence, a barcode domain, a common barcode domain, or other sequence that is constant among the oligonucleotides of the subset) and a variable region or domain (e.g., a random sequence, a random N-mer, or other sequence that is variable among the oligonucleotides of the subset). In some cases, the oligonucleotides may be releasably coupled to a bead, as described elsewhere herein. Oligonucleotides may be covalently or non-covalently linked to a bead via any suitable linkage, including types of covalent and non-covalent linkages described elsewhere herein. In some cases, an oligonucleotide may be covalently linked to a bead via a cleavable linkage such as, for example, a chemically cleavable linkage (e.g., a disulfide linkage), a photocleavable linkage, or a thermally cleavable linkage. Beads may comprise more than about or at least about 1, 10, 50, 100, 500, 1000, 5000, 10000, 50000, 100000, 500000, 1000000, 5000000, 10000000, 50000000, 100000000, 500000000, 1000000000, 5000000000, 10000000000, 50000000000, 100000000000, 500000000000, or 1000000000000 oligonucleotides comprising a constant region or domain and a variable region or domain.

In some cases, the oligonucleotides may each comprise an identical constant region or domain (e g, an identical barcode sequence, identical barcode domain, a common domain, etc.). In some cases, the oligonucleotides may each comprise a variable domain with a different sequence. In some cases, the percentage of the oligonucleotides that comprise an identical constant region (or common domain) may be at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, the percentage of the oligonucleotides that comprise a variable region with a different sequence may be at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, the percentage of beads in a plurality of beads that comprise oligonucleotides with different nucleotide sequences (including those comprising a variable and constant region or domain) is at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, the oligonucleotides may also comprise one or more additional sequences, such as, for example a primer binding site (e.g., a sequencing primer binding site), a universal primer sequence (e.g., a primer sequence that would be expected to hybridize to and prime one or more loci on any nucleic acid fragment of a particular length, based upon the probability of such loci being present within a sequence of such length) or any other desired sequence including types of additional sequences described elsewhere herein.

As described elsewhere herein, a plurality of beads may be generated to form, for example, a bead library (e.g., a barcoded bead library). In some cases, the sequence of a common domain (e.g., a common barcode domain) or region may vary between at least a subset of individual beads of the plurality. For example, the sequence of a common domain or region between individual beads of a plurality of beads may be different between 2 or more, 10 or more, 50 or more, 100 or more, 500 or more, 1000 or more, 5000 or more, 10000 or more, 50000 or more, 100000 or more, 500000 or more, 1000000 or more, 5000000 or more, 10000000 or more, 50000000 or more, 100000000 or more, 500000000 or more, 1000000000 or more, 5000000000 or more, 10000000000 or more, 50000000000 or more, or 100000000000 or more beads of the plurality. In some cases, each bead of a plurality of beads may comprise a different common domain or region. In some cases, the percentage of individual beads of a plurality of beads that comprise a different common domain or region may be at least about 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 100%. In some cases, a plurality of beads may comprise at least about 2, 10, 50, 100, 500, 1000, 5000, 10000, 50000, 100000, 500000, 1000000, 5000000, 10000000, 50000000, 100000000, 500000000, or more different common domains coupled to different beads in the plurality.

Figure 13A:
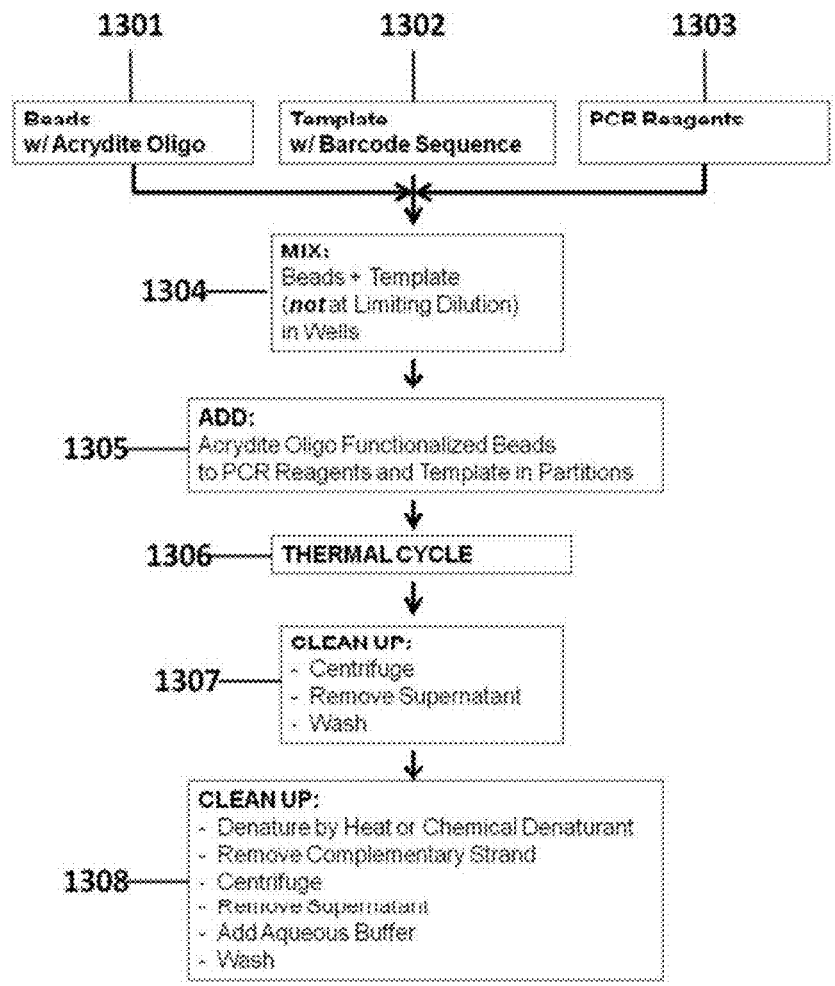
FIG. 13A is a flow diagram illustrating the addition of barcodes to beads using partitions.

As an alternative to limiting dilution (e.g., via droplets of an emulsion), other partitioning methods may be used to attach oligonucleotides to beads. As shown in FIG. 13A, the wells of a plate may be used. Beads comprising a primer (e.g., P5, primer linked to the bead via acrydite and, optionally, a disulfide bond) may be combined with a template oligonucleotide (e.g., a template oligonucleotide comprising a barcode sequence) and amplification reagents in the wells of a plate. Each well can comprise one or more copies of a unique template barcode sequence and one or more beads. Thermal cycling of the plate extends the primer, via hybridization of the template oligonucleotide to the primer, such that the bead comprises an oligonucleotide with a sequence complementary to the oligonucleotide template. Thermal cycling may continue for a desired number of cycles (e.g., at least about 1, 2, 5, 10, 15, 20, 25, 30, 35, 40, 45, 50 or more cycles) up until all primers have been extended.

Upon completion of thermal cycling, the beads may be pooled into a common vessel, washed (e.g., via centrifugation, magnetic separation, etc.), complementary strands denatured, washed again, and then subject to additional rounds of bulk processing if desired. For example, a random N-mer sequence may be added to the bead-bound oligonucleotides using the primer extension method described above for limiting dilution and as shown in FIG. 13B and FIGS. 4I-4M.

Figure 13B:
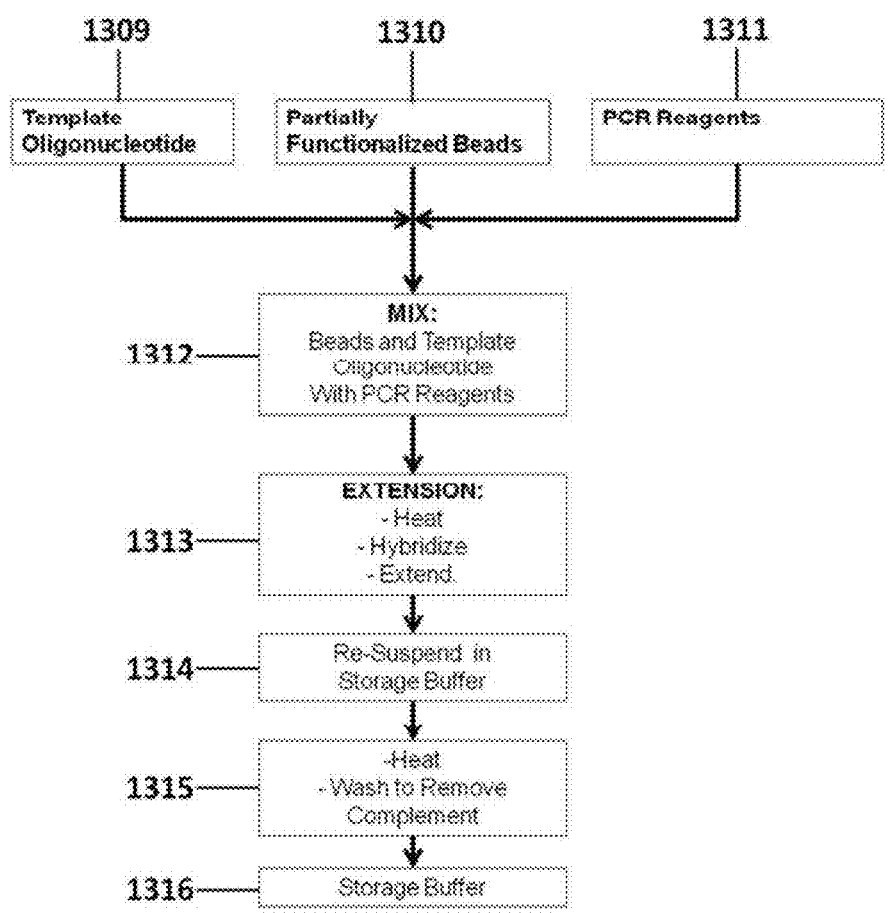
FIG. 13B is a flow diagram illustrating the addition of additional sequences to beads.
Figure 13C:
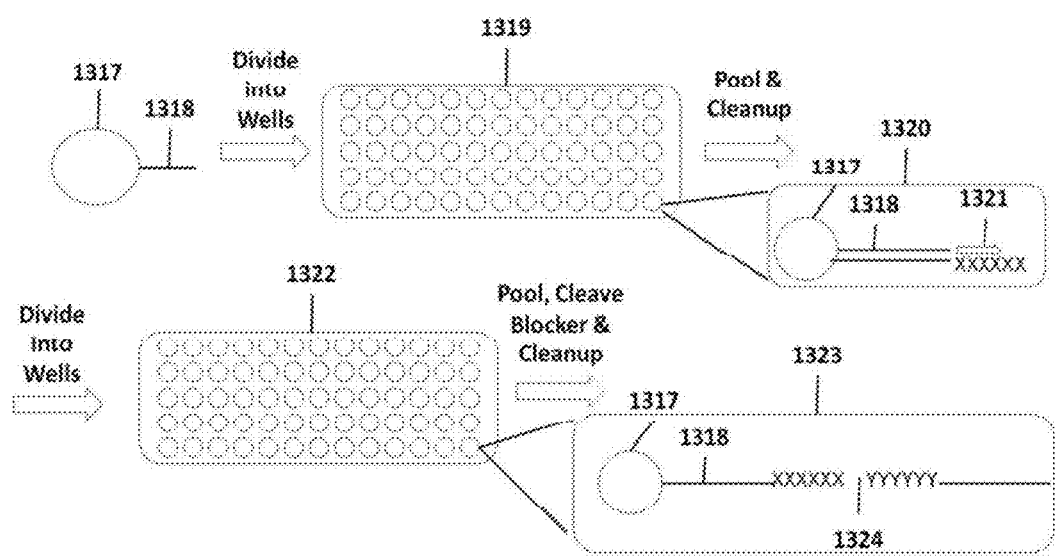
FIG. 13C is a diagram illustrating the use of a combinatorial approach in microwell plates to make barcoded beads.

As another alternative approach to limiting dilution, a combinatorial process involving partitioning in multiwell plates can be used to generate beads with oligonucleotide sequences as shown in FIG. 13C. In such methods, the wells may contain pre-synthesized oligonucleotides such as oligonucleotide templates. The beads (e.g., beads with preincorporated oligonucleotides such as primers) may be divided into the individual wells of the multiwell plate. For example, a mixture of beads containing P5 oligonucleotides may be divided into individual wells of a multiwell plate (e.g., 384 wells), wherein each well contains a unique oligonucleotide template (e.g., an oligonucleotide including a first partial barcode template or barcode template). A primer extension reaction may be performed within the individual wells using, for example, the oligonucleotides templates as the template and the primer attached to the beads as primers. Subsequently, all wells may be pooled together and the unreacted products may be removed.

The mixture of beads attached to the amplified product may be re-divided into wells of a second multiwell plate (e.g., 384-well plate), wherein each well of the second multiwell plate contains another oligonucleotide sequence (e.g., including a second partial barcode sequence and/or a random N-mer). In some cases, the oligonucleotide sequence may be attached (e.g., via hybridization) to a blocker oligonucleotide. Within the wells of the second multiwell plate, a reaction such as a single-stranded ligation reaction may be performed to add additional sequences to each bead (e.g., via ligation of the primer extension products attached to the beads as in the first step with the oligonucleotide in the wells of the second step). In some cases, a partial barcode sequence linked to the bead in the first step is ligated to a second partial barcode sequence in the second step, to generate beads comprising full barcode sequences. In some cases, the beads comprising full barcode sequences also comprise random sequences (e.g., random N-mers) and/or blocking oligonucleotides. In some cases, a PCR reaction or primer extension reaction is performed to attach the additional sequence to the beads. Beads from the wells may be pooled together, and the unreacted products may be removed. In some cases, the process is repeated with additional multi-well plates. The process may be repeated over 1, 2, 3, 4, 5, 6, 7, 8, 9, 10, 15, 20, 50, 100, 500, 1000, 5000, or 10000 times.

In some combinatorial approaches, ligation methods may be used to assemble oligonucleotide sequences comprising barcode sequences on beads (e.g., degradable beads as described elsewhere herein). For example, separate populations of beads may be provided to which barcode containing oligonucleotides are to be attached. These populations may include anchor components (or linkage) for attaching nucleotides, such as activatable chemical groups (phosphoramidites, acrydite moieties, or other thermally, optically or chemically activatable groups), cleavable linkages, previously attached oligonucleotide molecules to which the barcode containing oligonucleotides may be ligated, hybridized, or otherwise attached, DNA binding proteins, charged groups for electrostatic attachment, or any of a variety of other attachment mechanisms.

A first oligonucleotide or oligonucleotide segment that includes a first barcode sequence segment, is attached to the separate populations, where different populations include different barcode sequence segments attached thereto. Each bead in each of the separate populations may be attached to at least 2, 10, 50, 100, 500, 1000, 5000, 10000, 50000, 100000, 500000, 1000000, 5000000, 10000000, 50000000, 100000000, 500000000, 1000000000, or more first oligonucleotide molecules or oligonucleotide segment molecules. The first oligonucleotide or oligonucleotide segment may be releasably attached to the separate populations. In some cases, the first oligonucleotide or oligonucleotide segments may be attached directly to respective beads in the separate populations or may be indirectly attached (e.g., via an anchor component coupled to the beads, as described above) to respective beads in the separate populations.

In some cases, the first oligonucleotide may be attached to the separate populations with the aid of a splint (an example of a splint is shown as 2306 in FIG. 23A). A splint, as used herein, generally refers to a double-stranded nucleic acid, where one strand of the nucleic acid comprises an oligonucleotide to-be-attached to one or more receiving oligonucleotides and where the other strand of the nucleic acid comprises an oligonucleotide with a sequence that is in part complementary to at least a portion of the oligonucleotide to-be-attached and in part complementary to at least a portion of the one or more receiving oligonucleotides. In some cases, an oligonucleotide may be in part complementary to at least a portion of a receiving oligonucleotide via an overhang sequence as shown in FIG. 23A). An overhang sequence can be of any suitable length, as described elsewhere herein.

For example, a splint may be configured such that it comprises the first oligonucleotide or oligonucleotide segment hybridized to an oligonucleotide that comprises a sequence that is in part complementary to at least a portion of the first oligonucleotide or oligonucleotide segment and a sequence (e.g., an overhang sequence) that is in part complementary to at least a portion of an oligonucleotide attached to the separate populations. The splint can hybridize to the oligonucleotide attached to the separate populations via its complementary sequence. Once hybridized, the first oligonucleotide or oligonucleotide segment of the splint can then be attached to the oligonucleotide attached to the separate populations via any suitable attachment mechanism, such as, for example, a ligation reaction.

Following attachment of the first oligonucleotide or oligonucleotide segment to the separate populations, the separate populations are then pooled to create a mixed pooled population, which is then separated into a plurality of separate populations of the mixed, pooled population. A second oligonucleotide or segment including a second barcode sequence segment is then attached to the first oligonucleotides on the beads in each separate mixed, pooled population, such that different mixed pooled bead populations have a different second barcode sequence segment attached to it. Each bead in the separate populations of the mixed, pooled population may be attached to at least 2, 10, 50, 100, 500, 1000, 5000, 10000, 50000, 100000, 500000, 1000000, 5000000, 10000000, 50000000, 100000000, 500000000, 1000000000, or more second oligonucleotide molecules or oligonucleotide segment molecules.

In some cases, the second oligonucleotide may be attached to the first oligonucleotide with the aid of a splint. For example, the splint used to attach the first oligonucleotide or oligonucleotide segment to the separate populations prior to generating the mixed pooled population may also comprise a sequence (e.g., an overhang sequence) that is in part complementary to at least a portion of the second oligonucleotide. The splint can hybridize to the second oligonucleotide via the complementary sequence. Once hybridized, the second oligonucleotide can then be attached to the first oligonucleotide via any suitable attachment mechanism, such as, for example, a ligation reaction. The splint strand complementary to both the first and second oligonucleotides can then be then denatured (or removed) with further processing. Alternatively, a separate splint comprising the second oligonucleotide may be provided to attach the second oligonucleotide to the first oligonucleotide in analogous fashion as described above for attaching the first oligonucleotide to an oligonucleotide attached to the separate populations with the aid of splint. Also, in some cases, the first barcode segment of the first oligonucleotide and second barcode segment of the second oligonucleotide may be joined via a linking sequence as described elsewhere herein.

The separate populations of the mixed, pooled population can then be pooled and the resulting pooled bead population then includes a diverse population of barcode sequences, or barcode library that is represented by the product of the number of different first barcode sequences and the number of different second barcode sequences. For example, where the first and second oligonucleotides include, e.g., all 256 4-mer barcode sequence segments, a complete barcode library may include 65,536 diverse 8 base barcode sequences.

The barcode sequence segments may be independently selected from a set of barcode sequence segments or the first and second barcode sequence segments may each be selected from separate sets of barcode sequence segments. Moreover, the barcode sequence segments may individually and independently comprise from 2 to 20 nucleotides in length, preferably from about 4 to about 20 nucleotides in length, more preferably from about 4 to about 16 nucleotides in length or from about 4 to about 10 nucleotides in length. In some cases, the barcode sequence segments may individually and independently comprise at least 2, 3, 4, 5, 6, 7, 8, 9, 10, 11, 12, 13, 14, 15, 16, 17, 18, 19, 20, or more nucleotides in length. In particular, the barcode sequence segments may comprise 2-mers, 3-mers, 4-mers, 5-mers, 6-mers, 7-mers, 8-mers, 9-mers, 10-mers, 11-mers, 12-mers, 13-mers, 14-mers, 15-mers, 16-mers, 17-mers, 18-mers, 19-mers, 20-mers, or longer sequence segments.

Furthermore, the barcode sequence segments included within the first and second oligonucleotide sequences or sequence segments will typically represent at least 10 different barcode sequence segments, at least 50 different barcode sequence segments, at least 100 different barcode sequence segments, at least 500 different barcode sequence segments, at least 1,000 different barcode sequence segments, at least about 2,000 different barcode sequence segments, at least about 4,000 different barcode sequence segments, at least about 5,000 different barcode sequence segments, at least about 10,000 different barcode sequence segments, at least 50,000 different barcode sequence segments, at least 100,000 barcode sequence segments, at least 500,000 barcode sequence segments, at least 1,000,000 barcode sequence segments, or more. In accordance with the processes described above, these different oligonucleotides may be allocated amongst a similar or the same number of separate bead populations in either the first or second oligonucleotide addition step, e.g., at least 10, 100, 500, 1000, 2000, 4000, 5000, 10000, 50000, 100000, 500000, 1000000, etc., different barcode sequence segments being separately added to at least 10, 100, 500, 1000, 2000, 4000, 5000, 10000, 50000, 100000, 500000, 1000000, etc., separate bead populations.

As a result, resulting barcode libraries may range in diversity of from at least about 100 different barcode sequence segments to at least about 1,000,000, 2,000,000, 5,000,000, 10,000,000 100,000,000 or more different barcode sequence segments as described elsewhere herein, being represented within the library.

As noted previously, either or both of the first and second oligonucleotide sequences or sequence segments, or subsequently added oligonucleotides (e.g., addition of a third oligonucleotide to the second oligonucleotide, addition of a fourth oligonucleotide to an added third oligonucleotide, etc.), may include additional sequences, e.g., complete or partial functional sequences (e.g., a primer sequence (e.g., a universal primer sequence, a targeted primer sequence, a random primer sequence), a primer annealing sequence, an attachment sequence, a sequencing primer sequence, a random N-mer, etc.), for use in subsequent processing. These sequences will, in many cases, be common among beads in the separate populations, subsets of populations, and/or common among all beads in the overall population. In some cases, the functional sequences may be variable as between different bead subpopulations, different beads, or even different molecules attached to a single bead. Moreover, either or both of the first and second oligonucleotide sequences or sequence segments may comprise a sequence segment that includes one or more of a uracil containing nucleotide and a non-native nucleotide, as described elsewhere herein. In addition, although described as oligonucleotides comprising barcode sequences, it will be appreciated that such references includes oligonucleotides that are comprised of two, three or more discrete barcode sequence segments that are separated by one or more bases within the oligonucleotide, e.g., a first barcode segment separated from a second barcode segment by 1, 2, 3, 4, 5, 6, or 10 or more bases in the oligonucleotide in which they are contained. Preferably, barcode sequence segments will be located adjacent to each other or within 6 bases, 4 bases, 3 bases or two bases of each other in the oligonucleotide sequence in which they are contained. Together, whether contiguous within an oligonucleotide sequence, or separated by one or more bases, such collective barcode sequence segments within a given oligonucleotide are referred to herein as a barcode sequence, barcode sequence segment, or barcode domain.

An example combinatorial method for generating beads with sequences comprising barcode sequences as well as specific types of functional sequences is shown in FIGS. 23A-23D. Although described in terms of certain specific sequence segments for purposes of illustration, it will be appreciated that a variety of different configurations may be incorporated into the barcode containing oligonucleotides attached to the beads described herein, including a variety of different functional sequence types, primer types, e.g., specific for different sequencing systems, and the like. As shown in FIG. 23A, beads 2301 may be generated and covalently linked (e.g., via an acrydite moiety or other species) to a first oligonucleotide component to be used as an anchoring component and/or functional sequence or partial functional sequence, e.g., partial P5 sequence 2302. In each well of a plate (e.g., a 384-well plate) an oligonucleotide 2303, comprising the remaining P5 sequence and a unique first partial barcode sequence (indicated by bases "DDDDDD" in oligonucleotide 2303), can be hybridized to an oligonucleotide 2304 that comprises the complement of oligonucleotide 2303 and additional bases that overhang each end of oligonucleotide 2303. Hybridized product (a "splint") 2306 can thus be generated. Each overhang of the splint can be blocked (indicated with an "X" in FIG. 23A) with a blocking moiety to prevent side product formation. Non-limiting examples of blocking moieties include 3' Inverted dT, dideoxycytidine (ddC), and 3'C3 Spacer. Accordingly, in the example described, different splints can be generated, each with a unique first partial barcode sequence or its complement, e.g., 384 different splints, as described.

As shown in FIG. 23B, beads 2301 can be added to each well of the plate and the splint 2306 in each well can hybridize with the corresponding anchor sequence, e.g., partial P5 sequence 2302, of beads 2301, via one of the overhangs of oligonucleotide 2304. Limited stability of the overhang of oligonucleotide 2304 in hybridizing partial P5 sequence 2302 can permit dynamic sampling of splint 2306, which can aid in ensuring that subsequent ligation of oligonucleotide 2303 to partial P5 sequence 2302 is efficient. A ligation enzyme (e.g., a ligase) can ligate partial P5 sequence 2302 to oligonucleotide 2303. An example of a ligase would be T4 DNA ligase. Following ligation, the products can be pooled and the beads washed to remove unligated oligonucleotides.

As shown in FIG. 23C, the washed products can then be redistributed into wells of another plate (e.g., a 384-well plate), with each well of the plate comprising an oligonucleotide 2305 that has a unique second partial barcode sequence (indicated by "DDDDDD" in oligonucleotide 2305) and an adjacent short sequence (e.g., "CC" adjacent to the second partial barcode sequence and at the terminus of oligonucleotide 2305) complementary to the remaining overhang of oligonucleotide 2304. Oligonucleotide 2305 can also comprise additional sequences, such as R1 sequences and a random N-mer (indicated by "NNNNNNNNNN" in oligonucleotide 2305). In some cases, oligonucleotide 2305 may comprise a uracil containing nucleotide. In some cases, any of the thymine containing nucleotides of oligonucleotide 2305 may be substituted with uracil containing nucleotides. In some cases, in order to improve the efficiency of ligation of the oligonucleotide comprising the second partial barcode sequence, e.g., sequence 2305, to the first partial barcode sequence, e.g., sequence 2303, a duplex strand, e.g., that is complementary to all or a portion of oligonucleotide 2305, may be provided hybridized to some portion or all of oligonucleotide 2305, while leaving the overhang bases available for hybridization to splint 2304. As noted previously, splint 2304 and/or the duplex strand, may be provided blocked at one or both of their 3' and 5' ends to prevent formation of side products from or between one or both of the splint and the duplex strand. In preferred aspects, the duplex strand may be complementary to all or a portion of oligonucleotide 2305. For example, where oligonucleotide 2305 includes a random n-mer, the duplex strand may be provided that does not hybridize to that portion of the oligonucleotide.

Via the adjacent short sequence, oligonucleotide 2305 can be hybridized with oligonucleotide 2304, as shown in FIG. 23C. Again, the limited stability of the overhang in hybridizing the short complementary sequence of oligonucleotide 2305 can permit dynamic sampling of oligonucleotide 2305, which can aid in ensuring that subsequent ligation of oligonucleotide 2305 to oligonucleotide 2303 is efficient. A ligation enzyme (e.g., a ligase) can then ligate oligonucleotide 2305 to oligonucleotide 2303. Ligation of oligonucleotide 2305 to oligonucleotide 2303 can result in the generation of a full barcode sequence, via the joining of the first partial barcode sequence of oligonucleotide 2305 and the second partial barcode sequence of oligonucleotide 2303. As shown in FIG. 23D, the products can then be pooled, the oligonucleotide 2304 can be denatured from the products, and unbound oligonucleotides can then be washed away. Following washing, a diverse library of barcoded beads can be obtained, with each bead bound to, for example, an oligonucleotide comprising a P5 sequence, a full barcode sequence, an R1 sequence, and a random N-mer. In this example, 147,456 unique barcode sequences can be obtained (e.g., 384 unique first partial barcode sequence x 384 unique second partial barcode sequences).

Figures 24A, 24B:
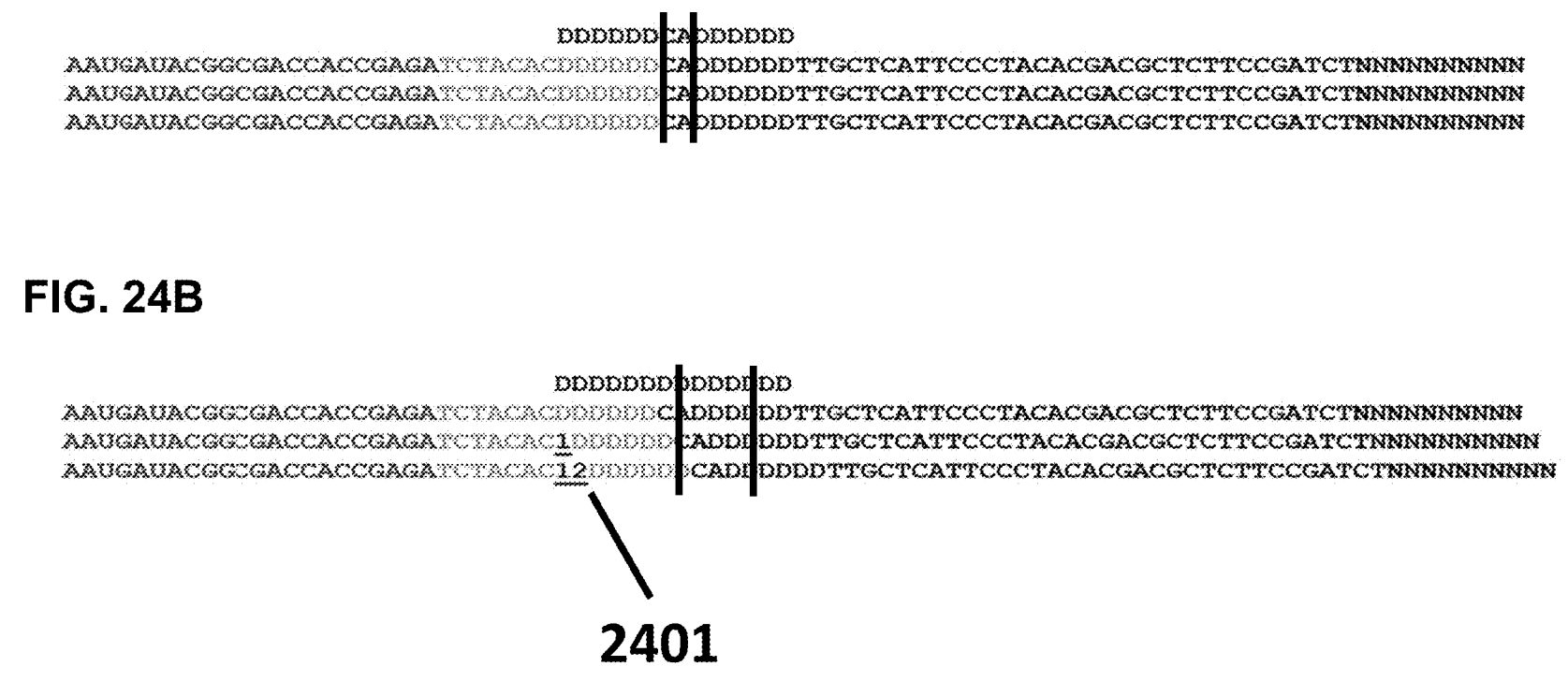

In some cases, the inclusion of overhang bases that aid in ligation of oligonucleotides as described above can result in products that all have the same base at a given position, including in between portions of a barcode sequence as shown in FIG. 24A. Limited or no base diversity at a given sequence position across sequencing reads may result in failed sequencing runs, depending upon the particular sequencing method utilized. Accordingly, in a number of aspects, the overhang bases may be provided with some variability as between different splints, either in terms of base identity or position within the overall sequenced portion of the oligonucleotide. For example, in a first example, one or more spacer bases 2401 (e.g., "1" "2" in FIG. 24B at 2401) can be added to some oligonucleotides used to synthesize larger oligonucleotides on beads, such that oligonucleotide products differ slightly in length from one another, and thus position the overhang bases at different locations in different sequences. Complementary spacer bases may also be added to splints necessary for sequence component ligations. A slight difference in oligonucleotide length between products can result in base diversity at a given read position, as shown in FIG. 24B.

In another example shown in FIGS. 25A-25C, splints comprising a random base overhang may be used to introduce base diversity at read positions complementary to splint overhangs. For example, a double-stranded splint 2501 may comprise a random base (e.g., "NN" in FIG. 25A) overhang 2503 and a determined base (e.g., "CTCT" in FIG. 25A) overhang 2506 on one strand and a first partial barcode sequence (e.g., "DDDDDD" in FIG. 25A) on the other strand. Using an analogous ligation scheme as described above for the Example depicted in FIGS. 23A-23D, the determined overhang 2506 may be used to capture sequence 2502 (which may be attached to a bead as shown in FIGS. 23A-23D) via hybridization for subsequent ligation with the upper strand (as shown in FIG. 25A) of splint 2501. Although overhang 2506 is illustrated as a four base determined sequence overhang, it will be appreciated that this sequence may be longer in order to improve the efficiency of hybridization and ligation in the first ligation step. As such determined base overhang 2506 may include 4, 6, 8, 10 or more bases in length that are complementary to partial P5 sequence 2502. Moreover, the random base overhang 2503 may be used to capture the remaining component (e.g., sequence 2504) of the final desired sequence. Sequence 2504 may comprise a second partial barcode sequence ("DDDDDD" in sequence 2504 of FIG. 25C), the complement 2505 (e.g., "NN" at 2505 in FIG. 25C) of the random base overhang 2503 at one end and a random N-mer 2507 at its other end (e.g., "NNNNNNNNNN" in sequence 2504 of FIG. 25C).

Due to the randomness of the bases in random base overhang 2503, bases incorporated into the ligation product at complement 2505 can vary, such that products comprise a variety of bases at the read positions of complement 2505. As will be appreciated, in preferred aspects, the second partial barcode sequence portion to be ligated to the first partial barcode sequence will typically include a population of such second partial barcode sequences that includes all of the complements to the random overhang sequences, e.g., a given partial barcode sequence will be present with, e.g., 16 different overhang portions, in order to add the same second partial barcode sequence to each bead in a given well where multiple overhang sequences are represented. While only two bases are shown for random overhang 2503 and complement 2505 in FIGS. 25A-25C, the example is not meant to be limiting. Any suitable number of random bases in an overhang may be used. Further, while described as random overhang sequences, in some cases, these overhang sequences may be selected from a subset of overhang sequences. For example, in some cases, the overhangs will be selected from subsets of overhang sequences that include fewer than all possible overhang sequences of the length of the overhang, which may be more than one overhang sequence, and in some cases, more than 2, more than 4, more than 10, more than 20, more than 50, or even more overhang sequences.

In another example, a set of splints, each with a defined overhang selected from a set of overhang sequences of a given length, e.g., a set of at least 2, 4, 10, 20 or more overhang sequences may be used to introduce base diversity at read positions complementary to splint overhangs. Again, because these overhangs are used to ligate a second partial barcode sequence to the first barcode sequence, it will be desirable to have all possible overhang complements represented in the population of second partial barcode sequences. As such, in many cases, it will be preferred to keep the numbers of different overhang sequences lower, e.g., less than 50, less than 20, or in some cases, less than 10 or less than 5 different overhang sequences. In many cases, the number of different linking sequences in a barcode library will be between 2 and 4096 different linking sequences, with preferred libraries having between about 2 and about 50 different linking sequences. Likewise it will typically be desirable to keep these overhang sequences of a relatively short length, in order to avoid introducing non-relevant bases to the ultimate sequence reads. As such, these overhang sequences will typically be designed to introduce no more than 10, no more than 9, no more than 8, no more than 7, no more than 6, no more than 5, no more than 4, and in some cases, 3 or fewer nucleotides to the overall oligonucleotide construct. In some cases, the length of an overhang sequence may be from about 1 to about 10 nucleotides in length, from about 2 to about 8 nucleotides in length, from about 2 to about 6 nucleotides in length, or from about 2 to about 4 nucleotides in length. In general, each splint in the set can comprise an overhang with a different sequence from other splints in the set, such that the base at each position of the overhang is different from the base in the same base position in the other splints in the set. An example set of splints is depicted in FIG. 26. The set comprises splint 2601 (comprising an overhang of "AC" 2602), splint 2603 (comprising an overhang of "CT" 2604), splint 2605 (comprising an overhang of "GA" 2606), and splint 2607 (comprising an overhang of "TG" 2608). Each splint can also comprise an overhang 2609 (e.g., "CTCT" in each splint) and first partial barcode sequence ("DDDDDD"). As shown in FIG. 26, each splint can comprise a different base in each position of its unique overhang (e.g., overhang 2602 in splint 2601, overhang 2604 in splint 2603, overhang 2606 in splint 2605, and overhang 2608 in splint 2607) such that no splint overhang comprises the same base in the same base position. Because each splint comprises a different base in each position of its unique overhang, products generated from each splint can also have a different base in each complementary position when compared to products generated from one of the other splints. Thus, base diversity at these positions can be achieved.

Such products can be generated by hybridizing the first component of the desired sequence (e.g., sequence 2502 in FIGS. 25B-25C comprising a first partial barcode sequence; the first component may also be attached to a bead) with the overhang common to each splint (e.g., overhang 2609 in FIG. 26); ligating the first component of the sequence to the splint; hybridizing the second part of the desired sequence (e.g., a sequence similar to sequence 2504 in FIG. 25C comprising a second partial barcode sequence, except that the sequence comprises bases complementary to the unique overhang sequence at positions 2505 instead of random bases) to the unique overhang of the splint; and ligating the second component of the desired sequence to the splint. The unligated portion of the splint (e.g., bottom sequence comprising the overhangs as shown in FIG. 26) can then be denatured, the products washed, etc. as described previously to obtain final products. As will be appreciated, and as noted previously, these overhang sequences may provide 1, 2, 3, 4, 5 or 6 or more bases between different partial barcode sequences (or barcode sequence segments), such that they provide a linking sequence between barcode sequence segments, with the characteristics described above. Such a linking sequence may be of varied length, such as for example, from about 2 to about 10 nucleotides in length, from about 2 to about 8 nucleotides in length, from about 2 to about 6 nucleotides in length, from about 2 to about 5 nucleotides in length, or from about 2 to about 4 nucleotides in length.

Figure 27:
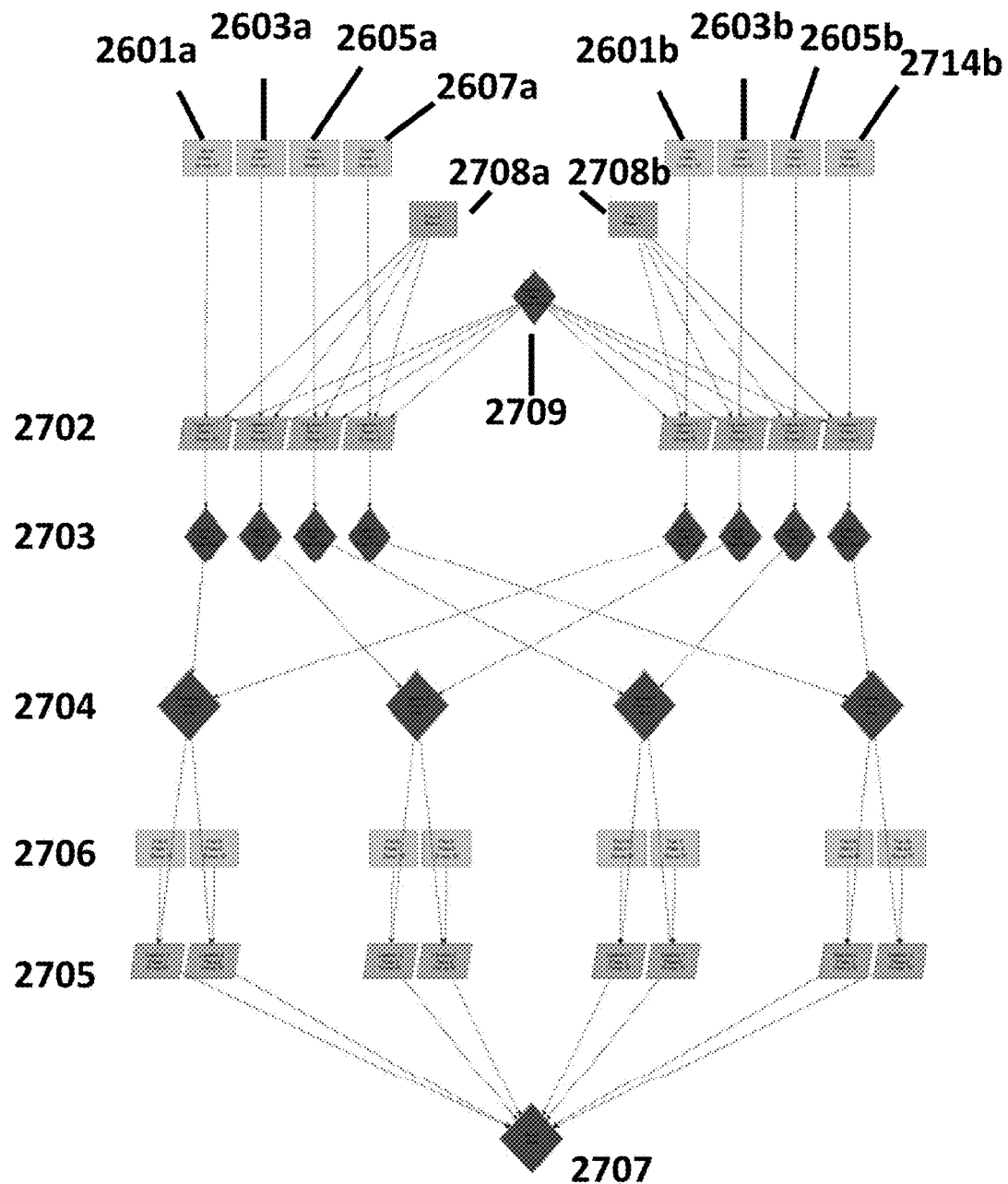
FIG. 27 is a schematic illustrating an example ligation-based combinatorial approach to make barcoded beads.

An example workflow using the set of splints depicted in FIG. 26 is shown in FIG. 27. For each splint in the set, the splint strand comprising the unique overhang sequence (e.g., the bottom strand of splints shown in FIG. 26) can be provided in each well of one or more plates. In FIG. 27, two 96-well plates of splint strands comprising a unique overhang sequence are provided for each of the four splint types, for a total of eight plates. Of the eight plates, two plates (2601a, 2601b) correspond to the bottom strand of splint 2601 comprising a unique overhang sequence ("AC") in FIG. 26, two plates (2603a, 2603b) correspond to the bottom strand of splint 2603 in FIG. 26 comprising a unique overhang sequence ("CT"), two plates (2605a, 2605b) correspond to the bottom strand of splint 2605 in FIG. 26 comprising a unique overhang sequence ("GA"), and two plates (2607a, 2607b) correspond to the bottom strand of splint 2607 in FIG. 26 comprising a unique overhang sequence ("TG"). The oligonucleotides in each 96-well plate (2601a, 2601b, 2603a, 2603b, 2605a, 2605b, 2607a, and 2607b) can be transferred to another set of 96-well plates 2702, with each plate transferred to its own separate plate (again, for a total of eight plates), and each well of each plate transferred to its corresponding well in the next plate.

The splint strand comprising a unique first partial barcode sequence (e.g., the upper strand of splints shown in FIG. 26) and a first partial P5 sequence can be provided in one or more plates. In FIG. 27, such splint strands are provided in two 96-well plates 2708a and 2708b, with each well of the two plates comprising an oligonucleotide with a unique first partial barcode sequence, for a total of 192 unique first partial barcode sequences across the two plates. Each well of plate 2708a can be added to its corresponding well in four of the plates 2702 and each well of plate 2708b can be added to its corresponding well in the other four of the plates 2702. Thus, the two splint strands in each well can hybridize to generate a complete splint. After splint generation, each well of two of the 96-well plates 2702 in FIG. 27 comprises a splint configured as splint 2601, splint 2603, splint 2605, or splint 2607 in FIG. 26 and a unique first partial barcode sequence, for a total of 192 unique first partial barcode sequences.

To each of the wells of the plates 2702, beads 2709 comprising a second partial P5 sequence (e.g., similar or equivalent to sequence 2502 in FIGS. 25B-25C) can then be added. The splints in each well can hybridize with the second partial P5 sequence via the common overhang sequence 2609 of each splint. A ligation enzyme (e.g., a ligase) can then ligate the second partial P5 sequence to the splint strand comprising the remaining first partial P5 sequence and the first partial barcode sequence. First products are, thus, generated comprising beads linked to a sequence comprising a P5 sequence and a first partial barcode sequence, still hybridized with the splint strand comprising the overhang sequences. Following ligation, first products from the wells of each plate can be separately pooled to generate plate pools 2703. The plate pools 2703 corresponding to each two-plate set (e.g., each set corresponding to a particular splint configuration) can also be separately pooled to generate first product pools 2704, such that each first product pool 2704 comprises products generated from splints comprising only one unique overhang sequence. In FIG. 27, four first product pools 2704 are generated, each corresponding to one of the four splint types used in the example. The products in each plate pool 2703 may be washed to remove unbound oligonucleotides, the products in each first product pool 2704 may be washed to remove unbound oligonucleotides, or washing may occur at both pooling steps. In some cases, plate pooling 2703 may be bypassed with the contents of each two-plate set entered directly into a first product pool 2704.

Next, each first product pool 2704 can be aliquoted into each well of two 96-well plates 2705, as depicted in FIG. 27, for a total of eight plates (e.g., two plates per product pool 2704). Separately, oligonucleotides that comprise a unique second partial barcode sequence, a terminal sequence complementary to one of the four unique overhang sequences, and any other sequence to be added (e.g., additional sequencing primer sites, random N-mers, etc.) can be provided in 96-well plates 2706. Such oligonucleotides may, for example, comprise a sequence similar to sequence 2504 in FIG. 25C, except that the sequence comprises bases complementary to a unique overhang sequence at position 2505 instead of random bases. For example, for splint 2601 shown in FIG. 26, the bases in position 2505 would be "TG", complementary to the unique overhang 2602 ("AC") of splint 2601. Of the plates 2706, sets of two plates can each comprise oligonucleotides comprising sequences complementary to one of the four unique overhang sequences, for a total of eight plates and four plate sets as shown in FIG. 27. Plates 2706 can be configured such that each well comprises a unique second partial barcode sequence, for a total of 768 unique second partial barcode sequences across the eight plates.

Each plate of plates 2706 can be paired with a corresponding plate of plates 2705, based on the appropriate unique overhang sequence of first products entered into the plate of plates 2705, as shown in FIG. 27. Oligonucleotides in each well of the plate from plates 2706 can be added to its corresponding well in its corresponding plate from plates 2705, such that each well comprises an aliquot of first products from the appropriate first product pool 2704 and oligonucleotides comprising a unique second barcode sequence and any other sequence (e.g., random N-mers) from plates 2706. In each well of the plates 2705, the unique overhang sequence of each first product can hybridize with an oligonucleotide comprising the second partial barcode sequence, via the oligonucleotide's bases complementary to the unique overhang sequence. A ligation enzyme (e.g., a ligase) can then ligate the oligonucleotides to the first products. Upon ligation, second products comprising complete barcode sequences are generated via joining of the first partial barcode sequence of the first products with the second partial barcode sequence of the second products. The second products obtained from plates 2705 can be removed and deposited into a common second product pool 2707. The splint strands comprising the overhangs (as shown in FIG. 26) can then be denatured in product pool 2707, and the products washed to obtain final products. A total of 147,456 unique barcode sequences can be obtained (e.g., 192 first partial barcode sequences x 768 second partial barcode sequences) with base diversity in base positions complementary to unique overhang sequences used during ligations.

The above example with respect to splint sets is not meant to be limiting, nor is the number and type (s) of plates used for combinatorial synthesis. A set of splints can comprise any suitable number of splints. Moreover, each set of splints may be designed with the appropriate first partial barcode sequence diversity depending upon, for example, the number of unique barcode sequences desired, the number of bases used to generate a barcode sequence, etc.

Using a combinatorial plate method, libraries of barcoded beads with high-diversity can be generated. For example, if two 384-well plates are used, each with oligonucleotides comprising partial barcode sequences pre-deposited in each well, it is possible that 384×384 or 147,456 unique barcode sequences can be generated. The combinatorial examples shown herein are not meant to be limiting as any suitable combination of plates may be used. For example, while in some cases, the barcode sequence segments added in each combinatorial step may be selected from the same sets of barcode sequence segments. However, in many cases, the barcode sequence segments added in each combinatorial step may be selected from partially or completely different sets of oligonucleotide sequences. For example, in some cases, a first oligonucleotide segment may include a barcode sequence from a first set of barcode sequences, e.g., 4-mer sequences, while the second oligonucleotide sequence may include barcode sequences from a partially or completely different set of barcode sequence segments, e.g., 4-mer sequences, 6-mer sequences, 8-mer sequences, etc., or even sequences of mixed lengths, e.g., where the second oligonucleotide segment is selected form a set of oligonucleotides having barcode sequences having varied lengths and sequences, to generate multiparameter variability in the generated barcodes, e.g., sequence and length.

With reference to the example above, for example, the number and type of plates (and barcodes) used for each step in a combinatorial method does not have to be the same. For example, a 384 well plate may be used for a first step and a 96 well plate may be used for a second step for a total of 36,864 unique barcode sequences generated. Furthermore, the number of bases of a full barcode sequence added in each combinatorial step does not need to be the same. For example, in a first combinatorial step, 4 bases of a 12 base barcode sequence may be added, with the remaining 8 bases added in a second combinatorial step. Moreover, the number of combinatorial steps used to generate a full barcode sequence may also vary. In some cases, about 2, 3, 4, 5, 6, 7, 8, 9, or 10 combinatorial steps are used.

The primer extension reactions and ligation reactions can be conducted with standard techniques and reagents in the multiwell plates. For example, the polymer, poly-ethylene glycol (PEG), may be present during the single-stranded ligation reaction at a concentration of about 15%, 20%, 25%, 30%, 35%, 40%, 45%, 50%, 55%, 60%, 65%, 70%, or 75%. In some cases, the PEG may be present during the ligation reaction at a concentration of more than about 6%, 10%, 18%, 20%, 30%, 36%, 40%, 50% or more. In some cases, the PEG may be present during the ligation reaction in the second plate at a concentration of less than about 6%, 10%, 18%, 20%, 30%, 36%, 40%, or 50%.

The methods provided herein may reduce nucleotide bias in ligation reactions. Better results may occur when the first extension in the first well plate may be run to completion. For the single-strand ligation step in the second well plate, no competition may be present when only one type of oligonucleotide sequence is used. The partitioning in wells method for attaching content to beads may avoid misformed adaptors with 8N ends, particularly when the first extension in the first well plate is run to completion.

Potential modifications to the partitioning in wells process may include replacing the single-strand ligation step with PCR by providing the second oligonucleotide sequence with degenerate bases, modifying the first oligonucleotide sequence to be longer than the second oligonucleotide sequence, and/or adding a random N-mer sequence in a separate bulk reaction after the single-strand ligation step, as this may save synthesis costs and may reduce N-mer sequence bias.

In some cases, the following sequence of processes may be used to attach a barcode sequence to a bead. The barcode sequence may be mixed with suitable PCR reagents and a plurality of beads in aqueous fluid. The aqueous fluid may be emulsified within an immiscible fluid, such as an oil, to form an emulsion. The emulsion may generate individual fluidic droplets containing the barcode sequence, the bead, and PCR reagents. Individual fluidic droplets may be exposed to thermocycling conditions, in which the multiple rounds of temperature cycling permits priming and extension of barcode sequences. The emulsion containing the fluidic droplets may be broken by continuous phase exchange, described elsewhere in this disclosure. Resulting barcoded beads suspended in aqueous solution may be sorted by magnetic separation or other sorting methods to obtain a collection of purified barcoded beads in aqueous fluid.

In some cases, the following sequence of processes may be used to attach an N-mer sequence to a bead. The N-mer sequence may be mixed with suitable PCR reagents and a plurality of pooled barcoded beads in aqueous fluid. The aqueous fluid may be heated to permit hybridization and extension of the N-mer sequence. Additional heating may permit removal of the complement strand.

The PCR reagents may include any suitable PCR reagents. In some cases, dUTPs may be substituted for dTTPs during the primer extension or other amplification reactions, such that oligonucleotide products comprise uracil containing nucleotides rather than thymine containing nucleotides. This uracil-containing section of the universal sequence may later be used together with a polymerase that will not accept or process uracil-containing templates to mitigate undesired amplification products.

Amplification reagents may include a universal primer, universal primer binding site, sequencing primer, sequencing primer binding site, universal read primer, universal read binding site, or other primers compatible with a sequencing device, e.g., an Illumina sequencer, Ion Torrent sequencer, etc. The amplification reagents may include P5, non cleavable 5'acrydite-P5, a cleavable 5' acrydite-SS-P5, R1c, Biotin R1c, sequencing primer, read primer, P5_Universal, P5_U, 52-BioR1-rc, a random N-mer sequence, a universal read primer, etc. In some cases, a primer may contain a modified nucleotide, a locked nucleic acid (LNA), an LNA nucleotide, a uracil containing nucleotide, a nucleotide containing a non-native base, a blocker oligonucleotide, a blocked 3' end, 3'ddCTP. FIG. 19 provides additional examples.

As described herein, in some cases oligonucleotides comprising barcodes are partitioned such that each bead is partitioned with, on average, less than one unique oligonucleotide sequence, less than two unique oligonucleotide sequences, less than three unique oligonucleotide sequences, less than four unique oligonucleotide sequences, less than five unique oligonucleotide sequences, or less than ten unique oligonucleotide sequences. Therefore, in some cases, a fraction of the beads does not contain an oligonucleotide template and therefore cannot contain an amplified oligonucleotide. Thus, it may be desirable to separate beads comprising oligonucleotides from beads not comprising oligonucleotides. In some cases, this may be done using a capture moiety.

In some embodiments, a capture moiety may be used with isolation methods such as magnetic separation to separate beads containing barcodes from beads, which may not contain barcodes. As such, in some cases, the amplification reagents may include capture moieties attached to a primer or probe. Capture moieties may allow for sorting of labeled beads from non-labeled beads to confirm attachment of primers and downstream amplification products to a bead. Exemplary capture moieties include biotin, streptavidin, glutathione-S-transferase (GST), cMyc, HA, etc. The capture moieties may be, or include, a fluorescent label or magnetic label. The capture moiety may comprise multiple molecules of a capture moiety, e.g., multiple molecules of biotin, streptavidin, etc. In some cases, an amplification reaction may make use of capture primers attached to a capture moiety (as described elsewhere herein), such that the primer hybridizes with amplification products and the capture moiety is integrated into additional amplified oligonucleotides during additional cycles of the amplification reaction. In other cases, a probe comprising a capture moiety may be hybridized to amplified oligonucleotides following the completion of an amplification reaction such that the capture moiety is associated with the amplified oligonucleotides.

A capture moiety may be a member of binding pair, such that the capture moiety can be bound with its binding pair during separation. For example, beads may be generated that comprise oligonucleotides that comprise a capture moiety that is a member of a binding pair (e.g., biotin). The beads may be mixed with capture beads that comprise the other member of the binding pair (e.g., streptavidin), such that the two binding pair members bind in the resulting mixture. The bead-capture bead complexes may then be separated from other components of the mixture using any suitable means, including, for example centrifugation and magnetic separation (e.g., including cases where the capture bead is a magnetic bead).

In many cases as described, individual beads will generally have oligonucleotides attached thereto, that have a common overall barcode sequence segment. As described herein, where a bead includes oligonucleotides having a common barcode sequence, it is generally meant that of the oligonucleotides coupled to a given bead, a significant percentage, e.g., greater than 70%, greater than 80%, greater than 90%, greater than 95% or even greater than 99% of the oligonucleotides of or greater than a given length, e.g., including the full expected length or lengths of final oligonucleotides and excluding unreacted anchor sequences or partial barcode sequences, include the same or identical barcode sequence segments. This barcode sequence segment or domain (again, which may be comprised of two or more sequence segments separated by one or more bases) may be included among other common or variable sequences or domains within a single bead. Also as described, the overall population of beads will include beads having large numbers of different barcode sequence segments. In many cases, however, a number of separate beads within a given bead population may include the same barcode sequence segment. In particular, a barcode sequence library having 1000, 10,000, 1,000,000, 10,000,000 or more different sequences, may be represented in bead populations of greater than 100,000, 1,000,000, 10,000,000, 100,000,000, 1 billion, 10 billion, 100 billion or more discrete beads, such that the same barcode sequence is represented multiple times within a given bead population or subpopulation. For example, the same barcode sequence may be present on two or more beads within a given analysis, 10 or more beads, 100 or more beads, etc.

A capture device, such as a magnetic bead, with a corresponding linkage, such as streptavidin, may be added to bind the capture moiety, for example, biotin. The attached magnetic bead may then enable isolation of the barcoded beads by, for example, magnetic sorting. Magnetic beads may also be coated with other linking entities besides streptavidin, including nickel-IMAC to enable the separation of His-tagged fusion proteins, coated with titanium dioxide to enable the separation of phosphorylated peptides, or coated with amine-reactive NHS-ester groups to immobilize protein or other ligands for separation.

In some embodiments, the capture moiety may be attached to a primer, to an internal sequence, to a specific sequence within the amplified product, to a barcode sequence, to a universal sequence, or to a complementary sequence. Capture moieties may be attached by PCR amplification or ligation. Capture moieties may include a universal tag such as biotin attached to a specific target such as a primer before added to the bead population. In other cases, capture moieties may include a specific tag that recognizes a specific sequence or protein or antibody that may be added to the bead population independently. In some embodiments, the capture moieties may be pre-linked to a sorting bead, such as a magnetic bead. In some cases, the capture moiety may be a fluorescent label, which may enable sorting via fluorescence-activated cell sorting (FACS).

In some cases, a nucleic acid label (e.g., fluorescent label) may be used to identify fluidic droplets, emulsions, or beads that contain oligonucleotides. Sorting (e.g., via flow cytometry) of the labeled droplets or beads may then be performed in order to isolate beads attached to amplified oligonucleotides. Exemplary stains include intercalating dyes, minor-groove binders, major groove binders, external binders, and bis-intercalators. Specific examples of such dyes include SYBR green, SYBR blue, DAPI, propidium iodide, SYBR gold, ethidium bromide, propidium iodide, imidazoles (e.g., Hoechst 33258, Hoechst 33342, Hoechst 34580, and DAPI), 7-AAD, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, EvaGreen, SYBR Green, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, and -63 (red).

Multi-Functional Beads

Beads may be linked to a variety of species (including non-nucleic acid species) such that they are multi-functional. For example, a bead may be linked to multiple types of oligonucleotides comprising a barcode sequence and an N-mer (e.g., a random N-mer or a targeted N-mer as described below). Each type of oligonucleotide may differ in its barcode sequence, its N-mer, or any other sequence of the oligonucleotide. Moreover, each bead may be linked to oligonucleotides comprising a barcode sequence and an N-mer and may also be linked to a blocker oligonucleotide capable of blocking the oligonucleotides comprising a barcode sequence and an N-mer. Loading of the oligonucleotide blocker and oligonucleotide comprising a barcode sequence and an N-mer may be completed at distinct ratios in order to obtain desired stoichiometries of oligonucleotide blocker to oligonucleotide comprising a barcode sequence and an N-mer. In general, a plurality of species may be loaded to beads at distinct ratios in order to obtain desired stoichiometries of the species on the beads.

Moreover, a bead may also be linked to one or more different types of multi-functional oligonucleotides. For example, a multi-functional oligonucleotide may be capable of functioning as two or more of the following: a primer, a tool for ligation, an oligonucleotide blocker, an oligonucleotide capable of hybridization detection, a reporter oligonucleotide, an oligonucleotide probe, a functional oligonucleotide, an enrichment primer, a targeted primer, a non-specific primer, and a fluorescent probe. Oligonucleotides that function as fluorescent probes may be used, for example, for bead detection or characterization (e.g., quantification of number of beads, quantification of species (e.g., primers, linkers, etc.) attached to beads, determination of bead size/topology, determination of bead porosity, etc.).

Other non-limiting examples of species that may also be attached or coupled to beads include whole cells, chromosomes, polynucleotides, organic molecules, proteins, polypeptides, carbohydrates, saccharides, sugars, lipids, enzymes, restriction enzymes, ligases, polymerases, barcodes, adapters, small molecules, antibodies, antibody fragments, fluorophores, deoxynucleotide triphosphates (dNTPs), dideoxynucleotide triphosphates (ddNTPs), buffers, acidic solutions, basic solutions, temperature-sensitive enzymes, pH-sensitive enzymes, light-sensitive enzymes, metals, metal ions, magnesium chloride, sodium chloride, manganese, aqueous buffer, mild buffer, ionic buffer, inhibitors, saccharides, oils, salts, ions, detergents, ionic detergents, non-ionic detergents, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, a locked nucleic acid (LNA) in whole or part, locked nucleic acid nucleotides, any other type of nucleic acid analogue, proteases, nucleases, protease inhibitors, nuclease inhibitors, chelating agents, reducing agents, oxidizing agents, probes, chromophores, dyes, organics, emulsifiers, surfactants, stabilizers, polymers, water, small molecules, pharmaceuticals, radioactive molecules, preservatives, antibiotics, aptamers, and combinations thereof. Both additional oligonucleotide species and other types of species may be coupled to beads by any suitable method including covalent and non-covalent means (e.g., ionic bonds, van der Waals interactions, hydrophobic interactions, encapsulation, diffusion of the species into the bead, etc.). In some cases, an additional species may be a reactant used for a reaction comprising another type of species on the bead. For example, an additional species coupled to a bead may be a reactant suitable for use in an amplification reaction comprising an oligonucleotide species also attached to the bead.

In some cases, a bead may comprise one or more capture ligands each capable of capturing a particular type of sample component, including components that may comprise nucleic acid. For example, a bead may comprise a capture ligand capable of capturing a cell from a sample. The capture ligand may be, for example, an antibody, antibody fragment, receptor, protein, peptide, small molecule or any other species targeted toward a species unique to and/or overexpressed on the surface of a particular cell. Via interactions with the cell target, the particular cell type can be captured from a sample such that it remains bound to the bead. A bead bound to a cell can be entered into a partition as described elsewhere herein to barcode nucleic acids obtained from the cell. In some cases, capture of a cell from a sample may occur in a partition. Lysis agents, for example, can be included in the partition such in order to release the nucleic acid from the cell. The released nucleic acid can be barcoded and processed using any of the methods described herein.

IV. Barcode Libraries

Beads may contain one or more attached barcode sequences. The barcode sequences attached to a single bead may be identical or different. In some cases, each bead may be attached to about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 identical barcode sequences. In some cases, each bead may be to about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 different barcode sequences. In some cases, each bead may be attached to at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more identical barcode sequences. In some cases, each bead may be attached to at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more different barcode sequences. In some cases, each bead may be attached to less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 1000000000, 5000000000, 10000000000, 50000000000, or 100000000000 identical barcode sequences. In some cases, each bead may be attached to less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 1000000000, 5000000000, 10000000000, 50000000000, or 100000000000 different barcode sequences.

An individual barcode library may comprise one or more barcoded beads. In some cases, an individual barcode library may comprise about 1, 5, 10, 50, 100, 500, 1000, 5000, 10000, 20000, 50000, 100000, 500000, 1000000, 5000000, 10000000, 50000000, 100000000, 500000000, 1000000000, 5000000000, 10000000000, 50000000000, or 100000000000 individual barcoded beads. In some cases, each library may comprise at least about 1, 5, 10, 50, 100, 500, 1000, 5000, 10000, 20000, 50000, 100000, 200000, 300000, 400000, 500000, 600000, 700000, 800000, 900000, 1000000, 2000000, 3000000, 4000000, 5000000, 6000000, 7000000, 8000000, 9000000, 10000000, 20000000, 30000000, 40000000, 50000000, 60000000, 70000000, 80000000, 90000000, 100000000, 200000000, 300000000, 400000000, 500000000, 600000000, 700000000, 800000000, 900000000, 1000000000, 2000000000, 3000000000, 4000000000, 5000000000, 6000000000, 7000000000, 8000000000, 9000000000, 10000000000, 20000000000, 30000000000, 40000000000, 50000000000, 60000000000, 70000000000, 80000000000, 90000000000, 100000000000 or more individual barcoded beads. In some cases, each library may comprise less than about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 500000, 1000000, 5000000, 10000000, 50000000, 100000000, 500000000, 1000000000, 5000000000, 10000000000, 50000000000, or 100000000000 individual barcoded beads. The barcoded beads within the library may have the same sequences or different sequences.

In some embodiments, each bead may have a unique barcode sequence. However, the number of beads with unique barcode sequences within a barcode library may be limited by combinatorial limits. For example, using four different nucleotides, if a barcode is 12 nucleotides in length, than the number of unique constructs may be limited to $4^{12}=16777216$ unique constructs. Since barcode libraries may comprise many more beads than 1677216, there may be some libraries with multiple copies of the same barcode. In some embodiments, the percentage of multiple copies of the same barcode within a given library may be 1%, 2%, 3%, 4%, 5%, 6%, 7%, 8%, 9%, 10%, 15%, 20%, 25%, 30%, 40%, or 50%. In some cases, the percentage of multiple copies of the same barcode within a given library may be more than 1%, 2%, 3%, 4%, 5%, 6%, 7%, 8%, 9%, 10%, 15%, 20%, 25%, 30%, 40%, 50% or more. In some cases, the percentage of multiple copies of the same barcode within a given library may be less than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, or 50%.

In some embodiments, each bead may comprise one unique barcode sequence but multiple different random N-mers. In some cases, each bead may have one or more different random N-mers. Again, the number of beads with different random N-mers within a barcode library may be limited by combinatorial limits. For example, using four different nucleotides, if an N-mer sequence is 12 nucleotides in length, than the number of different constructs may be limited to $4^{12}=16777216$ different constructs. Since barcode libraries may comprise many more beads than 16777216, there may be some libraries with multiple copies of the same N-mer sequence. In some embodiments, the percentage of multiple copies of the same N-mer sequence within a given library may be 1%, 2%, 3%, 4%, 5%, 6%, 7%, 8%, 9%, 10%, 15%, 20%, 25%, 30%, 40%, or 50%. In some cases, the percentage of multiple copies of the same N-mer sequence within a given library may be more than 1%, 2%, 3%, 4%, 5%, 6%, 7%, 8%, 9%, 10%, 15%, 20%, 25%, 30%, 40%, 50% or more. In some cases, the percentage of multiple copies of the same N-mer sequence within a given library may be less than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 40%, or 50%.

In some embodiments, the unique identifier sequence within the barcode may be different for each primer within each bead. In some cases, the unique identifier sequence within the barcode sequence may be the same for each primer within each bead.

V. Combining Barcoded Beads with Sample

Types of Samples

The methods, compositions, devices, and kits of this disclosure may be used with any suitable sample or species. A sample (e.g., sample material, component of a sample material, fragment of a sample material, etc.) or species can be, for example, any substance used in sample processing, such as a reagent or an analyte. Exemplary samples can include one or more of whole cells, chromosomes, polynucleotides, organic molecules, proteins, nucleic acids, polypeptides, carbohydrates, saccharides, sugars, lipids, enzymes, restriction enzymes, ligases, polymerases, barcodes (e.g., including barcode sequences, nucleic acid barcode sequences, barcode molecules), adaptors, small molecules, antibodies, fluorophores, deoxynucleotide triphosphate (dNTPs), dideoxynucleotide triphosphates (ddNTPs), buffers, acidic solutions, basic solutions, temperature-sensitive enzymes, pH-sensitive enzymes, light-sensitive enzymes, metals, metal ions, magnesium chloride, sodium chloride, manganese, aqueous buffer, mild buffer, ionic buffer, inhibitors, oils, salts, ions, detergents, ionic detergents, non-ionic detergents, oligonucleotides, template nucleic acid molecules (e.g., template oligonucleotides, template nucleic acid sequences), nucleic acid fragments, template nucleic acid fragments (e.g., fragments of a template nucleic acid generated from fragmenting a template nucleic acid during fragmentation, fragments of a template nucleic acid generated from a nucleic acid amplification reaction), nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, proteases, locked nucleic acids in whole or part, locked nucleic acid nucleotides, nucleases, protease inhibitors, nuclease inhibitors, chelating agents, reducing agents, oxidizing agents, probes, chromophores, dyes, organics, emulsifiers, surfactants, stabilizers, polymers, water, pharmaceuticals, radioactive molecules, preservatives, antibiotics, aptamers, and the like. In summary, the samples that are used will vary depending on the particular processing needs.

Samples may be derived from human and non-human sources. In some cases, samples are derived from mammals, non-human mammals, rodents, amphibians, reptiles, dogs, cats, cows, horses, goats, sheep, hens, birds, mice, rabbits, insects, slugs, microbes, bacteria, parasites, or fish. Samples may be derived from a variety of cells, including but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, etc. In some cases, a sample may comprise the contents of a cell, such as, for example, the contents of a single cell or the contents of multiple cells. Examples of single cell applications of the methods and systems described herein are set forth in U.S. Provisional Patent Application No. 62/017,558, filed of even date herewith. Samples may also be cell-free, such as circulating nucleic acids (e.g., DNA, RNA).

A sample may be naturally-occurring or synthetic. A sample may be obtained from any suitable location, including from organisms, whole cells, cell preparations and cell-free compositions from any organism, tissue, cell, or environment. A sample may be obtained from environmental biopsies, aspirates, formalin fixed embedded tissues, air, agricultural samples, soil samples, petroleum samples, water samples, or dust samples. In some instances, a sample may be obtained from bodily fluids, which may include blood, urine, feces, serum, lymph, saliva, mucosal secretions, perspiration, central nervous system fluid, vaginal fluid, or semen. Samples may also be obtained from manufactured products, such as cosmetics, foods, personal care products, and the like. Samples may be the products of experimental manipulation including recombinant cloning, polynucleotide amplification, polymerase chain reaction (PCR) amplification, purification methods (such as purification of genomic DNA or RNA), and synthesis reactions.

Methods of Attaching Barcodes to Samples

Barcodes (or other oligonucleotides, e.g. random N-mers) may be attached to a sample by joining the two nucleic acid segments together through the action of an enzyme. This may be accomplished by primer extension, polymerase chain reaction (PCR), another type of reaction using a polymerase, or by ligation using a ligase. When the ligation method is used to attach a sample to a barcode, the samples may or may not be fragmented prior to the ligation step. In some cases, the oligonucleotides (e.g., barcodes, random N-mers) are attached to a sample while the oligonucleotides are still attached to the beads. In some cases, the oligonucleotides (e.g., barcodes, random N-mers) are attached to a sample after the oligonucleotides are released from the beads, e.g., by cleavage of the oligonucleotides comprising the barcodes from the beads and/or through degradation of the beads.

The oligonucleotides may include one or more random N-mer sequences. A collection of unique random N-mer sequences may prime random portions of a DNA segment, thereby amplifying a sample (e.g., a whole genome). The resulting product may be a collection of barcoded fragments representative of the entire sample (e.g., genome).

The samples may or may not be fragmented before ligation to barcoded beads. DNA fragmentation may involve separating or disrupting DNA strands into small pieces or segments. A variety of methods may be employed to fragment DNA including restriction digest or various methods of generating shear forces. Restriction digest may utilize restriction enzymes to make intentional cuts in a DNA sequence by blunt cleavage to both strands or by uneven cleavage to generate sticky ends. Examples of shear-force mediated DNA strand disruption may include sonication, acoustic shearing, needle shearing, pipetting, or nebulization. Sonication, is a type of hydrodynamic shearing, exposing DNA sequences to short periods of shear forces, which may result in about 700 bp fragment sizes. Acoustic shearing applies high-frequency acoustic energy to the DNA sample within a bowl-shaped transducer. Needle shearing generates shear forces by passing DNA through a small diameter needle to physically tear DNA into smaller segments. Nebulization forces may be generated by sending DNA through a small hole of an aerosol unit in which resulting DNA fragments are collected from the fine mist exiting the unit.

In some cases, a ligation reaction is used to ligate oligonucleotides to sample. The ligation may involve joining together two nucleic acid segments, such as a barcode sequence and a sample, by catalyzing the formation of a phosphodiester bond. The ligation reaction may include a DNA ligase, such as an *E. coli* DNA ligase, a T4 DNA ligase, a mammalian ligase such as DNA ligase I, DNA ligase III, DNA ligase IV, thermostable ligases, or the like. The T4 DNA ligase may ligate segments containing DNA, oligonucleotides, RNA, and RNA-DNA hybrids. The ligation reaction may not include a DNA ligase, utilizing an alternative such as a topoisomerase. To ligate a sample to a barcode sequence, utilizing a high DNA ligase concentration and including PEG may achieve rapid ligation. The optimal temperature for DNA ligase, which may be 37° C., and the melting temperature of the DNA to be ligated, which may vary, may be considered to select for a favorable temperature for the ligation reaction. The sample and barcoded beads may be suspended in a buffer to minimize ionic effects that may affect ligation.

Although described in terms of ligation or direct attachment of a barcode sequence to a sample nucleic acid component, above, the attachment of a barcode to a sample nucleic acid, as used herein, also encompasses the attachment of a barcode sequence to a complement of a sample, or a copy or complement of that complement, e.g., when the barcode is associated with a primer sequence that is used to replicate the sample nucleic acid, as is described in greater detail elsewhere herein. In particular, where a barcode containing primer sequence is used in a primer extension reaction using the sample nucleic acid (or a replicate of the sample nucleic acid) as a template, the resulting extension product, whether a complement of the sample nucleic acid or a duplicate of the sample nucleic acid, will be referred to as having the barcode sequence attached to it.

In some cases, sample is combined with the barcoded beads (either manually or with the aid of a microfluidic device) and the combined sample and beads are partitioned, such as in a microfluidic device. The partitions may be aqueous droplets within a water-in-oil emulsion. When samples are combined with barcoded beads, on average less than two target analytes may be present in each fluidic droplet. In some embodiments, on average, less than three target analytes may appear per fluidic droplet. In some cases, on average, more than two target analytes may appear per fluidic droplet. In other cases, on average, more than three target analytes may appear per fluidic droplet. In some cases, one or more strands of the same target analyte may appear in the same fluidic droplet. In some cases, less than 1, 2, 3, 4, 5, 6, 7, 8, 9, 10, 50, 100, 1000, 5000, 10000, or 100000 target analytes are present within a fluidic droplet. In some cases, greater than 1, 2, 3, 4, 5, 6, 7, 8, 9, 10, 50, 100, 1000, 5000, 10000, or 100000 target analytes are present within a fluidic droplet. The partitions described herein are often characterized by having extremely small volumes. For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes.

When samples are combined with barcoded beads, on average less than one bead may be present in each fluidic droplet. In some embodiments, on average, less than two beads may be present in each fluidic droplet. In some embodiments, on average, less than three beads may be present per fluidic droplet. In some cases, on average, more than one bead may be present in each fluidic droplet. In other cases, on average, more than two beads may appear be present in each fluidic droplet. In other cases, on average, more than three beads may be present per fluidic droplet. In some embodiments, a ratio of on average less than one barcoded bead per fluidic droplet may be achieved using limiting dilution technique. Here, barcoded beads may be diluted prior to mixing with the sample, diluted during mixing with the sample, or diluted after mixing with the sample.

The number of different barcodes or different sets of barcodes (e.g., different sets of barcodes, each different set coupled to a different bead) that are partitioned may vary depending upon, for example, the particular barcodes to be partitioned and/or the application. Different sets of barcodes may be, for example, sets of identical barcodes where the identical barcodes differ between each set. Or different sets of barcodes may be, for example, sets of different barcodes, where each set differs in its included barcodes. In some cases, different barcodes are partitioned by attaching different barcodes to different beads (e.g., gel beads). In some cases, different sets of barcodes are partitioned by disposing each different set in a different partition. In some cases, though a partition may comprise one or more different barcode sets. For example, each different set of barcodes may be coupled to a different bead (e.g., a gel bead). Each different bead may be partitioned into a fluidic droplet, such that each different set of barcodes is partitioned into a different fluidic droplet. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes or different sets of barcodes may be partitioned. In some examples, about 1-5, 5-10, 10-50, 50-100, 100-1000, 1000-10000, 10000-100000, 100000-1000000, 10000-1000000, 10000-10000000, or 10000-100000000 different barcodes or different sets of barcodes may be partitioned.

Barcodes may be partitioned at a particular density. For example, barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 barcodes per partition. In some cases, partitioned barcodes may be coupled to one or more beads, such as, for example, a gel bead. In some cases, the partitions are fluidic droplets.

Barcodes may be partitioned such that identical barcodes are partitioned at a particular density. For example, identical barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more identical barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 identical barcodes per partition. In some cases, partitioned identical barcodes may be coupled to a bead, such as, for example, a gel bead. In some cases, the partitions are fluidic droplets.

Barcodes may be partitioned such that different barcodes are partitioned at a particular density. For example, different barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 different barcodes per partition. In some cases, partitioned different barcodes may be coupled to a bead, such as, for example, a gel bead. In some cases, the partitions are fluidic droplets.

The number of partitions employed to partition barcodes or different sets of barcodes may vary, for example, depending on the application and/or the number of different barcodes or different sets of barcodes to be partitioned. For example, the number of partitions employed to partition barcodes or different sets of barcodes may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2,000,000, 3,000,000, 4,000,000, 5,000,000, 10000000, 20000000 or more. The number of partitions employed to partition barcodes or different sets of barcodes may be at least about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1000000, 2000000, 3000000, 4000000, 5000000, 10000000, 20000000 or more. The number of partitions employed to partition barcodes or different sets of barcodes may be less than about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1000000, 2000000, 3000000, 4000000, 5000000, 10000000, or 20000000. The number of partitions employed to partition barcodes may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000. In some cases, the partitions may be fluidic droplets.

As described above, different barcodes or different sets of barcodes (e.g., each set comprising a plurality of identical barcodes or different barcodes) may be partitioned such that each partition generally comprises a different barcode or different barcode set. In some cases, each partition may comprise a different set of identical barcodes, such as an identical set of barcodes coupled to a bead (e.g., a gel bead). Where different sets of identical barcodes are partitioned, the number of identical barcodes per partition may vary. For example, about 100,000 or more different sets of identical barcodes (e.g., a set of identical barcodes attached to a bead) may be partitioned across about 100,000 or more different partitions, such that each partition comprises a different set of identical barcodes (e.g., each partition comprises a bead coupled to a different set of identical barcodes). In each partition, the number of identical barcodes per set of barcodes may be about 1,000,000 or more identical barcodes (e.g., each partition comprises 1,000,000 or more identical barcodes coupled to one or more beads). In some cases, the number of different sets of barcodes may be equal to or substantially equal to the number of partitions or may be less than the number of partitions. Any suitable number of different barcodes or different barcode sets, number of barcodes per partition, and number of partitions may be combined. Thus, as will be appreciated, any of the above-described different numbers of barcodes may be provided with any of the above-described barcode densities per partition, and in any of the above-described numbers of partitions.

Microfluidic Devices and Droplets

In some cases, this disclosure provides devices for making beads and for combining beads (or other types of partitions) with samples, e.g., for co-partitioning sample components and beads. Such a device may be a microfluidic device (e.g., a droplet generator). The device may be formed from any suitable material. In some examples, a device may be formed from a material selected from the group consisting of fused silica, soda lime glass, borosilicate glass, poly(methyl methacrylate) PMMA, PDMS, sapphire, silicon, germanium, cyclic olefin copolymer, polyethylene, polypropylene, polyacrylate, polycarbonate, plastic, thermosets, hydrogels, thermoplastics, paper, elastomers, and combinations thereof.

A device may be formed in a manner that it comprises channels for the flow of fluids. Any suitable channels may be used. In some cases, a device comprises one or more fluidic input channels (e.g., inlet channels) and one or more fluidic outlet channels. In some embodiments, the inner diameter of a fluidic channel may be about 10 µm, 20 µm, 30 µm, 40 µm, 50 µm, 60 µm, 65 µm, 70 µm, 75 µm, 80 µm, 85 µm, 90 µm, 100 µm, 125 µm, or 150 µm. In some cases, the inner diameter of a fluidic channel may be more than 10 µm, 20 µm, 30 µm, 40 µm, 50 µm, 60 µm, 65 µm, 70 µm, 75 µm, 80 µm, 85 µm, 90 µm, 100 µm, 125 µm, 150 µm or more. In some embodiments, the inner diameter of a fluidic channel may be less than about 10 µm, 20 µm, 30 µm, 40 µm, 50 µm, 60 µm, 65 µm, 70 µm, 75 µm, 80 µm, 85 µm, 90 µm, 100 µm, 125 µm, or 150 µm. Volumetric flow rates within a fluidic channel may be any flow rate known in the art.

As described elsewhere herein, the microfluidic device may be utilized to form beads by forming a fluidic droplet comprising one or more gel precursors, one or more cross-linkers, optionally an initiator, and optionally an aqueous surfactant. The fluidic droplet may be surrounded by an immiscible continuous fluid, such as an oil, which may further comprise a surfactant and/or an accelerator.

In some embodiments, the microfluidic device may be used to combine beads (e.g., barcoded beads or other type of first partition, including any suitable type of partition described herein) with sample (e.g., a sample of nucleic acids) by forming a fluidic droplet (or other type of second partition, including any suitable type of partition described herein) comprising both the beads and the sample. The fluidic droplet may have an aqueous core surrounded by an oil phase, such as, for example, aqueous droplets within a water-in-oil emulsion. The fluidic droplet may contain one or more barcoded beads, a sample, amplification reagents, and a reducing agent. In some cases, the fluidic droplet may include one or more of water, nuclease-free water, acetonitrile, beads, gel beads, polymer precursors, polymer monomers, polyacrylamide monomers, acrylamide monomers, degradable crosslinkers, non-degradable crosslinkers, disulfide linkages, acrydite moieties, PCR reagents, primers, polymerases, barcodes, polynucleotides, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, probes, dyes, organics, emulsifiers, surfactants, stabilizers, polymers, aptamers, reducing agents, initiators, biotin labels, fluorophores, buffers, acidic solutions, basic solutions, light-sensitive enzymes, pH-sensitive enzymes, aqueous buffer, oils, salts, detergents, ionic detergents, non-ionic detergents, and the like. In summary, the composition of the fluidic droplet will vary depending on the particular processing needs.

The fluidic droplets may be of uniform size or heterogeneous size. In some cases, the diameter of a fluidic droplet may be about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, or 1 mm. In some cases, a fluidic droplet may have a diameter of at least about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, 1 mm or more. In some cases, a fluidic droplet may have a diameter of less than about 1 µm, 5 µm, 10 µm, 20 µm, 30 µm, 40 µm, 45 µm, 50 µm, 60 µm, 65 µm, 70 µm, 75 µm, 80 µm, 90 µm, 100 µm, 250 µm, 500 µm, or 1 mm. In some cases, fluidic droplet may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In some embodiments, the device may comprise one or more intersections of two or more fluid input channels. For example, the intersection may be a fluidic cross. The fluidic cross may comprise two or more fluidic input channels and one or more fluidic outlet channels. In some cases, the fluidic cross may comprise two fluidic input channels and two fluidic outlet channels. In other cases, the fluidic cross may comprise three fluidic input channels and one fluidic outlet channel. In some cases, the fluidic cross may form a substantially perpendicular angle between two or more of the fluidic channels forming the cross.

In some cases, a microfluidic device may comprise a first and a second input channel that meet at a junction that is fluidly connected to an output channel. In some cases, the output channel may be, for example, fluidly connected to a third input channel at a junction. In some cases, a fourth input channel may be included and may intersect the third input channel and outlet channel at a junction. In some cases, a microfluidic device may comprise first, second, and third input channels, wherein the third input channel intersects the first input channel, the second input channel, or a junction of the first input channel and the second input channel.

As described elsewhere herein, the microfluidic device may be used to generate gel beads from a liquid. For example, in some embodiments, an aqueous fluid comprising one or more gel precursors, one or more crosslinkers and optionally an initiator, optionally an aqueous surfactant, and optionally an alcohol within a fluidic input channel may enter a fluidic cross. Within a second fluidic input channel, an oil with optionally a surfactant and an accelerator may enter the same fluidic cross. Both aqueous and oil components may be mixed at the fluidic cross causing aqueous fluidic droplets to form within the continuous oil phase. Gel precursors within fluidic droplets exiting the fluidic cross may polymerize forming beads.

As described elsewhere herein, the microfluidic device (e.g., a droplet generator) may be used to combine sample with beads (e.g., a library of barcoded beads) as well as an agent capable of degrading the beads (e.g., reducing agent if the beads are linked with disulfide bonds), if desired. In some embodiments, a sample (e.g., a sample of nucleic acids) may be provided to a first fluidic input channel that is fluidly connected to a first fluidic cross (e.g., a first fluidic junction). Pre-formed beads (e.g., barcoded beads, degradable barcoded beads) may be provided to a second fluidic input channel that is also fluidly connected to the first fluidic cross, where the first fluidic input channel and second fluidic input channel meet. The sample and beads may be mixed at the first fluidic cross to form a mixture (e.g., an aqueous mixture). In some cases, a reducing agent may be provided to a third fluidic input channel that is also fluidly connected to the first fluidic cross and meets the first and second fluidic input channel at the first fluidic cross. The reducing agent can then be mixed with the beads and sample in the first fluidic cross. In other cases, the reducing agent may be premixed with the sample and/or the beads before entering the microfluidic device such that it is provided to the microfluidic device through the first fluidic input channel with the sample and/or through the second fluidic input channel with the beads. In other cases, no reducing agent may be added.

In some embodiments, the sample and bead mixture may exit the first fluidic cross through a first outlet channel that is fluidly connected to the first fluidic cross (and, thus, any fluidic channels forming the first fluidic cross). The mixture may be provided to a second fluidic cross (e.g., a second fluidic junction) that is fluidly connected to the first outlet channel. In some cases, an oil (or other suitable immiscible) fluid may enter the second fluidic cross from one or more separate fluidic input channels that are fluidly connected to the second fluidic cross (and, thus, any fluidic channels forming the cross) and that meet the first outlet channel at the second fluidic cross. In some cases, the oil (or other suitable immiscible fluid) may be provided in one or two separate fluidic input channels fluidly connected to the second fluidic cross (and, thus, the first outlet channel) that meet the first outlet channel and each other at the second fluidic cross. Both components, the oil and the sample and bead mixture, may be mixed at the second fluidic cross. This mixing partitions the sample and bead mixture into a plurality of fluidic droplets (e.g., aqueous droplets within a water-in-oil emulsion), in which at least a subset of the droplets that form encapsulate a barcoded bead (e.g., a gel bead). The fluidic droplets that form may be carried within the oil through a second fluidic outlet channel exiting from the second fluidic cross. In some cases, fluidic droplets exiting the second outlet channel from the second fluidic cross may be partitioned into wells for further processing (e.g., thermocycling).

In many cases, it will be desirable to control the occupancy rate of resulting droplets (or second partitions) with respect to beads (or first partitions). Such control is described in, for example, U.S. Provisional patent application No. 61/977,804, filed Apr. 4, 2014, the full disclosure of which is incorporated herein by reference in its entirety for all purposes. In general, the droplets (or second partitions) will be formed such that at least 50%, 60%, 70%, 80%, 90% or more droplets (or second partitions) contain no more than one bead (or first partition). Additionally, or alternatively, the droplets (or second partitions) will be formed such that at least 50%, 60%, 70%, 80%, 90% or more droplets (or second partitions) include exactly one bead (or first partition). In some cases, the resulting droplets (or second partitions) may each comprise, on average, at most about one, two, three, four, five, six, seven, eight, nine, ten, eleven, twelve, thirteen, fourteen, fifteen, sixteen, seventeen, eighteen, nineteen, or twenty beads (or first partitions). In some cases, the resulting droplets (or second partitions) may each comprise, on average, at least about one, two, three, four, five, six, seven, eight, nine, ten, eleven, twelve, thirteen, fourteen, fifteen, sixteen, seventeen, eighteen, nineteen, twenty, or more beads (or first partitions).

In some embodiments, samples may be pre-mixed with beads (e.g., degradable beads) comprising barcodes and any other reagent (e.g., reagents necessary for sample amplification, a reducing agent, etc.) prior to entry of the mixture into a microfluidic device to generate an aqueous reaction mixture. Upon entry of the aqueous mixture to a fluidic device, the mixture may flow from a first fluidic input channel and into a fluidic cross. In some cases, an oil phase may enter the fluidic cross from a second fluidic input channel (e.g., a fluidic channel perpendicular to or substantially perpendicular to the first fluidic input channel) also fluidly connected to the fluidic cross. The aqueous mixture and oil may be mixed at the fluidic cross, such that an emulsion (e.g. a gel-water-oil emulsion) forms. The emulsion can comprise a plurality of fluidic droplets (e.g., droplets comprising the aqueous reaction mixture) in the continuous oil phase. In some cases, each fluidic droplet may comprise a single bead (e.g., a gel bead attached to a set of identical barcodes), an aliquot of sample, and an aliquot of any other reagents (e.g., reducing agents, reagents necessary for amplification of the sample, etc.). In some cases, though, a fluidic droplet may comprise a plurality of beads. Upon droplet formation, the droplet may be carried via the oil continuous phase through a fluidic outlet channel exiting from the fluidic cross. Fluidic droplets exiting the outlet channel may be partitioned into wells for further processing (e.g., thermocycling).

In cases where a reducing agent may be added to the sample prior to entering the microfluidic device or may be added at the first fluidic cross, the fluidic droplets formed at the second fluidic cross may contain the reducing agent. In this case, the reducing agent may degrade or dissolve the beads contained within the fluidic droplet as the droplet travels through the outlet channel leaving the second fluidic cross.

In some embodiments, a microfluidic device may contain three discrete fluidic crosses in parallel. Fluidic droplets may be formed at any one of the three fluidic crosses. Sample and beads may be combined within any one of the three fluidic crosses. A reducing agent may be added at any one of the three fluidic crosses. An oil may be added at any one of the three fluidic crosses.

The methods, compositions, devices, and kits of this disclosure may be used with any suitable oil. In some embodiments, an oil may be used to generate an emulsion. The oil may comprise fluorinated oil, silicon oil, mineral oil, vegetable oil, and combinations thereof.

In some embodiments, the aqueous fluid within the microfluidic device may also contain an alcohol. For example, an alcohol may be glycerol, ethanol, methanol, isopropyl alcohol, pentanol, ethane, propane, butane, pentane, hexane, and combinations thereof. The alcohol may be present within the aqueous fluid at about 5%, 6%, 7%, 8%, 9%, 10%, 11%, 12%, 13%, 14%, 15%, 16%, 17%, 18%, 19%, or 20% (v/v). In some cases, the alcohol may be present within the aqueous fluid at least about 5%, 6%, 7%, 8%, 9%, 10%, 11%, 12%, 13%, 14%, 15%, 16%, 17%, 18%, 19%, 20% or more (v/v). In some cases, the alcohol may be present within the aqueous fluid for less than about 5%, 6%, 7%, 8%, 9%, 10%, 11%, 12%, 13%, 14%, 15%, 16%, 17%, 18%, 19%, or 20% (v/v).

In some embodiments, the oil may also contain a surfactant to stabilize the emulsion. For example, a surfactant may be a fluorosurfactant, Krytox lubricant, Krytox FSH, an engineered fluid, HFE-7500, a silicone compound, a silicon compound containing PEG, such as bis krytox peg (BKP). The surfactant may be present at about 0.1%, 0.5%, 1%, 1.1%, 1.2%, 1.3%, 1.4%, 1.5%, 1.6%, 1.7%, 1.8%, 1.9%, 2%, 5%, or 10% (w/w). In some cases, the surfactant may be present at least about 0.1%, 0.5%, 1%, 1.1%, 1.2%, 1.3%, 1.4%, 1.5%, 1.6%, 1.7%, 1.8%, 1.9%, 2%, 5%, 10% (w/w) or more. In some cases, the surfactant may be present for less than about 0.1%, 0.5%, 1%, 1.1%, 1.2%, 1.3%, 1.4%, 1.5%, 1.6%, 1.7%, 1.8%, 1.9%, 2%, 5%, or 10% (w/w).

In some embodiments, an accelerator and/or initiator may be added to the oil. For example, an accelerator may be Tetramethylethylenediamine (TMEDA or TEMED). In some cases, an initiator may be ammonium persulfate or calcium ions. The accelerator may be present at about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (v/v). In some cases, the accelerator may be present at least about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (v/v) or more. In some cases, the accelerator may be present for less than about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (v/v).

VI. Amplification

DNA amplification is a method for creating multiple copies of small or long segments of DNA. The methods, compositions, devices, and kits of this disclosure may use DNA amplification to attach one or more desired oligonucleotide sequences to individual beads, such as a barcode sequence or random N-mer sequence. DNA amplification may also be used to prime and extend along a sample of interest, such as genomic DNA, utilizing a random N-mer sequence, in order to produce a fragment of the sample sequence and couple the barcode associated with the primer to that fragment.

For example, a nucleic acid sequence may be amplified by co-partitioning a template nucleic acid sequence and a bead comprising a plurality of attached oligonucleotides (e.g., releasably attached oligonucleotides) into a partition (e.g., a droplet of an emulsion, a microcapsule, or any other suitable type of partition, including a suitable type of partition described elsewhere herein). The attached oligonucleotides can comprise a primer sequence (e.g., a variable primer sequence such as, for example, a random N-mer, or a targeted primer sequence such as, for example, a targeted N-mer) that is complementary to one or more regions of the template nucleic acid sequence and, in addition, may also comprise a common sequence (e.g., such as a barcode sequence). The primer sequence can be annealed to the template nucleic acid sequence and extended (e.g., in a primer extension reaction or any other suitable nucleic acid amplification reaction) to produce one or more first copies of at least a portion of the template nucleic acid, such that the one or more first copies comprises the primer sequence and the common sequence. In cases where the oligonucleotides comprising the primer sequence are releasably attached to the bead, the oligonucleotides may be released from the bead prior to annealing the primer sequence to the template nucleic acid sequence. Moreover, in general, the primer sequence may be extended via a polymerase enzyme (e.g., a strand displacing polymerase enzyme as described elsewhere herein, an exonuclease deficient polymerase enzyme as described elsewhere herein, or any other type of suitable polymerase, including a type of polymerase described elsewhere herein) that is also provided in the partition. Furthermore, the oligonucleotides releasably attached to the bead may be exonuclease resistant and, thus, may comprise one or more phosphorothioate linkages as described elsewhere herein. In some cases, the one or more phosphorothioate linkages may comprise a phosphorothioate linkage at a terminal internucleotide linkage in the oligonucleotides.

In some cases, after the generation of the one or more first copies, the primer sequence can be annealed to one or more of the first copies and the primer sequence again extended to produce one or more second copies. The one or more second copies can comprise the primer sequence, the common sequence, and may also comprise a sequence complementary to at least a portion of an individual copy of the one or more first copies, and/or a sequence complementary to the variable primer sequence. The aforementioned steps may be repeated for a desired number of cycles to produce amplified nucleic acids.

The oligonucleotides described above may comprise a sequence segment that is not copied during an extension reaction (such as an extension reaction that produces the one or more first or second copies described above). As described elsewhere herein, such a sequence segment may comprise one or more uracil containing nucleotides and may also result in the generation of amplicons that form a hairpin (or partial hairpin) molecule under annealing conditions.

In another example, a plurality of different nucleic acids can be amplified by partitioning the different nucleic acids into separate first partitions (e.g., droplets in an emulsion) that each comprise a second partition (e.g., beads, including a type of bead described elsewhere herein). The second partition may be releasably associated with a plurality of oligonucleotides. The second partition may comprise any suitable number of oligonucleotides (e.g., more than 1,000 oligonucleotides, more than 10,000 oligonucleotides, more than 100,000 oligonucleotides, more than 1,000,000 oligonucleotides, more than 10,000,000 oligonucleotides, or any other number of oligonucleotides per partition described herein). Moreover, the second partitions may comprise any suitable number of different barcode sequences (e.g., at least 1,000 different barcode sequences, at least 10,000 different barcode sequences, at least 100,000 different barcode sequences, at least 1,000,000 different barcode sequences, at least 10,000,000 different barcode sequence, or any other number of different barcode sequences described elsewhere herein).

Furthermore, the plurality of oligonucleotides associated with a given second partition may comprise a primer sequence (e.g., a variable primer sequence, a targeted primer sequence) and a common sequence (e.g., a barcode sequence). Moreover, the plurality of oligonucleotides associated with different second partitions may comprise different barcode sequences. Oligonucleotides associated with the plurality of second partitions may be released into the first partitions. Following release, the primer sequences within the first partitions can be annealed to the nucleic acids within the first partitions and the primer sequences can then be extended to produce one or more copies of at least a portion of the nucleic acids with the first partitions. In general, the one or more copies may comprise the barcode sequences released into the first partitions.

Amplification within Droplets and Sample Indexing

Nucleic acid (e.g., DNA) amplification may be performed on contents within fluidic droplets. As described herein, fluidic droplets may contain oligonucleotides attached to beads. Fluidic droplets may further comprise a sample. Fluidic droplets may also comprise reagents suitable for amplification reactions which may include Kapa HiFi Uracil Plus, modified nucleotides, native nucleotides, uracil containing nucleotides, dTTPs, dUTPs, dCTPs, dGTPs, dATPs, DNA polymerase, Taq polymerase, mutant proof reading polymerase, 9 degrees North, modified (NEB), exo (–), exo (–) Pfu, Deep Vent exo (–), Vent exo (–), and acyclonucleotides (acyNTPS).

Oligonucleotides attached to beads within a fluidic droplet may be used to amplify a sample nucleic acid such that the oligonucleotides become attached to the sample nucleic acid. The sample nucleic acids may comprise virtually any nucleic acid sought to be analyzed, including, for example, whole genomes, exomes, amplicons, targeted genome segments e.g., genes or gene families, cellular nucleic acids, circulating nucleic acids, and the like, and, as noted above, may include DNA (including gDNA, cDNA, mtDNA, etc.) RNA (e.g., mRNA, rRNA, total RNA, etc.). Preparation of such nucleic acids for barcoding may generally be accomplished by methods that are readily available, e.g., enrichment or pull-down methods, isolation methods, amplification methods etc. In order to amplify a desired sample, such as gDNA, the random N-mer sequence of an oligonucleotide within the fluidic droplet may be used to prime the desired target sequence and be extended as a complement of the target sequence. In some cases, the oligonucleotide may be released from the bead in the droplet, as described elsewhere herein, prior to priming. For these priming and extension processes, any suitable method of DNA amplification may be utilized, including polymerase chain reaction (PCR), digital PCR, reverse-transcription PCR, multiplex PCR, nested PCR, overlap-extension PCR, quantitative PCR, multiple displacement amplification (MDA), or ligase chain reaction (LCR). In some cases, amplification within fluidic droplets may be performed until a certain amount of sample nucleic acid comprising barcode may be produced. In some cases, amplification may be performed for about 1, 2, 3, 4, 5, 6, 7, 8, 9, 10, 11, 12, 13, 14, 15, 16, 17, 18, 19, or 20 cycles. In some cases, amplification may be performed for more than about 1, 2, 3, 4, 5, 6, 7, 8, 9, 10, 11, 12, 13, 14, 15, 16, 17, 18, 19, 20 cycles, or more. In some cases, amplification may be performed for less than about 2, 3, 4, 5, 6, 7, 8, 9, 10, 11, 12, 13, 14, 15, 16, 17, 18, 19, or 20 cycles.

Figure 38A:
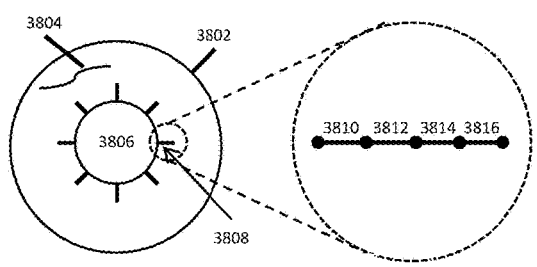
FIGS. 38A-38F provide a schematic illustration of an exemplary nucleic acid barcoding and amplification process.

An exemplary amplification and barcoding process as described herein, is schematically illustrated in FIGS. 38A-38F. As shown, oligonucleotides that include a barcode sequence are co-partitioned in, e.g., a droplet 3802 in an emulsion, along with a sample nucleic acid 3804. As noted elsewhere herein, the oligonucleotides 3808 may be provided on a bead 3806 that is co-partitioned with the sample nucleic acid 3804, which oligonucleotides are preferably releasable from the bead 3806, as shown in FIG. 38A. The oligonucleotides 3808 include a barcode sequence 3812, in addition to one or more functional sequences, e.g., sequences 3810, 3814 and 3816. For example, oligonucleotide 3808 is shown as comprising barcode sequence 3812, as well as sequence 3810 that may function as an attachment or immobilization sequence for a given sequencing system, e.g., a P5 sequence used for attachment in flow cells of an Illumina Hiseq or Miseq system. As shown, the oligonucleotides also include a primer sequence 3816, which may include a random or targeted N-mer for priming replication of portions of the sample nucleic acid 3804. Also included within oligonucleotide 3808 is a sequence 3814 which may provide a sequencing priming region, such as a "read1" or R1 priming region, that is used to prime polymerase mediated, template directed sequencing by synthesis reactions in sequencing systems. In many cases, the barcode sequence 3812, immobilization sequence 3810 and R1 sequence 3814 will be common to all of the oligonucleotides attached to a given bead. The primer sequence 3816 may vary for random N-mer primers, or may be common to the oligonucleotides on a given bead for certain targeted applications.

Figure 38B:
Figure 38C:
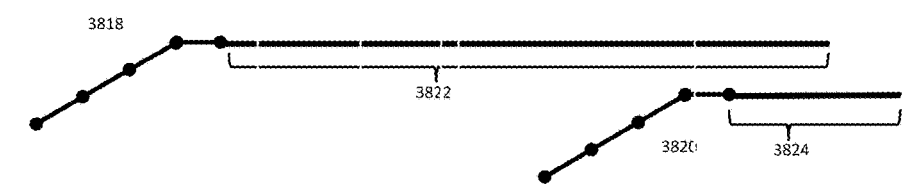

Based upon the presence of primer sequence 3816, the oligonucleotides are able to prime the sample nucleic acid as shown in FIG. 38B, which allows for extension of the oligonucleotides 3808 and 3808a using polymerase enzymes and other extension reagents also co-partitioned with the bead 3806 and sample nucleic acid 3804. As described elsewhere herein, these polymerase enzymes may include thermostable polymerases, e.g., where initial denaturation of double stranded sample nucleic acids within the partitions is desired. Alternatively, denaturation of sample nucleic acids may precede partitioning, such that single stranded target nucleic acids are deposited into the partitions, allowing the use of non-thermostable polymerase enzymes, e.g., Klenow, phi29, Pol 1, and the like, where desirable. As shown in FIG. 38C, following extension of the oligonucleotides that, for random N-mer primers, would anneal to multiple different regions of the sample nucleic acid 3804; multiple overlapping complements or fragments of the nucleic acid are created, e.g., fragments 3818 and 3820. Although including sequence portions that are complementary to portions of sample nucleic acid, e.g., sequences 3822 and 3824, these constructs are generally referred to herein as comprising fragments of the sample nucleic acid 3804, having the attached barcode sequences. In some cases, it may be desirable to artificially limit the size of the replicate fragments that are produced in order to maintain manageable fragment sizes from the first amplification steps. In some cases, this may be accomplished by mechanical means, as described above, e.g., using fragmentation systems like a Covaris system, or it may be accomplished by incorporating random extension terminators, e.g., at low concentrations, to prevent the formation of excessively long fragments.

Figure 38D:
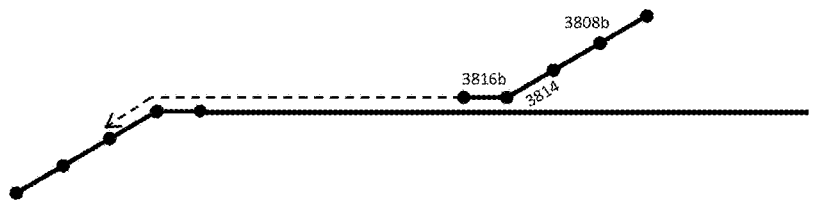
Figure 38E:
Figure 38F:
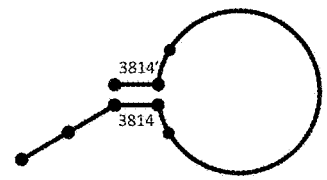

These fragments may then be subjected to sequence analysis, or they may be further amplified in the process, as shown in FIG. 38D. For example, additional oligonucleotides, e.g., oligonucleotide 3808b, also released from bead

3806, may prime the fragments 3818 and 3820. This shown in for fragment 3818. In particular, again, based upon the presence of the random N-mer primer 3816b in oligonucleotide 3808b (which in many cases will be different from other random N-mers in a given partition, e.g., primer sequence 3816), the oligonucleotide anneals with the fragment 3818, and is extended to create a complement 3826 to at least a portion of fragment 3818 which includes sequence 3828, that comprises a duplicate of a portion of the sample nucleic acid sequence. Extension of the oligonucleotide 3808b continues until it has replicated through the oligonucleotide portion 3808 of fragment 3818. As noted elsewhere herein, and as illustrated in panel D, the oligonucleotides may be configured to prompt a stop in the replication by the polymerase at a desired point, e.g., after replicating through sequences 3816 and 3814 of oligonucleotide 3808 that is included within fragment 3818. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 3812 to cause a non-uracil tolerant polymerase to cease replication of that region. As a result, a fragment 3826 is created that includes the full-length oligonucleotide 3808b at one end, including the barcode sequence 3812, the attachment sequence 3810, the R1 primer region 3814, and the random n-mer sequence 3816b. At the other end of the sequence will be included the complement 3816' to the random n-mer of the first oligonucleotide 3808, as well as a complement to all or a portion of the R1 sequence, shown as sequence 3814'. The R1 sequence 3814 and its complement 3814' are then able to hybridize together to form a partial hairpin structure 3828. As will be appreciated because the random-n-mers differ among different oligonucleotides, these sequences and their complements would not be expected to participate in hairpin formation, e.g., sequence 3816', which is the complement to random N-mer 3816, would not be expected to be complementary to random n-mer sequence 3816b. This would not be the case for other applications, e.g., targeted primers, where the N-mers may be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 3826.

Following attachment of the barcode to the sample, additional amplification steps (e.g. PCR) may be performed to amplify the barcoded fragments prior to sequencing, as well as to optionally add additional functional sequences to those barcoded fragments, e.g., additional primer binding sites (e.g. Read2 sequence primer, Index primer) that is compatible with a sequencing device (e.g. Illumina MiSeq) and optionally, one or more additional barcode sequences (e.g., see FIG. 14C), as well as other functional sequences, e.g., additional immobilization sequences or their complements, e.g., P7 sequences. In some cases, an additional barcode sequence may serve as a sample index, with the original barcode and sample index permitting multiplexed sequencing (e.g., simultaneous molecular tagging and sample identification). The original barcode can be used during sequencing to align a sequence read corresponding to the nucleic acid molecule associated with the barcode (e.g., identified via the barcode). A different sample index can be included in sequencer-ready products generated from each different sample. Thus, the sample index can be used during sequencing for identifying the sample to which a particular sequence read belongs and multiplexing can be achieved.

In some cases, a sample index can be added to a sample nucleic acid after the addition of the original barcode to the sample nucleic acid, with or without the use of partitions or the generation of additional partitions. In some cases, the sample index is added in bulk. In some cases, the addition of a sample index to a sample nucleic acid may occur prior to the addition of a barcode to the sample nucleic acid. In some cases, the addition of a sample index to a sample nucleic acid may occur simultaneous to or in parallel to the addition of a sample index to the sample nucleic acid.

In some cases, a sample index may be added to a sample nucleic acid after addition of a barcode sequence to the sample nucleic acid. For example, as described elsewhere herein, amplification methods may be used to attach a barcode sequence and other sequences (e.g., P5, R1, etc.) to a sample nucleic acid. In some cases, a random amplification scheme, such as Partial Hairpin Amplification for Sequencing (PHASE—as described elsewhere herein), for example, may aid in attaching a barcode sequence and other sequences to a sample nucleic acid. In one example, a plurality of primers, each comprising a different random N-mer, a sequencer attachment or immobilization site (e.g., P5), a barcode sequence (e.g., an identical barcode sequence), and a sequencing primer binding site (e.g., R1) are used to randomly prime and amplify a sample nucleic acid. Any of the sequencer primer binding site, the barcode sequence, and/or sequencing primer binding site may comprise uracil containing nucleotides. The primer may also include an oligonucleotide blocker hybridized to the primer at one or more sequences of the primer to ensure that priming of the sample nucleic acid occurs only via the random N-mer. A schematic representation of an example primer is as follows (oligonucleotide blocker not shown):
P5-Barcode-R1-RandomNMer Random priming of the sample nucleic acid and multiple rounds of amplification can generate amplicons comprising a portion of the sample nucleic acid linked at one end to the sequencer attachment or immobilization site (e.g., P5), the barcode, the sequencing primer binding site (e.g., R1), and the random N-mer. At its other end, the portion of the sample nucleic acid can be linked to a region (e.g., R1c, or R1c partial) that is complementary or partially complementary to the sequencing primer binding site. A schematic representation of an example sequence (in a linear configuration) is as follows:
P5-Barcode-R1-RandomNmer-Insert-R1c,partial
where "Insert" corresponds to the portion of the sample nucleic acid copied during amplification. The sequencing primer binding site (e.g., R1) and its partial complement (e.g., R1c, partial) at the opposite end of the portion of the copied sample nucleic acid (Insert) can intramolecularly hybridize to form a partial hairpin structure as described elsewhere herein.

Following creation of the barcoded fragments of the sample nucleic acid, and as noted above, it may be desirable to further amplify those fragments, as well as attach additional functional sequences to the amplified, barcoded fragments. This amplification may be carried out using any suitable amplification process, including, e.g., PCR, LCR, linear amplification, or the like. Typically, this amplification may be initiated using targeted primers that prime against the known terminal sequences in the created fragments, e.g., priming against one or both of the attachment sequence

3810, in FIGS. 38A-38F, and sequence 3814'. Further by incorporating additional functional sequences within these primers, e.g., additional attachment sequences such as P7, additional sequencing primers, e.g., a read 2 or R2 priming sequence, as well as optional sample indexing sequences, one can further configure the amplified barcoded fragments.

By way of example, following generation of partial hairpin amplicons, intramolecular hybridization of the partial hairpin amplicons can be disrupted by contacting the partial hairpin amplicons with a primer that is complementary to the duplex portion of the hairpin, e.g., sequence 3814', in order to disrupt the hairpin and prime extension along the hairpin structure. In many cases, it will be desirable to provide these primers with a stronger hybridization affinity than the hairpin structure in order to preferentially disrupt that hairpin. As such, in at least one example, the primer comprises a locked nucleic acid (LNAs) or locked nucleic acid nucleotides. LNAs include nucleotides where the ribonucleic acid base comprises a molecular bridge connecting the 2'-oxygen and 4'-carbon of the nucleotide's ribose moiety. LNAs generally have higher melting temperatures and lower hybridization energies. Accordingly, LNAs can favorably compete with intramolecular hybridization of the partial hairpin amplicons by binding to any of the hybridized sequences of a partial hairpin amplicon. Subsequent amplification of the disrupted amplicons via primers comprising LNAs and other primers can generate linear products comprising any additional sequences (including a sample index) to be added to the sequence.

Figure 14A:
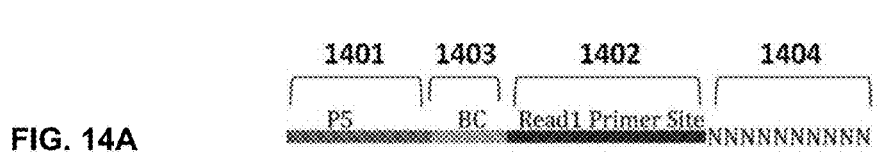
FIGS. 14A-14C are diagrams of oligonucleotides containing universal sequences (R1, P5) and uracil containing nucleotides.
Figure 14B:
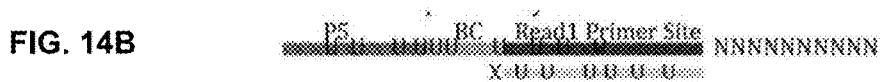
Figure 14C:
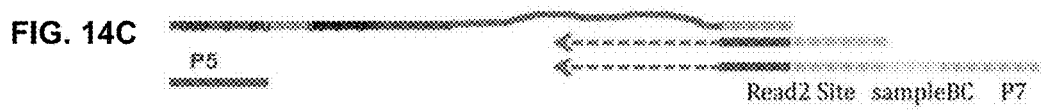

For the example partial hairpin P5-Barcode-R1-RandomNmer-Insert-R1c,partial configuration described above, the partial hairpin can be contacted with a primer comprising LNAs and a sequence complementary to R1c,partial (e.g., see FIG. 14C). The primer may also comprise the complement of any additional sequence to be added to the construct. For example, the additional sequence (e.g., R2partial) may be a sequence that, when coupled to R1c,partial, generates an additional sequencing primer binding site (e.g., R2). Hybridization of the primer with the partial hairpin can disrupt the partial hairpin's intramolecular hybridization and linearize the construct. Hybridization may occur, for example, such that the primer hybridizes with R1c,partial via its complementary sequence (e.g., see FIG. 14C). Extension of the primer can generate a construct comprising the primer linked to a sequence complementary to the linearized partial hairpin amplicon. A schematic of an example construct is as follows:
P5c-Barcode,c-R1c-RandomNmer,c-Insert,c-R1,partial-R2partial,c
where P5c corresponds to the complement of P5, Barcode,c corresponds to the complement of the barcode, RandomNmer,c corresponds to the complement of the random N-mer, Insert,c corresponds to the complement of the portion of the Insert, and R1,partial-R2partial,c corresponds to the complement of R2.

Upon a further round of amplification with a second primer (e.g., P5, hybridizing at P5c), a linear construct comprising the partial hairpin amplicon sequence and a sequence complementary to the primer can be generated. A schematic representation of an example configuration is as follows:
P5-Barcode-R1-RandomNmer-Insert-R1c,partial-R2partial
or
P5-Barcode-R1-RandomNmer-Insert-R2
where the combined sequence of R1c,partial and R2partial can correspond to an additional sequencing primer binding site (e.g., R2).

Additional sequences can be added to the construct using additional rounds of such amplification, for however many additional sequences/rounds of amplification are desired. For the example P5-Barcode-R1-RandomNmer-Insert-R2 construct described above, a primer comprising a sequence complementary to R2 (e.g., R2c), the complement of a sample index sequence (e.g., SIc, SampleBarcode), and the complement of an additional sequencer primer binding site sequence (e.g., P7c) can be hybridized to the construct at R2, via R2c of the primer (e.g., see FIG. 14C). Extension of the primer can generate a construct comprising the primer linked to a sequence complementary to the construct. A schematic representation of an example configuration is as follows:
P5c-Barcode,c-R1c-RandomNmer,c-Insert,c-R2,c-SIc-P7c
Upon a further round of amplification with a second primer (e.g., P5, hybridizing at P5c), a sequencer-ready construct comprising the construct sequence and a sequence complementary to the primer can be generated. A schematic representation of an example configuration of such a sequencer-ready construct is as follows:
P5-Barcode-R1-RandomNmer-Insert-R2-SampleIndex-P7 As an alternative, the starting primer may comprise a barcode sequence, P7, and R2 (instead of P5 and R1). A schematic representation of an example primer is as follows:
P7-Barcode-R2-RandomNmer
Using an analogous amplification scheme as described above (e.g., amplification with primers comprising LNAs, additional rounds of amplification, etc.), an insert comprising a portion of a sample nucleic acid to be sequenced, P5, R1, and a sample index can be added to the primer to generate a sequencer-ready product. A schematic representation of an example product is as follows:
P7-Barcode-R2-RandomNmer-Insert-R1-SampleIndex-P5
In other cases, a sample index may be added to a sample nucleic acid concurrently with the addition of a barcode sequence to the sample nucleic acid. For example, a primer used to generate a barcoded sample nucleic acid may comprise both a barcode sequence and a sample index, such that when the barcode is coupled to the sample nucleic acid, the sample index is coupled simultaneously. The sample index may be positioned anywhere in the primer sequence. In some cases, the primer may be a primer capable of generating barcoded sample nucleic acids via random amplification, such as PHASE amplification. Schematic representations of examples of such primers include:
P5-Barcode-R1-SampleIndex-RandomNmer
P5-Barcode-SampleIndex-R1-RandomNmer
P5-SampleIndex-Barcode-R1-RandomNmer
Upon random priming of a sample nucleic acid with a respective primer and amplification of the sample nucleic acid in the partition, partial hairpin amplicons comprising a barcode sequence and a sample index sequence can be generated. Schematic representations (shown in linear form) of examples of such partial hairpin amplicons generated from the above primers include, respectively:
P5-Barcode-R1-SampleIndex-RandomNmer-Insert-R1c, partial
P5-Barcode-SampleIndex-R1-RandomNmer-Insert-R1c, partial
P5-SampleIndex-Barcode-R1-RandomNmer-Insert-R1c, partial
R1c, partial can intramolecularly hybridize with its complementary sequence in R1 to form a partial hairpin amplicon.

By way of example, in some cases, following the generation of partial hairpin amplicons, additional sequences (e.g., functional sequences like R2 and P7 sequences) can be added to the partial hairpin amplicons, such as, for example, in bulk. In analogous fashion to amplification methods described elsewhere herein, primers that include these additional functional sequences may be used to prime the replication of the partial hairpin molecule, e.g., by priming against the 5' end of the partial hairpin, e.g., the R1c sequence, described above. In many cases, it will be desirable to provide a higher affinity primer sequence, e.g., to outcompete rehybridization of the hairpin structure, in order to provide greater priming and replication. In such cases, tighter binding primer sequences, e.g., that include in their sequence one or more higher affinity nucleotide analogues, like LNAs or the like, may be used to disrupt partial hairpin amplicons and add additional sequences to the amplicons. For example, with reference to the example described above, a primer may comprise LNAs, a sequence complementary to R1c,partial and a sequence comprising the complement to R2partial, such that when the primer is extended and the resulting product further amplified via a P5 primer, R1c, partial and R2partial are joined to generate R2. Schematic representations of examples of such constructs generated from the above primers include, respectively:
P5-Barcode-R1-SampleIndex-RandomNmer-Insert-R2
P5-Barcode-SampleIndex-R1-RandomNmer-Insert-R2
P5-SampleIndex-Barcode-R1-RandomNmer-Insert-R2

As noted above, additional rounds of amplification cycles may be used to add additional sequences to the constructs. For example, a primer may comprise a sequence complementary to R2 and a sequence comprising the complement to P7, such that when the primer is extended and the resulting product further amplified via a P5 primer, P7 is linked to R2 and a sequencer-ready construct is generated. Schematic representations of examples of such sequencer-ready constructs generated from the above primers include, respectively:
P5-Barcode-R1-SampleIndex-RandomNmer-Insert-R2-P7
P5-Barcode-SampleIndex-R1-RandomNmer-Insert-R2-P7
P5-SampleIndex-Barcode-R1-RandomNmer-Insert-R2-P7

Combining a barcode and a sample index into a primer capable of amplifying regions of a sample nucleic acid (e.g., via PHASE amplification) may enable parallelization of sample indexing. Sets of primers may be used to index nucleic acids from different samples. Each set of primers may be associated with nucleic acid molecules obtained from a particular sample and comprise primers comprising a diversity of barcode sequences and a common sample index sequence.

In some cases, it may be desirable to attach additional sequence segments to the 5' end of the partial hairpin molecules described herein, not only to provide additional functionality to the amplified fragment of the sample nucleic acid as described above, but also to ensure more efficient subsequent processing, e.g., amplification and/or sequencing, of those molecules. For example, where a partial hairpin molecule is subjected to extension reaction conditions, it may be susceptible to filling in of the partial hairpin structure, by priming its own 'filling in' reaction through extension at the 5' terminus. As a result, a complete hairpin structure may be created that is more difficult to amplify, by virtue of the greater stability of its duplex portion. In such cases, it may be desirable to preferentially attach additional sequence segment(s) that is not complementary to the opposing end sequence, in order to prevent the formation of a complete hairpin structure. In one exemplary process, the LNA primers described above for the amplification of the partial hairpin structures, may be provided with additional overhanging sequence, including, e.g., the R2 complementary sequence described above, as well as potentially complementary sequences to other functional sequence components, e.g., attachment sequences like P7, sample index sequences, and the like. Subjecting the partial hairpin and primer to the extension reaction described above for amplification of that partial hairpin, will also result in extension of the partial hairpin along the overhanging sequence on the LNA primer. The extended sequence may comprise simply a non-complementary sequence, or it may comprise additional functional sequences, or their complements as noted above, such that the extension reaction results in attachment of those functional sequences to the 5' terminus of the partial hairpin structure.

Figure 40:
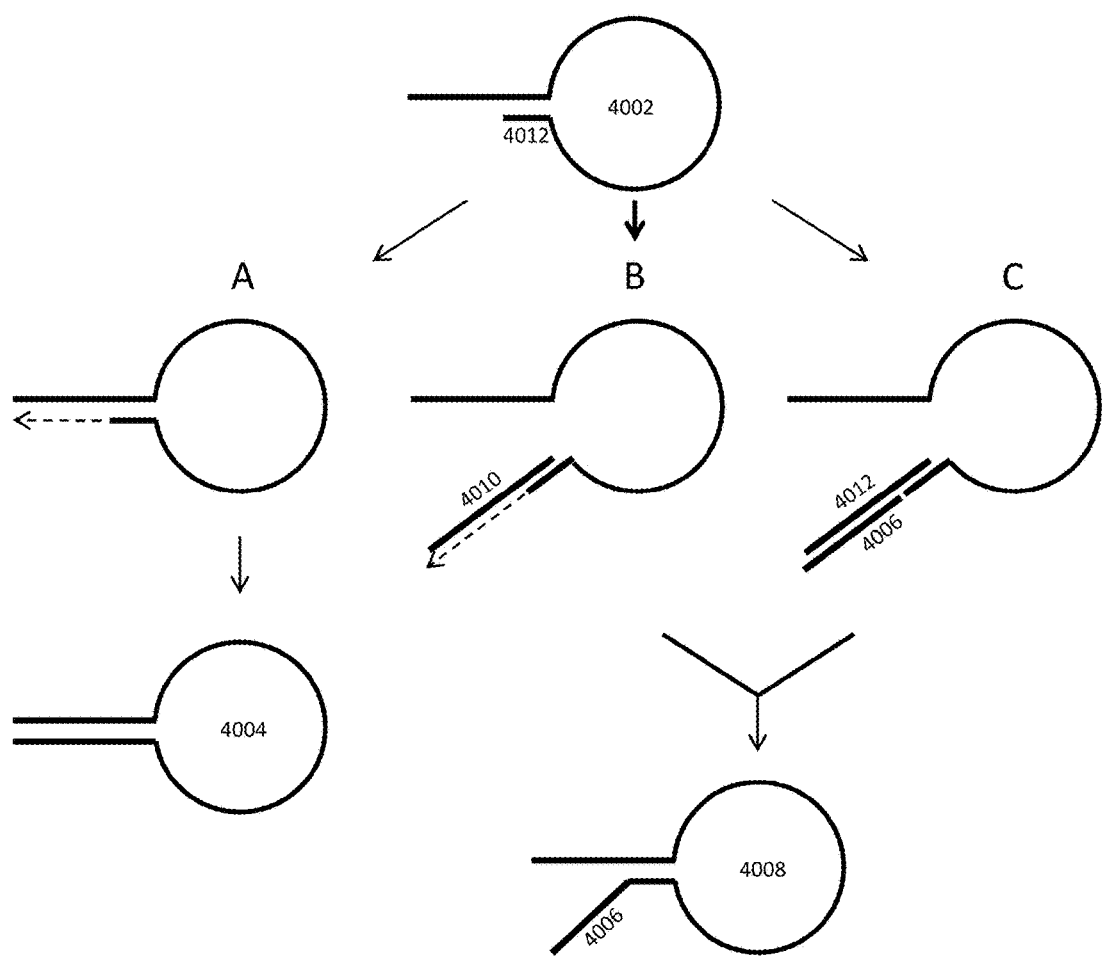
FIG. 40 presents examples of alternative processing steps following barcoding and amplification of nucleic acids, as described herein.

In alternative aspects, additional sequence segments may be ligated to the 5' end of the partial hairpin structure where such sequence segments are not complementary to the non-overlapped portion of the hairpin structure. The foregoing are schematically illustrated in FIG. 40. As shown in path A, a partial hairpin structure, when subjected to primer extension conditions, may act as its own primer and have its 5' sequence extended, as shown by the dashed arrow, until it forms a complete or nearly complete hairpin structure, e.g., with little or no overhang sequence. This full hairpin structure will possess far greater duplex stability, thereby potentially negatively impacting the ability to disrupt the hairpin structure to prime its replication, even when employing higher affinity primers, e.g., LNA containing primers/probes.

In order to minimize this possibility, as shown in both paths B and C, a separate sequence segment 4006 is added to the 5' end of the hairpin structure, to provide a partial hairpin with non-complementary tail sequences 4008, in order to prevent the generation of the complete or nearly complete hairpin structure. As shown, this may be accomplished in a number of different ways. For example, in a first process shown in path B, an invading probe 4010 may be used to disrupt the partial hairpin structure and hybridize to sequence segment 4012. Such invading probes may be provided with higher affinity binding than the inherent partial hairpin structure, e.g., through use of higher affinity nucleotide analogues such as LNAs or the like. In particular, that portion of the invader sequence 4010 that hybridizes to sequence segment 4012 may comprise LNAs within its sequence in the same fashion described herein for use with LNA primer sequences used in subsequent amplification.

Extension of the 5' portion of the partial hairpin (and sequence segment 4012) as shown by the dashed arrow in path B, then appends the sequence 4006 to the 5' terminus of the partial hairpin structure to provide structure 4008. Alternatively, sequence 4006 may be ligated to the 5' end of the partial hairpin structure 4002 (or sequence segment 4012). As shown in path C, this achieved through the use of a splint sequence 4014 that is partially complementary to sequence 4006 and partially complementary to sequence 4012, in order to hold sequence 4006 adjacent to sequence segment 4012 for ligation. As will be appreciated, the splint sequence 4014 may again utilize a higher affinity invading probe, like probe 4010, to disrupt the hairpin structure and hybridize to sequence segment 4012. In particular, again, that portion of splint sequence 4014 that is intended to hybridize to sequence segment 4012 may be provided with one or more LNA nucleotide analogues within its sequence, in order to preferentially disrupt the partial hairpin structure 4002, and allow ligation of sequence 4006 to its 5' end.

In some cases, a microfluidic device (e.g., a microfluidic chip) may be useful in parallelizing sample indexing. Such a device may comprise parallel modules each capable of adding a barcode sequence and a sample index to nucleic acid molecules of a sample via primers comprising both the barcode sequence and the sample index. Each parallel module may comprise a primer set comprising a different sample index, such that the sample processed in each module is associated with a different sample index and set of barcodes. For example, a microfluidic device with 8 modules may be capable of sample indexing 8 different samples. Following barcoding and sample indexing via attachment of the sequences to a sample nucleic acid, bulk addition of additional sequences (e.g., R2, P7, other barcode sequences) via, for example, serial amplification can be used to generate sequencer-ready products as described elsewhere herein.

In some cases, sample indexing may be achieved during barcoding without the inclusion of a separate sample index sequence in a primer used to attach a barcode to a sample nucleic acid. In such cases, a barcode sequence, for example, may also serve as a sample index. An example configuration of a sequencer-ready construct with a sequence functioning as both a barcode sequence and a sample index is as follows:
P5-BSI-R1-RandomNmer-Insert-R2-P7
where "BSI" is the sequence functioning as both a barcode sequence and a sample index. A sequencer-ready product may comprise a barcode sequence that can be used to align sequence reads and provide a sequence for a sample nucleic acid. The sequencer-ready product may be generated, for example, using PHASE amplification and subsequent bulk amplification as described elsewhere herein. Moreover, the barcode sequence may belong to a particular set of known barcode sequences. The set of barcode sequences may be associated with a particular sample, such that identification of the sample from which a particular sequencing read originates can be achieved via the read barcode sequence. Each sample can be associated with a set of known barcode sequences, with each barcode sequence set comprising barcode sequences that do not overlap with barcode sequence in other barcode sets associated with other samples. Thus, the uniqueness of a barcode sequence and its uniqueness amongst different sets of barcode sequences may be used for multiplexing.

For example, a sequencing read may comprise the barcode sequence "GAGCCG". Barcode sequence "GAGCCG" may be a barcode sequence in a set of known barcode sequences associated with Sample A. The sequence is not found in a set of known barcode sequences associated with another sample. Upon reading the sequence "GAGCCG", it can be determined that the sequence read is associated with Sample A because the sequence "GAGCCG" is unique to the set of barcode sequences associated with Sample A. Moreover, another sequencing read may comprise the barcode sequence "AGCAGA". Barcode sequence "AGCAGA" may be a barcode sequence in a set of known barcode sequences associated with Sample B. The sequence is not found in a set of known barcode sequences associated with another sample. Upon reading the sequence "AGCAGA", it can be determined that the sequence read is associated with Sample B because "AGCAGA" is unique to the set of barcode sequences associated with Sample B.

In another example, a sample index sequence may be embedded in a random sequence of a primer used in one or more amplification reactions to attach a barcode to a sample nucleic acid. For example, a primer may comprise a barcode sequence and a random sequence that can be used to randomly prime a sample nucleic acid and attach the barcode sequence to the sample nucleic acid. In some cases, the random sequence may be a pseudo-random sequence such that particular bases of the random sequence are conserved between all primers. The pattern of the conserved bases may be used as a sample index, such that all sequencer-ready products obtained from a particular sample all comprise the conserved pattern of bases in the random sequence region. Each sample can be associated with a different pattern of conserved bases and, thus, multiplexing can be achieved. In some cases, the pattern is a contiguous sequence region of a pseudo-random sequence (e.g., "NNNATACNNN" (SEQ ID NO: 1)) or in other cases, the pattern is a non-contiguous sequence region of a pseudo-random sequence (e.g., "NCNGNNAANN" (SEQ ID NO: 2)), where "N" corresponds to a random base. Moreover, any suitable number of bases may be conserved in a pseudo-random sequence in any pattern and the examples described herein are not meant to be limiting. An example configuration of a sequencer-ready construct with a sequence functioning as both a barcode sequence and a sample index is as follows:
P5-Barcode-R1-NQNQNNQQNN-Insert-R2-P7
where "Q" is a conserved base in the random region For example, a sequencer-ready product may comprise a 10-mer pseudo-random sequence "NCNGNNAANN" (SEQ ID NO: 2), where the second base ("C"), fourth base ("G"), seventh base ("A"), and eighth base ("A") of the pseudo-random sequence are conserved for all sequencer-ready products generated from Sample A. A sequencing read may comprise such a pattern of conserved bases in the random sequence region. Upon reading the conserved base pattern, it can be determined that the sequence read is associated with Sample A because the "NCNGNNAANN" (SEQ ID NO: 2) conserved pattern of bases is associated with Sample A. Moreover, a sequencer-ready product may comprise a 10-mer pseudo-random sequence "NNGCNGNGNN" (SEQ ID NO: 3), where the third base ("G"), fourth base ("C"), sixth base ("G"), and eighth base ("G") of the pseudo-random sequence are conserved for all sequencer-ready products generated from Sample B. A sequencing read may comprise such a pattern of conserved bases in the random sequence region. Upon reading the conserved base pattern, it can be determined that the sequence read is associated with Sample B because the "NNGCNGNGNN" (SEQ ID NO: 3) conserved pattern of bases is associated with Sample B.

In other cases, a sample index may be added to a sample nucleic acid prior to the addition of a barcode sequence to the sample nucleic acid. For example, a sample nucleic acid may be pre-amplified in bulk such that resulting amplicons are attached to a sample index sequence prior to barcoding. For example, sample may be amplified with a primer comprising a sample index sequence such that the sample index sequence can be attached to the sample nucleic acid. In some cases, the primer may be a random primer (e.g., comprising a random N-mer) and amplification may be random. Produced amplicons that comprise the sample index can then be barcoded using any suitable method, including barcoding methods described herein.

Sample nucleic acid molecules can be combined into partitions (e.g., droplets of an emulsion) with the primers described above. In some cases, each partition can comprise a plurality of sample nucleic acid molecules (e.g., smaller pieces of a larger nucleic acid). In some cases, no more than one copy of a unique sample nucleic acid molecule is present per partition. In some cases, each partition can generally comprise primers comprising an identical barcode sequence and a sample priming sequence (e.g., a variable random-Nmer, a targeted N-mer), with the barcode sequence generally differing between partitions. In such cases, each partition (and, thus, sample nucleic acid in the partition) can be associated with a unique barcode sequence and the unique barcode sequence can be used to determine a sequence for the barcoded sample nucleic acid generated in the partition.

In some cases, upon generation of barcoded sample nucleic acids, the barcoded sample nucleic acids can be released from their individual partitions, pooled, and subject to bulk amplification schemes to add additional sequences (e.g., additional sequencing primer binding sites, additional sequencer primer binding sites, additional barcode sequences, sample index sequences) common to all downstream sequencer-ready products. In cases where the partitions are droplets of an emulsion, the emulsion may be broken and the barcoded sample nucleic acids pooled. A sample index can be added in bulk to the released, barcoded sample nucleic acids, for example, using the serial amplification methods described herein. Where a sample index is added in bulk, each sequencer-ready product generated from the same sample will comprise the same sample index that can be used to identify the sample from which the read for the sequencer-ready product was generated. Where a sample index is added during barcoding, each primer used for barcoding may comprise an identical sample index sequence, such that each sequencer-ready product generated from the same sample will comprise the same sample index sequence.

Partitioning of sample nucleic acids to generate barcoded (or barcoded and sample indexed) sample nucleic acids and subsequent addition of additional sequences (e.g., including a sample index) to the barcoded sample nucleic acids can be repeated for each sample, using a different sample index for each sample. In some cases, a microfluidic droplet generator may be used to partition sample nucleic acids. In some cases, a microfluidic chip may comprise multiple droplet generators, such that a different sample can be processed at each droplet generator, permitting parallel sample indexing. Via each different sample index, multiplexing during sequencing can be achieved.

Upon the generation of sequencer-ready oligonucleotides, the sequencer-ready oligonucleotides can then be provided to a sequencing device for sequencing. Thus, for example, the entire sequence provided to the sequencing device may comprise one or more adaptors compatible with the sequencing device (e.g. P5, P7), one or more barcode sequences, one or more primer binding sites (e.g. Read1 (R1) sequence primer, Read2 (R2) sequencing primer, Index primer), an N-mer sequence, a universal sequence, the sequence of interest, and combinations thereof. The barcode sequence may be located at either end of the sequence. In some cases, the barcode sequence may be located between P5 and Read1 sequence primer binding site. In other cases, the barcode sequence may be located between P7 and Read 2 sequence primer binding site. In some cases, a second barcode sequence may be located between P7 and Read 2 sequence primer binding site. The index sequence primer binding site may be utilized in the sequencing device to determine the barcode sequence.

The configuration of the various components (e.g., adaptors, barcode sequences, sample index sequences, sample sequence, primer binding sites, etc.) of a sequence to be provided to a sequencer device may vary depending on, for example the particular configuration desired and/or the order in which the various components of the sequence is added. Any suitable configuration for sequencing may be used and any sequences can be added to oligonucleotides in any suitable order. Additional sequences may be added to a sample nucleic acid prior to, during, and after barcoding of the sample nucleic acid. For example, a P5 sequence can be added to a sample nucleic acid during barcoding and P7 can be added in bulk amplification following barcoding of the sample nucleic acid. Alternatively, a P7 sequence can be added to a sample nucleic acid during barcoding and a P5 sequence can be added in bulk amplification following barcoding of the sample nucleic acid. Example configurations displayed as examples herein are not intended to be limiting. Moreover, the addition of sequence components to an oligonucleotide via amplification is also not meant to be limiting. Other methods, such as, for example, ligation may also be used. Furthermore, adaptors, barcode sequences, sample index sequences, primer binding sites, sequencer-ready products, etc. described herein are not meant to be limiting. Any type of oligonucleotide described herein, including sequencer-ready products, may be generated for any suitable type of sequencing platform (e.g., Illumina sequencing, Life Technologies Ion Torrent, Pacific Biosciences SMRT, Roche 454 sequencing, Life Technologies SOLiD sequencing, etc.) using methods described herein.

Sequencer-ready oligonucleotides can be generated with any adaptor sequence suitable for a particular sequencing platform using methods described herein. For example, sequencer-ready oligonucleotides comprising one or more barcode sequences and P1 and A adaptor sequences useful in Life Technologies Ion Torrent sequencing may be generated using methods described herein. In one example, beads (e.g., gel beads) comprising an acrydite moiety linked to a P1 sequence via a disulfide bond may be generated. A barcode construct may be generated that comprises a P1sequence, a barcode sequence, and a random N-mer sequence. The barcode construct may enter an amplification reaction (e.g., in a partition, such as a fluidic droplet) to barcode sample nucleic acid. Barcoded amplicons may then be subject to further amplification in bulk to add the A sequence and any other sequence desired, such as a sample index. Alternatively, P1 and A sequences can be interchanged such that A is added during sample barcoding and P1 is added in bulk. The complete sequence can then be entered into an Ion Torrent sequencer. Other adaptor sequences (e.g., P1 adaptor sequence for Life Technologies SOLiD sequencing, A and B adaptor sequences for Roche 454, etc.) for other sequencing platforms can be added in analogous fashion.

Although described herein as generating partial hairpin molecules, and in some cases, preventing formation of complete hairpins, in some cases, it may be desirable to provide complete hairpin fragments that include the barcode sequences described herein. In particular, such complete hairpin molecules may be further subjected to conventional sample preparation steps by treating the 3' and 5' end of the single hairpin molecule as one end of a double stranded duplex molecule in a conventional sequencing workflow. In particular, using conventional ligation steps, one could readily attach the appropriate adapter sequences to both the 3' and 5' end of the hairpin molecule in the same fashion as those are attached to the 3' and 5' termini of a duplex molecule. For example, in case of an Illumina based sequencing process, one could attach a standard Y adapter that includes the P5 and P7 adapters and R1 and R2 primer sequences, to one end of the hairpin as if it were one end of a duplex molecule, using standard Illumina protocols.

Methods for Reducing Undesired Amplification Products (Partial Hairpin Amplification for Sequencing (PHASE))

A random N-mer sequence may be used to randomly prime a sample, such as genomic DNA (gDNA). In some embodiments, the random N-mer may comprise a primer. In some cases, the random N-mer may prime a sample. In some cases, the random N-mer may prime genomic DNA. In some cases, the random N-mer may prime DNA fragments.

Additionally, a random N-mer sequence may also be attached to another oligonucleotide. This oligonucleotide may be a universal sequence and/or may contain one or more primer read sequences that may be compatible with a sequencing device (e.g. Read 1 primer site, Read 2 primer site, Index primer site), one or more barcode sequences, and one or more adaptor segments that may be compatible with a sequencing device (e.g. P5, P7). Alternatively, the oligonucleotide may comprise none of these and may include another sequence.

Via subsequent amplification methods, priming of a sample nucleic acid with a random N-mer may be used to attach an oligonucleotide sequence (e.g., an oligonucleotide sequence comprising a barcode sequence) linked to a random N-mer to the sample nucleic acid, including a sample nucleic acid to be sequenced. Utilizing random primers to prime a sample may introduce significant sequence read errors, due to, for example, the production of undesired amplification products.

To mitigate undesired amplification products, at least a subsection of an oligonucleotide sequence may be substituted with dUTPs or uracil containing nucleotides in place of dTTPs or thymine containing nucleotides, respectively. In some cases, substitution may be complete (e.g., all thymine containing nucleotides are substituted with uracil containing nucleotides), or may be partial such that a portion of an oligonucleotide's thymine containing nucleotides are substituted with uracil containing nucleotides. In some cases, thymine containing nucleotides in all but the last about 10 to about 20, last about 10 to 30, last about 10 to 40, or last about 5 to 40 nucleotides of an oligonucleotide sequence adjacent to a random N-mer sequence are substituted with dUTPs or uracil containing nucleotides. In addition, a polymerase that does not accept or process uracil-containing templates may be used for amplification of the sample nucleic acid. In this case, the non-uracil containing portion of about 10 to about 20 nucleotides may be amplified and the remaining portion containing the dUTPs or uracil containing nucleotides may not be amplified. In some cases, the portion of an oligonucleotide sequence comprising dUTPs or uracil containing nucleotides may be adjacent to the N-mer sequence. In some cases, the portion of an oligonucleotide sequence comprising dUTPs or uracil containing nucleotides may be adjacent to the barcode sequence. Any portion of an oligonucleotide sequence, including an adaptor segment, barcode, or read primer sequence may comprise dUTPs or uracil containing nucleotides (e.g., substituted for thymine containing nucleotides), depending upon the configuration of the oligonucleotide sequence.

Moreover, the number and positioning of uracil containing nucleotide-for-thymine containing nucleotide substitutions in an oligonucleotide may be used, for example, to tune the size of partial hairpin products obtained with amplification methods described below and/or to tune the binding of the polymerase enzyme with a uracil containing primer sequence. Additionally, free uracil containing nucleotides, e.g., UTP or an analogue thereof, may also be provided within the reaction mixture, e.g., within the partition, at a desired concentration to mediate polymerase/uracil-primer binding kinetics. In some cases, smaller partial hairpin products may give rise to more accurate sequencing results. Accordingly, an oligonucleotide may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more uracil containing nucleotide-for-thymine containing nucleotide substitutions depending upon, for example, the desired length of partial hairpin products generated from the oligonucleotide.

Upon random priming of a sample nucleic acid with a random N-mer linked to an oligonucleotide sequence (e.g., an oligonucleotide sequence comprising uracil containing nucleotides described above) FIG. 15A, a first round of amplification (e.g., using a polymerase that does not accept or process a uracil containing nucleotide as a template) may result in the attachment of the oligonucleotide sequence to a complement of the sample nucleic acid, FIG. 15B and FIG. 15C. Upon priming (via the random N-mer) and further amplification of the amplification product with another copy of the oligonucleotide sequence comprising the random N-mer (FIG. 15D), an amplification product comprising the oligonucleotide sequence, a portion of the sample nucleic acid sequence, and a partial complementary oligonucleotide sequence (e.g., complementary to the portion of the oligonucleotide sequence not comprising uracil containing nucleotides) at an end of the amplification product opposite the oligonucleotide sequence, can be generated. The partial complementary oligonucleotide sequence and the oligonucleotide sequence can hybridize to form a partial hairpin that, in some cases, can no longer participate in nucleic acid amplification. A partial hairpin can be generated because a portion of the original oligonucleotide sequence comprising uracil containing nucleotides was not copied. Amplification can continue for a desired number of cycles (e.g., 5, 10, 15, 20, 25, 30, 35, 40, 45, or 50 cycles), up until all oligonucleotide sequences comprising random N-mers have been exhausted (FIGS. 15E-15G).

In some embodiments, to ensure priming of sample nucleic acid (e.g., genomic DNA (gDNA)) with only a random N-mer and not portions of an attached oligonucleotide sequence, the oligonucleotide sequence may be blocked via hybridization of a blocker oligonucleotide (e.g., black dumbbell in FIGS. 15A-15G). A blocker oligonucleotide (also referred to as an oligonucleotide blocker elsewhere herein) may be hybridized to any portion of an oligonucleotide sequence, including a barcode sequence, read primer site sequence, all or a portion of a uracil containing portion of the oligonucleotides, or all or any other portion of the oligonucleotides, or other sequence therein. A blocker oligonucleotide may be DNA or RNA. In some cases, a blocker oligonucleotide may comprise uracil containing nucleotide-for-thymine containing nucleotide substitutions. In some cases, all of the thymine containing nucleotides of a blocker oligonucleotide may be substituted with uracil containing nucleotides. In some cases, a portion of the thymine containing nucleotides of a blocker oligonucleotide may be substituted with uracil containing nucleotides. In some cases, a blocker oligonucleotide may comprise locked nucleic acid (LNA), an LNA nucleotide, bridged nucleic acid (BNA), and/or a BNA nucleotide. Moreover a blocker oligonucleotide may be of any suitable length necessary for blocker functionality. A blocker oligonucleotide may be of length suitable to block a portion of an oligonucleotide or may be of the same or of substantially the same length of an oligonucleotide it is designed to block. The blocker oligonucleotide may ensure that only random N-mers bind to the sample nucleic acid (e.g., genomic DNA) and not other portions of the oligonucleotide sequence.

The stoichiometric ratio of a blocker oligonucleotide to oligonucleotide (e.g., blocker oligonucleotide:oligonucleotide) may vary. For example, the blocker oligonucleotide:oligonucleotide stoichiometric ratio may be about 0.01, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.10, 2.20, 2.30, 2.40, 2.50, 2.60, 2.70, 2.80, 2.90, 3.00, 3.50, 4.00, 4.50, 5.0, 5.5, 6.0, 6.5, 7.0, 7.5, 8.0, 8.5, 9.0, 10.0, 20, 30, 40, 50, 100 or more. In some cases, the blocker oligonucleotide:oligonucleotide stoichiometric ratio may be at least about 0.01, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.10, 2.20, 2.30, 2.40, 2.50, 2.60, 2.70, 2.80, 2.90, 3.00, 3.50, 4.00, 4.50, 5.0, 5.5, 6.0, 6.5, 7.0, 7.5, 8.0, 8.5, 9.0, 10.0, 20, 30, 40, 50, 100 or more. In some cases, the blocker oligonucleotide:oligonucleotide stoichiometric ratio may be at most about 0.01, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.10, 2.20, 2.30, 2.40, 2.50, 2.60, 2.70, 2.80, 2.90, 3.00, 3.50, 4.00, 4.50, 5.0, 5.5, 6.0, 6.5, 7.0, 7.5, 8.0, 8.5, 9.0, 10.0, 20, 30, 40, 50, or 100.

Moreover, incorporation of a blocker moiety (e.g., via a dideoxynucleotide (ddNTP), ddCTP, ddATP, ddGTP, ddTTP, etc. at the 3' or 5' end of the blocker oligonucleotide) to a blocker oligonucleotide and/or the inclusion of uracil containing nucleotides (e.g., substituted for all or a portion of thymine containing nucleotides) in a blocker oligonucleotide may prevent preferential binding of blocked portions of the blocked oligonucleotide sequence to the sample nucleic acid. Additional examples of blocker moieties include 3' phosphate, a blocked 3' end, 3'ddCTP, C3 Spacer (/3SpC3/), Dideoxy-C (/3ddC/). Blocker oligonucleotides may be cleaved from an oligonucleotide sequence by RNAse, RNAseH, an antisense DNA oligonucleotide, and/or alkaline phosphatase.

In some cases, an oligonucleotide sequence may be blocked with a blocker oligonucleotide such that the oligonucleotide sequence comprises a blocked 5' end, comprises a blocked 3' end, may be entirely blocked (e.g., may be entirely blocked, except for its random N-mer sequence), or may be blocked at another location (e.g., a partial sequence of the oligonucleotide, different from an oligonucleotide sequence's random N-mer). In some cases, an oligonucleotide sequence may comprise a plurality of blockers, such that multiple sites of the oligonucleotide are blocked. In some cases, an oligonucleotide sequence may comprise both a blocked 3' end and uracil containing nucleotides. In some cases, an oligonucleotide sequence comprising uracil containing nucleotides and a blocked 3' end may be adjacent to the N-mer sequence. In some cases, an oligonucleotide sequence may comprise a blocked 3' end. In some cases, an oligonucleotide sequence may comprise uracil containing nucleotides. In some cases, an oligonucleotide sequence may comprise both a blocked 5' end and uracil containing nucleotides.

In some cases, the oligonucleotide sequence comprising uracil containing nucleotides and a blocked 3' end may be adjacent to the N-mer sequence. In some cases, the oligonucleotide sequence comprising uracil containing nucleotides and a blocked 3' end may be adjacent to the barcode sequence. In some cases, the oligonucleotide sequence may comprise a blocked 3' end. In some cases, the oligonucleotide sequence may comprise uracil containing nucleotides. In some cases, the oligonucleotide sequence may comprise both the blocked 3' end and uracil containing nucleotides. Addition of a blocker oligonucleotide may prevent preferential binding to portions of the universal sequence, which may not be desired to be amplified.

In some cases, an oligonucleotide suitable for priming a sample nucleic acid via its random N-mer may also comprise a blocking sequence that can function in the same role as a blocker oligonucleotide. For example, an oligonucleotide may be arranged in a hairpin configuration with a blocking sequence that can function in the same role as a blocker oligonucleotide. An example oligonucleotide comprising a random N-mer, an R1c sequence, a P5 sequence, a barcode sequence, and an R1 sequence may be configured as follows:

5'-RandomNmer-R1c-P5-Barcode-R1-3'

The R1 sequence and R1c sequence of the oligonucleotide may hybridize to generate a hairpin with a hairpin loop comprising the P5 and Barcode sequences. The R1c sequence can function in the same role as a blocker oligonucleotide such that priming of sample nucleic acid with the oligonucleotide occurs via only the oligonucleotide's random N-mer. In some cases, one or more cleavage sites (e.g., a restriction site, a cleavage site, an abasic site, etc.) may be included in an oligonucleotide arranged as a hairpin with a blocking sequence, including an oligonucleotide's hairpin loop, to separate sequence components of the oligonucleotide downstream, if desired. Separation may occur, for example, via an enzymatic reaction, oxidation-reduction, radiation (e.g., UV-light), the addition of heat, or other suitable means.

Figure 16A:
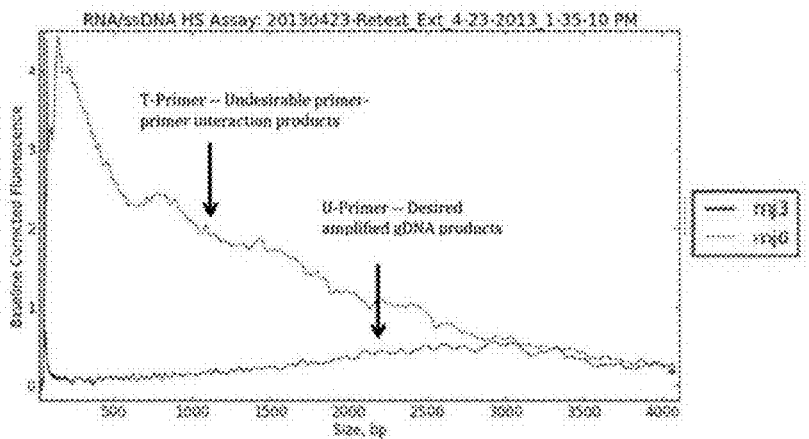
FIG. 16A is a graphic depiction of including uracil containing nucleotides in the universal portion of the primer.
Figure 16B:
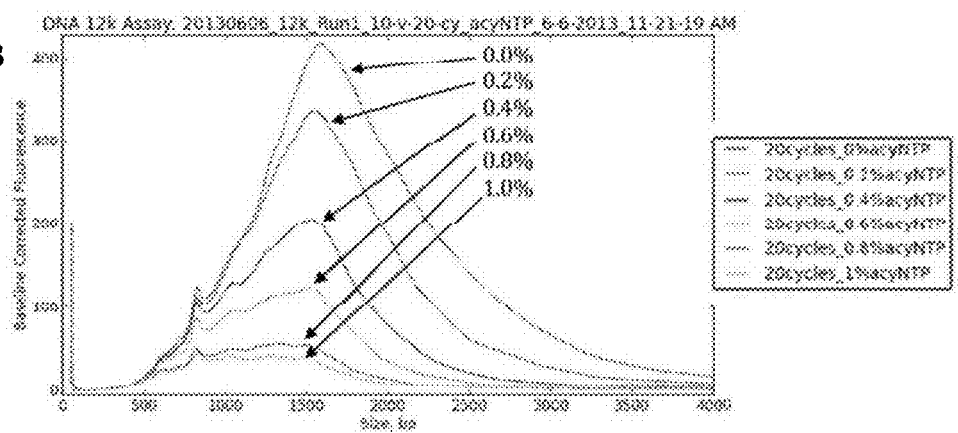
FIG. 16B is a graphic depiction of controlling amplification product length by including acyNTPs in the reaction mixture.

An example uracil containing nucleotide-substituted oligonucleotide sequence linked to a random N-mer is depicted in FIG. 14B. Specifically, a random primer (e.g., a random N-mer), of about 8N-12N in length, 1404, may be linked with an oligonucleotide sequence. The random N-mer may be used to randomly prime and extend from a sample nucleic acid, such as, genomic DNA (gDNA). The oligonucleotide sequence comprises: (1) sequences for compatibility with a sequencing device, such as, a flow cell (e.g. Illumina's P5, 1401, and Read 1 Primer sites, 1402) and (2) a barcode (BC), 1403, (e.g., 6-12 base sequences). Furthermore, the Read 1 Primer site 1402 of the oligonucleotide sequence may be hybridized with a blocking oligonucleotide comprising uracil containing nucleotides and a blocker moiety at its 3' end (e.g. 3'ddCTP, indicated by an "X"). The blocking oligonucleotide can be used to promote priming of a sample nucleic acid with only the random N-mer sequence and prevent preferential binding of the oligonucleotide sequence to portions of the sample nucleic acid that are complementary to the Read 1 Primer site, 1402. Optionally, to further limit product lengths, a small percentage of terminating nucleotides (e.g., 0.1-2% acyclonucleotides (acyNTPs)) (FIG. 16B) may be included in oligonucleotide sequences to reduce undesired amplification products.

An example of partial hairpin amplification for attaching a uracil containing nucleotide-substituted oligonucleotide sequence comprising a random N-mer to a sample nucleic acid (e.g., genomic DNA (gDNA)) is depicted in FIGS. 15A-15G. First, initial denaturation of the sample nucleic acid may be achieved at a denaturation temperature (e.g., 98° C., for 2 minutes) followed by priming of a random portion of the sample nucleic acid with the random N-mer sequence at a priming temperature (e.g., 30 seconds at 4° C.), FIG. 15A. The oligonucleotide sequence is hybridized with a blocking oligonucleotide (black dumbbell in FIGS. 15A-15G), to ensure that only the random N-mer primes the sample nucleic acid and not another portion of the oligonucleotide sequence. Subsequently, sequence extension (e.g., via polymerase that does not accept or process a uracil containing nucleotide as a template) may follow as the temperature ramps to higher temperature (e.g., at 0.1° C./second to 45° C. (held for 1 second)) (FIG. 15A). Extension may then continue at elevated temperatures (e.g., 20 seconds at 70° C.), continuing to displace upstream strands and create a first phase of redundancy (FIG. 15B). Denaturation of the amplification product may then occur at a denaturing temperature (e.g., 98° C. for 30 seconds) to release the sample nucleic acid and amplification product for additional priming.

After the first cycle, amplification products have a single 5' tag (FIG. 15C) comprising the oligonucleotide sequence. These aforementioned steps are repeated to prime the amplification product and sample nucleic acid with the oligonucleotide sequence via its random N-mer. The black sequence indicates portions of the added 5' tags (added in cycle 1) that comprise uracil containing nucleotides and thus, will not be copied upon priming and amplification of the amplification product (FIG. 15D). Following a second round of amplification, both 5' tagged products and 3' & 5' tagged products may be generated (FIG. 15E). The 3' & 5' tagged products comprise a full oligonucleotide sequence at one end, the sample nucleic acid sequence, and a sequence partially complementary to the oligonucleotide sequence (e.g., complementary to regions of the oligonucleotide sequence not comprising uracil containing nucleotides) at the other end of the oligonucleotide. The oligonucleotide sequence may hybridize with its partially complementary sequence to generate a partial hairpin structure (FIG. 15F. Amplification can continue repeatedly for a desired number of cycles (e.g., up to 20 times), up until all oligonucleotide sequences have been exhausted (FIG. 15G).

Partial hairpin formation may prevent generating a copy of a copy and may instead encourage only copies of the original template to be produced, thus reducing potential amplification bias, and other artifacts. Partial hairpin formation may encourage segregation of the desired product and may reduce production of copies.

Desirable properties for the uracil-non-reading polymerase to form the partial hairpin may include an exonuclease deficient polymerase (e.g., having low exonuclease activity, having substantially no exonuclease activity, having no exonuclease activity), strand displacing capabilities (e.g., a thermostable strand displacing polymerase enzyme), residual activity at temperatures <50° C., and discrimination against uracil containing nucleotides v thymine containing nucleotides. Examples of such polymerases may include 9 degrees North, modified (NEB), exo minus Pfu, Deep Vent exo minus, Vent exo minus, and homologs thereof. Moreover, a polymerase with low exonuclease activity may be a polymerase with less than 90%, less than 80%, less than 70%, less than 60%, less than 50%, less than 40%, less than 30%, less than 20%, less than 10%, less than 5%, or 0% exonuclease activity of a thermally stable polymerase with normal exonuclease activity (e.g., Taq polymerase). In some cases, a polymerase used for partial hairpin amplification may be capable of strand-displacement. In some cases, limiting the length of the amplified sequence may reduce undesired amplification products, wherein longer length products may include undesired upstream portions such as a barcode sequence. The amplified product length may be limited by inclusion of terminating nucleotides. An example of a terminating nucleotide may include an acyclonucleotide (acyNTPs). Terminating nucleotides may be present at about 0%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, or 2.5% of the amplified product length. In some cases, terminating nucleotides may be present at more than about 0%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, or more of the amplified product length. In some cases, terminating nucleotides may be present at less than about 0%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, or 2.5% of the amplified product length.

Amplification product length may also be controlled by pre-amplification of sample nucleic acid prior to initiation of PHASE amplification. For example, a random N-mer may be used for pre-amplification of the sample nucleic acid. A random N-mer may be used to prime a sample nucleic acid followed by extension of the primer using suitable thermal cycling conditions. Product length can be controlled by thermal cycling conditions (e.g., number of thermal cycles, temperatures utilized, cycle time, total run time, etc.) in addition to the random priming of the sample nucleic acid. In some cases, pre-amplification products smaller than the original sample nucleic acid can be obtained. Amplification products generated during pre-amplification may then be entered into a PHASE amplification and barcoded as described above.

Figure 17:
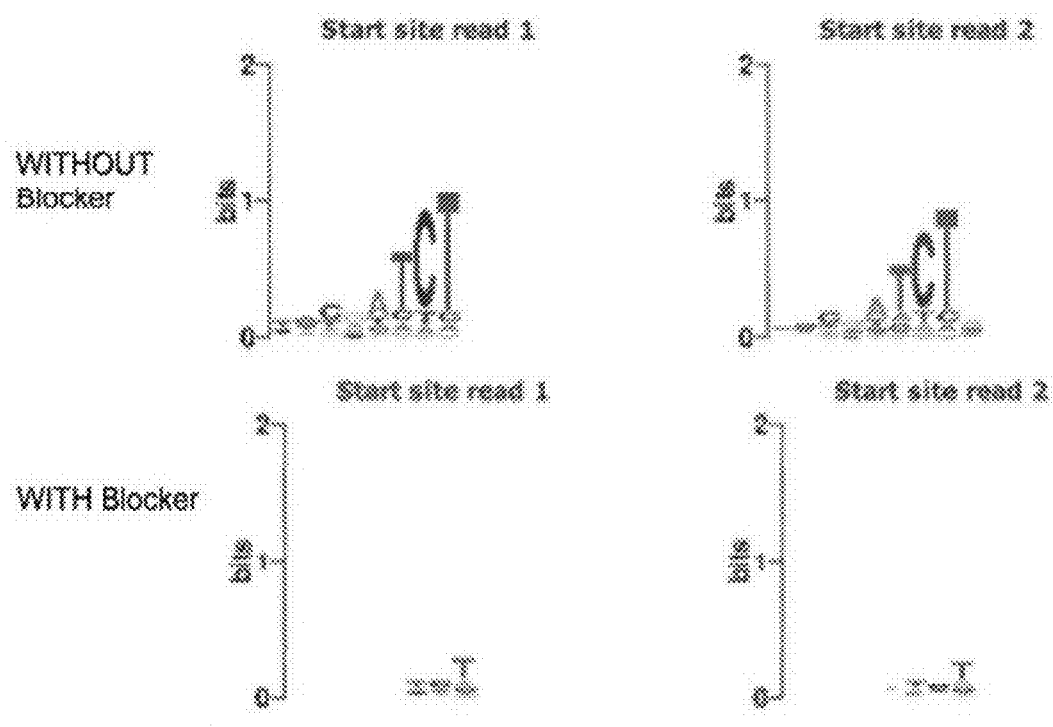
FIG. 17 is a graphic depiction of reducing start site bias by adding a blocker oligonucleotide.

As shown in FIG. 17, addition of a blocking oligonucleotide may reduce start site bias by 50%. Incorporation of uracil containing nucleotides instead of thymine containing nucleotides into the universal sequence and using a polymerase that does not accept or process uracil-containing templates, may significantly reduce sequencing errors, as reported in FIG. 21 and FIG. 22. For example, Q40 error may be reduced from about 0.002 to about 0.001, unmapped fraction ends may be reduced from about 0.996 to about 0.03, median insert size may be reduced from about 399 to about 310, IQR insert size may be reduced from about 413 to about 209, and zero coverage fraction may be reduced from about 0.9242 to about 0.0093.

Figure 34A:
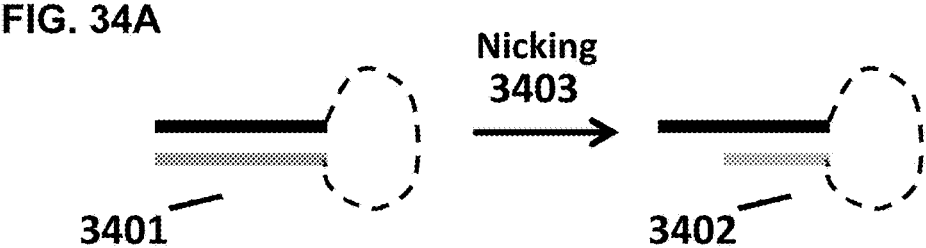
FIGS. 34A-34C are schematics of example hairpin constructs.

Amplification schemes that do not involve the substitution of thymine containing nucleotides with uracil containing nucleotides are also envisioned for generating partial hairpin species. In some cases, other species unable to be recognized or be copied by a polymerase (e.g., methylated bases, abasic sites, bases linked to bulky side groups, etc.) may be used in place of uracil containing nucleotides to generate partial hairpin amplicons. In some cases, full hairpin amplicons may be generated and processed post-synthesis to generate partial hairpin species. In some cases, full hairpin amplicons may be generated and portions subsequently removed to generate partial hairpin species. For example, as shown in FIG. 34A, full hairpin amplicons 3401 can be generated via the amplification scheme depicted in FIGS. 15A-15G when oligonucleotide primers comprising random N-mers do not comprise uracil containing nucleotides and/or a polymerase capable of accepting or processing a uracil containing template is used for amplification. Upon generation of the full hairpin amplicons 3401, the full hairpin amplicons can be enzymatically (e.g., via a restriction enzyme or other site specific enzyme such as a nickase) or chemically nicked 3403 at one or more appropriate sites to generate partial hairpin species 3402.

Figure 34B:
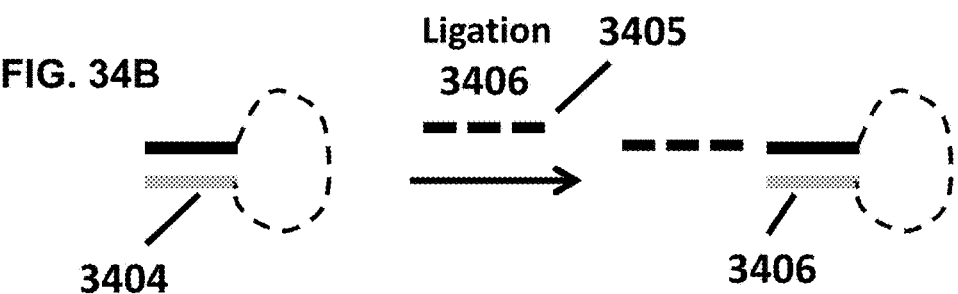

In some cases, full hairpin amplicons may be generated and portions added to the full hairpin amplicons to generate partial hairpin species. For example, a primer comprising a sequencing primer binding site (e.g., R1) coupled to a random N-mer and not comprising uracil containing nucleotides may be used to amplify sample nucleic acid and generate full hairpin amplicons (e.g., a full hairpin comprising the sequencing primer binding site (e.g., R1), the copied sample nucleic acid, and the complement to the sequencing primer binding site hybridized with the sequencing primer binding site (e.g., R1c)—3404 in FIG. 34B) via the amplification scheme depicted in FIGS. 15A-15G. Upon generation of the full hairpin amplicons 3404, the full hairpin amplicons can have additional sequences (e.g., a sequence comprising a P5 sequence and a barcode sequence) 3405 added, for example, via ligation 3406.

Figure 34C:
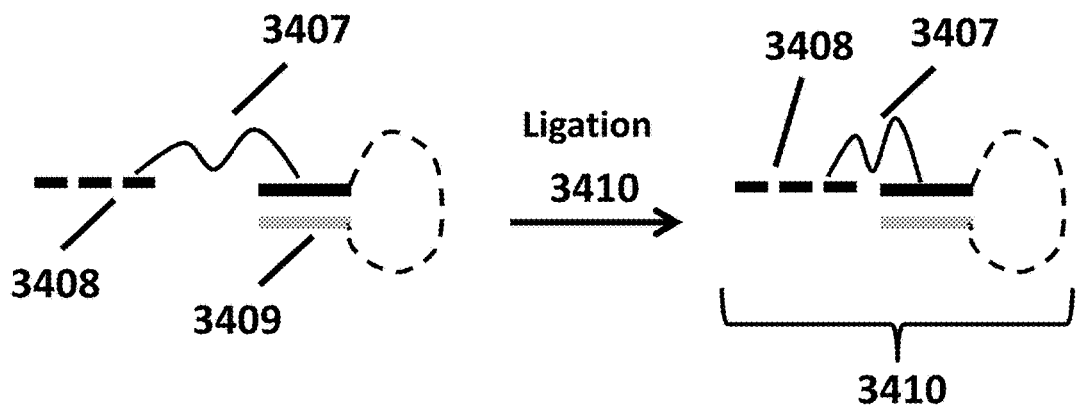

In some cases, primers (e.g., oligonucleotides comprising a random N-mer) used to generate full hairpin amplicons may be covalently modified to comprise an additional sequence via, for example, a linker (e.g., a linker not comprising nucleic acid or a linker comprising nucleic acid that does not participate in amplification). In some cases, the linker may be polyethylene glycol or a carbon-based linker. Full hairpin amplicons generated from the primers (e.g., via an amplification scheme depicted in FIGS. 15A-15G), thus, can also be covalently linked to the additional sequence via the linker. The attached sequence can then be ligated to the full hairpin amplicon to generate a partial hairpin species. An example of a full hairpin amplicon 3409 comprising an additional sequence 3408 via a linker 3407 is shown in FIG. 34C. Following full hairpin generation, the additional sequence 3408 can be ligated to the full hairpin amplicon 3409 such that a partial hairpin species (3410) comprising the additional sequence 3408 can be generated.

Targeted N-mers and Targeted Amplification

In addition to random amplification schemes, barcode constructs (e.g., oligonucleotides comprising a barcode sequence and an N-mer for priming a sample nucleic acid) comprising targeted priming sequences (e.g., a targeted N-mer) and targeted amplification schemes are also envisioned. Targeted amplification schemes may be useful, for example, in detecting a particular gene or sequence of interest via sequencing methods, may be useful in detecting a particular type of nucleic acid, may be useful in detecting the a particular strand of nucleic acid comprising a sequence, and combinations thereof. In general, targeted amplification schemes rely on targeted primers to complete amplification of a particular nucleic acid sequence. In some examples, PCR methods may be used for targeted amplification, via the use of primers targeted toward a particular gene sequence of interest or a particular sequence upstream of a particular gene sequence of interest, such that the particular gene sequence of interest is amplified during PCR.

The PHASE amplification reaction described above may also be modified such that target amplification of sample nucleic acid is achieved. Barcode constructs comprising a targeted priming sequence (e.g., a targeted N-mer), rather than a random sequence (e.g., a random N-mer), as described above, may be used to prime a specific sequence during PHASE amplification. The specific sequence, for example, may be a particular gene sequence of interest such that generation of amplicons is indicative of the sequence's presence. Or, the specific sequence may be a sequence known to be upstream from a particular gene sequence of interest. Such constructs may be generated, and, if desired, coupled to beads, using any of the methods described herein, including limiting dilution schemes depicted in FIGS. 4A-4N and the combinatorial plate schemes described elsewhere herein.

For example, as described previously with respect to FIGS. 4A-4N, a construct comprising a primer 403 (e.g., P5), a barcode sequence 408, and a read primer binding site (e.g., R1) 415 can be generated (see FIGS. 4A-4H). As shown in FIG. 4I, an additional sequence 413 can be added (optionally in bulk) to the construct via primer comprising a sequence 412 complementary to read primer binding site 415. Sequence 413 may serve as a targeted sequence (e.g., a targeted N-mer) such that the targeted sequence corresponds to a particular target sequence of interest. The construct may also comprise an oligonucleotide blocker, as described elsewhere herein, in order to ensure that only the targeted sequence, and not other sequence portions of the construct, primes the sample nucleic acid. Upon entry of the completed construct into a PHASE reaction with sample nucleic acid, for example, the targeted construct may prime the sample nucleic acid (e.g., at the desired sequence site) and the amplification reaction can be initiated to generate partial hairpins from the sample nucleic acid as described above. In some cases, a combination of targeted N-mer primers and random N-mer primers are used to generate partial hairpin amplicons. In some cases, targeted amplification may be useful in controlling the size (e.g., sequence length) of partial hairpin amplicons that are generated during amplification for a particular target.

In some cases, a plurality of constructs comprising a barcode sequence and a targeted N-mer may be coupled to a bead (e.g., a gel bead). In some cases, the plurality of constructs may comprise an identical barcode sequence and/or an identical targeted N-mer sequence. In some cases, the targeted N-mer sequence may vary amongst individual constructs of the plurality such that a plurality of target sequences on a sample nucleic acid may be primed via the various targeted N-mers. As described above, the beads may be partitioned (e.g., in fluidic droplets) with sample nucleic acid, the bead(s) in each partition degraded to release the coupled constructs into the partition, and the sample nucleic acid amplified via the targeted N-mer of the constructs. Post processing (e.g., addition of additional sequences (e.g., P7, R2), addition of a sample index, etc.) of the generated amplicons may be achieved with any method described herein, including bulk amplification methods (e.g., bulk PCR) and bulk ligation.

In a partition, constructs comprising a barcode sequence and a targeted N-mer may be coupled to a bead, may be free in solution (e.g., free in the aqueous interior of a fluidic droplet), or both. Moreover, a partition may comprise both targeted constructs (e.g., constructs comprising a targeted N-mer sequence) and non-targeted constructs (e.g., constructs comprising a random N-mer sequence). Each of the targeted and non-targeted constructs may be coupled to a bead, one of the two may be coupled to a bead, and either construct may also be in solution within a partition.

Where each type of construct is present in a partition, both targeted and non-targeted amplification of sample nucleic acids may take place. For example, with respect to a PHASE amplification reaction, a targeted barcode construct may be used to initially prime and extend a sample nucleic acid. In general, these steps correspond to the first cycle of PHASE amplification described above with respect to FIGS. 15A-15C, except that the targeted construct is used for initial priming. The extension products can then be primed with a barcode construct comprising a random N-mer such that a partial hairpin is generated, these steps corresponding to the second cycle of PHASE described above with respect to FIGS. 15D-15F. Amplification can continue for additional rounds (e.g., FIG. 15G) until the desired number of rounds are complete. Post processing (e.g., addition of additional sequences (e.g., P7, R2), addition of a sample index, etc.) of the generated partial hairpin amplicons may be achieved with any method described herein, including bulk amplification methods (e.g., bulk PCR) and bulk ligation.

Moreover, targeted barcode constructs may be generated such that the construct's targeted N-mer is directed toward nucleic acid species other than DNA, such as, for example, an RNA species. In some cases, the targeted barcode construct's targeted N-mer may be directed toward a particular RNA sequence, such as, for example, a sequence corresponding to transcribed gene or other sequence on a messenger RNA (mRNA) transcript. In some cases, sequencing of barcoded products generated from RNA (e.g., an mRNA) may aid in determining the expression level of a gene transcribed by the RNA. In some cases, the targeted N-mer may be a poly-thymine (e.g., poly-T sequence) sequence capable of hybridizing with a poly-adenine (poly-A sequence) that can, for example, be found at the 3' end of an mRNA transcript. Upon priming of an mRNA with a targeted barcode construct comprising a poly-T sequence via hybridization of the barcode construct's poly-T sequence with the mRNA's poly-A sequence, the targeted barcode construct can be extended via a reverse transcription reaction to generate a complementary DNA (cDNA) product comprising the barcode construct. In some cases, a targeted barcode construct comprising a poly-T targeted N-mer may also comprise an oligonucleotide blocker as described elsewhere herein, such that only the poly-T sequence hybridizes with RNA.

Targeted barcode constructs to RNA species may also be useful in generating partial hairpin amplicons via, for example, a PHASE amplification reaction. For example, a targeted barcode construct comprising a poly-T sequence can hybridize with an mRNA via its poly-A sequence. The targeted barcode construct can be extended via a reverse transcription reaction (e.g., via the action of a reverse transcriptase) such that a cDNA comprising the barcode construct is generated. These steps can correspond to the first cycle of PHASE amplification described above with respect to FIGS. 15A-15C, except that reverse transcription is used to generate the extension product. Following reverse transcription (e.g., a first PHASE cycle), a barcode construct comprising a random N-mer may prime the extension products such that a partial hairpin is generated as described above with respect to FIGS. 15D-15F. Amplification can continue for additional rounds until the, FIG. 15G) until the desired number of rounds are complete.

In some cases, a plurality of targeted constructs comprising a barcode sequence and a targeted N-mer comprising a poly-T sequence may be coupled to a bead (e.g., a gel bead). In some cases, the plurality of constructs may comprise an identical barcode sequence. The beads may be partitioned (e.g., in fluidic droplets) with sample nucleic acid comprising RNA, the bead(s) in each partition degraded to release the coupled constructs into the partition, and the sample RNA captured via the targeted N-mer of the constructs. Partitions may also comprise barcode constructs (e.g., with barcode sequences identical to the targeted constructs) that comprise a random N-mer. In a first amplification cycle, extension of the targeted constructs can occur via reverse transcription within each partition, to generate extension products comprising the targeted construct. The extension products in each partition can then be primed with the barcode constructs comprising the random N-mer to generate partial hairpin amplicons as described above with respect to FIGS. 15A-15G. Post processing (e.g., addition of additional sequences (e.g., P7, R2), addition of a sample index, etc.) of the generated amplicons may be achieved with any method described herein, including bulk amplification methods (e.g., bulk PCR) and bulk ligation.

In some cases, reverse transcription of RNA in a sample may also be used without the use of a targeted barcode construct. For example, sample nucleic acid comprising RNA may be first subject to a reverse transcription reaction with other types of reverse transcription primers such that cDNA is generated from the RNA. The cDNA that is generated may then undergo targeted or non-targeted amplification as described herein. For example, sample nucleic acid comprising RNA may be subject to a reverse transcription reaction such that cDNA is generated from the RNA. The cDNA may then enter a PHASE amplification reaction, using a barcode construct with a random N-mer as described above with respect to FIGS. 15A-15G, to generate partial hairpin amplicons comprising the construct's barcode sequence. Post processing (e.g., addition of additional sequences (e.g., P7, R2), addition of a sample index, etc.) of the generated partial hairpin amplicons may be achieved with any method described herein, including bulk amplification methods (e.g., bulk PCR) and bulk ligation.

Targeted barcode constructs may also be generated toward specific sequences (e.g., gene sequences) on specific strands of a nucleic acid such that strandedness information is retained for sequencer-ready products generated for each strand. For example, a sample nucleic may comprise double stranded nucleic acid (e.g., double-stranded DNA), such that each strand of nucleic acid comprises one or more different target gene sequences. Complementary DNA strands can comprise different gene sequences due to the opposite 5' to 3' directionalities and/or base composition of each strand. Targeted barcode constructs can be generated for each strand (based on 5' to 3' directionality of the strand) based on the targeted N-mer and configuration of the barcode construct. Example sets of targeted barcode constructs directed to forward and reverse strands of a double-stranded sample nucleic acid are shown in FIG. 28A.

Figure 28A:
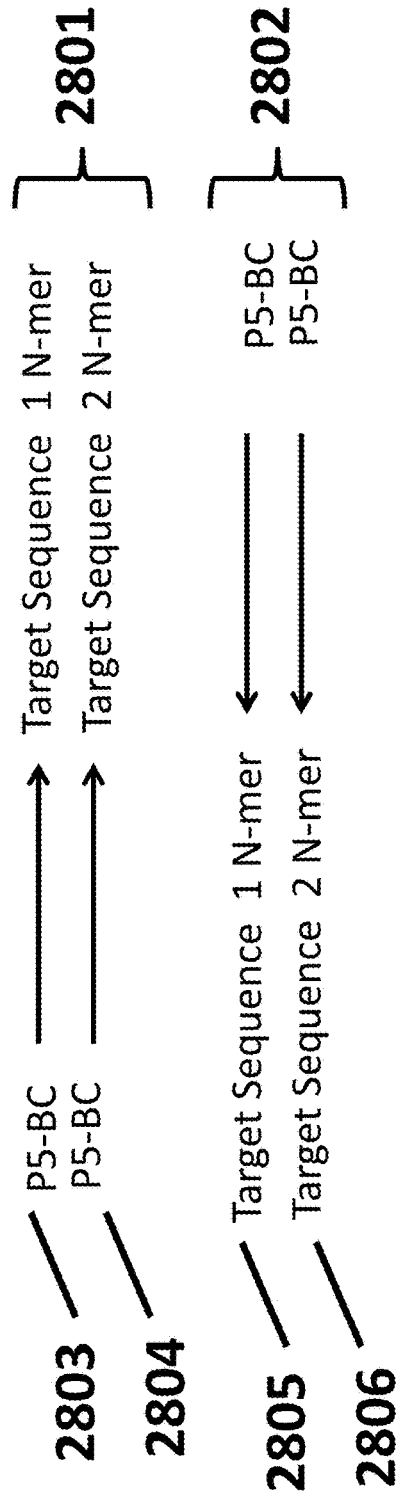
FIGS. 28A-28B are schematic representations of example targeted barcode constructs suitable for strand-specific amplification.

Example sets 2801 and 2802 of targeted barcode constructs each targeted to either of a forward (2801) strand and reverse (2802) strand of a double-stranded sample nucleic acid are shown in FIG. 28A. Set 2801 comprises targeted barcode constructs 2803 and 2804 comprising a P5 sequence, a barcode sequence, and a targeted N-mer to either of a first target sequence (2803) or a second target sequence (2804). Set 2802 comprises targeted barcode constructs 2805 and 2806 comprising a P5 sequence, a barcode sequence, and a targeted N-mer to either of the first target sequence (2805) and the second target sequence (2806). Each construct can also comprise any additional sequences between the barcode and the targeted N-mer (indicated by an arrow in each construct shown in FIG. 28A).

The barcode constructs in set 2801 are configured to prime their respective target sequences on the forward strand of the double-stranded sample nucleic acid. The barcode constructs of set 2802 are configured to prime their respective target sequences on the reverse strand of the double-stranded sample nucleic acid. As shown, the targeted barcode constructs in each set are configured in opposite directionality corresponding to the opposite directionality of forward and reverse strands of the double-stranded sample nucleic acid. Each barcode construct can prime its respective target sequence on its respective strand of sample nucleic acid to generate barcoded amplicons via an amplification reaction, such as any amplification reaction described herein.

Figure 28B:
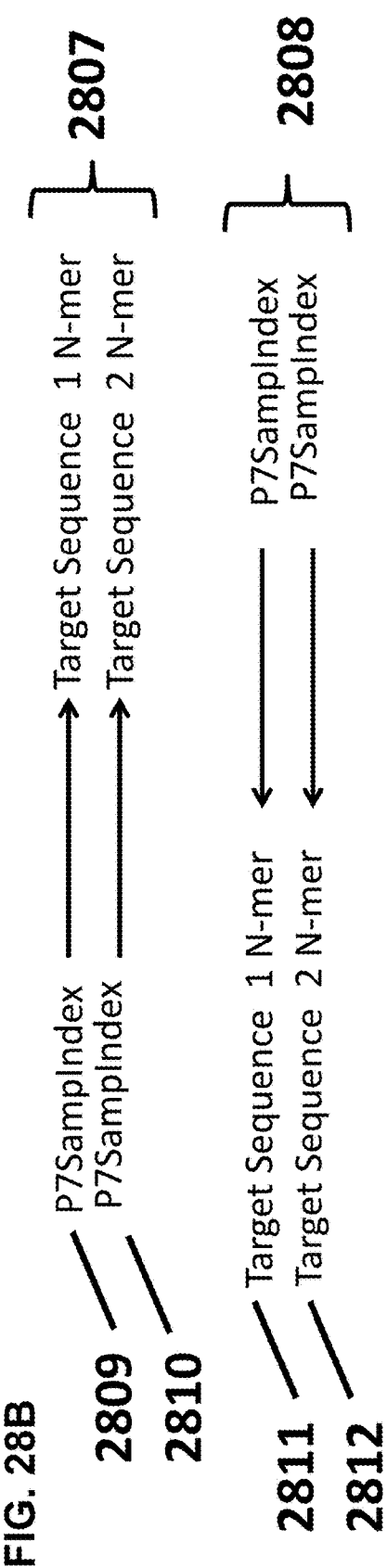

Additional sequences can be added to barcoded amplicons using amplification methods described herein, including bulk amplification, bulk ligation, or a combination thereof. Example sets of primers that may be used to add a sample index and P7 sequence to amplicons generated from the targeted barcode constructs in FIG. 28A are shown in FIG. 28B. Primer set 2808 corresponds to targeted barcode construct set 2801 (e.g., targeted barcode construct 2803 corresponds to primer 2811, targeted barcode construct 2804 corresponds to primer 2812) and primer set 2808 corresponds to targeted barcode construct set 2801 (e.g., targeted barcode construct 2505 corresponds to primer 2809, targeted barcode construct 2806 corresponds to primer 2810). Each primer can prime its respective target sequence on its respective strand and bulk amplification (e.g., bulk PCR) initiated to generate sequencer-ready constructs that include the P7 and sample index sequences in analogous fashion to bulk amplification methods described elsewhere herein. Based on the configuration and directionality of the various components of each sequencer-ready construct (e.g., P5, barcode, targeted N-mer, sample insert, etc.), the strand from which the sequencer-ready product is generated can be determined/is retained.

Libraries of barcode constructs (e.g., targeted barcode constructs) may be generated for both forward and reverse strands of a double stranded nucleic acid. For example, two libraries of beads (e.g., gel beads) comprising targeted barcode constructs may be generated using methods described herein, such that one library comprises targeted barcode constructs for forward strands of sample nucleic acids and the other library comprises targeted barcode constructs for reverse strands of sample nucleic acids. In some cases, each library may comprise beads each comprising an identical targeted N-mer. In some cases, each library may comprise two or more sets of beads, with each bead in a set comprising an identical targeted N-mer (e.g., a targeted N-mer targeted toward a particular gene) and different sets comprising different targeted N-mers. In some cases, the two libraries may be combined such that a library of forward strand and reverse strand beads is generated.

For example, a library can comprise two types of forward strand beads and two types of reverse strand beads, for a total of four types of beads. Each bead in the library may comprise a unique barcode sequence. One type of the forward strand beads and one type of the reverse strand beads may comprise targeted N-mers corresponding to a target sequence (e.g., a target gene sequence). For example, one type of forward strand beads may comprise a targeted barcode construct as shown in 2803 in FIG. 28A and one type of reverse strand beads may comprise a targeted barcode construct as shown in 2805 in FIG. 28A. Analogously, the second type of forward strand beads may comprise a targeted barcode construct as shown in 2804 in FIG. 28A and one type of reverse strand beads may comprise a targeted barcode construct as shown in 2806 in FIG. 28A.

A barcode library comprising forward strand and reverse strand beads (e.g., gel beads), with each bead comprising a unique barcode sequence may be partitioned to barcode sample nucleic acids as described elsewhere herein. For example, the mixed library of two types of forward strand and two types of reverse strand beads described above may be partitioned with a sample nucleic acid (e.g., genomic DNA) and any other desired reagents (e.g., reagents necessary for amplification of the sample nucleic acid, a reducing agent). The partitions may be, for example, fluidic droplets such as droplets of an emulsion. In general, each partition may comprise a bead (e.g., a forward strand bead or a reverse strand bead) coupled to a targeted barcode construct comprising a unique barcode sequence and a targeted N-mer.

In some cases, though, one or more of the partitions may comprise multiple beads of the same type or of different types. The targeted barcode constructs may be released from the bead (e.g., via degradation of the bead—for example, via a reducing agent in cases where the bead is a gel bead comprising disulfide bonds) in the partition and allowed to prime their target sequence on their respective strand (e.g., forward strand or reverse strand) of sample nucleic acid.

A first product strand synthesis may take place in each partition via extension of the hybridized targeted barcode construct, via, for example, linear amplification of the sample nucleic acid. Additional rounds of linear amplification of the sample nucleic acid with the targeted barcode construct, for example, may be used to generate additional copies of the first product strand. First product strands may then be removed from the partitions (e.g., in cases where the partitions are droplets of an emulsion, the emulsion may be broken to release first products) and pooled. The first products may be washed to remove targeted barcode constructs and any other waste products. In some cases, an optional double-stranded digestion may be completed to digest sample nucleic acid and remove it from the first product strands.

Next, the first product strands may be subject to bulk amplification to add additional sequences (e.g., P7, a sample index, etc.) to the first product strands, resulting in the generation of second product strands. The bulk amplification reaction mixture may comprise a plurality of primers, with each primer in the plurality corresponding to one of the bead types (and, thus, type of targeted barcode construct) used to generate the first products strands. For the example library comprising two types of forward strand beads and two types of reverse strand beads described above, primers shown as 2809, 2810, 2811, and 2812 in FIG. 28B may be used to add additional sample index and P7 sequences to first product strands generated from targeted barcode constructs 2803, 2804, 2805, and 2806 respectively via bulk amplification. Second product strands may then be washed to remove primers from the reaction mixture. Fresh primers (e.g., primers comprising P5 and P7 for the example described above) may then be added one or more additional rounds of amplification (e.g., via PCR) to generate final, sequencer-ready products. Thus, final products can comprise the original targeted barcode construct, the strand of sample nucleic acid amplified, and the additional sequences (e.g., P7, sample index) added to first product strands.

Methods described herein may be useful in whole genome amplification. In some embodiments of whole genome amplification, a random primer (e.g., a random N-mer sequence) can be hybridized to a genomic nucleic acid. The random primer can be a component of a larger oligonucleotide that may also include a universal nucleic acid sequence (including any type of universal nucleic acid sequence described herein) and a nucleic acid barcode sequence. In some cases, the universal nucleic acid sequence may comprise one or more uracil containing nucleotides. Moreover, in some cases, the universal nucleic acid sequence may comprise a segment of at least 1, 2, 3, 4, 5, 6, 7, 8, 9, 10, 11, 12, 13, 14, 15, 16, 17, 18, 19, 20, or more nucleotides that do not comprise uracil. The random primer can be extended (e.g., in a primer extension reaction or any other suitable type of nucleic acid amplification reaction) to form an amplified product.

As described elsewhere herein, the amplified product may undergo an intramolecular hybridization reaction to form a hairpin molecule such as, for example, a partial hairpin molecule. In some cases, whole genome amplification may occur in the presence of an oligonucleotide blocker (also referred to as a blocker oligonucleotide elsewhere herein) that may or may not comprise a blocker moiety (e.g., C3 spacer (/3SpC3/), Dideoxy-C (/3ddC/), 3' phosphate, or any other type of blocker moiety described elsewhere herein). Furthermore, the oligonucleotide blocker may be capable of hybridizing to at least a portion of the universal nucleic acid sequence or any other part of an oligonucleotide comprising the random primer.

In some embodiments of whole genome amplification, a genomic component (e.g., a chromosome, genomic nucleic acid such as genomic DNA, a whole genome of an organism, or any other type of genomic component described herein) may be fragmented in a plurality of first fragments. The first fragments can be co-partitioned into a plurality of partitions with a plurality of oligonucleotides. The oligonucleotides in each of the partitions may comprise a primer sequence (including a type of primer sequence described elsewhere herein) and a common sequence (e.g., a barcode sequence). Primer sequences in each partition can then be annealed to a plurality of different regions of the first fragments within each partition. The primer sequences can then be extended along the first fragments to produce amplified first fragments within each partition of the plurality of partitions. The amplified first fragments within the partitions may comprise any suitable coverage (as described elsewhere herein) of the genomic component. In some cases, the amplified first fragments within the partitions may comprise at least 1× coverage, at least 2× coverage, at least 5× coverage, at least 10× coverage, at least 20× coverage, at least 40× coverage, or greater coverage of the genomic component.

VII. Digital Processor

The methods, compositions, devices, and kits of this disclosure may be used with any suitable processor, digital processor or computer. The digital processor may be programmed, for example, to operate any component of a device and/or execute methods described herein. The digital processor may be capable of transmitting or receiving electronic signals through a computer network, such as for example, the Internet and/or communicating with a remote computer. One or more peripheral devices such as screen display, printer, memory, data storage, and/or electronic display adaptors may be in communication with the digital processor. One or more input devices such as keyboard, mouse, or joystick may be in communication with the digital processor. The digital processor may also communicate with detector such that the detector performs measurements at desired or otherwise predetermined time points or at time points determined from feedback received from pre-processing unit or other devices.

Figure 18:
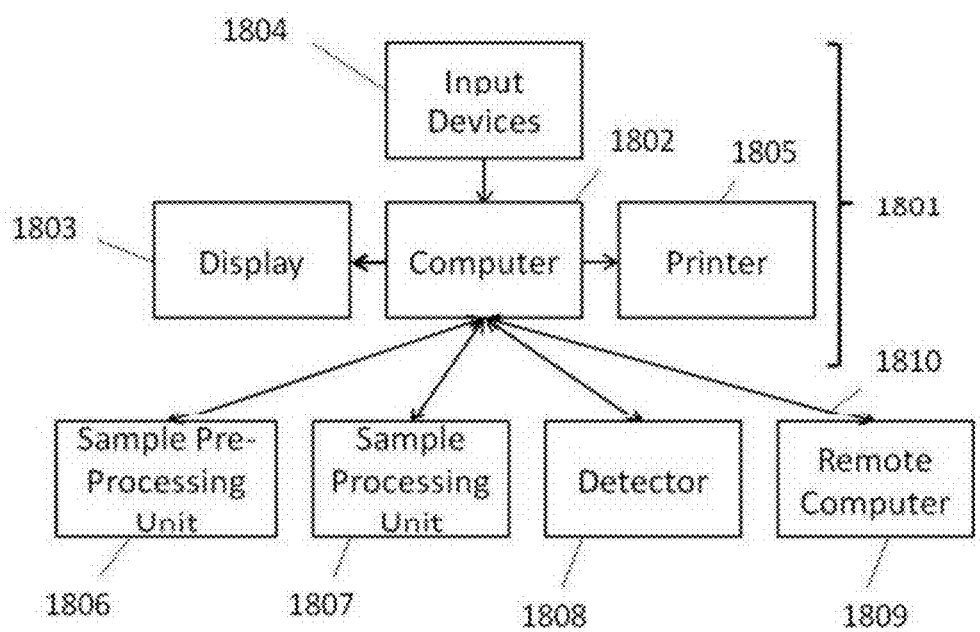
FIG. 18 is a flow diagram of a digital processor and its related components.

A conceptual schematic for an example control assembly is shown in FIG. 18. A computer, serves as the central hub for control assembly. The computer is in communication with a display, one or more input devices (e.g., a mouse, keyboard, camera, etc.), and optionally a printer. The control assembly, via its computer, is in communication with one or more devices: optionally a sample pre-processing unit, one or more sample processing units (such as a sequence, thermocycler, or microfluidic device), and optionally a detector. The control assembly may be networked, for example, via an Ethernet connection. A user may provide inputs (e.g., the parameters necessary for a desired set of nucleic acid amplification reactions or flow rates for a microfluidic device) into the computer, using an input device. The inputs are interpreted by the computer, to generate instructions. The computer communicates such instructions to the optional sample pre-processing unit, the one or more sample processing units, and/or the optional detector for execution.

Moreover, during operation of the optional sample pre-processing unit, one or more sample processing units, and/or the optional detector, each device may communicate signals back to computer. Such signals may be interpreted and used by computer to determine if any of the devices require further instruction. The computer may also modulate the sample pre-processing unit such that the components of a sample are mixed appropriately and fed, at a desired or otherwise predetermined rate, into the sample processing unit (such as the microfluidic device).

The computer may also communicate with a detector such that the detector performs measurements at desired or otherwise predetermined time points or at time points determined from feedback received from pre-processing unit or sample processing unit. The detector may also communicate raw data obtained during measurements back to the computer for further analysis and interpretation.

Analysis may be summarized in formats useful to an end user via a display and/or printouts generated by a printer. Instructions or programs used to control the sample pre-processing unit, the sample processing unit, and/or the detector; data acquired by executing any of the methods described herein; or data analyzed and/or interpreted may be transmitted to or received from one or more remote computers, via a network, which, for example, could be the Internet.

In some embodiments, the method of bead formation may be executed with the aid of a digital processor in communication with a droplet generator. The digital processor may control the speed at which droplets are formed or control the total number of droplets that are generated. In some embodiments, the method of attaching samples to barcoded beads may be executed with the aid of a digital processor in communication with the microfluidic device. Specifically, the digital processor may control the volumetric amount of sample and/or beads injected into the input channels and may also control the flow rates within the channels. In some embodiments, the method of attaching oligonucleotides, primers, and the like may be executed with the aid of a digital processor in communication with a thermocycler or other programmable heating element. Specifically, the digital processor may control the time and temperature of cycles during ligation or amplification. In some embodiments, the method of sequencing a sample may be executed with the aid of a digital processor in communication with a sequencing device.

VIII. Kits

In some cases, this disclosure provides a kit comprising a microfluidic device, a plurality of barcoded beads, and instructions for utilizing the microfluidic device and combining barcoded beads with customer sample to create fluidic droplets containing both. As specified throughout this disclosure, any suitable sample may be incorporated into the fluidic droplets. As described throughout this disclosure, a bead may be designed to be degradable or non-degradable. In this case, the kit may or may not include a reducing agent for bead degradation.

In some cases, this disclosure provides a kit comprising a plurality of barcoded beads, suitable amplification reagents, e.g., optionally including one or more of polymerase enzymes, nucleoside triphosphates or their analogues, primer sequences, buffers, and the like, and instructions for combining barcoded beads with customer sample. As specified throughout this disclosure, any suitable sample may be used. As specified throughout this disclosure, the amplification reagents may include a polymerase that will not accept or process uracil-containing templates. A kit of this disclosure may also provide agents to form an emulsion, including an oil and surfactant.

IX. Applications

Barcoding Sample Materials

The methods, compositions and systems described herein are particularly useful for attaching barcodes, and particularly barcode nucleic acid sequences, to sample materials and components of those sample materials. In general, this is accomplished by partitioning sample material components into separate partitions or reaction volumes in which are co-partitioned a plurality of barcodes, which are then attached to sample components within the same partition.

In an exemplary process, a first partition is provided that includes a plurality of oligonucleotides (e.g., nucleic acid barcode molecules) that each comprise a common nucleic acid barcode sequence. The first partition may comprise any of a variety of portable partitions, e.g., a bead (e.g., a degradable bead, a gel bead), a droplet (e.g., an aqueous droplet in an emulsion), a microcapsule, or the like, to which the oligonucleotides are releasably attached, releasably coupled, or are releasably associated. Moreover, any suitable number of oligonucleotides may be included in the first partition, including numbers of oligonucleotides per partition described elsewhere herein. For example, the oligonucleotides may be releasably attached to, releasably coupled to, or releasably associated with the first partition via a cleavable linkage such as, for example, a chemically cleavable linkage (e.g., a disulfide linkage, or any other type of chemically cleavable linkage described herein), a photo-cleavable linkage, and/or a thermally cleavable linkage. In some cases, the first partition may be a bead and the bead may be a degradable bead (e.g., a photodegradable bead, a chemically degradable bead, a thermally degradable bead, or any other type of degradable bead described elsewhere herein). Moreover, the bead may comprise chemically-cleavable cross-linking (e.g., disulfide cross-linking) as described elsewhere herein.

The first partition is then co-partitioned into a second partition, with a sample material, sample material component, fragment of a sample material, or a fragment of a sample material component. The sample material (or component or fragment thereof) may be any appropriate sample type, including the example sample types described elsewhere herein. In cases where a sample material or component of a sample material comprises one or more nucleic acid fragments, the one or more nucleic acid fragments may be of any suitable length, including, for example, nucleic acid fragment lengths described elsewhere herein. The second partition may include any of a variety of partitions, including for example, wells, microwells, nanowells, tubes or containers, or in preferred cases droplets (e.g., aqueous droplets in an emulsion) or microcapsules in which the first partition may be co-partitioned. In some cases, the first partition may be provided in a first aqueous fluid and the sample material, sample material component, or fragment of a sample material component may be provided in a second aqueous fluid. During co-partitioning, the first aqueous fluid and second aqueous fluid may be combined within a droplet within an immiscible fluid. In some cases, the second partition may comprise no more than one first partition. In other cases, the second partition may comprise no more than one, two, three, four, five, six, seven, eight, nine, or ten first partitions. In other cases, the second partition may comprise at least one, two, three, four, five, six, seven, eight, nine, ten, or more first partitions.

Once co-partitioned, the oligonucleotides comprising the barcode sequences may be released from the first partition (e.g., via degradation of the first partition, cleaving a chemical linkage between the oligonucleotides and the first partition, or any other suitable type of release, including types of release described elsewhere herein) into the second partition, and attached to the sample components co-partitioned therewith. In some cases, the first partition may comprise a bead and the crosslinking of the bead may comprise a disulfide linkage. In addition, or as an alternative, the oligonucleotides may be linked to the bead via a disulfide linkage. In either case, the oligonucleotides may be released from the first partition by exposing the first partition to a reducing agent (e.g., DTT, TCEP, or any other exemplary reducing agent described elsewhere herein).

As noted elsewhere herein, attachment of the barcodes to sample components includes the direct attachment of the barcode oligonucleotides to sample materials, e.g. through ligation, hybridization, or other associations. Additionally, in many cases, for example, in barcoding of nucleic acid sample materials (e.g., template nucleic acid sequences, template nucleic acid molecules), components or fragments thereof, such attachment may additionally comprise use of the barcode containing oligonucleotides that also comprise as priming sequences. The priming sequence can be complementary to at least a portion of a nucleic acid sample material and can be extended along the nucleic acid sample materials to create complements to such sample materials, as well as at least partial amplification products of those sequences or their complements.

In another exemplary process, a plurality of first partitions can be provided that comprise a plurality of different nucleic acid barcode sequences. Each of the first partitions can comprise a plurality of nucleic acid barcode molecules having the same nucleic acid barcode sequence associated therewith. Any suitable number of nucleic acid barcode molecules may be associated with each of the first partitions, including numbers of nucleic acid barcode molecules per partition described elsewhere herein. The first partitions may comprise any suitable number of different nucleic acid barcode sequences, including, for example, at least about 2, 10, 100, 500, 1000, 5000, 10000, 50000, 100000, 500000, 1000000, 5000000, 10000000, 50000000, or 1000000000, or more different nucleic acid barcode sequences.

In some cases, the plurality of first partitions may comprise a plurality of different first partitions where each of the different first partitions comprises a plurality of releasably attached, releasably coupled, or releasably associated oligonucleotides comprising a common barcode sequence, with the oligonucleotides associated with each different first partitions comprising a different barcode sequence. The number of different first partitions may be, for example, at least about 2, 10, 100, 500, 1000, 5000, 10000, 50000, 100000, 500000, 1000000, 5000000, 10000000, 50000000, or 1000000000, or more different first partitions.

The first partitions may be co-partitioned with sample materials, fragments of a sample material, components of a sample material, or fragments of a component(s) of a sample material into a plurality of second partitions. In some cases, a subset of the second partitions may comprise the same nucleic acid barcode sequence. For example, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more of the second partitions may comprise the same nucleic acid barcode sequence. Moreover, the distribution of first partitions per second partition may also vary according to, for example, occupancy rates described elsewhere herein. In cases where the plurality of first partitions comprises a plurality of different first partitions, each different first partition may be disposed within a separate second partition.

Following co-partitioning, the nucleic acid barcode molecules associated with the first partitions can be released into the plurality of second partitions. The released nucleic acid barcode molecules can then be attached to the sample materials, sample material components, fragments of a sample material, or fragments of sample material components, within the second partitions. In the case of barcoded nucleic acid species (e.g., barcoded sample nucleic acid, barcoded template nucleic acid, barcoded fragments of one or more template nucleic acid sequences, etc.), the barcoded nucleic acid species may be sequenced as described elsewhere herein.

In another exemplary process, an activatable nucleic acid barcode sequence may be provided and partitioned with one or more sample materials, components of a sample material, fragments of a sample material, or fragments of a component(s) of a sample material into a first partition. With the first partition, the activatable nucleic acid barcode sequence may be activated to produce an active nucleic acid barcode sequence. The active nucleic acid barcode sequence can then be attached to the one or more sample materials, components of a sample material, fragments of a sample material, or fragments of a component(s) of a sample material.

In some cases, the activatable nucleic acid barcode sequence may be coupled to a second partition that is also partitioned in the first partition with the activatable nucleic acid barcode sequence. As described elsewhere herein, an activatable nucleic acid barcode sequence may be activated by releasing the activatable nucleic acid barcode sequence from an associated partition (e.g., a bead). Thus, in cases where an activatable nucleic acid barcode sequence is associated with a second partition (e.g., a bead) that is partitioned in a first partition (e.g., a fluidic droplet), the activatable nucleic acid barcode sequence may be activated by releasing the activatable nucleic acid barcode sequence from its associated second partition. In addition, or as an alternative, an activatable barcode may also be activated by removing a removable blocking or protecting group from the activatable nucleic acid barcode sequence.

In another exemplary process, a sample of nucleic acids may be combined with a library of barcoded beads (including types of beads described elsewhere herein) to form a mixture. In some cases, the barcodes of the beads may, in addition to a barcode sequence, each comprise one or more additional sequences such as, for example, a universal sequence and/or a functional sequence (e.g., a random N-mer or a targeted N-mer, as described elsewhere herein). The mixture may be partitioned into a plurality of partitions, with at least a subset of the partitions comprising at most one barcoded bead. Within the partitions, the barcodes may be released from the beads, using any suitable route, including types of release described herein. A library of barcoded beads may be generated via any suitable route, including the use of methods and compositions described elsewhere herein. In some cases, the sample of nucleic acids may be combined with the library of barcoded beads and/or the resulting mixture partitioned with the aid of a microfluidic device, as described elsewhere herein. In cases where the released barcodes also comprise a primer sequence (e.g., such as a targeted N-mer or a random N-mer as described elsewhere herein), the primer sequences of the barcodes may be hybridize with the sample nucleic acids and, if desired, an amplification reaction can be completed in the partitions.

Polynucleotide Sequencing

Generally, the methods and compositions provided herein are useful for preparation of oligonucleotide fragments for downstream applications such as sequencing. In particular, these methods, compositions and systems are useful in the preparation of sequencing libraries. Sequencing may be performed by any available technique. For example, sequencing may be performed by the classic Sanger sequencing method. Sequencing methods may also include: high-throughput sequencing, pyrosequencing, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, Maxim-Gilbert sequencing, primer walking, and any other sequencing methods known in the art.

For example, a plurality of target nucleic acid sequences may be sequenced by providing a plurality of target nucleic sequences and separating the target nucleic acid sequences into a plurality of separate partitions. Each of the separate partitions can comprise one or more target nucleic acid sequences and a plurality of oligonucleotides. The separate partitions may comprise any suitable number of different barcode sequences (e.g., at least 1,000 different barcode sequences, at least 10,000 different barcode sequences, at least 100,000 different barcode sequences, at least 1,000,000 different barcode sequences, at least 10,000,000 different barcode sequences, or any other number of different barcode sequences as described elsewhere herein). Moreover, the oligonucleotides in a given partition can comprise a common barcode sequence. The oligonucleotides and associated common barcode sequence in a given partition can be attached to fragments of the one or more target nucleic acids or to copies of portions of the target nucleic acid sequences within the given partition. Following attachment, the separate partitions can then be pooled. The fragments of the target nucleic acids or the copies of the portions of the target nucleic acids and attached barcode sequences can then be sequenced.

In another example, a plurality of target nucleic acid sequences may be sequenced by providing the target nucleic acid sequences and separating them into a plurality of separate partitions. Each partition of the plurality of separate partitions can include one or more of the target nucleic acid sequences and a bead having a plurality of attached oligonucleotides. The oligonucleotides attached to a given bead may comprise a common barcode sequence. The oligonucleotides associated with a bead can be attached to fragments of the target nucleic acid sequences or to copies of portions of the target nucleic acid sequences within a given partition, such that the fragments or copies of the given partition are also attached to the common barcode sequence associated with the bead. Following attachment of the oligonucleotides to the fragments of the target nucleic acid sequences or the copies of the portions of the target nucleic acid sequences, the separate partitions can then be pooled. The fragments of the target nucleic acid sequences or the copies of the portions of the target nucleic acid sequences and any attached barcode sequences can then be sequenced (e.g., using any suitable sequencing method, including those described elsewhere herein) to provide barcoded fragment sequences or barcoded copy sequences. The barcoded fragment sequences or barcoded copy sequences can be assembled into one or more contiguous nucleic acid sequence based, in part, upon a barcode portion of the barcoded fragment sequences or barcoded copy sequences.

In some cases, varying numbers of barcoded-oligonucleotides are sequenced. For example, in some cases about 30%-90% of the barcoded-oligonucleotides are sequenced. In some cases, about 35%-85%, 40%-80%, 45%-75%, 55%-65%, or 50%-60% of the barcoded-oligonucleotides s are sequenced. In some cases, at least about 30%, 40%, 50%, 60%, 70%, 80%, or 90% of barcoded-oligonucleotides are sequenced. In some cases, less than about 30%, 40%, 50%, 60%, 70%, 80%, or 90% of the barcoded-oligonucleotides are sequenced.

In some cases, sequences from fragments are assembled to provide sequence information for a contiguous region of the original target polynucleotide that may be longer than the individual sequence reads. Individual sequence reads may be about 10-50, 50-100, 100-200, 200-300, 300-400, or more nucleotides in length. Examples of sequence assembly methods include those set forth in U.S. Provisional Patent Application No. 62/017,589, filed of even date herewith.

The identities of the barcodes may serve to order the sequence reads from individual fragments as well as to differentiate between haplotypes. For example, when combining individual sample fragments and barcoded beads within fluidic droplets, parental polynucleotide fragments may be separated into different droplets. With an increase in the number of fluidic droplets and beads within a droplet, the likelihood of a fragment from both a maternal and paternal haplotype contained within the same fluidic droplet associated with the same bead may become negligibly small Thus, sequence reads from fragments in the same fluidic droplet and associated with the same bead may be assembled and ordered.

In at least one example, the present disclosure provides nucleic acid sequencing methods, systems compositions, and combinations of these that are useful in providing myriad benefits in both sequence assembly and read-length equivalent, but do so with very high throughput and reduced sample preparation time and cost.

In general, the sequencing methods described herein provide for the localized tagging or barcoding of fragments of genetic sequences. By tagging fragments that derive from the same location within a larger genetic sequence, one can utilize the presence of the tag or barcode to inform the assembly process as alluded to above. In addition, the methods described herein can be used to generate and barcode shorter fragments from a single, long nucleic acid molecule. Sequencing and assembly of these shorter fragments provides a long read equivalent sequence, but without the need for low throughput longer read-length sequencing technologies.

Figure 39:
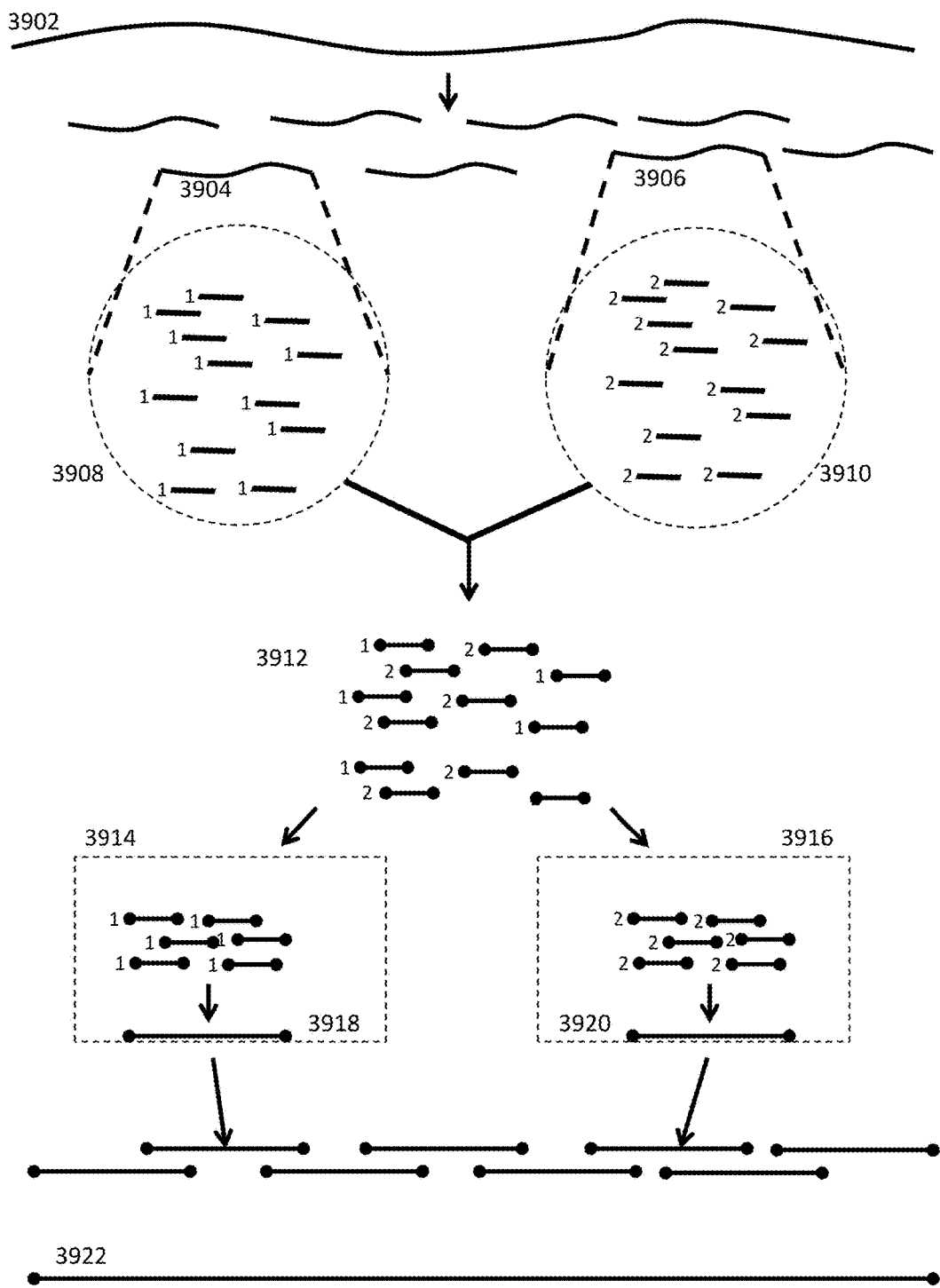
FIG. 39 provides a schematic illustration of an exemplary application of the methods described herein to nucleic acid sequencing and assembly.

FIG. 39 provides a schematic illustration of an example sequencing method. As shown, a first genetic component 3902 that may comprise, for example, a chromosome or other large nucleic acid molecule, is fragmented into a set of large first nucleic acid fragments, e.g., including fragments 3904 and 3906. The fragments of the large genetic component may be non-overlapping or overlapping, and in some cases, may include multifold overlapping fragments, in order to provide for high confidence assembly of the sequence of the larger component. In some cases, the fragments of the larger genetic component provide 1×, 2×, 5×, 10×, 20×, 40× or greater coverage of the larger component.

One or more of the first fragments 3904 is then processed to separately provide overlapping set of second fragments of the first fragment(s), e.g., second fragment sets 3908 and 3910. This processing also provides the second fragments with a barcode sequence that is the same for each of the second fragments derived from a particular first fragment. As shown, the barcode sequence for second fragment set 3908 is denoted by "1" while the barcode sequence for fragment set 3910 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 3908 and 3910, may then be pooled for sequencing. Once sequenced, the sequence reads 3912 can be attributed to their respective fragment set, e.g., as shown in aggregated reads 3914 and 3916, at least in part based upon the included barcodes, and optionally, and preferably, in part based upon the sequence of the fragment itself. The attributed sequence reads for each fragment set are then assembled to provide the assembled sequence for the first fragments, e.g., fragment sequences 3918 and 3920, which in turn, may be assembled into the sequence 3922 of the larger genetic component.

In accordance with the foregoing, a large genetic component, such as a long nucleic acid fragment, e.g., 1, 10, 20, 40, 50, 75, 100, 1000 or more kb in length, a chromosomal fragment or whole chromosome, or part of or an entire genome (e.g., genomic DNA) is fragmented into smaller first fragments. Typically, these fragments may be anywhere from about 1000 to about 100000 bases in length. In certain preferred aspects, the fragments will be between about 1 kb and about 100 kb, or between about 5 kb and about 50 kb, or from about 10 kb to about 30 kb, and in some cases, between about 15 kb and about 25 kb. Fragmentation of these larger genetic components may be carried out by any of a variety of convenient available processes, including commercially available shear based fragmenting systems, e.g., Covaris fragmentation systems, size targeted fragmentation systems, e.g., Blue Pippin (Sage Sciences), enzymatic fragmentation processes, e.g., using restriction endonucleases, or the like. As noted above, the first fragments of the larger genetic component may comprise overlapping or non-overlapping first fragments. Although described here as being fragmented prior to partitioning, it will be appreciated that fragmentation may optionally and/or additionally be performed later in the process, e.g., following one or more amplification steps, to yield fragments of a desired size for sequencing applications.

In preferred aspects, the first fragments are generated from multiple copies of the larger genetic component or portions thereof, so that overlapping first fragments are produced. In preferred aspects, the overlapping fragments will constitute greater than 1× coverage, greater than 2× coverage, greater than 5× coverage, greater than 10× coverage, greater than 20× coverage, greater than 40× coverage, or even greater coverage of the underlying larger genetic component or portion thereof. The first fragments are then segregated to different reaction volumes. In some cases, the first fragments may be separated so that reaction volumes contain one or fewer first fragments. This is typically accomplished by providing the fragments in a limiting dilution in solution, such that allocation of the solution to different reaction volumes results in a very low probability of more than one fragment being deposited into a given reaction volume. However, in most cases, a given reaction volume may include multiple different first fragments, and can even have 2, 5, 10, 100, 100 or even up to 10,000 or more different first fragments in a given reaction volume. Again, achieving a desired range of fragment numbers within individual reaction volumes is typically accomplished through the appropriate dilution of the solution from which the first fragments originate, based upon an understanding of the concentration of nucleic acids in that starting material.

The reaction volumes may include any of variety of different types of vessels or partitions. For example, the reaction volumes may include conventional reaction vessels, such as test tubes, reaction wells, microwells, nanowells, or they may include less conventional reaction volumes, such as droplets within a stabilized emulsion, e.g., a water in oil emulsion system. In preferred aspects, droplets are preferred as the reaction volumes for their extremely high multiplex capability, e.g., allowing the use of hundreds of thousands, millions, tens of millions or even more discrete droplet/reaction volumes within a single container. Within each reaction volume, the fragments that are contained therein are then subjected to processing that both derives sets of overlapping second fragments of each of the first fragments, and also provides these second fragments with attached barcode sequences. As will be appreciated, in preferred aspects, the first fragments are partitioned into droplets that also contain one or more microcapsules or beads that include the members of the barcode library used to generate and barcode the second fragments.

In preferred aspects, the generation of these second fragments is carried out through the introduction of primer sequences that include the barcode sequences and that are capable of hybridizing to portions of the first fragment and be extended along the first fragment to provide a second fragment including the barcode sequence. These primers may comprise targeted primer sequences, e.g., to derive fragments that overlap specific portions of the first fragment, or they may comprise universal priming sequences, e.g., random primers, that will prime multiple different regions of the first fragments to create large and diverse sets of second fragments that span the first fragment and provide multifold overlapping coverage. These extended primer sequences may be used as the second fragments, or they may be further replicated or amplified. For example, iterative priming against the extended sequences, e.g., using the same primer containing barcoded oligonucleotides. In certain preferred aspects, the generation of the second sets of fragments generates the partial hairpin replicates of portions of the first fragment, as described elsewhere herein that each include barcode sequences, e.g., for PHASE amplification as described herein. As noted elsewhere herein, the formation of the partial hairpin is generally desired to prevent repriming of the replicated strand, e.g., making a copy of a copy. As such, the partial hairpin is typically preferentially formed from the amplification product during annealing as compared to a primer annealing to the amplification product, e.g., the hairpin will have a higher Tm than the primer product pair.

The second fragments are generally selected to be of a length that is suitable for subsequent sequencing. For short read sequencing technologies, such fragments will typically be from about 50 bases to about 1000 bases in sequenceable length, from about 50 bases to about 900 bases in sequenceable length, from about 50 bases to about 800 bases in sequenceable length, from about 50 bases to about 700 bases in sequenceable length, from about 50 bases to about 600 bases in sequenceable length, from about 50 bases to about 500 bases in sequenceable length, from about 50 bases to about 400 bases in sequenceable length, from about 50 bases to about 300 bases in sequenceable length, from about 50 bases to about 250 bases in sequenceable length, from about 50 bases to about 200 bases in sequenceable length, or from about 50 bases to about 100 bases in sequenceable length, including the barcode sequence segments, and functional sequences that are subjected to the sequencing process.

Once the overlapping, barcoded second fragment sets are generated, they may be pooled for subsequent processing and ultimately, sequencing. For example, in some cases, the barcoded fragments may be subsequently subjected to additional amplification, e.g., PCR amplification, as described elsewhere herein. Likewise, these fragments may additionally, or concurrently, be provided with sample index sequences to identify the sample from which collections of barcoded fragments have derived, as well as providing additional functional sequences for use in sequencing processes.

In addition, clean up steps may also optionally be performed, e.g., to purify nucleic acid components from other impurities, to size select fragment sets for sequencing, or the like. Such clean up steps may include purification and/or size selection upon SPRI beads (such as Ampure® beads, available from Beckman Coulter, Inc.). In some cases, multiple process steps may be carried out in an integrated process while the fragments are associated with SPRI beads, e.g., as described in Fisher et al., Genome Biol. 2011:12(1): R1 (E-pub Jan. 4, 2011), which is incorporated herein by reference in its entirety for all purposes.

As noted previously, in many cases, short read sequencing technologies are used to provide the sequence information for the second fragment sets. Accordingly, in preferred aspects, second fragment sets will typically comprise fragments that, when including the barcode sequences, will be within the read length of the sequencing system used. For example, for Illumina HiSeq® sequencing, such fragments may be between generally range from about 100 bases to about 200 bases in length, when carrying out paired end sequencing. In some cases, longer second fragments may be sequenced when accessing only the terminal portions of the fragments by the sequencing process.

As noted above with reference to FIG. 39, the sequence reads for the various second fragments are then attributed to their respective starting nucleic acid segment based in part upon the presence of a particular barcode sequence, and in some cases, based in part on the actual sequence of the fragment, i.e., a non-barcode portion of the fragment sequence. As will be appreciated, despite being based upon short sequence data, one can infer that two sequences sharing the same barcode likely originated from the same longer first fragment sequence, especially where such sequences are otherwise assemble-able into a contiguous sequence segment, e.g., using other overlapping sequences bearing the common barcode. Once the first fragments are assembled, they may be assembled into larger sequence segments, e.g., the full length genetic component.

In one exemplary process, one or more fragments of one or more template nucleic acid sequences may be barcoded using a method described herein. A fragment of the one or more fragments may be characterized based at least in part upon a nucleic acid barcode sequence attached thereto. Characterization of the fragment may also include mapping the fragment to its respective template nucleic acid sequence or a genome from which the template nucleic acid sequence was derived. Moreover, characterization may also include identifying an individual nucleic acid barcode sequence and a sequence of a fragment of a template nucleic acid sequence attached thereto.

In some cases, sequencing methods described herein may be useful in characterizing a nucleic acid segment or target nucleic acid. In some example methods, a nucleic acid segment may be characterized by co-partitioning the nucleic acid segment and a bead (e.g., including any suitable type of bead described herein) comprising a plurality of oligonucleotides that include a common nucleic acid barcode sequence, into a partition (including any suitable type of partition described herein, such as, for example, a droplet). The oligonucleotides may be releasably attached to the bead (e.g., releasable from the bead upon application of a stimulus to the bead, such as, for example, a thermal stimulus, a photo stimulus, and a chemical stimulus) as described elsewhere herein, and/or may comprise one or more functional sequences (e.g., a primer sequence, a primer annealing sequence, an immobilization sequence, any other suitable functional sequence described elsewhere herein, etc.) and/or one or more sequencing primer sequences as described elsewhere herein. Moreover, any suitable number of oligonucleotides may be attached to the bead, including numbers of oligonucleotides attached to beads described elsewhere herein.

Within the partition, the oligonucleotides may be attached to fragments of the nucleic segment or to copies of portions of the nucleic acid segment, such that the fragments or copies are also attached to the common nucleic barcode sequence. The fragments may be overlapping fragments of the nucleic acid segment and may, for example, provide greater than 2× coverage, greater than 5× coverage, greater than 10× coverage, greater than 20× coverage, greater than 40× coverage, or even greater coverage of the nucleic acid segment. In some cases, the oligonucleotides may comprise a primer sequence capable of annealing with a portion of the nucleic acid segment or a complement thereof. In some cases, the oligonucleotides may be attached by extending the primer sequences of the oligonucleotides to replicate at least a portion of the nucleic acid segment or complement thereof, to produce a copy of at least a portion of the nucleic acid segment comprising the oligonucleotide, and, thus, the common nucleic acid barcode sequence.

Following attachment of the oligonucleotides to the fragments of the nucleic acid segment or to the copies of the portions of the nucleic acid segment, the fragments of the nucleic acid segment or the copies of the portions of the nucleic acid segment and the attached oligonucleotides (including the oligonucleotide's barcode sequence) may be sequenced via any suitable sequencing method, including any type of sequencing method described herein, to provide a plurality of barcoded fragment sequences or barcoded copy sequences. Following sequencing, the fragments of the nucleic acid segment or the copies of the portions of the nucleic acid segment can be characterized as being linked within the nucleic acid segment at least in part, upon their attachment to the common nucleic acid barcode sequence. As will be appreciated, such characterization may include sequences that are characterized as being linked and contiguous, as well as sequences that may be linked within the same fragment, but not as contiguous sequences. Moreover, the barcoded fragment sequences or barcoded copy sequences generated during sequencing can be assembled into one or more contiguous nucleic acid sequences based at least in part on the common nucleic acid barcode sequence and/or a non-barcode portion of the barcoded fragment sequences or barcoded copy sequences.

In some cases, a plurality of nucleic acid segments (e.g., fragments of at least a portion of a genome, as described elsewhere herein) may be co-partitioned with a plurality of different beads in a plurality of separate partitions, such that each partition of a plurality of different partitions of the separate partitions contains a single bead. The plurality of different beads may comprise a plurality of different barcode sequences (e.g., at least 1,000 different barcode sequences, at least 10,000 different barcode sequences, at least 100,000 different barcode sequences, at least 1,000,000 different barcodes sequences, or any other number of different barcode sequences as described elsewhere herein). In some cases, two or more, three or more, four or more, five or more, six or more, seven or more of the plurality of separate partitions may comprise beads that comprise the same barcode sequence. In some cases, at least 0.01%, 0.1%, 1%, 5%, 10%, 15%, 20%, 25%, 30%, 35%, 40%, 45%, 50%, 55%, 60%, 65%, 70%, 75%, 80%, 85%, 90%, 95%, or 99% of the separate partitions may comprise beads having the same barcode sequence. Moreover, each bead may comprise a plurality of attached oligonucleotides that include a common nucleic acid barcode sequence.

Following co-partitioning, barcode sequences can be attached to fragments of the nucleic acid segments or to copies of portions of the nucleic acid segments in each partition. The fragments of the nucleic acid segments or the copies of the portions of the nucleic acid segments can then be pooled from the separate partitions. After pooling, the fragments of the nucleic acid segments or copies of the portions of the nucleic acid segments and any associated barcode sequences can be sequenced (e.g., using any suitable sequencing method, including those described herein) to provide sequenced fragment or sequenced copies. The sequenced fragments or sequenced copies can be characterized as deriving from a common nucleic acid segment, based at least in part upon the sequenced fragments or sequenced copies comprising a common barcode sequence. Moreover, sequences obtained from the sequenced fragments or sequenced copies may be assembled to provide a contiguous sequence of a sequence (e.g., at least a portion of a genome) from which the sequenced fragments or sequenced copies originated. Sequence assembly from the sequenced fragments or sequenced copies may be completed based, at least in part, upon each of a nucleotide sequence of the sequenced fragments and a common barcode sequence of the sequenced fragments.

In another example method, a target nucleic acid may be characterized by partitioning fragments of the target nucleic acid into a plurality of droplets. Each droplet can comprise a bead attached to a plurality of oligonucleotides comprising a common barcode sequence. The common barcode sequence can be attached to fragments of the fragments of the target nucleic acid in the droplets. The droplets can then be pooled and the fragments and associated barcode sequences of the pooled droplets sequenced using any suitable sequencing method, including sequencing methods described herein. Following sequencing, the fragments of the fragments of the target nucleic acid may be mapped to the fragments of the target nucleic acid based, at least in part, upon the fragments of the fragments of the target nucleic acid comprising a common barcode sequence.

The application of the methods, compositions and systems described herein in sequencing may generally be applicable to any of a variety of different sequencing technologies, including NGS sequencing technologies such as Illumina MiSeq, HiSeq and X10 Sequencing systems, as well as sequencing systems available from Life Technologies, Inc., such as the Ion Torrent line of sequencing systems. While discussed in terms of barcode sequences, it will be appreciated that the sequenced barcode sequences may not include the entire barcode sequence that is included, e.g., accounting for sequencing errors. As such, when referring to characterization of two barcode sequences as being the same barcode sequence, it will be appreciated that this may be based upon recognition of a substantial portion of a barcode sequence, e.g., varying by fewer than 5, 4, 3, 2 or even a single base.

Sequencing from Small Numbers of Cells

Methods provided herein may also be used to prepare polynucleotides contained within cells in a manner that enables cell-specific information to be obtained. The methods enable detection of genetic variations from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method may comprise partitioning a cellular sample (or crude cell extract) such that at most one cell (or extract of one cell) is present within a partition, e.g., fluidic droplet, and is co-partitioned with the barcode oligonucleotides, e.g., as described above. Processing then involves lysing the cells, fragmenting the polynucleotides contained within the cells, attaching the fragmented polynucleotides to barcoded beads, pooling the barcoded beads, and sequencing the resulting barcoded nucleic acid fragments.

As described elsewhere herein, the barcodes and other reagents may be encapsulated within, coated on, associated with, or dispersed within a bead (e.g. gel bead). The bead may be loaded into a fluidic droplet contemporaneously with loading of a sample (e.g. a cell), such that each cell is contacted with a different bead. This technique may be used to attach a unique barcode to oligonucleotides obtained from each cell. The resulting tagged oligonucleotides may then be pooled and sequenced, and the barcodes may be used to trace the origin of the oligonucleotides. For example, oligonucleotides with identical barcodes may be determined to originate from the same cell, while oligonucleotides with different barcodes may be determined to originate from different cells.

The methods described herein may be used to detect a specific gene mutation that may indicate the presence of a disease, such as cancer. For example, detecting the presence of a V600 mutation in the BRAF gene of a colon tissue sample may indicate the presence of colon cancer. In other cases, prognostic applications may include the detection of a mutation in a specific gene or genes that may serve as increased risk factors for developing a specific disease. For example, detecting the presence of a BRCA1 mutation in a mammary tissue sample may indicate a higher level of risk to developing breast cancer than a person without this mutation. In some examples, this disclosure provides methods of identifying mutations in two different oncogenes (e.g., KRAS and EGRF). If the same cell comprises genes with both mutations, this may indicate a more aggressive form of cancer. In contrast, if the mutations are located in two different cells, this may indicate that the cancer may be more benign, or less advanced.

Analysis of Gene Expression

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

Cells may be placed directly into a fluidic droplet and lysed. After lysis, the methods of the disclosure may be used to fragment and barcode the oligonucleotides of the cell for sequencing. Oligonucleotides may also be extracted from cells prior to introducing them into a fluidic droplet used in a method of the disclosure. Reverse transcription of mRNA may be performed in a fluidic droplet described herein, or outside of such a fluidic droplet. Sequencing cDNA may provide an indication of the abundance of a particular transcript in a particular cell over time, or after exposure to a particular condition.

Partitioning Polynucleotides from Cells or Proteins

In one example the compositions, methods, devices, and kits provided in this disclosure may be used to encapsulate cells or proteins within the fluidic droplets. In one example, a single cell or a plurality of cells (e.g., 2, 10, 50, 100, 1000, 10000, 25000, 50000, 10000, 50000, 1000000, or more cells) may be loaded onto, into, or within a bead along with a lysis buffer within a fluidic droplet and incubated for a specified period of time. The bead may be porous, to allow washing of the contents of the bead, and introduction of reagents into the bead, while maintaining the polynucleotides of the one or more cells (e.g. chromosomes) within the fluidic droplets. The encapsulated polynucleotides of the one or more cells (e.g. chromosomes) may then be processed according to any of the methods provided in this disclosure, or known in the art. This method can also be applied to any other cellular component, such as proteins.

Epigenetic Applications

Compositions, methods, devices, and kits of this disclosure may be useful in epigenetic applications. For example, DNA methylation can be in indicator of epigenetic inheritance, including single nucleotide polymorphisms (SNPs). Accordingly, samples comprising nucleic acid may be treated in order to determine bases that are methylated during sequencing. In some cases, a sample comprising nucleic acid to be barcoded may be split into two aliquots. One aliquot of the sample may be treated with bisulfite in order to convert unmethylated cytosine containing nucleotides to uracil containing nucleotides. In some cases, bisulfite treatment can occur prior to sample partitioning or may occur after sample partitioning. Each aliquot may then be partitioned (if not already partitioned), barcoded in the partitions, and additional sequences added in bulk as described herein to generate sequencer-ready products. Comparison of sequencing data obtained for each aliquot (e.g., bisulfite-treated sample vs. untreated sample) can be used to determine which bases in the sample nucleic acid are methylated.

In some cases, one aliquot of a split sample may be treated with methylation-sensitive restriction enzymes (MSREs). Methylation specific enzymes can process sample nucleic acid such that the sample nucleic acid is cleaved as methylation sites. Treatment of the sample aliquot can occur prior to sample partitioning or may occur after sample partitioning and each aliquot may be partitioned used to generate barcoded, sequencer-ready products. Comparison of sequencing data obtained for each aliquot (e.g., MSRE-treated sample vs. untreated sample) can be used to determine which bases in the sample nucleic acid are methylated.

Low Input DNA Applications

Compositions and methods described herein may be useful in the analysis and sequencing of low polynucleotide input applications. Methods described herein, such as PHASE, may aid in obtaining good data quality in low polynucleotide input applications and/or aid in filtering out amplification errors. These low input DNA applications include the analysis of samples to sequence and identify a particular nucleic acid sequence of interest in a mixture of irrelevant or less relevant nucleic acids in which the sequence of interest is only a minority component, to be able to individually sequence and identify multiple different nucleic acids that are present in an aggregation of different nucleic acids, as well as analyses in which the sheer amount of input DNA is extremely low. Specific examples include the sequencing and identification of somatic mutations from tissue samples, or from circulating cells, where the vast majority of the sample will be contributed by normal healthy cells, while a small minority may derive from tumor or other cancer cells. Other examples include the characterization of multiple individual population components, e.g., in microbiome analysis applications, where the contributions of individual population members may not otherwise be readily identified amidst a large and diverse population of microbial elements. In a further example, being able to individually sequence and identify different strands of the same region from different chromosomes, e.g., maternal and paternal chromosomes, allows for the identification of unique variants on each chromosome. Additional examples of low polynucleotide input applications of the compositions, methods, and systems described herein are set forth in U.S. Provisional Patent Application No. 62/017,580, filed of even date herewith.

The advantages of the methods and systems described herein are clearer upon a discussion of the problems confronted in the present state of the art. In analyzing the genetic makeup of sample materials, e.g., cell or tissue samples, most sequencing technologies rely upon the broad amplification of target nucleic acids in a sample in order to create enough material for the sequencing process. Unfortunately, during these amplification processes, majority present materials will preferentially overwhelm portions of the samples that are present at lower levels. For example, where a genetic material from a sample is comprised of 95% normal tissue DNA, and 5% of DNA from tumor cells, typical amplification processes, e.g., PCR based amplification, will quickly amplify the majority present material to the exclusion of the minority present material. Furthermore, because these amplification reactions are typically carried out in a pooled context, the origin of an amplified sequence, in terms of the specific chromosome, polynucleotide or organism will typically not be preserved during the process.

In contrast, the methods and systems described herein partition individual or small numbers of nucleic acids into separate reaction volumes, e.g., in droplets, in which those nucleic acid components may be initially amplified. During this initial amplification, a unique identifier may be coupled to the components to the components that are in those separate reaction volumes. Separate, partitioned amplification of the different components, as well as application of a unique identifier, e.g., a barcode sequence, allows for the preservation of the contributions of each sample component, as well as attribution of its origin, through the sequencing process, including subsequent amplification processes, e.g., PCR amplification.

Non-Overlapping Fragmentation

This disclosure provides methods, compositions, systems, and devices for processing polynucleotides. In one example, a method provided herein comprises: (a) providing a target polynucleotide; (b) fragmenting the target polynucleotide to generate a plurality of non-overlapping first polynucleotide fragments; (c) partitioning the first polynucleotide fragments to generate partitioned first polynucleotide fragments, wherein at least one partition of the partitioned first polynucleotide fragments comprises a first polynucleotide fragment with a unique sequence within the at least one partition; and (d) fragmenting the partitioned first polynucleotide fragments, to generate a plurality of non-overlapping second polynucleotide fragments.

In some of the methods provided in this disclosure, a third and fourth set of polynucleotide fragments are generated by performing the method described above and additionally performing a method comprising: (a) fragmenting the target polynucleotide to generate a plurality of non-overlapping third polynucleotide fragments; (b) partitioning the third polynucleotide fragments to generate partitioned third polynucleotide fragments, wherein at least one partition of the partitioned third polynucleotide fragments comprises a third polynucleotide fragment with a unique sequence within the at least one partition; and (c) fragmenting the partitioned third polynucleotide fragments to generate a plurality of non-overlapping fourth polynucleotide fragments.

The third polynucleotide fragments may overlap with the first polynucleotide fragments. The fourth polynucleotide fragments may overlap with the second polynucleotide fragments.

The target polynucleotide may be, for example, DNA, RNA, cDNA, or any other polynucleotide.

In some cases, at least one of the first, second, third, and fourth polynucleotide fragments are generated by an enzyme. The enzyme may be a restriction enzyme. The restriction enzyme used to generate the first polynucleotide fragments may be different from the restriction enzyme used to generate the third polynucleotide fragments. The restriction enzyme used to generate the second polynucleotide fragments may be different from the restriction enzyme used to generate the fourth polynucleotide fragments. The restriction enzymes may have a recognition site of at least about six nucleotides in length.

The fragments can be of a variety of lengths. For example, the first and/or third polynucleotide fragments may have a median length of least about 10,000 nucleotides. The second or fourth polynucleotide fragments may have a median length of less than about 200 nucleotides.

The fragments can be attached to barcodes. For example, the second polynucleotide fragments and/or the fourth polynucleotide fragments may be attached to barcodes, to generate barcoded second and/or fourth polynucleotide fragments. The barcodes may be polynucleotide barcodes. The attachment of the barcodes to the polynucleotide fragments may be performed using an enzyme. The enzyme may be a ligase. The barcoded fragments may be pooled. Unpooled or pooled barcoded fragments may be sequenced.

In some cases, one or more steps of the methods described in this disclosure may be performed within a device. The device may comprise at least one well. The well may be a microwell. Any of the partitioning steps described in this disclosure may be performed by dispensing into a microwell.

The microwell (or well) may comprise reagents. These reagents may be any reagent, including, for example, barcodes, enzymes, adapters, and combinations thereof. The reagents may be physically separated from a polynucleotide sample placed in the microwell. This physical separation may be accomplished by containing the reagents within a microcapsule that is placed within a microwell. The physical separation may also be accomplished by dispensing the reagents in the microwell and overlaying the reagents with a layer that is, for example, dissolvable, meltable, or permeable prior to introducing the polynucleotide sample into the microwell. This layer may be, for example, an oil, wax, membrane, or the like. The microwell may be sealed at any point, for example after addition of the microcapsule, after addition of the reagents, or after addition of either of these components plus a polynucleotide sample.

Partitioning may also be performed by a variety of other means, including through the use of fluid flow in microfluidic channels, by emulsification, using spotted arrays, by surface acoustic waves, and by piezoelectric droplet generation.

Additional methods of fragmenting nucleic acids that are compatible with the methods provided herein include mechanical disruption, sonication, chemical fragmentation, treatment with UV light, and heating, and combinations thereof. These methods may be used to fragment, for example, the partitioned first or third polynucleotide fragments described above.

Partitioning may be done at any time. For example, the first polynucleotide fragments and/or the third polynucleotide fragments may each be further partitioned into two or more partitions before further processing.

Pseudo-Random Fragmentation

This disclosure provides methods for pseudo-random fragmentation of polynucleotides. In some cases, such methods comprise: (a) providing a target polynucleotide; (b) fragmenting the target polynucleotide to generate a plurality of first polynucleotide fragments; (c) partitioning the first polynucleotide fragments to generate partitioned first polynucleotide fragments, such that at least one partition comprises a first polynucleotide fragment with a unique sequence within the at least one partition; and (d) fragmenting the partitioned first polynucleotide fragments with at least one restriction enzyme in at least one partition, to generate a plurality of second polynucleotide fragments, wherein the partitioned first polynucleotide fragment is fragmented with at least two restriction enzymes across all partitions.

In some cases, at least two restriction enzymes are disposed within the same partition. In some cases, at least two restriction enzymes are disposed across a plurality of different partitions.

The pseudo-random fragmentation methods can be performed in order to yield fragments of a certain size. In some cases, at least about 50% of the nucleotides within a target polynucleotide are within about 100 nucleotides of a restriction site of a restriction enzyme used to perform pseudo-random fragmentation. In some cases, at most about 25% of the nucleotides within a target polynucleotide are within about 50 nucleotides of a restriction site of a restriction enzyme used to perform pseudo-random fragmentation. In some cases, at most about 10% of the nucleotides within a target polynucleotide are more than about 200 nucleotides from a restriction site a restriction enzyme used to perform pseudo-random fragmentation.

A polynucleotide may be treated with two or more restriction enzymes concurrently or sequentially.

The pseudo-randomly fragmented polynucleotides may be attached to barcodes, to generate barcoded polynucleotide fragments. The barcoded polynucleotides may be pooled and sequenced.

The number of partitions holding the partitioned first polynucleotide fragments may be at least about 1,000 partitions. The volume of these partitions may be less than about 500 nanoliters.

Each enzyme may occupy an equivalent number of partitions, or each enzyme may occupy a different number of partitions.

Restriction Enzyme-Mediated Recycling

This disclosure provides methods for recycling certain unwanted reaction side products back into starting materials that can be used to generate a desired product. In some cases, these methods comprise: (a) providing a first polynucleotide, a second polynucleotide, a first restriction enzyme, and a second restriction enzyme, wherein the first polynucleotide comprises a target polynucleotide or a fragment thereof; and (b) attaching the first polynucleotide to the second polynucleotide, to generate a polynucleotide product, wherein the first restriction enzyme cuts a polynucleotide generated by attachment of the first polynucleotide to itself, the second restriction enzyme cuts a polynucleotide generated by attachment of the second polynucleotide to itself, and neither the first restriction enzyme nor the second restriction enzyme cuts the polynucleotide product.

The first polynucleotide may be generated in the same reaction volume as the polynucleotide product, or in a different reaction volume. The target polynucleotide may be, for example, a fragment of genomic DNA.

The second polynucleotide may be generated in the same reaction volume as the polynucleotide product, or in a different reaction volume. The second polynucleotide may be, for example, a barcode or an adapter.

The first restriction enzyme may have a recognition site of at most about four nucleotides in length. The second restriction enzyme may have a recognition site of at least about six nucleotides in length. The first restriction enzyme may have a recognition site of about four nucleotides in length. The second restriction enzyme may have a recognition site of at least about five nucleotides in length.

The first and second restriction enzymes may generate ligation compatible ends. These ends may have single-stranded overhangs (i.e., "sticky ends") or be blunt. The sticky ends may match in sequence and orientation, to allow ligation. The attachment step may be performed by ligation.

The sequence 5' to the ligation compatible end generated by the first restriction enzyme may be different from the sequence 5' to the ligation compatible end generated by the second restriction enzyme. This will ensure that the desired product cannot be re-cut by either restriction enzyme.

The sequence 3' to the ligation compatible end generated by the first restriction enzyme may be different from the sequence 3' to the ligation compatible end generated by the second restriction enzyme. This will ensure that the desired product cannot be re-cut by either restriction enzyme. Given the criteria provided throughout this specification, one of ordinary skill in the art will recognize that many pairs of enzymes are suitable for use with this method.

The recycling may provide increased yield of the desired product, for example at least about 75% (w/w).

Also provided by this disclosure is a polynucleotide fragment generated by any of the methods provided herein, devices for performing the methods provided herein, and systems for performing the methods provided herein.

The methods provided in this disclosure (and portions thereof) may also be used with each other. For example, the non-overlapping fragmentation methods may be used alone and/or with the pseudo-random fragmentation methods and/or with the restriction enzyme-mediated recycling methods. Likewise, the pseudo-random fragmentation methods may be used alone and/or with the non-overlapping fragmentation methods and/or with the restriction enzyme-mediated recycling methods. Similarly, the restriction enzyme-mediated recycling methods may be used alone and/or with the non-overlapping fragmentation methods and/or with the pseudo-random fragmentation methods.

The term "about," as used herein and throughout the disclosure, generally refers to a range that may be 15% greater than or 15% less than the stated numerical value within the context of the particular usage. For example, "about 10" would include a range from 8.5 to 11.5.

As will be appreciated, the instant disclosure provides for the use of any of the compositions, libraries, methods, devices, and kits described herein for a particular use or purpose, including the various applications, uses, and purposes described herein. For example, the disclosure provides for the use of the compositions, methods, libraries, devices, and kits described herein in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in polynucleotide phasing (see e.g., U.S. Provisional Patent Application No. 62/017,808 filed of even date herewith), in sequencing polynucleotides from small numbers of cells, in analyzing gene expression, in partitioning polynucleotides from cells, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, such as circulating tumor cell (CTC) sequencing, in a combination thereof, and in any other application, method, process or use described herein.

Any concentration values provided herein are provided as admixture concentration values, without regard to any in situ conversion, modification, reaction, sequestration or the like. Moreover, where appropriate, the sensitivity and/or specificity of methods (e.g., sequencing methods, barcoding methods, amplification methods, targeted amplification methods, methods of analyzing barcoded samples, etc.) described herein may vary. For example, a method described herein may have specificity of greater than 50%, 70%, 75%, 80%, 85%, 86%, 87%, 88%, 89%, 90%, 91%, 92%, 93%, 94%, 95%, 96%, 97%, 98%, 99%, or 99.5% and/or a sensitivity of greater than 50%, 70%, 75%, 80%, 85%, 86%, 87%, 88%, 89%, 90%, 91%, 92%, 93%, 94%, 95%, 96%, 97%, 98%, 99%, or 99.5%.

X. Examples

Example 1

Creation of Gel Beads Functionalized with Acrydite Primer

Figure 2:
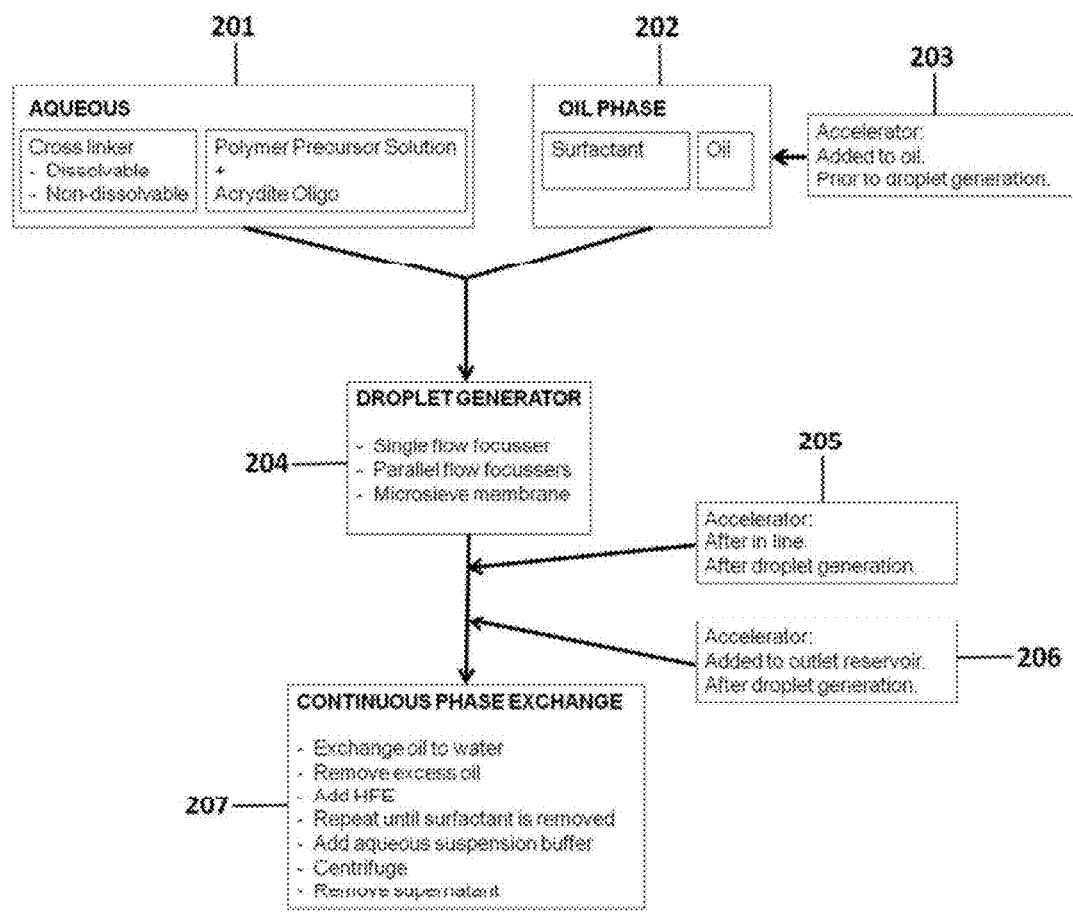
FIG. 2 is a flow diagram for making beads.

Gel beads are produced according to the method illustrated in FIG. 2. In nuclease free water, 1 mL stock solutions are prepared at the following concentrations: an acrylamide precursor (Compound A)=40% (v/v) stock solution, a cross-linker (Bis-acryloyl cystamine—Compound B)=3.19 mg/mL in 50:50 mix of acetonitrile:water, an initiator (Compound C)=20 mg/mL, and di-sulfide acrydite primer (Compound D)=1 mM. From these stock solutions, 1 mL of an aqueous Gel Bead (GB) working solution is prepared by mixing the following volumes: nuclease free water=648 µL, Compound A=150 µL, Compound B=100 µL, Compound C=100 µL, and Compound D=2 µL. Stock solutions of Compound A and B and GB working solutions are prepared daily.

The Gel Bead (GB) working solution, 201, is an aqueous fluid that contains the crosslinker, BAC, and a polymer precursor solution with di-sulfide-modified acrydite oligonucleotides at a concentration of between about 0.1 and about 100 µm. The second fluid, 202, is a fluorinated oil containing the surfactant, Krytox FSH 1.8% w/w HFE 7500. The accelerator, tetramethylethylenediamine (TEMED) is added a) to the oil prior to droplet generation, 203, b) in the line after droplet generation, 205, and/or c) to the outlet reservoir after droplet generation, 206 to give a final concentration of 1% (v/v). TEMED is made fresh daily. Gel beads are generated by sending the aqueous and oil phase fluids to a droplet generator, 204. Polymerization is initiated immediately after droplet generation and continues to the outlet well. Gelation is considered complete after 15-20 minutes. After gelation, generated gel beads are subjected to continuous phase exchange by washing in HFE 7500, 207, to remove excess oil, and re-suspending the beads in aqueous solution. In some cases, the resulting beads may be present in an agglomeration. The agglomeration of gel beads are separated into individual gel beads with vortexing. Gel beads are visualized under a microscope.

Example 2

Creation of Barcoded Gel Beads by Limiting Dilution

Figure 3A:
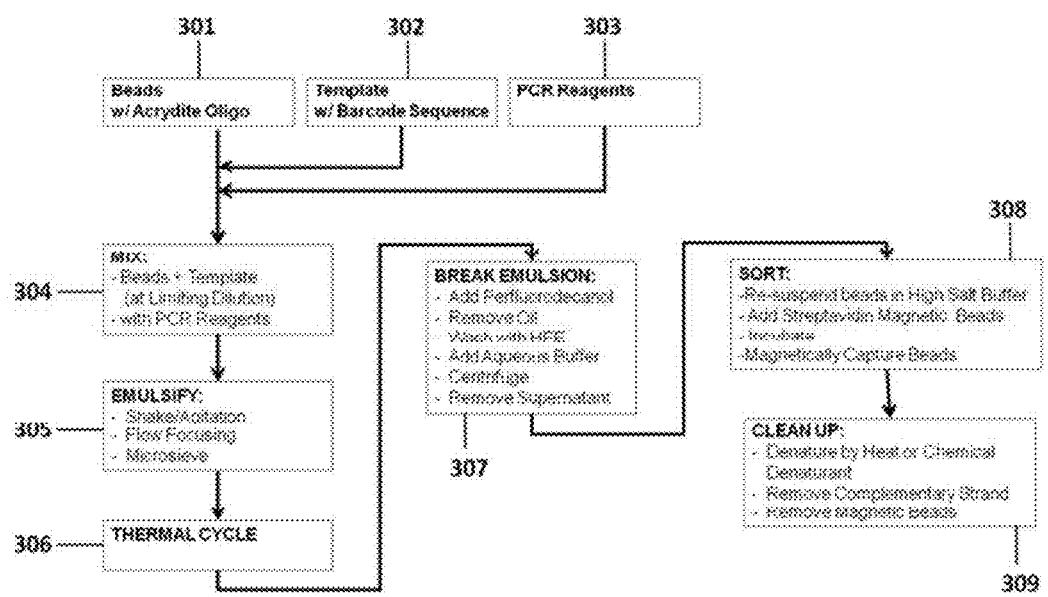
FIG. 3A is a flow diagram for adding barcodes to beads by limiting dilution.

Functionalized gel beads are produced by limiting dilution according to the method illustrated in FIG. 3A and FIGS. 4A-4N. Gel beads with acrydite oligonucleotides (with or without a di-sulfide modification), 301, 401, are mixed with barcode-containing template sequences, 302, at a limiting dilution. PCR reagents, 303, including a biotin labeled read primer, 406, are mixed with the gel beads and template sequences, 304. The beads, barcode template, and PCR reagents are emulsified into a gel-water-oil emulsion by shaking/agitation, flow focusing, or microsieve, 305, preferably such that at most one barcode template is present in a partition (e.g., droplet) within the emulsion. The emulsion is exposed to one or more thermal cycles, 306. The first thermocycle incorporates the complement barcode sequence, 408, and immobilizes it onto the gel bead.

Continued thermal cycling is performed to clonally amplify the barcode throughout the gel bead and to incorporate the 5' biotin labeled primer into the complementary strand for downstream sorting of beads which contain barcode sequences from those that do not. The emulsion is broken, 307, by adding perfluorodecanol, removing the oil, washing with HFE-7500, adding aqueous buffer, centrifuging, removing supernatant, removing undesired products (e.g. primer dimers, starting materials, deoxynucleotide triphosphates (dNTPs), enzymes, etc.) and recovering degradable gel beads into an aqueous suspension. The functionalized gel beads are re-suspended in high salt buffer, 308. Streptavidin-labeled magnetic beads are added to the re-suspension, which is then incubated to allow binding to gel beads attached to biotinylated barcodes 308, 410. A magnetic device is then used to separate positive barcoded gel beads from beads that are not attached to barcode, 308. Denaturation conditions, 309, (e.g. heat or chemical denaturant) are applied to the gel beads in order to separate the biotinylated complementary strand from the barcoded beads. The magnetic beads are subsequently removed from the solution; and the resulting solution of partially-functionalized barcoded beads is pooled for further processing.

Example 3

Further Functionalization of Barcoded Beads

Figure 3B:
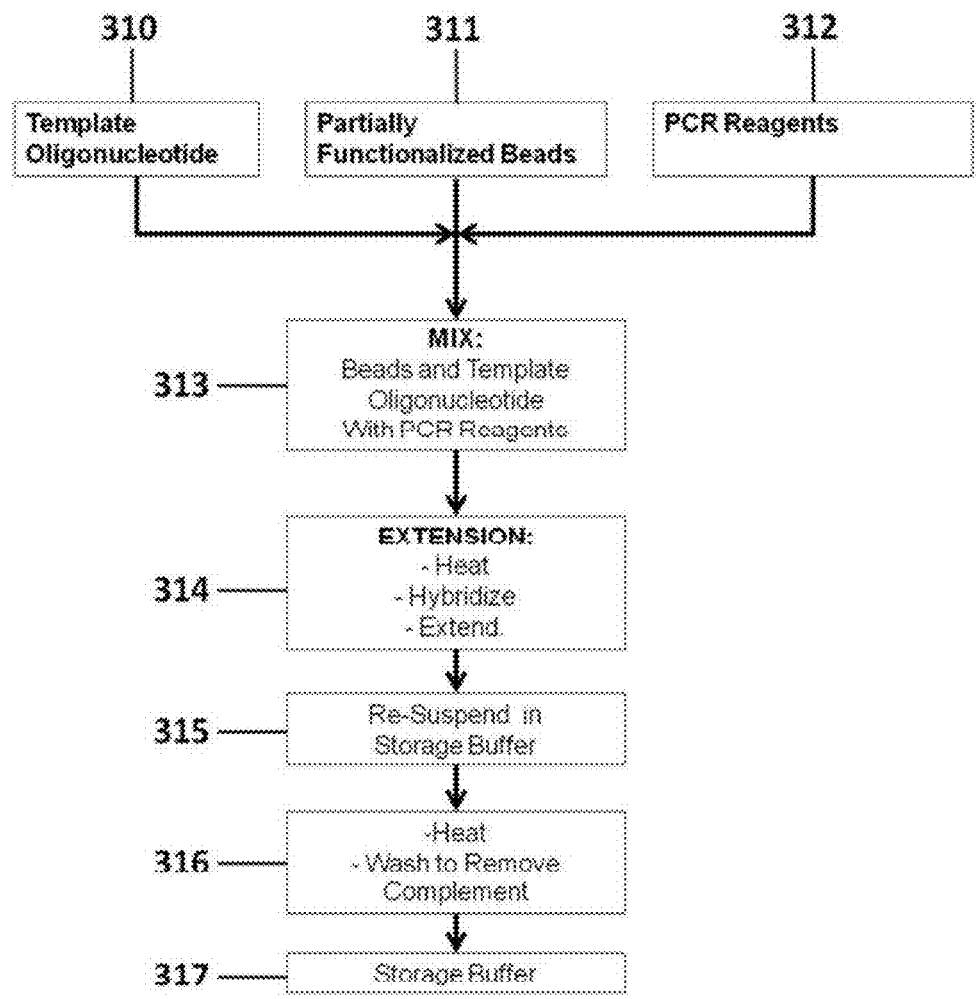
FIG. 3B is a flow diagram for adding additional sequences to oligonucleotides attached to beads.

As shown in FIG. 3B, the barcoded gel beads, 311, from Example 2, are further functionalized as follows. The beads are combined with an additional template oligonucleotide, 310, (such as an oligonucleotide containing a random N-mer sequence, 413, as shown in FIGS. 4I and 4J), and PCR reagents, 312, 313, and subjected to conditions to enable hybridization of the template oligonucleotide with the read primer attached to the gel bead. An extension reaction is performed so that the barcode strands are extended, 314, thereby incorporating the complementary sequence of the template oligonucleotide. Resulting functionalized gel beads are re-suspended in aqueous buffer, 315, and exposed to heating conditions to remove complement strands, 316, and placed into aqueous storage buffer, 317.

Example 4

Step-by-Step Description of Bead Functionalization

FIGS. 4A-4N provides a step-by-step description of an example process of functionalizing the gel beads with barcodes and random N-mers. As shown in FIG. 4A, the process begins with gel beads, 401, that are attached to a universal primer, such as a P5 primer (or its complement), 403. The beads may be linked to the primer via a di-sulfide bond, 402. The gel beads are provided in an aqueous solution (g/w). Using a limiting dilution and partitioning, unique barcode sequence templates, 405, are combined with the beads such that at most one unique barcode sequence occupies the same partition as a gel bead. Generally, the partitions are aqueous droplets within a gel/water/oil (g/w/o) emulsion. As shown in FIG. 4B, the barcode sequence template, 405, is contained within a larger nucleotide strand that contains a sequence, 404, that is complementary to the universal primer 403, as well as a sequence, 407, that is identical in sequence to a biotin labeled read primer, 406.

As shown in FIG. 4C, an amplification reaction is then conducted to incorporate the complement, 408, of the barcode template, 405, onto the strand that is attached to the bead. The amplification reaction also results in incorporation of a sequence, 415, that is complementary to sequence, 407. Additional amplification cycles result in hybridization of the biotin labeled read primer, 406, to sequence, 415 (FIG. 4D), and the biotin labeled read primer is then extended (FIG. 4E). The emulsion may then be broken, and the gel beads may then be pooled into a gel/water common solution.

Figure 5A:
FIGS. 5A-5E provides an illustration of a gel bead attached to an oligonucleotide (FIG. 5A), an image of a microfluidic chip used to make Gel Beads in Emulsions (GEM) (FIG. 5B), as well as images of GEMs (FIGS. 5C, 5D, and 5E).

In the gel/water solution, magnetic capture beads, 409, are then used to capture the biotinylated nucleic acids attached to the gel beads, which are then isolated from beads that only contain the original primer (FIGS. 4F and 4G). The biotinylated strand is then removed from the strand attached to the gel bead (FIG. 4H). Random N-mer sequences, 414, may then be attached to the strands attached to the gel bead. For each gel bead, an identical barcode sequence, 408, is attached to each primer throughout the gel bead; each barcode sequence is then functionalized with a random N-mer sequence, 414, such that multiple different random N-mer sequences are attached to each bead. For this process, a random N-mer template sequence, 413, linked to a sequence, 412, complementary to sequence, 415, is introduced to the solution containing the pooled beads (FIG. 4I). The solution is subjected to conditions to enable hybridization of the template to the strand attached to the bead and sequence 415 is extended to include the random N-mer, 414. (FIG. 4J). The fully functionalized beads (FIG. 4K) are then combined with a sample nucleic acid and a reducing agent (e.g., dithiothreitol (DTT) at a concentration of 1 mM) and partitioned within droplets of a gel/water/oil emulsion (FIG. 4L). This combining step may be conducted with a microfluidic device (FIG. 5A). The gel beads are then degraded within each partition (e.g., droplet) such as by the action of a reducing agent, and the barcoded sequence is released from the droplet (FIGS. 4M and 4N). The random N-mer within the barcoded sequence may serve as a primer for amplification of the sample nucleic acid.

Example 5

Figure 5B:
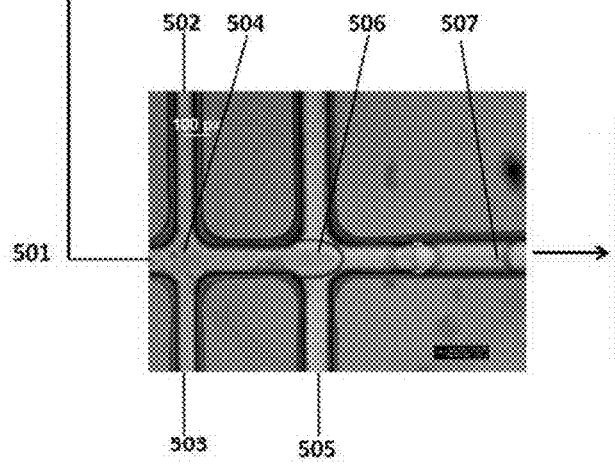
Figure 5C:
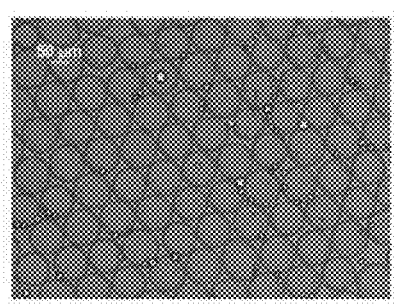
Figure 5D:
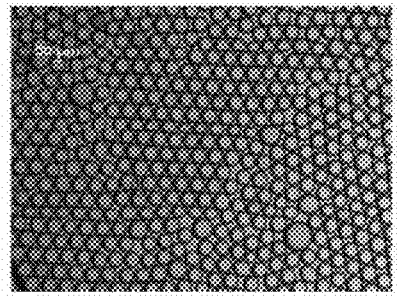
Figure 5E:
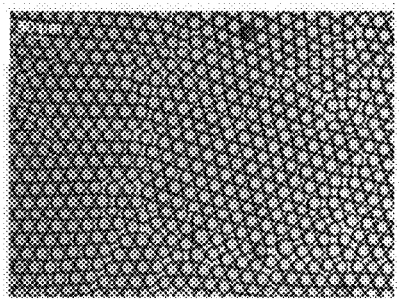

Use of a Microfluidic Chip to Combine the Gel-Beads-in Emulsions (GEMS) with Sample The functionalized gel beads may be combined with sample using a double-cross microfluidic device illustrated in FIG. 5B. Degradable gel beads are introduced to the fluidic input, 501, in a fluid stream, which contains about 7% glycerol. The experimental sample of interest is introduced to the fluidic input, 502, in a fluid stream, which is aqueous phase. The reducing agent, dithiothreitol (DTT) at a concentration of about 1 mM is introduced to the fluidic input, 503, in a fluid stream, which contains about 7% glycerol. Fluidic inputs 501, 502, and 503 mix at a microfluidic cross junction, 504, and enter a second microfluidic cross junction, 506. The second microfluidic cross junction can be used to produce emulsified (w/o) droplets containing the el beads. Fluidic input, 505, is used to introduce oil with 2% (w/w) bis krytox peg (BKP). Individual droplets exiting from the second microfluidic cross junction, 507, are added into microplate wells, FIG. 5C, for further downstream applications. FIG. 5D is an image of droplets generated in the absence of DTT (and therefore containing gel beads). FIG. 5E is an image of droplets generated with DTT that caused the internal gel beads to degrade.

Example 6

Fluorescent Identification of Positive Gel Beads

Figure 6A:
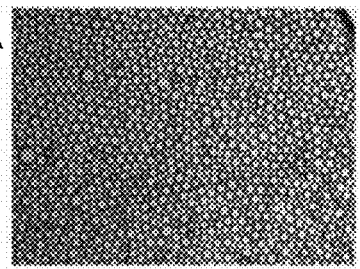
FIGS. 6A-6F provides bright-field (FIGS. 6A, 6C, and 6E) and fluorescent (FIGS. 6B, 6D, and 6F) images of beads with attached oligonucleotides.
Figure 6B:
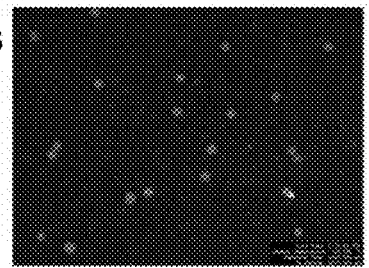
Figure 6C:
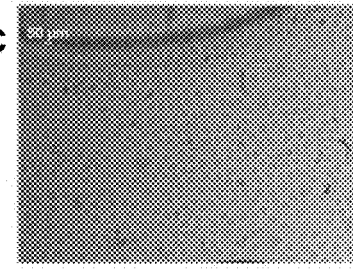
Figure 6D:
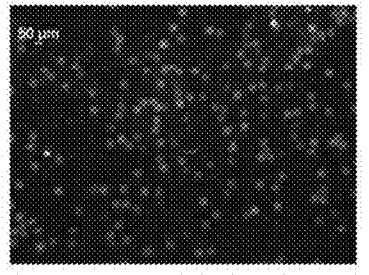
Figure 6E:
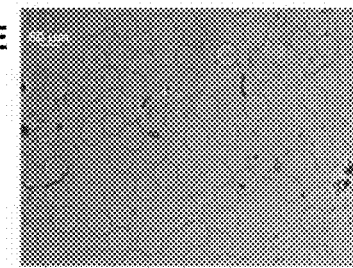
Figure 6F:
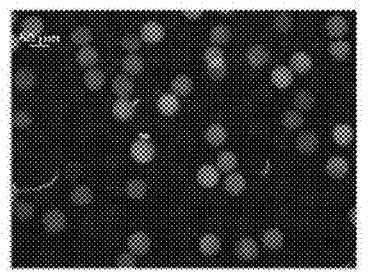

FIGS. 6A-6F depicts images of gel beads containing amplified nucleic acids that have been labeled with a fluorescent label. Functionalization of the gel beads is first performed using a limiting dilution so that only a portion of the gel beads are functionalized with barcodes. Gel beads suspended in a bis krytox peg (BKP) emulsion are imaged at 4× magnification following PCR thermocycling but before washing. The bright field image, FIG. 6A, shows all emulsion-generated droplets, and the fluorescent image, FIG. 6B, shows only positive functionalized gel beads. Many non-fluorescent droplets are generated indicating empty droplets, which do not contain either gel bead and/or oligonucleotide. Empty droplets are washed away by multiple re-suspensions and washing in HFE-7500. FIGS. 6C and 6D show positive gel bead enrichment following emulsion breaking and further wash steps. The bright field images (4×), FIG. 6C, and (10×) FIG. 6E, show all gel beads. The fluorescent images (4×), FIG. 6D, and (10×), FIG. 6F, show 30% positive beads from SYBR staining. The 30% positive bead result matches predicted value from gDNA input.

FIGS. 7A-7C shows images of gel beads containing single stranded (ss) DNA, double-stranded (ds) DNA, and denatured, ssDNA. Gel beads stained with 1× EvaGreen are brighter in the presence of dsDNA as evident from the fluorescent images taken at step 1: Make (ssDNA), FIG. 7A, step 2: Extension (dsDNA), FIG. 7B, and step 3: Denature (ssDNA), FIG. 7C. Fluorescent images show that beads become brighter after extension and become dimmer after denaturation.

Example 7

Enrichment of Positive Gel Beads Using Streptavidin-Coated Magnetic Beads

Figure 8A:
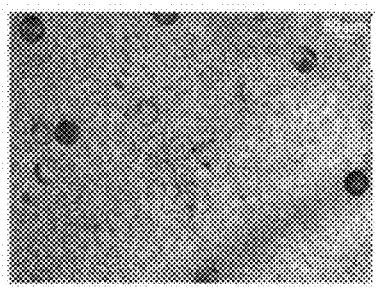
FIGS. 8A-F provide images of barcode-enriched populations of beads.
Figure 8B:
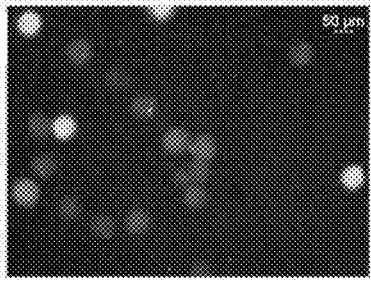
Figure 8C:
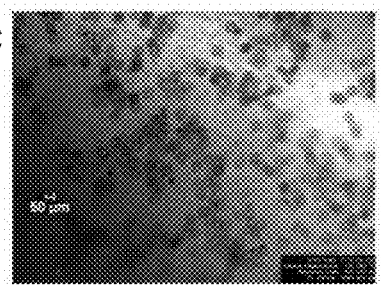
Figure 8D:
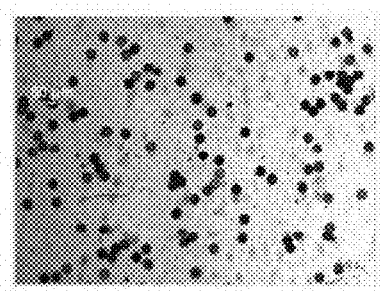
Figure 8E:
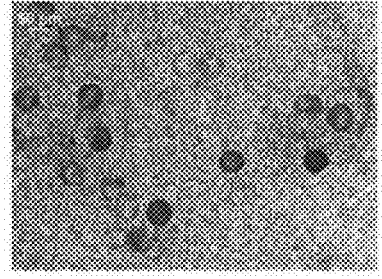
Figure 8F:
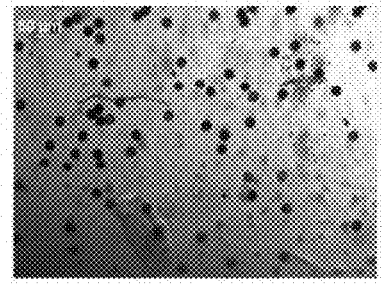
Figure 9A:
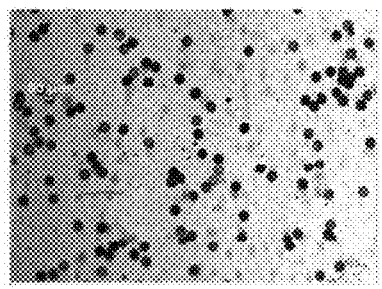
FIGS. 9A-9D provide images of the dissolution of beads by heating.
Figure 9B:
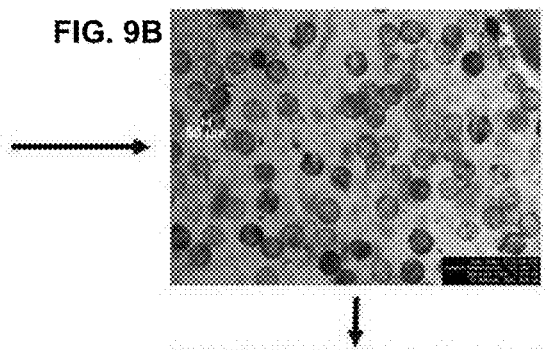
Figure 9D:
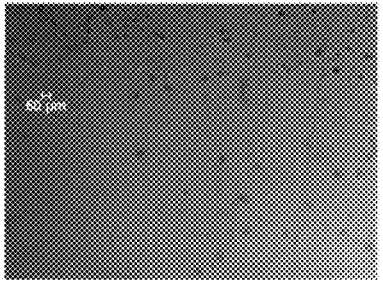
Figure 9C:
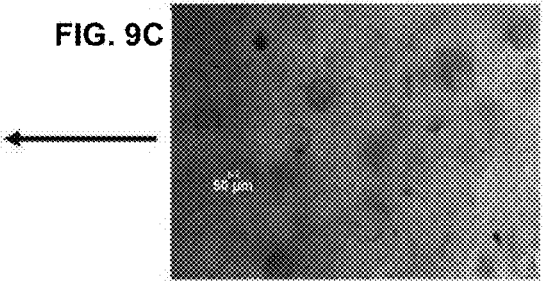

Enrichment of positive gel beads using streptavidin-coated magnetic beads is depicted in FIGS. 8A-8F. FIG. 8A (bright field) and FIG. 8B (fluorescent) provides images of SYBR-stained gel beads 24 hours following the addition of magnetic beads. Magnetic coated positive gel beads are brighter due to SYBR staining. Bright field images before, FIG. 8C, and after sorting, FIG. 8D, at a magnetic bead concentration of 40 mg/mL, show positive gel bead enrichment, where coated beads are optically brighter. Bright field images before, FIG. 8E, and after sorting, FIG. 8F, at a magnetic bead concentration of 60 mg/mL, show positive gel bead enrichment, where coated beads are optically brighter. At each magnetic bead working concentration, a single gel bead is coated by about 100-1000 magnetic beads.

Example 8

Dissolution of Gel Beads

Figure 10A:
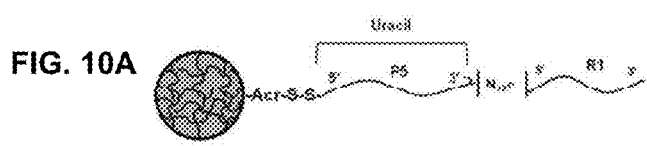
FIG. 10A provides a schematic of a functionalized bead.
Figures 10B, 10C, 10D, 10E, 10F, 10G:
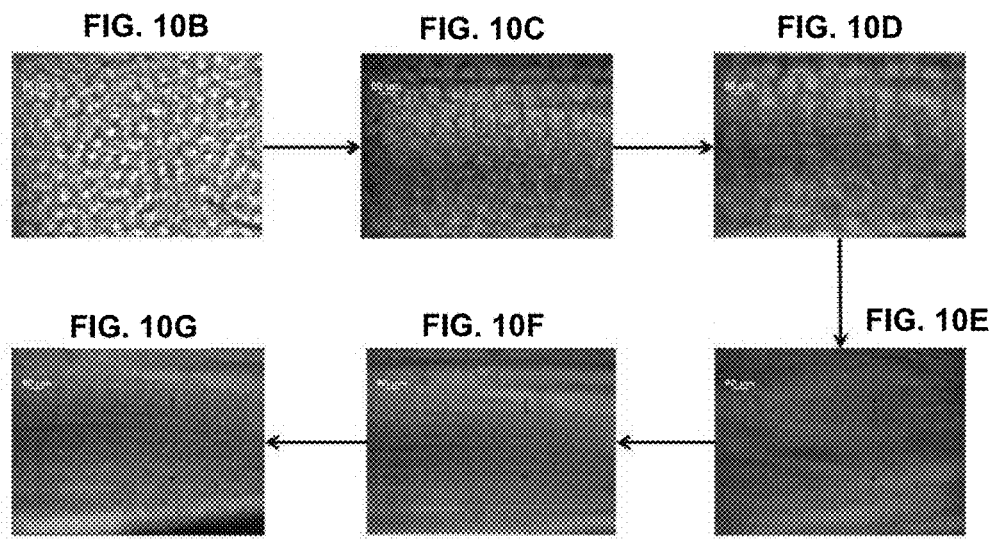
FIGS. 10B-10G provide images of beads dissolved with a reducing agent.
Figure 11C:
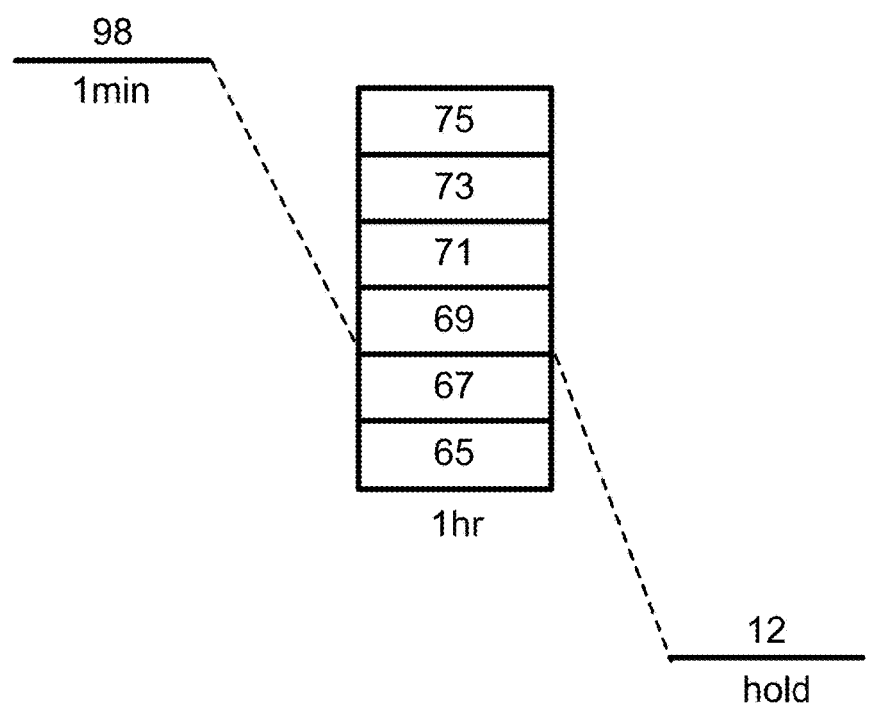
Figure 11D:
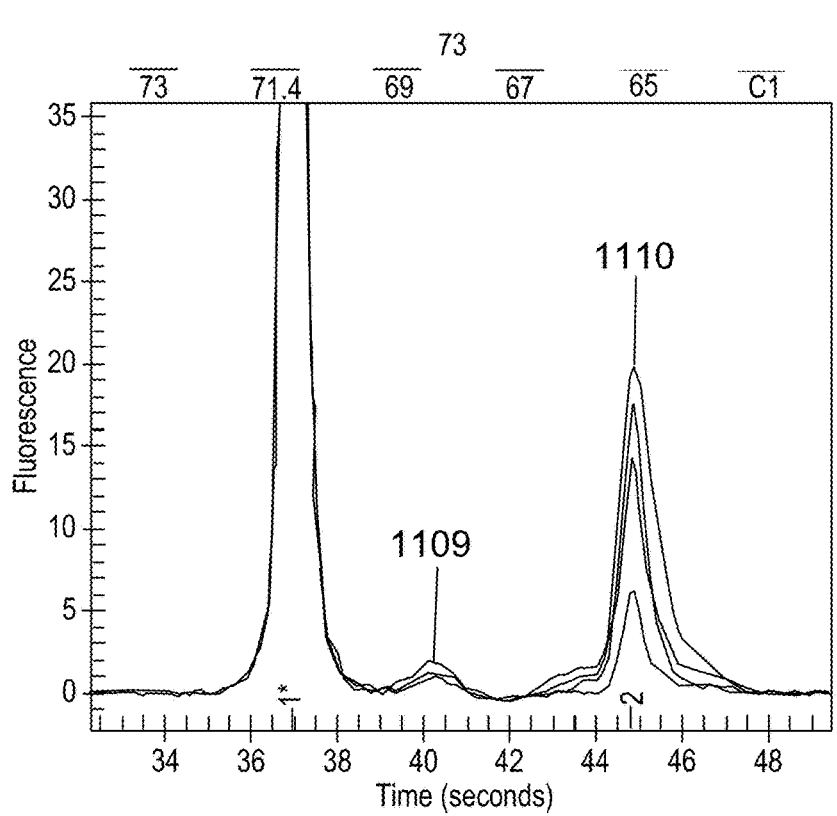
Figure 12:
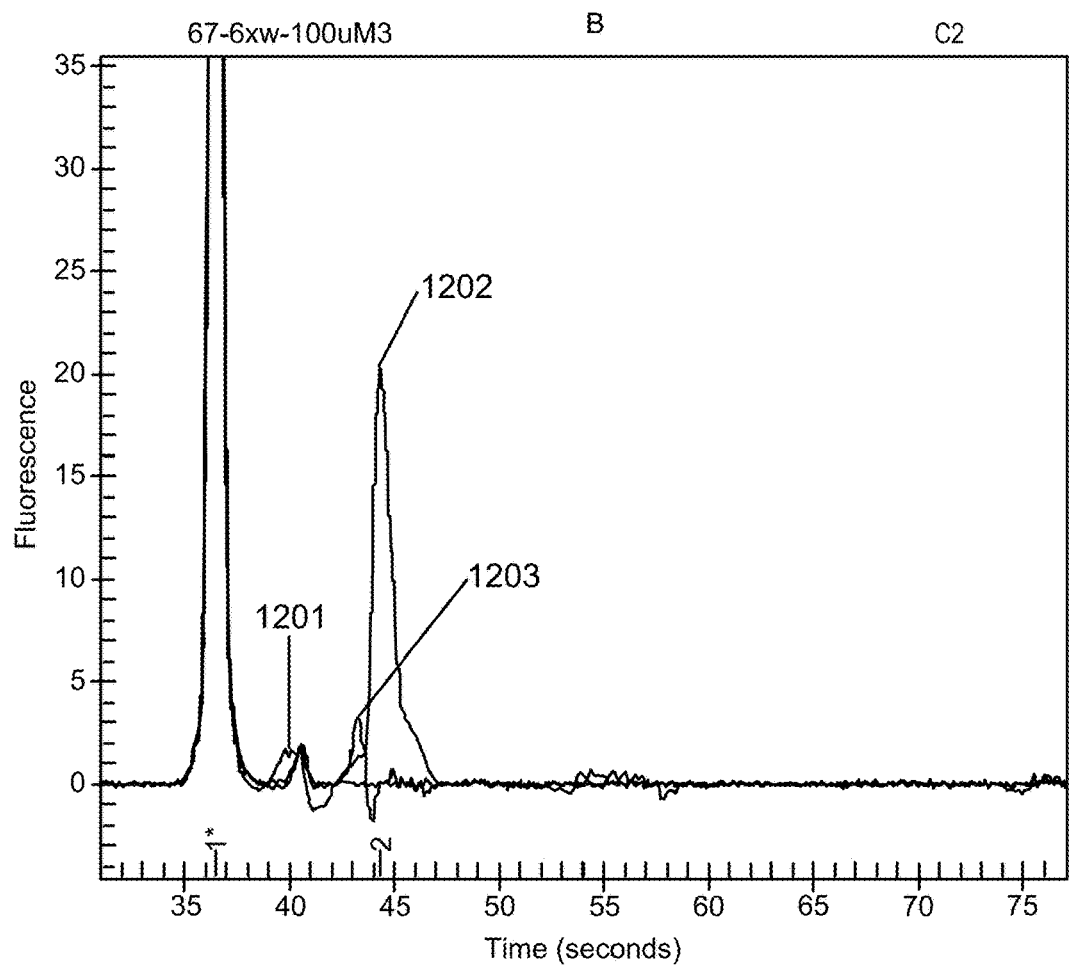
FIG. 12 is a graphic depiction of content attached to beads.

Heating gel beads in basic solution degrades the gel beads as evident in FIGS. 9A-9D. Gel beads are heated in basic solution at 95° C. and monitored at 5 minute heating intervals: t=0 min, FIG. 9A, t=5 min, FIG. 9B, t=10 min, FIG. 9C, t=15 min, FIG. 9D. Following 15 minutes, gel beads are completely degraded. Gel beads more than double in size while they are degrading. FIGS. 10A-10G depicts dissolution of the gel beads using tris(2-carboxyethyl)phosphine (TCEP), which is an effective and irreversible di-sulfide bond reducing agent. Functionalized gel beads, FIG. 10A, are placed into basic solution, pH=8, with 1 mM TCEP and monitored at 2 minute intervals: t=0 min, FIG. 10B, t=2 min, FIG. 10C, t=4 min, FIG. 10D, t=6 min, FIG. 10E, t=8 min, FIG. 10F, and t=10 min, FIG. 10G. Between about 6 and about 10 minutes, the functionalized gel beads are completely degraded.

Example 9

Analysis of Content After Dissolution Gel Beads (GB)

An analysis of content attached to gel beads is provided in FIGS. 11A-11D, and FIG. 12. Gel beads are functionalized, 1101, with barcode or barcode complement (N12C) and a random N-mer (8mer) that is 8 nucleotides in length, 1102. The random N-mer is attached by performing a primer extension reaction using a template construct containing R1C and a random N-mer 1102. The length of the entire oligonucleotide strand (including the bar code and random N-mer) is 82 bp, 1101. The strand length of the random N-mer and the R1C is 42 base pairs (bp), 1102. The extension reaction is performed using a KAPA HIFI RM Master Mix under high primer concentration (10 μm) at 65° C. for one hour. Increasing the number of wash steps before the step of degrading the gel beads results in a reduction in the amount of primer dimers within the sample. When no washes are performed, 1103, both 42 bp products, 1106, and 80 bp products, 1107, can be observed. After three washes, the level of primer dimer, 1104, is reduced relative to the no-wash experiment. After six washes, 1105, 80 bp products, 1107, are observed, but no primer dimers are observed.

The six-wash experiment can also be performed using six different temperatures (65° C., 67° C., 69° C., 71° C., 73° C., 75° C., FIG. 11C) for the extension step. In this specific example, a high primer concentration (10 μm) is used and the extension step lasts one hour. It appears that 67° C. is the optimal temperature for both optimizing the level of 80 bp products and minimizing the number of 42 bp products, 1109.

The temperature, 67° C., is chosen for subsequent denaturation studies. Heat denaturation of the complementary strand, wherein the sample is heated to 95° C. six times and washed to remove complementary strand, results in an 84 bp peak, 1202, before denaturation, and shows a reduced peak, 1201, following denaturation. The control value measured from step 1 is shown at 1203.

Example 10

Creation of Barcoded Gel Beads by Partitioning in Wells

Functionalized beads are produced by partitioning in wells according to the method illustrated in FIGS. 13A and 13B. The first functionalization step is outlined in FIG. 13A, the second functionalization step is outlined in FIG. 13B. An example multiplex adaptor creation scheme is outlined in FIG. 13C and described in Example 11. As shown in FIG. 13A, functionalized beads, 1301 (e.g., beads with acrydite oligos and primer (e.g., 5'-AAUGAUACGGCGACCAC-CGAGA-3' (SEQ ID NO: 4)), the template with barcode sequence, 1302 (e.g., 5'-XXXXXXTCTCGGTGGTCGC-CGTATCATT-3' (SEQ ID NO: 5)), and appropriate PCR reagents, 1303, are mixed together, 1304/1305 and divided into 384 wells of a multi-well plate. Each well comprises multiple copies of a unique barcode sequence and multiple beads. Thermocycling, 1306, with an extension reaction is performed in each individual well to form beads with attached barcodes. All wells are pooled together and cleaned up in bulk, 1307/1308.

To add a random N-mer, the partially functionalized beads, 1310, the template random N-mer oligonucleotides, 1309, and the appropriate PCR reagents, 1311, are mixed together, 1312, and the functionalized beads 1310 subjected to extension reactions 1313 to add a random N-mer sequence complementary to the random N-mer template, to the beads. Following thermal cycling, the beads are cleaned up in bulk, 1314-1316.

Example 11

Combinatorial Plate Technique

As shown in FIG. 13C, beads 1317 attached to primers (e.g., P5 oligomers, 5'-AAUGAUACGGCGACCAC- CGAGA-3' (SEQ ID NO: 4)) 1318 are partitioned into wells of a multi-well plate (such as a 5X-1 384-well plate 1319) with multiple copies of a template 1321 comprising a unique template partial barcode sequence (e.g., 5'-XXXXXX-TCTCGGTGGTCGCCGTATCATT-3 (SEQ ID NO: 5)). Extension reactions (e.g., extension of primer 1318 via template 1321) are performed to generate Bead-P5-[5X-1], 1320 comprising an extension product (e.g., an oligonucleotide comprising primer 1318 and a partial barcode sequence complementary to the template partial barcode sequence) in each well. The beads are removed from the wells are pooled together and a clean-up step is performed in bulk.

The pooled mixture is then re-divided into wells of a second multiwell plate such as a 384-well plate with 5X-2, 1322, with each well also comprising an oligonucleotide comprising a second unique partial barcode sequence and a random N-mer (e.g., 5'P-YYYYYYCGCACACUCUUC-CCUACACGACGCUCUUCCGAUCUNNNNNNNN-BLOCK (SEQ ID NO: 6)). The oligonucleotide may have a blocker oligonucleotide attached (e.g., via hybridization) (e.g., "BLOCK"). Single-stranded ligation reactions 1324 are performed between the extension product bound to the bead and the oligonucleotide comprising the second partial barcode sequence and random N-mer. Following the ligation reaction, beads comprising a full barcode sequence (e.g., XXXXXXYYYYYY) and a random N-mer are generated, 1323 (e.g., Bead-P5-[5X-1][5X-2]R1[8N-Blocker]). The beads also comprise the blocker oligonucleotide. All wells are then pooled together, the blocking groups are cleaved, and the bead products are cleaned up in bulk. Beads comprising a large diversity of barcode sequences are obtained.

Example 12

Partial Hairpin Amplification for Sequencing (PHASE) Reaction

Partial Hairpin Amplification for Sequencing (PHASE) reaction is a technique that can be used to mitigate undesirable amplification products according to the method outlined in FIGS. 14A-14C and FIGS. 15A-15G by forming partial hairpin structures. Specifically, random primers, of about 8N-12N in length, 1404, tagged with a universal sequence portion, 1401/1402/1403, may be used to randomly prime and extend from a nucleic acid, such as, genomic DNA (gDNA). The universal sequence comprises: (1) sequences for compatibility with a sequencing device, such as, a flow cell (e.g. Illumina's P5, 1401, and Read 1 Primer sites, 1402) and (2) a barcode (BC), 1403, (e.g., 6 base sequences). In order to mitigate undesirable consequences of such a long universal sequence portion, uracil containing nucleotides are substituted for thymine containing nucleotides for all but the last 10-20 nucleotides of the universal sequence portion, and a polymerase that will not accept or process uracil-containing templates is used for amplification of the nucleic acid, resulting in significant improvement of key sequencing metrics, FIG. 16A, FIG. 21, and FIG. 22. Furthermore, a blocking oligonucleotide comprising uracil containing nucleotides and a blocked 3' end (e.g. 3'ddCTP) are used to promote priming of the nucleic acid by the random N-mer sequence and prevent preferential binding to portions of the nucleic acid that are complementary to the Read 1 Primer site, 1402. Additionally, product lengths are further limited by inclusion of a small percentage of terminating nucleotides (e.g., 0.1-2% acyclonucleotides (acyNTPs)) (FIG. 16B) to reduce undesired amplification products.

An example of partial hairpin formation to prevent amplification of undesired products is provided here. First, initial denaturation is achieved at 98° C. for 2 minutes followed by priming a random portion of the genomic DNA sequence by the random N-mer sequence acting as a primer for 30 seconds at 4° C. (FIG. 15A). Subsequently, sequence extension follows as the temperature ramps at 0.1° C./second to 45° C. (held for 1 second) (FIG. 15A). Extension continues at elevated temperatures (20 seconds at 70° C.), continuing to displace upstream strands and creating a first phase of redundancy (FIG. 15B). Denaturation occurs at 98° C. for 30 seconds to release genomic DNA for additional priming After the first cycle, amplification products have a single 5' tag (FIG. 15C). These aforementioned steps are repeated up to 20 times, for example by beginning cycle 2 at 4° C. and using the random N-mer sequence to again prime the genomic DNA where the black sequence indicates portions of the added 5' tags (added in cycle 1) that cannot be copied (FIG. 15D). Denaturation occurs at 98° C. to again release genomic DNA and the amplification product from the first cycle for additional priming After a second round of thermocycling, both 5' tagged products and 3' & 5' tagged products exist (FIG. 15E). Partial hairpin structures form from the 3' & 5' tagged products preventing amplification of undesired products (FIG. 15F). A new random priming of the genomic DNA sequence begins again at 4° C. (FIG. 15G).

Example 13

Adding Additional Sequences by Amplification

For the completion of sequencer-ready libraries, an additional amplification (e.g., polymerase chain reaction (PCR) step) is completed to add additional sequences, FIG. 14C. In order to out-compete hairpin formation, a primer containing locked nucleic acid (LNAs) or locked nucleic acid nucleotides, is used. Furthermore, in cases where the inclusion of uracil containing nucleotides is used in a previous step, a polymerase that does not discriminate against template uracil containing nucleotides is used for this step. The results presented in FIG. 17 show that a blocking oligonucleotide reduces start site bias, as measured by sequencing on an Illumina MiSeq sequencer. The nucleic acid template in this case is yeast gDNA.

Example 14

Digital Processor

A conceptual schematic for an example control assembly, 1801, is shown in FIG. 18. A computer, 1802, serves as the central hub for control assembly, 1801. Computer, 1802, is in communication with a display, 1803, one or more input devices (e.g., a mouse, keyboard, camera, etc.) 1804, and optionally a printer, 1805. Control assembly, 1801, via its computer, 1802, is in communication with one or more devices: optionally a sample pre-processing unit, 1806, one or more sample processing units (such as a sequence, thermocycler, or microfluidic device) 1807, and optionally a detector, 1808. The control assembly may be networked, for example, via an Ethernet connection. A user may provide inputs (e.g., the parameters necessary for a desired set of nucleic acid amplification reactions or flow rates for a microfluidic device) into computer, 1802, using an input device, 1804. The inputs are interpreted by computer, 1802, to generate instructions. The computer, 1802, communicates such instructions to the optional sample pre-processing unit, 1806, the one or more sample processing units, 1807, and/or the optional detector, 1808, for execution. Moreover, during operation of the optional sample pre-processing unit, 1806, one or more sample processing units, 1807, and/or the optional detector, 1808, each device may communicate signals back to computer, 1802. Such signals may be interpreted and used by computer, 1802, to determine if any of the devices require further instruction. Computer, 1802, may also modulate sample pre-processing unit, 1806, such that the components of a sample are mixed appropriately and fed, at a desired or otherwise predetermined rate, into the sample processing unit (such as the microfluidic device), 1807. Computer, 1802, may also communicate with detector, 1808, such that the detector performs measurements at desired or otherwise predetermined time points or at time points determined from feedback received from pre-processing unit, 1806, or sample processing unit, 1807. Detector, 1808, may also communicate raw data obtained during measurements back to computer, 1802, for further analysis and interpretation. Analysis may be summarized in formats useful to an end user via display, 1803, and/or printouts generated by printer, 1805. Instructions or programs used to control the sample pre-processing unit, 1806, the sample processing unit, 1807, and/or detector, 1808; data acquired by executing any of the methods described herein; or data analyzed and/or interpreted may be transmitted to or received from one or more remote computers, 1809, via a network, 1810, which, for example, could be the Internet.

Example 15

Combinatorial Technique Via Ligation

As shown in FIG. 23A, beads 2301 are generated and covalently linked (e.g., via an acrydite moiety) to a partial P5 sequence 2302. Separately, in 50 μL of each well of 4 96 well plates, an oligonucleotide 2303, comprising the remaining P5 sequence and a unique partial barcode sequence (indicated by bases "DDDDDD" in oligonucleotide 2303), is hybridized to an oligonucleotide 2304 that comprises the reverse complement to oligonucleotide 2303 and additional bases that overhang each end of oligonucleotide 2303. Splint 2306 is generated. Each overhang is blocked (indicated with an "X" in FIG. 23) with 3' C3 Spacer, 3' Inverted dT, or dideoxy-C (ddC) to prevent side product formation.

As shown in FIG. 23B, splints 2306 are each added to 4 96 deep well plates, with each well comprising 2 mL beads 2301 and a splint comprising a unique partial barcode sequence. In each well, the splint 2306 hybridizes with the partial P5 sequence 2302 of beads 2301, via the corresponding overhang of oligonucleotide 2304. Following hybridization, partial P5 sequence 2302 is ligated to oligonucleotide 2303 (which will typically have been 5' phosphorylated) via the action of a ligase, e.g., a T4 ligase, at 16° C. for 1 hour. Following ligation, the products are pooled and the beads washed to remove unligated oligonucleotides.

As shown in FIG. 23C, the washed products are then redistributed into wells of 4 new 96 well plates, with each well of the plate comprising 2 mL of beads 2301 and an oligonucleotide 2305 that has a unique partial barcode sequence (indicated by "DDDDDD" in oligonucleotide 2305) and an adjacent short sequence (e.g., "CC" adjacent to the partial barcode sequence and at the terminus of oligonucleotide 2305) complementary to the remaining overhang of oligonucleotide 2304. Oligonucleotide 2305 also comprises a random N-mer (indicated by "NNNNNNNNNN" in oligonucleotide 2305). Via the adjacent short sequence, oligonucleotide 2305 is hybridized with oligonucleotide 2304 via the remaining overhang of oligonucleotide 2304. Oligonucleotide 2305 is then ligated to oligonucleotide 2303 via the action of a ligase at 16° C. for 1 hour. Ligation of oligonucleotide 2305 to oligonucleotide 2303 results in the generation of a full barcode sequence. As shown in FIG. 23D, the products are then pooled, the oligonucleotide 2304 is denatured from the products, and the unbound oligonucleotides are then washed away. Following washing, a diverse library of barcoded beads is obtained, with each bead bound to an oligonucleotide comprising a P5 sequence, a full barcode sequence, and a random N-mer. The generated library comprises approximately 147,000 different barcode sequences.

Example 16

Figure 33A:
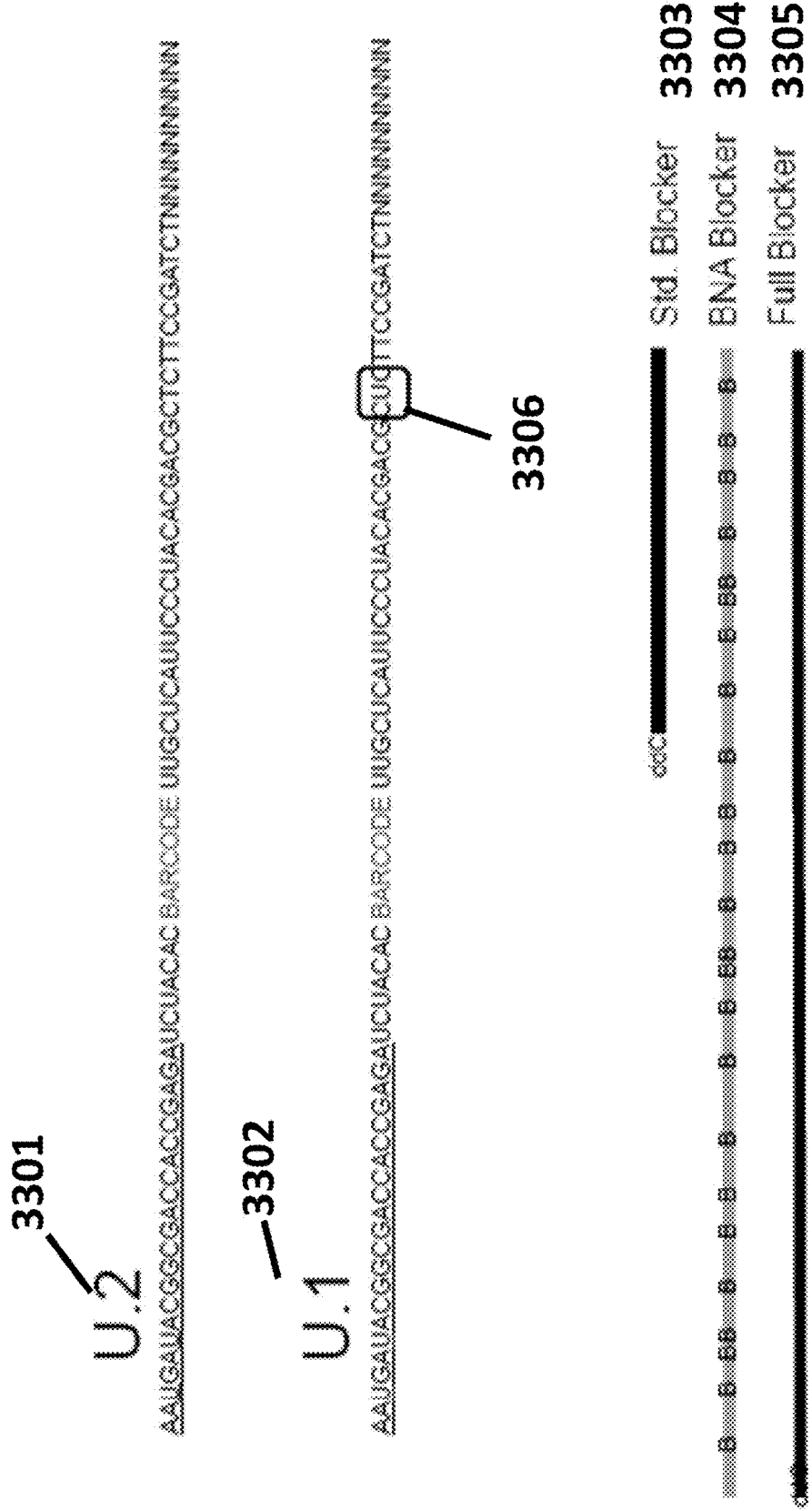
FIG. 33A is a schematic depiction of barcode primers (SEQ ID NOS 23 and 24, respectively, in order of appearance).

Substitution of Uracil Containing Nucleotides for Thymine Containing Nucleotides in Barcode Primers As shown in FIG. 33A, two barcode primers 3301 and 3302 suitable for PHASE amplification were used to amplify sample nucleic acid obtained from a yeast genome. Following PHASE amplification, additional sequences were added (e.g., via bulk PCR) to generate sequencer-ready products. Barcode primers 3301 (also shown as U.2 in FIG. 33A) and 3302 (also shown at U.1 in FIG. 33A) comprised an identical sequence except that barcode primer 3301 comprised an additional uracil containing nucleotide-for-thymine containing nucleotide substitution at position 3306. Sets of amplification experiments were run for each barcode primer, with each set corresponding to a particular blocker oligonucleotide mixed with the respective barcode primer at various stoichiometries. For barcode primer 3302, sets of amplification experiments corresponding to a standard blocker oligonucleotide 3303, a full blocker oligonucleotide comprising bridged nucleic acid (BNAs) 3304 (also shown as BNA blocker in FIG. 33A), or a full blocker oligonucleotide 3305 were conducted. Blocker oligonucleotides 3303 and 3305 comprised uracil containing nucleotide-for-thymine containing nucleotide substitutions at all thymine containing nucleotide positions and a ddC blocked end. In each set, the blocker oligonucleotide:barcode primer stoichiometry was either 0, 0.4, 0.8, or 1.2. For barcode primer 3301, each type of blocker oligonucleotide 3303, 3304, and 3305 was tested at a 0.8 blocker oligonucleotide:barcode primer stoichiometry.

Figure 33B:
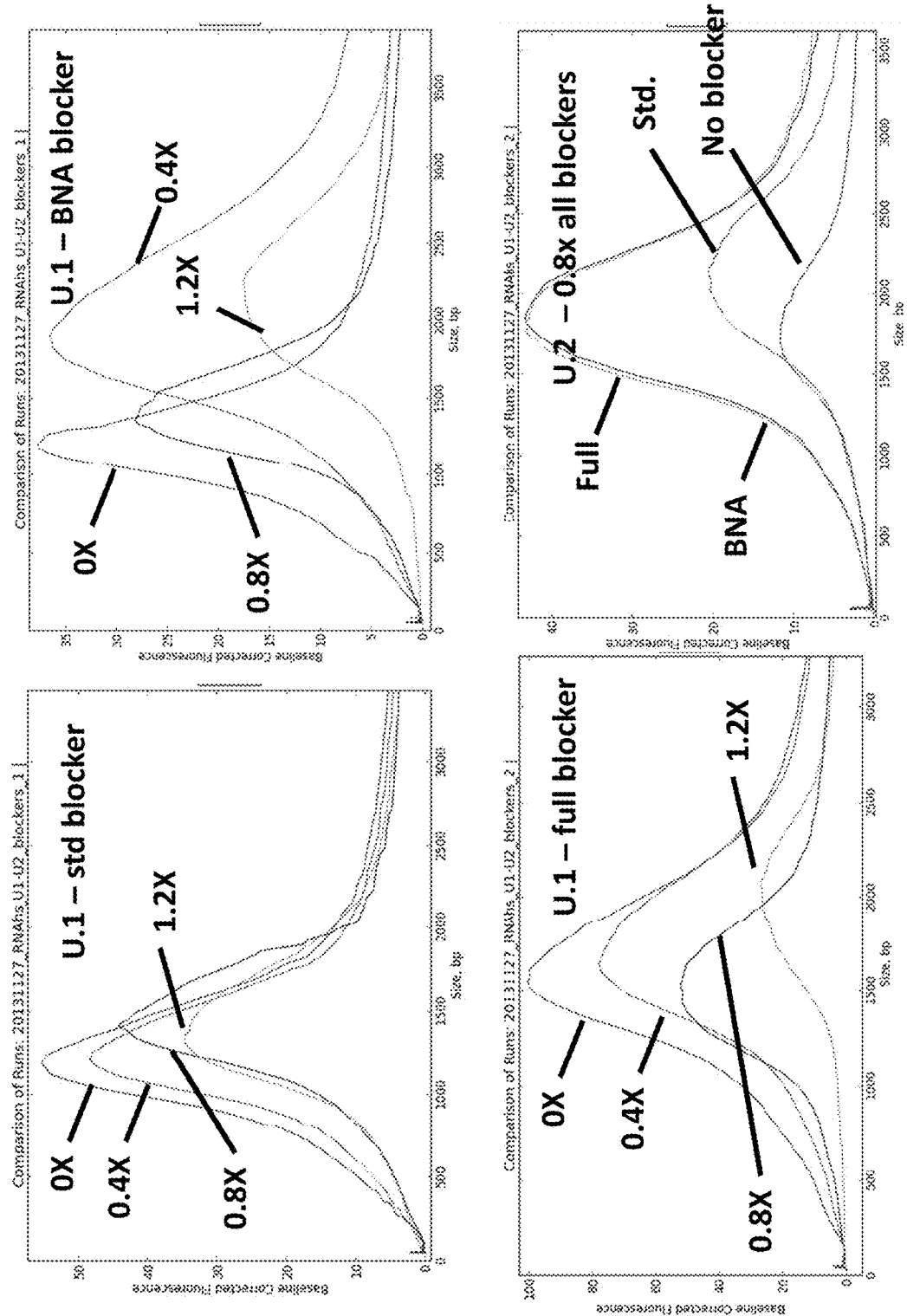
Figure 33C:
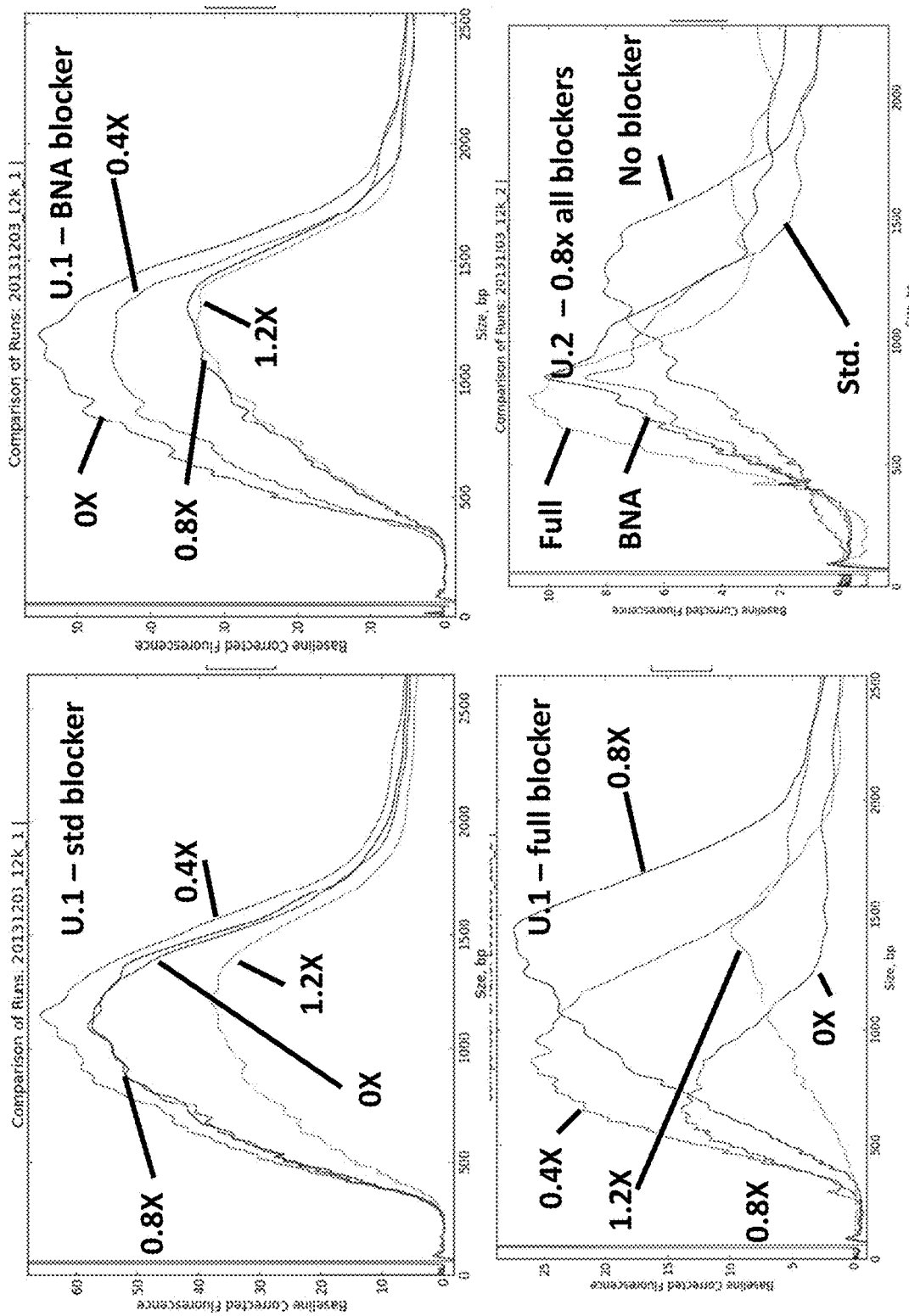

The size results of PHASE amplification products are depicted in FIG. 33B. As shown, barcode primer 3302 (e.g., comprising the extra uracil containing nucleotide-for-thymine containing nucleotide substitution) coupled to blocker oligonucleotide 3303 generally produced the smallest amplification products across the stoichiometries tested. Results for barcode primer 3302 with respect to blocker oligonucleotides 3304 and 3305 varied, with sizes generally larger than results for blocker oligonucleotide 3303. For barcode primer 3301, amplification product sizes were also generally larger than those obtained for barcode primer 3301 coupled to blocker oligonucleotide 3303 across the blocker oligonucleotides tested. The size results of sequencer-ready products are depicted in FIG. 33C.

Key sequencing metrics obtained from the amplification products are depicted in FIG. 33D. As shown, the fraction of unmapped reads (panel I in FIG. 33D) was generally lower for sequencing runs for amplification products generated from barcode primer 3302. For example, the fraction of unmapped reads for amplification products generated from barcode primer 3302 and blocker oligonucleotide 3303 at 0.8 blocker oligonucleotide:barcode primer stoichiometry was approximately 7-8%, whereas results obtained using barcode primer 3301 at the same conditions was approximately 17-18%. Moreover, Q40 error rates (panel II in FIG. 33D) were also lower for barcode primer 3302. For example, Q40 error rate for amplification products generated from barcode primer 3302 and blocker oligonucleotide 3303 at 0.8 blocker oligonucleotide:barcode primer stoichiometry was approximately 0.105%, whereas results obtained using barcode primer 3301 at the same conditions was approximately 0.142%. Read 1start site (panel III) and Read 2 start site (panel IV) relative entropies determined during sequencing are shown in FIG. 33E.

Example 17

Post-Synthesis Functionalization of Gel Beads Via Disulfide Exchange

Gel beads comprising disulfide bonds were generated according to one or more methods described herein. The gel beads were then reacted with TCEP at ratios of molecules of TCEP to gel beads (TCEP:GB). The tested ratios were 0, 2.5 billion, and 10.0 billion. The TCEP functions as a reducing agent to generate free thiols within the gel beads. Following reduction, the gel beads were washed once to remove the TCEP. Next, the generated free thiols of the gel beads were reacted with an acrydite-S—S-P5 species (e.g., 3505 in FIG. 35A) to link the acrydite-S—S-P5 to the gel beads via Michael addition chemistry as shown in FIG. 35A. Different ratios of acrydite-S—S-P5 to each type (e.g., ratio of TCEP:GB used to generate free thiols on the gel beads) of the activated gel beads were tested. The tested ratios of acrydite-S—S-P5 species to activated gel beads (P5:GB) were 50 million, 500 million, and 5 billion.

Figure 36:
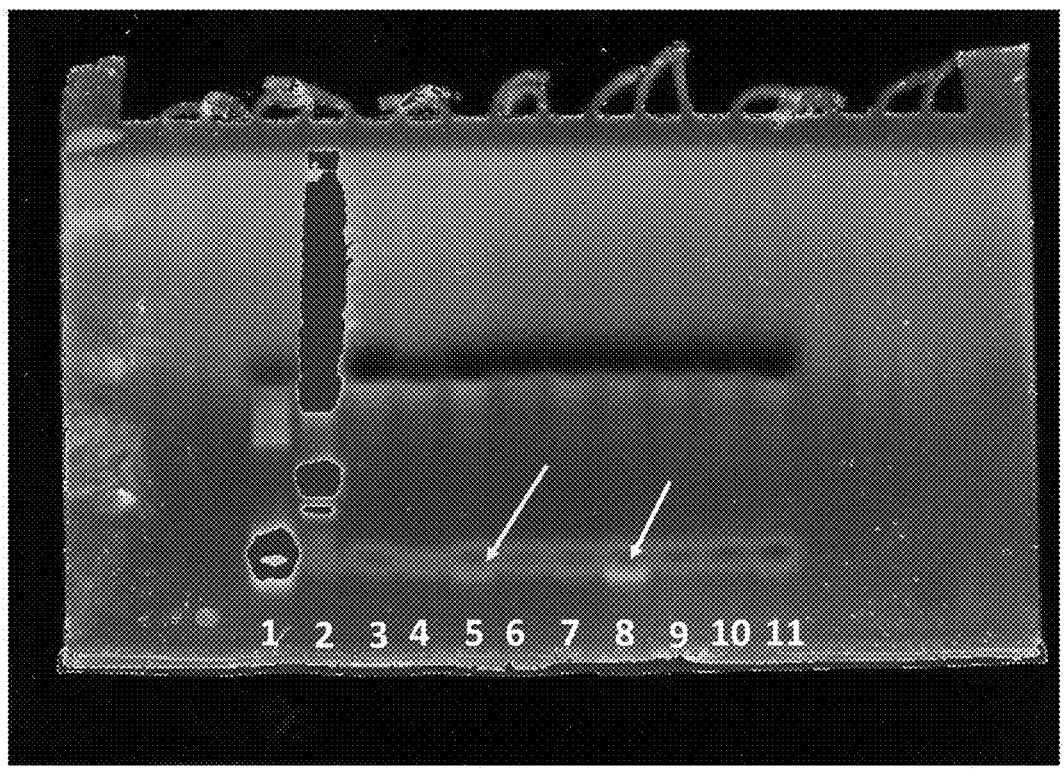
FIG. 36 is a photograph of a gel obtained during a gel electrophoresis experiment described in Example 17.

Following syntheses, the gel beads from each reaction were washed and treated with DTT in a reaction mixture to degrade the gel beads and release any bound acrydite-S—S-P5 species. An aliquot of each reaction mixture was entered into a lane of a gel and free oligonucleotides subject to gel electrophoresis as shown in FIG. 36 (e.g., lanes 3-11 in FIG. 36). A 50 picomole acrydite-S—S-P5 standard was also run (e.g., lane 1 in FIG. 36) along with a 25 base pair ladder (e.g., lane 2 in FIG. 36). Bands corresponding to loaded acrydite-S—S-P5 were generated in lanes 5 and 8 (indicated by arrows in FIG. 36). Lane 5 corresponds to gel beads treated at a TCEP:GB ratio of 2.5 billion and the TCEP treated gel beads reacted with acrydite-S—S-P5 at a P5:GB ratio of 5 billion. Lane 8 corresponds to gel beads treated at a TCEP:GB ratio of 10.0 billion and the TCEP treated gel beads reacted with acrydite-S—S-P5 at a P5:GB ratio of 5 billion.

Example 18

Post-Synthesis Functionalization of Gel Beads Via Disulfide Exchange

Gel beads comprising disulfide bonds were generated according to one or more methods described herein. The gel beads were then reacted with TCEP in 0.1M phosphate buffer at a concentration of 4 μg TCEP/100,000 gel beads. The TCEP can function as a reducing agent to generate gel beads with free thiol groups. Following reduction, the gel beads were washed once to separate the gel beads from the TCEP. Next, the free thiols of the gel beads were reacted with 2,2'-dithiopyridine (e.g., 3507 in FIG. 35B) in a saturated solution (~0.2 mM) of 2,2'-dithiopyridine to link pyridine groups to the gel beads via disulfide exchange chemistry as shown in FIG. 35B. Following synthesis, the gel beads were washed three times to remove excess 2,2'-dithiopyridine.

Figure 37A:
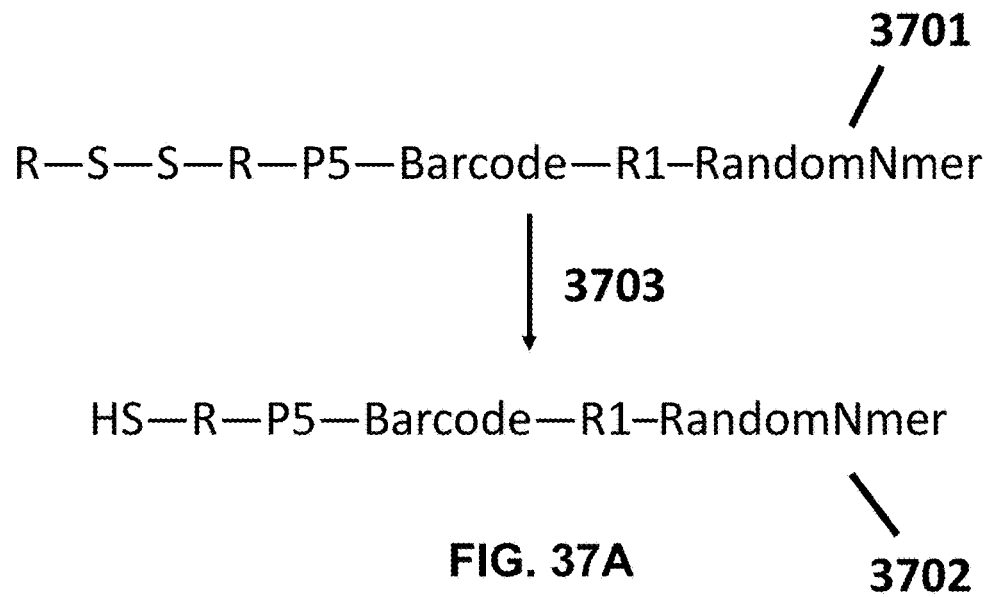
FIG. 37A is a schematic depiction of oligonucleotides described in Example 18.

The washed gel beads were then reacted with an oligonucleotide 3702 comprising a full construct barcode (FCBC—e.g., an oligonucleotide comprising P5, a barcode sequence, R1, and a random N-mer) sequence at one end and a free thiol group at its other end. Two reactions were completed at two different ratios of molecules of FCBC to gel beads (e.g., FCBC:GB) and the reactions were allowed to proceed overnight. The tested FCBC:GB ratios were 400 million and 1.6 billion. Oligonucleotide 3702 was initially supplied with its free thiol group protected in a disulfide bond, shown as 3701 in FIG. 37A. To generate the free thiol as in oligonucleotide 3702, oligonucleotide 3701 was treated with 0.1 M DTT in 1× Tris-EDTA buffer (TE) buffer for 30 minutes. Salt exchange on a Sephadex (NAP-5) column was used to remove DTT after reduction and purify oligonucleotide 3702. For each reaction, purified oligonucleotides 3702 were then reacted with the dithio-pyridine species of the gel beads via thiol-disulfide exchange (e.g., see FIG. 35B) to generate gel beads comprising oligonucleotide 3702. Following the reaction, the gel beads were purified by washing the beads three times.

For comparison purposes, gel beads comprising disulfide bonds and the FCBC sequence were also generated via polymerization of monomers as described elsewhere herein. The FCBC was linked to a monomer comprising an acrydite species that was capable of participating in a polymerization with acrylamide and bis(acryloyl)cystamine to generate the gel beads. The FCBC sequence was linked to the gel beads via the acrydite moiety.

Figure 37B:
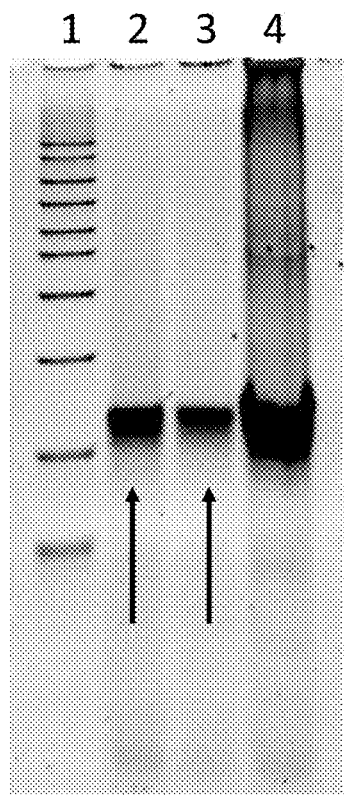
FIG. 37B is a photograph of a gel obtained during a gel electrophoresis experiment described in Example 18.

Following syntheses, the gel beads from each reaction were washed and treated with DTT in a reaction mixture to degrade the gel beads and release any bound oligonucleotide 3702. Gel beads comprising the FCBC sequence that were synthesized via polymerization were also treated with DTT in a reaction mixture. An aliquot of each reaction mixture was entered into a lane of a gel and free oligonucleotides subject to gel electrophoresis as shown in FIG. 37B. As shown in the gel photograph depicted in FIG. 37B, lane 1 corresponds to a 50 base pair ladder; lane 2 corresponds to gel beads functionalized via disulfide exchange chemistry at an FCBC:GB ratio of 400 million; lane 3 corresponds to gel beads functionalized via disulfide exchange chemistry at an FCBC:GB ratio of 1.6 billion; and lane 4 corresponds to functionalized gel beads generated via polymerization of acrydite species. Bands corresponding to loaded oligonucleotides were generated for functionalized gel beads generated at both FCBC:GB ratios and were at a similar position to the band generated for functionalized gel beads generated via polymerization of acrydite species.

Figure 37C:
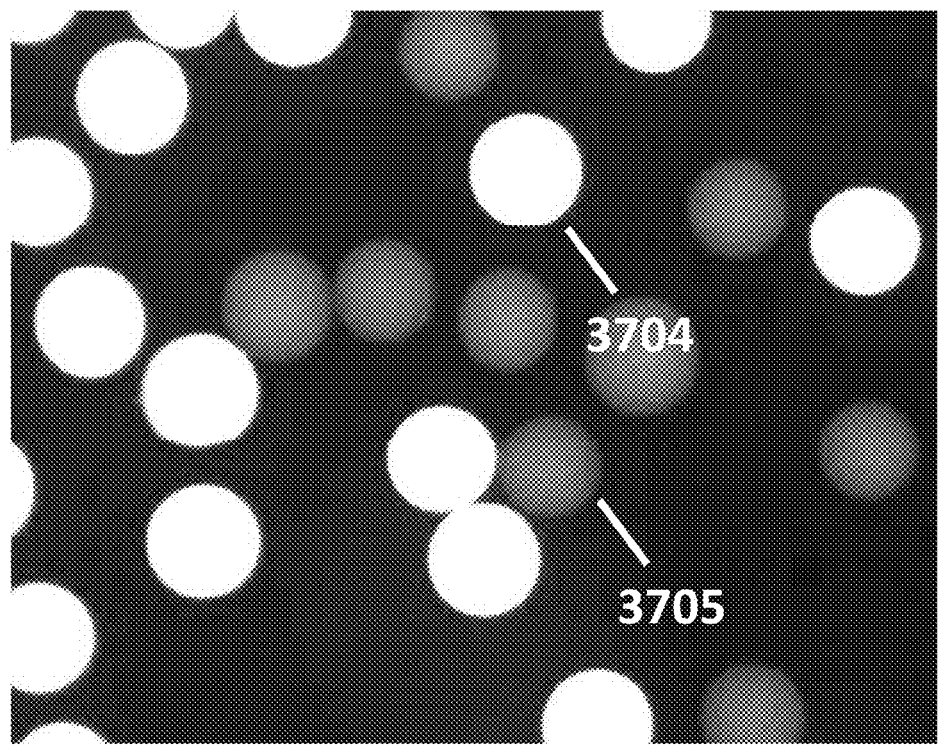
FIG. 37C is a micrograph of beads obtained during a fluorescence microscopy experiment described in Example 18.

Following syntheses, gel beads from each reaction were also washed and stained with SYBR Gold fluorescent stain. Gel beads comprising the FCBC sequence that were synthesized via polymerization were also stained with SYBR Gold. SYBR Gold can stain functionalized beads by intercalating any bound oligonucleotides. Following staining, the beads were pooled and imaged using fluorescence microscopy, as shown in the micrograph depicted in FIG. 37C. Brighter beads (3704) in FIG. 37C correspond to beads functionalized during polymerization of the beads and dim beads (still showing SYBR gold signal) (3705) correspond to beads functionalized with disulfide exchange chemistry after gel bead generation. Loading of oligonucleotides via disulfide-exchange was approximately 30% of that achieved with functionalization of beads during gel bead polymerization.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:
1. A method for polynucleotide barcoding, comprising:
   (a) providing a first set of partitions comprising (i) a first set of nucleic acid barcode molecules comprising barcode sequences and (ii) a plurality of polynucleotides and attaching said first set of nucleic acid barcode molecules to said plurality of polynucleotides to generate a first set of barcoded polynucleotides;
   (b) pooling contents of said first set of partitions;
   (c) partitioning (i) a second set of nucleic acid barcode molecules comprising barcode sequences and (ii) at least a portion of said contents from (b) into a second set of partitions different than said first set of partitions; and
   (d) in said second set of partitions, attaching said second set of nucleic acid barcode molecules to said first set of barcoded polynucleotides to generate a second set of barcoded polynucleotides.

2. The method of claim 1, wherein a subset of barcoded polynucleotides of said first set of barcoded polynucleotides have identical barcode sequences.

3. The method of claim 1, wherein at least a subset of barcoded polynucleotides of said second set of barcoded polynucleotides have different barcode sequences.

4. The method of claim 1, wherein said plurality of polynucleotides is attached to beads.

5. The method of claim 1, wherein said plurality of polynucleotides is a plurality of cellular polynucleotides.

6. The method of claim 1, wherein said first set of partitions are a first set of wells and said second set of partitions are a second set of wells.

7. The method of claim 1, wherein said first set of partitions are a first set of droplets and said second set of partitions are a second set of droplets.

8. The method of claim 1, wherein said first set of nucleic acid barcode molecules are attached to said plurality of polynucleotides by a nucleic acid reaction or (ii) said second set of nucleic acid barcode molecules are attached to said first set of barcoded polynucleotides by a nucleic acid reaction.

9. The method of claim 1, wherein (i) said first set of nucleic acid barcode molecules are attached to said plurality of polynucleotides by a nucleic acid primer extension reaction or (ii) said second set of nucleic acid barcode molecules are attached to said first set of barcoded polynucleotides by a nucleic acid primer extension reaction.

10. The method of claim 1, wherein (i) said first set of nucleic acid barcode molecules are attached to said plurality of polynucleotides by a nucleic acid amplification reaction or (ii) said second set of nucleic acid barcode molecules are attached to said first set of barcoded polynucleotides by a nucleic acid amplification reaction.

11. The method of claim 1, wherein (i) said first set of nucleic acid barcode molecules are attached to said plurality of polynucleotides by ligation or (ii) said second set of nucleic acid barcode molecules are attached to said first set of barcoded polynucleotides by ligation.

12. The method of claim 1, wherein said first set of barcoded polynucleotides or said second set of barcoded polynucleotides are coupled to a plurality of beads.

13. The method of claim 12, wherein said first set of barcoded polynucleotides or said second set of barcoded polynucleotides are releasable from said plurality of beads.

14. The method of claim 12, wherein said plurality of beads is a plurality of gel beads.

15. The method of claim 14, wherein each gel bead of said plurality of gel beads is dissolvable or disruptable.

16. The method of claim 1, wherein each nucleic acid barcode molecule of said first set of nucleic acid barcode molecules or said second set of nucleic acid barcode molecules further comprises a primer sequence.

17. The method of claim 16, wherein said primer sequence is a targeted primer sequence or a random primer sequence.

18. The method of claim 1, wherein each nucleic acid barcode molecule of said first set of nucleic acid barcode molecules or said second set of nucleic acid barcode molecules further comprises a random N-mer.

19. The method of claim 1, wherein said barcode sequences of said first set of nucleic acid barcode molecules or said barcode sequences of said second set of nucleic acid barcode molecules are greater than 4 nucleic acid bases in length.

20. The method of claim 1, wherein said barcode sequences of said first set of nucleic acid barcode molecules or said barcode sequences of said second set of nucleic acid barcode molecules are 4 to 20 nucleic acid bases in length.

21. The method of claim 1, wherein each barcoded polynucleotide of said second set of barcoded polynucleotides comprises a barcode sequence that is at least 15 nucleic acid bases in length.

22. The method of claim 1, wherein said second set of barcoded polynucleotides comprises at least 100,000 different barcode sequences.

23. The method of claim 1, wherein said second set of barcoded polynucleotides comprises at least 1,000,000 different barcode sequences.

24. The method of claim 1, wherein said second set of barcoded polynucleotides comprises at least 10,000,000 different barcode sequences.

25. The method of claim 1, further comprising:
   (e) pooling contents of said second set of partitions;
   (f) partitioning (i) a third set of nucleic acid barcode molecules comprising barcode sequences and (ii) at least a portion of said contents from (e) into a third set of partitions different than said first set of partitions and said second set of partitions; and
   (g) in said third set of partitions, attaching said third set of nucleic acid barcode molecules to said second set of barcoded polynucleotides to generate a third set of barcoded polynucleotides.

26. The method of claim 25, further comprising:
   (h) pooling contents of said third set of partitions;
   (i) partitioning (i) a fourth set of nucleic acid barcode molecules comprising barcode sequences and (ii) at least a portion of said contents from (h) into a fourth set of partitions different than said first set of partitions, said second set of partitions, and said third set of partitions; and
   (j) in said fourth set of partitions, attaching said fourth set of nucleic acid barcode molecules comprising barcode sequences to said third set of barcoded polynucleotides to provide a fourth set of barcoded polynucleotides.

27. The method of claim 26, wherein said first set of nucleic acid barcode molecules are attached to said plurality of polynucleotides by a nucleic acid primer extension reaction, wherein said second set of nucleic acid barcode molecules are attached to said first set of barcoded polynucleotides by ligation, wherein said third set of nucleic acid barcode molecules are attached to said second set of barcoded polynucleotides by ligation, and wherein said fourth set of nucleic acid barcode molecules are attached to said third set of barcoded polynucleotides by a nucleic acid amplification reaction.

28. The method of claim 1, wherein said first set of barcoded polynucleotides and said second set of barcoded polynucleotides are coupled to a plurality of beads.

\* \* \* \* \*

SEQUENCE LISTING

```
<160> NUMBER OF SEQ ID NOS: 24

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (8)..(10)
<223> OTHER INFORMATION: a, c, t, g, unknown or other

<400> SEQUENCE: 1 nnnatacnnn                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 2 ncngnnaann                                                          10

<210> SEQ ID NO 3
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (9)..(10)
<223> OTHER INFORMATION: a, c, t, g, unknown or other

<400> SEQUENCE: 3 nngcngngnn                                                          10

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 4
aaugauacgg cgaccaccga ga                                            22

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, t, g, unknown or other

<400> SEQUENCE: 5
nnnnnntctc ggtggtcgcc gtatcatt                                      28

<210> SEQ ID NO 6
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (43)..(50)
<223> OTHER INFORMATION: a, c, u, g, unknown or other

<400> SEQUENCE: 6
nnnnnncgca cacucuuucc cuacacgacg cucuuccgau cunnnnnnnn               50

<210> SEQ ID NO 7
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
gcgtcgtgta gggaaagagt gt                                              22

<210> SEQ ID NO 8
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(34)
<223> OTHER INFORMATION: a, c, t, g, unknown or other

<400> SEQUENCE: 8
gcgtcgtgta gggaaagagt gtnnnnnnnn nnnngtgtag atctcggtgg tcgccgtatc     60
att                                                                   63

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 9
nnnnnnnnag atcggaagag cgtcgtgtag ggaaagagtg t                         41

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(13)
<223> OTHER INFORMATION: a, c, t, g, unknown or other

<400> SEQUENCE: 10
tctacacnnn nnn                                                        13

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 11
ggnnnnnngt gtagatctc                                                  19
```

```
<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(35)
<223> OTHER INFORMATION: a, c, t, g, unknown or other

<400> SEQUENCE: 12
aaugauacgg cgaccaccga gatctacacn nnnnn                               35

<210> SEQ ID NO 13
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(35)
<223> OTHER INFORMATION: a, c, t, g, unknown or other
<220> FEATURE:
<221> NAME/KEY: modified_base
<222> LOCATION: (38)..(43)
<223> OTHER INFORMATION: a, c, t, g, unknown or other
<220> FEATURE:
<221> NAME/KEY: modified_base
<222> LOCATION: (77)..(86)
<223> OTHER INFORMATION: a, c, t, g, unknown or other

<400> SEQUENCE: 13
aaugauacgg cgaccaccga gatctacacn nnnnccnnn nnnttgctca ttccctacac     60
gacgctcttc cgatctnnnn nnnnnn                                        86

<210> SEQ ID NO 14
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(35)
<223> OTHER INFORMATION: a, c, t, g, unknown or other
<220> FEATURE:
<221> NAME/KEY: modified_base
<222> LOCATION: (38)..(43)
<223> OTHER INFORMATION: a, c, t, g, unknown or other
<220> FEATURE:
<221> NAME/KEY: modified_base
<222> LOCATION: (77)..(86)
<223> OTHER INFORMATION: a, c, t, g, unknown or other

<400> SEQUENCE: 14
aaugauacgg cgaccaccga gatctacacn nnnncannn nnnttgctca ttccctacac     60
gacgctcttc cgatctnnnn nnnnnn                                        86
```

<210> SEQ ID NO 15
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(36)
<223> OTHER INFORMATION: a, c, t, g, unknown or other
<220> FEATURE:
<221> NAME/KEY: modified_base
<222> LOCATION: (39)..(44)
<223> OTHER INFORMATION: a, c, t, g, unknown or other
<220> FEATURE:
<221> NAME/KEY: modified_base
<222> LOCATION: (78)..(87)
<223> OTHER INFORMATION: a, c, t, g, unknown or other

<400> SEQUENCE: 15
aaugauacgg cgaccaccga gatctacacn nnnnnncann nnnnttgctc attccctaca      60
cgacgctctt ccgatctnnn nnnnnnn                                         87

<210> SEQ ID NO 16
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(37)
<223> OTHER INFORMATION: a, c, t, g, unknown or other
<220> FEATURE:
<221> NAME/KEY: modified_base
<222> LOCATION: (40)..(45)
<223> OTHER INFORMATION: a, c, t, g, unknown or other
<220> FEATURE:
<221> NAME/KEY: modified_base
<222> LOCATION: (79)..(88)
<223> OTHER INFORMATION: a, c, t, g, unknown or other

<400> SEQUENCE: 16
aaugauacgg cgaccaccga gatctacacn nnnnnncan nnnnttgct cattccctac       60 acgacgctct tccgatctnn nnnnnnnn                                        88

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 17
nnnnnnnngt gtagatctc                                                  19

<210> SEQ ID NO 18

```
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (30)..(43)
<223> OTHER INFORMATION: a, c, t, g, unknown or other
<220> FEATURE:
<221> NAME/KEY: modified_base
<222> LOCATION: (77)..(86)
<223> OTHER INFORMATION: a, c, t, g, unknown or other

<400> SEQUENCE: 18
aaugauacgg cgaccaccga gatctacacn nnnnnnnnnn nnnttgctca ttccctacac      60
gacgctcttc cgatctnnnn nnnnnn                                          86

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 19
cannnnnngt gtagatctc                                                  19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 20
tcnnnnnngt gtagatctc                                                  19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 21
agnnnnnngt gtagatctc                                                  19

<210> SEQ ID NO 22
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(8)
<223> OTHER INFORMATION: a, c, t, g, unknown or other

<400> SEQUENCE: 22
gtnnnnnngt gtagatctc                                                    19

<210> SEQ ID NO 23
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (63)..(72)
<223> OTHER INFORMATION: a, c, t, g, unknown or other
<220> FEATURE:
<221> NAME/KEY: misc_feature
<222> LOCATION: (29)..(30)
<223> OTHER INFORMATION: Nucleotides at these positions are
      non-consecutive and are separated by an undisclosed barcode
      sequence

<400> SEQUENCE: 23
aaugauacgg cgaccaccga gaucuacacu ugcucauucc cuacacgacg ctcttccgat        60
ctnnnnnnnn nn                                                           72

<210> SEQ ID NO 24
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (63)..(72)
<223> OTHER INFORMATION: a, c, t, g, unknown or other
<220> FEATURE:
<221> NAME/KEY: misc_feature
<222> LOCATION: (29)..(30)
<223> OTHER INFORMATION: Nucleotides at these positions are
      non-consecutive and are separated by an undisclosed barcode
      sequence

<400> SEQUENCE: 24
aaugauacgg cgaccaccga gaucuacacu ugcucauucc cuacacgacg cucttccgat        60
ctnnnnnnnn nn                                                           72
```